United States Patent [19]
Murphy et al.

[11] Patent Number: 5,508,384
[45] Date of Patent: Apr. 16, 1996

[54] POLYPEPTIDE DERIVED FROM A POPAMINE RECEPTOR, AND COMPOSITIONS AND METHODS THEREOF

[75] Inventors: Randall B. Murphy, Irvington, N.Y.; David I. Schuster, Wilton, Conn.

[73] Assignee: New York University, New York, N.Y.

[21] Appl. No.: 118,270

[22] Filed: Sep. 9, 1993

Related U.S. Application Data

[63] Continuation-in-part of Ser. No. 943,236, Sep. 10, 1992, abandoned.

[51] Int. Cl.$^6$ .................................................... C07K 14/705
[52] U.S. Cl. ............................................................ 530/324
[58] Field of Search ................................... 514/12, 13, 2; 530/300, 324

[56] References Cited

PUBLICATIONS

FASEB, J. 3:1825–1832, May 1984, Strader et al. Structural Basis of β–adrenergic receptor function.
Pharmac. Ther. 50:425–442, 1991, Jackson Structure and Function of G Protein Coupled Receptors.
Science 246:1310–1316, 03 Jun., 1988, Kobilka et al. Chimeric $\alpha_2,\beta_2$–Adrenergic Receptors: Delineation of Domains Involved in Effects–Coupling and Ligand Binding.
Nature 336:783–787, 22 Dec. 1988, Bunzow et al, Cloning and Expression of a rat $D_2$ dopamine receptor cDNA.

*Primary Examiner*—Garnette D. Draper
*Assistant Examiner*—John A. Ulm
*Attorney, Agent, or Firm*—Browdy and Neimark

[57] ABSTRACT

Compounds, compositions and methods involving purified, isolated and/or synthetic G-protein coupled receptor (GPR) polypeptides that comprise fragments, derivatives and/or consensus peptides of transmembrane domains of G-coupled receptor proteins, wherein the GPR polypeptide has biological activity selected from binding of a GPR ligand to a GPR or modulating the binding of a GPR ligand to a GPR.

1 Claim, 18 Drawing Sheets

FIG. 1

LSLLLSLLSLLLSLLSLLLSLYYY

FIG. 2

DDIFVTLDVLFSTASILNLSAISLKKK

FIG. 3

DYAIFVLYASAWLSFNCPFIVTLNIK

FIG. 4

KAVVYSSIVSFYVFID

FIG. 5

DCDVFVFVDIMLCTASIFNLCAISVGK

FIG. 8A(1)

1. Dictyostelium cAMP receptor (Klein et al., 1988)
2. Dog adenosine A2 receptor (RDC8) (Libert et al., 1989b)
3. Dog adenosine A1 receptor (RDC7) (Libert et al., 1989b)

4. Human m1 muscarinic acetylcholine receptor (Peralta et al., 1987)
5. Human m2 muscarinic acetylcholine receptor (Peralta et al., 1987)
6. Human m3 muscarinic acetylcholine receptor (Peralta et al., 1987)
7. Human m4 muscarinic acetylcholine receptor (Peralta et al., 1987)
8. Human m5 muscarinic acetylcholine receptor (Bonner et al., 1988)

9. Human beta 1 adrenergic receptor (Frielle et al., 1987)
10. Human beta 1 adrenergic receptor (Kobilka et al., 1987a)
11. Human beta 1 adrenergic receptor (Emorine et al., 1989)
12. Cow alpha 1 adrenergic receptor (Schwinn et al., 1990)
13. Rat alpha 1B adrenergic receptor (Voight, et al., 1990)
14. Human alpha 2 C4 adrenergic receptor (Regan et al., 1988)
15. Human alpha 2 C2 adrenergic receptor (Lomasney et al., 1990)
16. Human alpha 2 C10 adrenergic receptor (Kobilka et al., 1987c)
17. Rat alpha 2 adrenergic receptor R20 (Lanier et al., 1991)
18. Drosophila octopamine receptor (Arakawa et al., 1990)
19. Human dopamine D1 receptor (Dearry et al., 1990)
20. Human dopamine D5 receptor (Sunahara et al., 1991)
21. Human dopamine D2 receptor (Grandy et al., 1989)
22. Human dopamine D3 receptor (Giros et al., 1990)
23. Human dopamine D4 receptor (Van Tol et al., 1991)
24. Human serotonin 1d receptor [RDC4] (Hamblin and Metcalf, 1991)
25. Human serotonin 1a receptor (Kobilka et al., 1987b)
26. Rat serotonin 1c receptor (Julius et al., 1988)
27. Rat serotonin 2 receptor (Julius et al., 1990)
28. Human histamine H2 receptor (Gantz et al., 1991)
29. Human N-formyl peptide receptor (Boulay et al., 1990)
30. Human C5a anaphylatoxin receptor. (Gerard and Gerard, 1991)
31. Human thrombin receptor (Vu et al., 1991)
32. Human thromboxane A2 receptor (Hirata et al., 1991)
33. Human IL-8 receptor (Murphy and Tiffany, 1991)
34. Guinea-pig platelet-activating factor receptor (Honda et al., 1991)
35. Cow endothelin 1 receptor (Arai et al., 1990)
36. Rat non-isopeptide selective endothelin receptor (Sakurai et al., 1990)
37. Mouse bombesin/gastrin releasing peptide receptor (Spindel et al., 1991)

FIG. 8A(2)

38. Rat neuromedin B preferring bombesin receptor (Wada et al., 1991)
39. Human vasoactive intestinal peptide (Sreedharan et al., 1991)
40. Rat neurotensin receptor (Tanaka et al., 1990)
41. Rat bradykinin receptor (McEachern et al., 1991)
42. Mouse thyrotropin-releasing hormone receptor (Straub et al., 1990)
43. Human neurokinin A (SK) receptor (Gerard et al., 1990)
44. Rat substance P receptor (Yokota et al., 1989)
45. Rat neuromedin K receptor (Shigemoto et al., 1990)
46. Bovine adrenal angiotensin II type-1 receptor (Sasaki et al., 1991)
47. Human mas oncogene (angiotensin) receptor (Young et al., 1986)

48. Human lutropin-choriogonadotropin receptor (Frazier et al., 1990)
49. Human thyrotropin receptor (Libert et al., 1989a)
50. Human follicle stimulating hormone receptor (Minegish et al., 1991)

51. Human rhodopsin (Nathans and Hogness, 1984)
52. Human green opsin (Nathans et al., 1986)
53. Human red opsin (Nathans et al., 1986)
54. Human blue opsin (Nathans et al., 1986)

55. Odorant receptor F3 (Buck and Axel, 1991)
56. Odorant receptor F5 (Buck and Axel, 1991)
57. Odorant receptor F6 (Buck and Axel, 1991)
58. Odorant receptor F12 (Buck and Axel, 1991)
59. Odorant receptor I3 (Buck and Axel, 1991)
60. Odorant receptor I7 (Buck and Axel, 1991)
61. Odorant receptor I8 (Buck and Axel, 1991)
62. Odorant receptor I9 (Buck and Axel, 1991)
63. Odorant receptor I14 (Buck and Axel, 1991)
64. Odorant receptor I15 (Buck and Axel, 1991)

65. Human cannabinoid receptor (Matsuda et al., 1990)
66. Mouse Glucocorticoid-induced receptor (Harrigan et al., 1991)
67. Rat FC5R (Eva et al., 1990)
68. Human endothelial cell GPR (Hla and Maciag, 1990)
69. Rat testis G-protein coupled receptor 1 (Meyerhof et al. 1991a)
70. Rat RGHJP (Meyerhof, DNA and Cell Biology, in press, 1991b).
71. Human thoracic aorta GPR (Ross et al., 1990)
72. Cytomegalovirus (Human) GPR, US33 (Chee et al., 1990)
73. Cytomegalovirus (Human) GPR, US27 (Chee et al., 1990)
74. Cytomegalovirus (Human) GPR, US28 (Chee et al., 1990)

FIG. 8B(1)

1. MGLLDGNPANET
2. MSTMGSW
3. MPPAISAFQA
4. MNTSAPPAVSPNITVLAPGKGPWQ
5. MTLHNNSTTSSPLFPNISSSWIHSPSDAGLPPGTVTHFGSYNVSRAAGNFSSNDGTTDDPLGGHTVWQ
6. MNNSTNSSNNSLALTSPYKTFE
7. MANFTPVNGSSGNQSVRLVTSSSHNRYETVE
8. MEGDSYHNATTVNGTPVNHQPLERHRLWE
9. MGAGVLVLGASEPGNLSSAAPLPDGAATAARLLVPASPPALLPPASESPEPLSQQW
10. MAPWPHENSSLAPWPDLPTLAPNTANTSGLPGVPWE
11. MGQPGNGSAFLLAPNRSHAPDHDVTQQRDEVW
12. MVFLSGNASDSSNCTHPPPPVNISK
13. MNPDLDTGHNTSAPAHWGELKDDNFTGPNQTSSNSTLPQLDVTR
14. MASPALAAALAVAAAGPNASGAGERGSGGVANASGASWGPPRGQYSAGA
15. MDHQDPYSVQA
16. MGSLQPDAGNASWNGTEAPGGGARATPYSLQV
17. MGSLQPDAGNSSWNGTEAPGGGTRATPYSLQV
18. MPSADQILFVNVTTTVAAAALTAAAAVSTTKSGNAARGYTDSDDDAGMGTEAVANISGSLVEGLTTVTAALS-(35)
19. MRTLNTSAMDGTGLVVERDFSV
20. MLPPGSNGTAYPGQFALYQQLAQGNAVGGSAGAPPLGPS
21. MDPLNLSWYDDDLERQNWSRPFNGSDGKADRPH
22. MASLSQLSSHLNSTCGAENSTGASQARPH
23. MGNRSTADADGLLAGRGPAAGASAGASAGLAGQ
24. MSPLNQSAEGLPQESNRSLNATETSEAWNPRTLQAL
25. MDVLSPGQGNNTTSPPAPFETGGNTTGISDVTVSYQ
26. MVNLGNAVSLLMHIGLLVWQFDISISPVAGIVTDTFNSSDGGRLFQFPDGV
27. MEILCEDNISLSSIPNSLMQLGDGPRLYHNDFNSRDANTSEASNWTIDAENRTNLSCEGYLPPTCLSILHLQE
28. MAPNGTASSFCLDSTACK

FIG. 8B(2)

```
29                                                                                              METNSSLPTNISGGTPAVSAGYLFLD
30                                                                    MNSFNYTTPDYGHYDDKDTLDLNTPVDKTSNTLRVP
31  MGPRRLLLVAACFSLCGPLLSARTRARRPESKATNATLDPRSFLLLRNPNDKYEPFWEDEEKNESGLTEYRLVSINKSSPLQKQLPAFISEDASGYLTSSWL
32                                                                                      MWPNGSSLGPCFRPRTNITLEERR
33                                                       MESDSFEDFWKGEDLSNYSYSSTLPPFLLDAAPCEPESLEIN
34                                                                                                 MELNSSSRVDSFRYT
35             METFWLRLSFWVALVGGVISDNPESYSTNLSIHVDSVATFHGTELSFVVTHQPTNLALPSNGSMHNYCPQQTKITSAFK
36  MQSSASRCGRALVALLACGLLGVWGEKRGFPPAQATPSLLGTKEVMTPPTKTSWTRGSNSSLMRFRTAEVTKGGRVAGVPPRSFPPPCQRKIEINKTFK
37                                                                MMAPNNCSHLNLDVDPFLSCNDTFNQSLSPPKMDNWFHPGF
38                                                                       MPPRSLPNLSLPTEASESELEPEWENDFLPDSDGTTAELVIR
39                                                    MDLHLFDYAEPGNFSDISWPCNSSDCIVDTVMCPNIMPNKSVLL
40                                         MHLNSSVPQGTPGEPDAQPFSGPQSEMEATFLALSLSNGSGNTSESDTAGPNSDLDVNTDIYS
41                                                                    MFNITTQALGSAHNGTSFEVNCPDTEWWSWLN
42                                                                         MENDTVSEMNQTELQPQAAVALEYQVVT
43                                                                            MGTCDIVTEANISSGPESNTTGITAFSMPSWQ
44                                                                       MDNVLPMDSDLFPNISTNTSESNQFVQPTWQ
45              MASVPRGENWTDGTVEVGTHTGNLSSALGVTEWLALQAGNFSSALGLPATTQAPSQVRANLTNQFVQPSWR
46                                                                  MDGSNVTSFVVEEPTNISTGRNASVGNAHRQIP
47                                                                  MDGSNVTSFVVEEPTNISTGRNASVGNAHRQIP
48  MKQRFSPLQLLKLLLL LQAP LP RALRRI CPEPCN-(248)-LPTKE LNFSHS ISENFSKQCESTVRKSELSGWDYEYGFCLPKTPRCAPEPDAFNPCEDIMG
49  MRPADLLQLVLLLDLPRDLGGMGCSSPPCEECHQE-(318)-YVFFEEQEDEIIGFGQELKNPQEETLQAFDSHYDYTICGDSEDMVCTPKSDEFNPCEDIMG
50  MALLLVSLLAFLSLSGSGCHHRICHCSNRVFLCQE-(266)-VDYMTQARGQRSSLAEDNESSYSRGFDMTYTEFDYDLCNEVDVTCSPKPDAFNPCEDIMG
51                                                                          MNGTEGPNFYVPFSNATGWVRSPFEYPQYYLAEPWQF
52                                                      MAQQWSLQRLAGRHPQDSYEDSTQSSIFTYTNSNSTRGPFEGPNYHIAPRWVYHLTSVW
53                                                      MAQQWSLQRLAGRHPQDSYEDSTQSSIFTYTNSNSTRGPFEGPNYHIAPRWVYHLTSVW
54                                                                  MRKMSEEEFYLFKNISSVGPWDGPQYHAIPVWAFYL
```

FIG. 8B(3)

```
55                                                                          MDSSNRTRVSEFLLLGFVENKDLQP
56                                                                          MSSTNQSSVTEFLLLGLSRQPQQQQ
57                                                                          MAWSTGQNLSTPGPFILLGFPGPRSMRI
58                                                                          MESGNSTRRFSSFFLLGFTENPQLHF
59                                                                          MNNQTFITQFLLLGLPIPEEHQH
60                                                                          MERRNHSGRVSEFVLLGLPAPAPLRV
61                                                                          MNNKTVTHFLLLGLPIPPEHQQ
62                                                                          MTRRNQTAISQFFLLGLPFPPEYQH
63                                                                          MTGNNQTLILEFLLLGLPIPSEYHL
64                                                                          MTEENQTVISQFLLLFLPIPSEHQH
65  MKSILDGLADTTFRTITTDLLYVGSNDIQYEDIK-(21)-SPFQEKMTAGDNSPLVPAGDTTNITEFYNKSLSSFKENEENIQCGENFMDMECFMILNPSQQ
66                                                                          KVPPVLLFLLSSVRATEQPQVVTEHPSWEAALTGPNASSHFWANYTFSDWQNFVGRRRYGAESQNPTV
67                                                                          MNSTLSFRVENYSVHYMNVSENSPFLAFENDDCHLPLAV
68                                                                          MGPTSVPLVKAHRSSVSDYVNYDIIVRHYNYTGKLNISADKENSIK
69                                                                          MKANNTTTSALWLQ
70                                                                          MFPNGTAPSPTSSPSSSPGGCGEGVCSRGPGSGAADGMEEPGRNSSQNGTLSEGQGS
71                                                                          MAGNCSWEAHSTNQNKMCPGMSEALELYSRGFLTIEQIATLPPPA
72                                                                          MTGPLFAIR
73                                                                          MTTSTNNQTLTQVSNMTNHTLNSTEIYQLFEYTR
74                                                                          MTPTTTAELTTEFDYDEDATPCVFTDVLNQSK
```

FIG. 8C(1)

| # | 1 | | 2 | |
|---|---|---|---|---|
| 1 | ------SLVLLLFADFSSMLGCMAVLI | GFWRKLLRNHVTK | -VIACFCATSFCKDFPSTILTLT- | |
| 2 | --VYITVELAIAVLATGNVLVCHAV- | -WLNSNLONVTN | -YFWSLAAADIAVGVIAIPFAIT | |
| 3 | --AYIGIEVLIALVSVPGNVLVIHAV- | ---KVNQALRDATF | -CFIVSIAVADVAVGALVIPLAIL | |
| 4 | VAFIGITTGLLSIATVTGNLLVLISF- | ---KVNTELKTVNN | -YFLLSLACADLIIGTFSMNLYTT | ----YLLMGH-HALGTLA------CD |
| 5 | VVFIVLVAGSLSLVTIIGNILVMVSI- | ---KVNRHLQTVNN | -YLFSIACADLIIGVFSMNLYTL | ----YTVIGY-HPLGPVV------CD |
| 6 | VVFIAFLTGILALVTIIGNILVIVSF- | ---KVNKQLKTVNN | -YFLLSLACADLIIGVISMNLFTT | ----YIIMNR-HALGNLA------CD |
| 7 | MVFIATVRGSLSLVTVVGNILVLMLSI- | ---KVNRQLQTVNN | -YFLFSIACADLIIGAFSMNLYTV | ----YIIKGY-HPLGAVV------CD |
| 8 | VITIAVVTAVVSLMTIVGNVLVMISF- | ---KVNSQLKTVNN | -YLLSIACADLIIGIFSMNLYTT | ----YILMGR-HALGSLA------CD |
| 9 | TAGMGLIMALIVLLIVAGNVLVIAIA | ---KTPR-LQTLTN | -LFIMSIASADLVMLLLLVPPFCAT | ----LVVHGR-WEYGSFF------CE |
| 10 | VVGNGIVMSLIVLAIVFGNVLVITAIA | ---KFER-LQTVTN | -YFITSIACADLVMGLAVVPFGAA | ----HILMKN-WTFGNFW------CE |
| 11 | AALAGALLALAVLATVGGNLLVIAIA | ---WTPR-LQTMTN | -VFVTSLAAADLVMGLLVVPPAAT | ----LALTGH-WPLGATG------CE |
| 12 | AILLGVILGGLILFGVLGNVLVLSVA | ---CHRHLHSVTH | -YIVNLAVADLLTSTVLPFSAI | ----FEILGY-WKFGRVF------CN |
| 13 | AISVGLVLGAFILFAIVGNILVLSVA | ---CNRHLRTPTN | -YFIVNIAIADLLSFTVLPFSAT | ----LEVLGY-WVLGRIF------CD |
| 14 | VAGLAAVVGFLIVFTVVGNVLVIAVL | ---TSRALRAPQN | -LFVSIASADILVATLVMPFSLA | ----NELMAY-WYFGQVW------CG |
| 15 | TAAIAAAITFLILFTIFGNALVIAVL | ---TSRSLRAPQN | -LFVSIAAADILVATLIIPFSLA | ----NELLGY-WYFRRTW------CE |
| 16 | TLTLVCLAGLLMLLTVFGNVLVIAVF | ---TSRALKAPQN | -LFVSIASADILVATLVIPFSLA | ----NEVNGY-WYFGKTW------CE |
| 17 | TLTLVCIAGLIMLFTVFGNVLVIIAVF | ---TSRALKAPQN | -LFLVSIASADILVATLVIPFSLA | ----NEVMGY-WYFGKVW------CE |
| 18 | LLTALVLSVIIVL-TIIGNILVLSVF | ---TYKPLRIVQN | -FFIVSLAVADLTVALLVLPFNVA | ----YSILGR-WEFGIHL------CK |
| 19 | RILTACFLSLSLLILSTLLGNTLVCAAVI | ---RFRHLRSKVTN | -FFVISLAVSDLLVAVLVMPKAV | ----AEIAGF-WPFGSF-------CN |
| 20 | QVVTACLLTLLINTLLGNVLVCAAIV | ---RSRHLRANMIN | -VFIVSIAVSDLFVALLVMTHKAY | ----AEVAGY-WPFGAF-------CD |
| 21 | YNYATLLTLLIAVFGNVLVCMAVS | ---REKALQTTTN | -YLIVSLAVADLLVATLVMPWVVY | ----LEVVGE-WKFSRIH------CD |
| 22 | -AYYALSYCALILAIVFGNGLVCMAVL | ---REKALQTTTN | -YLVWSLAVADLLVATLVMPWVVY | ----LEVTGGVWNFSRIC------CD |
| 23 | GAAALVGGVLLICAVLAGNSLVCVSVA | ---TERALQTPTN | -SFIVSLAADLLALLVLPLFVY | ----SEVQGAAWLLSPRL------CD |
| 24 | KISLAVVLSVITLATVLSNAFVLTRIL | ---LTRKLHTPAN | -YLIGSLATTDLLVSILVMPISIA | ----YTITHT-WNFGQIL------CD |
| 25 | VITSLLGTLIFC-AVLGNACVAAIA | ---LERSLQNVAN | -YLIGSLAVRDLMVSVLVLPMAAL | ----YQVLNK-WTLGQVT------CD |
| 26 | QNWPALSIVVIINTIGGNILVIMAVS | ---MEKKLHHATN | -YFLMSLAIADMLVGFLVMPLSLL | ----AILYDVWPLPRYL------CP |
| 27 | KNWSALLTVVIILTIAGNILVIMAVS | ---LEKKLQNATH | -YFLMSLAIADMLLGFLVMPVSML | ----TILYGYRWPLPSKL------CA |
| 28 | -ITITVVLAVLLITVAGNVVVCIAVG | ---LNRRLRNLTN | -CFIVSLAITDLLLGLLVLPFSAI | ----YQLSCK-WSFGKVF------CN |
| 29 | -IITYLVFAVRFVLGVLGNGLVIWVAG | ------FRMTHTVT | -ISYLNLNAVADFCFTSTLPFFHVR | ----KAMGGHWPFGWFL-------CK |
| 30 | DILALVIFAVVFLVGVLGNALVVVTA | -----FEAKRTINA- | -IWFLNIAVADFLSCLALPILFTS | ----IVQHHHWPFGGAA-------CS |
| 31 | TLFVPSVYTGVFVVSLPLNIMAIVFI | ----LKMKVKPAV | -VYMLHLATADVLFVSVLPFKISY | ----YFSGSDWQFGSEL-------CR |
| 32 | -YNTVISCTIFIVGMVGNATLLRIIY | ----QNKCMRNGPN | -ALIASIALGDLIYVVIDLPINVP | ----KLLAGRWPFEQNDFGVFLCK |
| 33 | KYFVVIYALVFLLSLLGNSLVMLVIL | ----YSRGVRSVTD | -VYLLNIAIADLFALTLPIHAAS | ----KVNGWIFGTFL--------CK |
| 34 | --LFPIVYSIFVLGIIANGYVLVVFA | --RLYPSKKNEIK- | -IFMVNLTVADLFLITLPLHIVY | ----YSNQGNWFLPKFL------CN |
| 35 | -YINTIVSCLVFVLGIIGNSTLLRIIY | ----KNKCMRNGPN | -ILIASIALGDLLHIIDIPIMAY | ----KLLAGDWPF-----GAEMCK |
| 36 | LIASPWFAASFCVVGLASNLLALSVLA | GARQSSSHTRSSFL | -TFLCGLVLTDFLGLLVTGTIVVS | ----QHAALFEWHAVDPGCRL--CR |
| 37 | IYVIPAVYGLLIVIGLIVIGLIGNITLIKIF- | ---CTVKSMRNVPN | -LFISSLALGDLLLLVTCAPVDAS | ----KYLADRHLFGRIG-------CK |

```
                                                                                 3
     1  IVITYGSFACWLWTLCLAISIY    ---MLIVKREPEPELFEK----    ---YYYLLCWGLPLISTIVMLA---    ----------------KNTVQFVGN
     2  FFACFVLVLTQSSIFSLLAIAI    DRYIAIRIPLRYNGLVTGTR---   -AKGIIAVCWVLSFAIGLTPML-GW   ----------------NNCSQPKEGRNYSQ
     3  MVACPVLILTQSSIALLAIAV     DRYLRVKIPLRYKTVVTPRR---   -AAVAIAGCWILSFVVGLTPLF-GW   ----NRLGEAQRAWAANGSGGEPVI

4  LWLALDYVASNASVLNLLISF     DRYFSVTRPLSYRAKRT-PRR--   -AAIMIGIAWLVSFVL-WAPAILFW   ----------------QYLVGERTMLAG
     5  LWLALDYVVSNASVMNLLIISF    DRYFCVTKPLTYPVKRT-TKM--   -AGMMIAAAWVLSFIL-WAPAILFW   ----------------QFIVGVRTVEDG
     6  LWIAIDYVASNASVLNLLVISF    DRYFSITRPLTYRAKRT-TKR--   -AGVMIGLAWVISFVL-WAPAILFW   ----------------QYFVGKRTVPPG
     7  LWLALDYVVSNASVMNLLIISF    DRYFCVTKPLTYPARRT-TKM--   -AGIMIAAAWVLSFVL-WAPAILFW   ----------------QFVVGKRTVPDN
     8  LWLAIDYVASNASVLNLLVISF    DRYFSITRPLTYRAKRT-PKR--   -AGIMIGIAWLISFIL-WAPAILCW   ----------------QYLVGKRTVPID

9  LWTSVDVLCVTASIETLCVIAL    DRYLAITSPFRYQSLLTRAR---   -ARGLVCTVWAISALVSFPLIMHW    ----------------WRAESDEAR
    10  FWTSIDVLCVTASIETLCVIAV    DRYLFAITSPFKYQSLLTKNK---  -ARVIILMVWTVSGLTSFLPIQMHW   ----------------YRATHQEAI
    11  LWTSVDVLCVTASIETLCAIAV    DRYLAVTNPLRYGALVTKRC--    -ARTAVVLVWVSAAVSFAPIMSQW    ----------------WRVGADAEAQ
    12  VWAAVDVLCCTASIMLLCIISI    DRYIGVSYPLRYPTIVTQKR--    -GLMALLCVWAALSLVISIGPLF-GW  ----------------RQPAPEDET
    13  IWAAVDVLCCTASILSLCAISI    DRYIGVRYSLQYPTLVTRRK--    -AIIALLSVWVLSTVISIGPLL-GW   ----------------KEPAPNDDK
    14  VYLAIDVLFCTSSIVHLCAISL    DRYWSVTQAVEYNLKRTPRR--    -VKATIVAVWLISAVISFPPLVSLY   ----------------RQPDGAAYP
    15  VYLALDVLFCTSSIVHLCAISL    DRYWAVSRALEYNSKRTPRR--    -IKCIILTVWLIAAVISLPPLIYKG   ----------------DQGPQPRGRP
    16  IYLALDVLFCTSSIVHLCAISL    DRYWSITQAIEYNLKRTPRR--    -IKAIIITVWVISAVISFPPLISI-   ----------EKKGGGGPQPAEP
    17  IYLAIDVLFCTSSIVHLCAISL    DRYWSITQAIEYNLKRTPRR--    -IKAIIVTVWVISAVISFPPLLISI   ----------EKKGAGGQQPAEP
    18  LWLTCDVLCCTSSILNLCAIAL    DRYWAITDPINYAQKRTVGR--    -VLLISGVWLLSLLISSPPLI-GW    ----------------NDWPDEFTSAT
    19  IWVAFDIMCSTASILNLCVISV    DRYWAISSPFRYERKKrP-KA--   -AFILISVAWTLSVLISFIPVQLSW   ---HKAKPTSPSDGMATSLAETID
    20  VWVAFDIMCSTASILNLCVISV    DRYWAISRPFRYRKMTCH---     -ALVMGLAWTLSILISFIPVQLNW    ---NRDQAASWGGLDLPNN-(2C)
    21  IFVTLDVMMCTASILNLCAISI    DRYTAVAMPMLYN--TRYSSKRR   -VTVMISIVWVSFTISC-PLLFGL    ----------------NNADQN
    22  VFVTLDVMMCTASILNLCAISI    DRYTAVVMPVHYQHGTGQSSCRR   -VAIMITAVWVLAFAVSC-PLLFGF   ----------------NTTGDPT
    23  ALMAMDVMLCTASIFNLCAISV    DRFVAVAVPLRYN---RQGGSRR   -QLLLIGATWLLSAAVAA-PVLCGL   ----------------NDVRGRDPA
    24  IWLSSDITCCTASILHLCVIAL    DRYWAITDALEYSKRRTAGH--    -AATMIAIVWAISICISIPPLF--W   ----------------RQAKAQEEMS
    25  LFIALDVLCCTSSILHLCAIAL    DRYWAITDPIDYVNKRTPR---    -PRALISLTWLIGFLISIPPM-LGW   ----------------RTPEDRSDPD
    26  VWISLDVLFSTASIMHLCAISL    DRYVAIRNPIEHSRF-SRTK--    -AIWKIAIVWAISIGVSV-PIPVIG   ----------------LRDESKVFVNNT
    27  IWIYLDVLFSTASIMHLCAISL    DRYVAIQNPIHHSRFNSRTK--    -AFLKIIAVWTISVGISM-PIPVFG   ----------------LQDDSKVFKEG
    28  IYTSLDVMLCTASILNLFMISL    DRYCAVMDPLRYPVLVRPVR--    -VAISLVLIWVISITLSFLSIHLGW   ----------------NSRNETSKGNHTTS

29  FLFTIVDINLFGSVFLIALIAL    DRCVCVLHPVWTQNHRTVSLAK-   -KVIIGPWVMALLL-TLPVII--     ----------------RVTIVPGKTGTV
    30  ILPSLILLNMYASILLLATISA    DRFLLVFKPIWCQNFRGAGL--    -AWIACAVWGIALL-TIPSFLY-     ----------------RVVREEYFPPKV
    31  FVTAAFYCNMYASILLMTVISI    DRFIAVVYPMQSLSWRTLGR--    -ASFTCIAIWAIAIAG-V-PLVL--   ----------------KEQTIQVPGLNIT
    32  FMGVVMIFFGLSPLLLGAAMAS    ERYLGITRPFSRPAVASQRR--    -AWATVGLVWAAALALGLLPLL-GV   ----------------GRYTVQYPGS
    33  VSSLLKEVNFYSGILLLACISV    DRYLAIVRATRTLTQKRHLVK--   ---FICLSIWGLSLLL-ALPVLL--   ----------------FRRTYYSSNVSP
    34  LAGCLFFINTYCSVAFLGVITY    NRFQAVKYPIKTAQATTRKR--    -GIALSLVIWVAIVAA-ASYFLVMM   ----------------DSTNVVSNKAGSGNIT
    35  LPFFLQKSSVGITVLNLCALSV    DRYRAVASWSRIKGIGVPK---    -TAIEIVSIWILHLVVVSFIL-AIPEAIGF ----------------WMVPFEYKGAQHR
    36  LVPFIQKASVGITVLSLCALSI    DRYRAVASHSRIKGIGVPK---    WTAVEIVLIWVVSVL-AVPEAIGF    ----------------DTTSDYKGKPLR
    37  LIPFIQLTSVGVSVFLTALSA     DRYKAIVRPMDIQASHALWK---   -ICLKAALIWIVSML-AIPEAVF-    ----------------SDLHPFHVKDTNQTFI
    38  LIPAIQLTSVGVSVPTLTALSA    DRYRAINPMDMQTSGVVL----    -WTSVAVGIWVSVLL-AVPEAVF-    ----------------SEVARI-GSSDNSSFT
```

FIGURE 8D(2)

```
   3                                                                  4
39 VTHLIFSINLFSGIFFLTCMSV    DRYLSITYFTNTPSSRKKMVRR-   ---AVCILVLLAFCV-SLPDTYYL   ----------KTVTSASNNET
40 GYYFLRDACTYATALNVASLSV    ERYLAICHPFKAKTLMSRSRTK-   ---KFISAIWLASALL-AIPMLFT-  --MGLQNRSGDGTHPGGL
41 VVNIMYMNLYSSICFLMLVSI     DRYLALVKIMSMGRMRGVR----   WAKLYSLVIWSCTLLL-SSPMLVFR  ----TMKDYREEGHNV
42 CITYLQYLGINASSCSITAFTI    ERYIAICHPIKAQFLCTFSR---   -AKKIIFVWAFTSIYCMLWLFLLD   ----LNISTYKNAVVV
43 FQNLFPITAMFVSIYSMTAIAA    DRYMAIVHPFQPRLSAPSTK---   --AVIAGIWLVAI-KL-AFPQCFY-  ----STVTMDQGAT
44 FHNFFPIAALFASIYSMTAVAF    DRYMAIIDPLPQPRLSATATK--   ---VVIFVIWVIALL-ASPQGYY-   ----STTETMPSRV
45 FQNFFPITAVFSIYSM-AIAV     DRYMAIIDPLPQPRLSATATK--   ----IVIGSIWIALL-AFPQCLY-   ----SKIKVMPGRC
46 IASASVSFNLYASVFLLTCLSI    DRYLAIVHPMKSRLRRIML----   VAKVTCIIWLLAGIA-SLPTIIHR   ----NFFIENTNIT
47 TLSVTFLFGYNTGLYLLTAISV    ERCLSVLYPIWYRCHRPKY----   QSALVCALLWALSCLVTTME-YVM-  ----CIDRFEESHSRN

48 TAGFFTVLASELSVYTLTVITL    ERWHTITYAIHIDQKLRLRH---   -AILIMLGGWLFSSLIAMLPLVGVS  ----------NYMKVS
49 TAGFFTVFASELSVYTLTVITL    ERWYAITFAMRLDRKIRLRH---   -ACAIMVGGWVCCFLLALLPLVGIS  ----------SYAKVS
50 AAGFFTVFASELSVYTLTAITL    ERWHTITHIMQIDCKVQLRH---   -AASVMVMGWIFAFAAALFPIFGIS  ----------SYMKVS

51 LEGFFATLGGEIALWSLVVLAI    ERYVVVCKPMSNRFGEN------   HAIMGVAFTWVMALA-CAAPPLAGW  ----SRYIPEGLQC
52 LEGYTVSLCGITGLWSLAIISW    ERMHVVCKPFGNVRFDAK-----   LAIVGIAFSWIWAAV-WTAPPIFGW  ----SRYWPHGLKT
53 LEGYTVSLCGITGLWSLAIISW    ERWLVCKPFGNVRFDAK-----    LAIVGIAFSWIWSAV-WTAPPIFGW  ----SRYWPHGLKT
54 LEGFLGTVAGLVTGWSLAFLAF    ERYIVICKPFGNRFSSK------   HALTVVIATWTIGIG-VSIPPFFGW  ----SRFIPEGLQC

55 TQIYFLLFVELDNFLLTIMAY     DRYAICHPMHYTVIMNYK-----   LCGFLVLSWIVSVLHALFQSLMML   ----ALPFCTHLEIPHY
56 TQLYFLAVFGNMDNFLLAVMSY    DRYAICHPLHYTTKMIRQ-----   LCVLLVVGSWVANNNCLLHILIMA   ----RKSFCADNMLPHF
57 TQKYFVFSLGCTEYFLLAVMAY    DRYLAICLPLRYGGIMIPG----   LAMRLALGSWLCGFSAITVPATLIA  ----RLSFCGSRVINHF
58 SQMCVFLVFAELGNFLLAVMAY    DRYAXCHPLCYTVIVNHR-----   LCILLLLSWVISIFRAFIQSLIVL   ----QLTFCGDVKIPHF
59 AQTYFMVFGDMESFLLVAMAY     DRYAICFLPHYTSIMSPK-----   LCTCLVLLLMLTTSHAMMHTLLAA   ----RLSFCENNVVLNF
60 TQLYFFLGLGCTECVLLAVMAY    DRYAICHPLHYPVIVSSR-----   LCVQMAAGSWAGGFGISMVKVFLIS  ----RLSYCGPNTINHF
61 TQIFFFLLFGYLGNFLLVAMAY    DRYAICFPLHYTNIMSHK-----   LCTCLLLVFWIMTSSHAMMHTLLAA  ----RLSFCENNVLLNF
62 AQIYFLFFGDLGNFLLVAMAY     DRYAICFPLHYMSIMSPK-----   LCVSLVVLSWVLTTFHAMLHTLIMA  ----RLSFCEDSVIPHY
63 TQLYFFMVFGDMESFLLVVMAY    DRYAICFPLRYTTIMSTK-----   FCASLVLLLWLTMRHALLHTLLIA   ----RLSFCEDSVILHF
64 TQLYFLYFADLESFLLVAMAY     DRYAICFPLHYMSIMSPK-----   LCVSLVVLSWVLTTFHAMLHTLIMA  ----RLSFCADNMIPHF

65 FKLGGVTASFTASVGSLFLTAI    DRYISIHPPIAYKRIVTRPK---   -AVVAFCLMWTIAIVIAVLPLL-GW  ----------NCKKLQS
66 VSRFAQYCSLHVSALILTAIAV    DRHQVIMHPLKPRISITKG----   --VIYIAVIWWMATFF-SLPHAIC-  ----QKLFTFKYSEDIVRS
67 LNPFVQCVSITVSIFSLVLIAV    ERHQLIINPRGWRPNNRH-----   -AYIGITVIWVIAVAS-SLPFVIY-  ----QILTDEPFQNVSLAAFKDKY
68 LREGSMFVALSLSVFSLLAIAI    ERYITMLKMKLHNGSNNFR----   -LFLLISACWVISLILGGLPIM-GW  ----------NCISALS
69 FMSCVLLVFTHASIMSLLAIAV    DRLRVKLTVRYRTVTQRR-----   -IWLFLGLCWLVSFLVGLTPMF-GW  ----NRKVTLELSQNSSTL
70 LVLSVDAVNMFTSIYCLTVLSV    DRYVAVVHPIKAARYRRPT----   VAKVWNLGVWVLSLLV-ILPIVVFS  ----RTAANSDGTV
71 VSRIVGLCTFAGVSLLPAISI     ERCVSVIFPMWYWRRRPKR----   LSAGVCALLLWLSFLV-TSIHNYF-  ----------CMFLGHEASGT
72 FLSVIYYSSCTVGFATVALIAA    DRYLHKRTYARGSYR--------   STYMILLLTWLAGLI-FSVPAAVYT  ----TVVMHHDANDTNNTNGHA
73 GLNACFYICLFAGVCFLINLSM    DRYCIVIWGVELNRVRNNKR---   ATCVVVIF-WIIAVL-MGMPHYIMY  ----------SHTNN
74 LLTACFYVAITASLCFITEIALI   DRYYAIVYMRY----RPVK----   CACLFSIFWWIFAVI-IAIPHFMVV  ----------TQKDN
```

FIGURE 8E(1)

```
                                                                    5
1   WCWIGVSFTGYRFG----------  -LFYPFLFIWAISAVLVGLT----  SRYTYVVIHNGVSDN---------------------------------
2   GCGEGQVACLFEDVVPHN------  YMVYNFFAFVLVPLLLMLGVYL-  RIFLAARRQLKQMESQPLPGERARSTLQ--------------------
3   KCEFEKVISME-------------  YMVFNFFVWLPLLLMVLIYL-  EVFYLIRRQLGKKVSASSGDPQKYYG----------------------

4   QCYIQFLSQP--------------  IITFGTAMAAFYMPVTVMCTLYW-  RIYRETENRARELAALQGSETPGKGGGSSSSSERSQPGAEGSPETP
5   ECYIQFFSNP--------------  AVTFGTAIAAFYLPVIIMIVLYW-  HISRASKSRIKKDKKEPVANQDPVSPSLVQGRIVKPNNNAMPSSDD
6   ECFIQFLSEP--------------  TITFGTAIAAFYMPVTIMRILYW-  RIYKETEKRTKELAGLQASGTEAETENFVHPTGSSRSCSSYELQQQ
7   QCFIQFLSNP--------------  AVTFGTAIAAFYLPVVIMIVLYI-  HISLASRSRVHKRPEGPKEKKAKTIAFLKSPLMKQSVKKPPPGEA
8   ECQIQFLSEP--------------  TITFGTAIAAFYIPVSIMRILYC-  RIYRETEKRTKDLADLQGSDSVYKAEKRKPAHRALFRSCLRCPRPT

9   RCYNDPKCCDFVTNR---------  AYAIASSVVSFYVPLCIMAFVYL-  RVFREAQKQVKIDSCERRFLGGPARPPSPSPSVPAPAPPGPPRP
10  NCYANETCCDFFTNQ---------  AYA-ASSAVSFYVPLVIMVFVYS-  RVFQEAKRQLQKIDKSEGRFHVQNLSQVEQDGRTGHGLRRSSKFCL
11  RCHSNPRCCAFASNM---------  PYVLLSSSVSFYLPLLVMLFVYA-  RVFVVATRQLRLLRGELGRFPPEESPPAPSRSLAPAPVGTGAPPEG
12  ICQINEEP----------------  GYVLFSALGSFYVPLTIILVMYC-  RVYVVAKRESRGLKSGLKTDKSDSEQVTLRIHRKNAQVGGSGVTSA
13  ECVTEEP-----------------  FCALFCSLGSFYIPIAVILVMYC-  RVYIVAKRTTKNLEAGVMKEMSNSKFLTLRIHWSKNFHEDTLSSTK
14  QCGLNDET----------------  WYILSSCIGSFFAPCLIYLLVYA-  RIYRVAKRTRTLSEKRAPVGPDGASPTTENGLGAAAGEARTGTAR
15  QCKLNQEA----------------  WYILASSIGSFFAPCLIMILVYL-  RIYLIAKRSNRGRPRAKCGPGQGESKQPRPDHGGAIASAKLPAIAS
16  RCEINDQK----------------  WYVISSCIGSFFAPCLIMILVVV-  RIYQIAKRTRVPPSRRDPDAVAAPPGGTERRPNGLGPERSAGPGG
17  SCKINDQK----------------  WYVISSIGSFFAPCLINHLVYV-  RIYQIAKRTRVPPSRRGPDACSAPPGGADRRPNAVGPERGAGTAG
18  PCELTSQRI---------------  GYYIYSLGSFFIPIAIMRIVYI-  EIFVATRRRLRERARANKINTIALKSTELEPMANSSPVAASNSGSK
19  NCDSSLSR----------------  TYAISSSVISFYIPVALMIVTYT-  RIYRIAQKQIRRIAALERAAVHAKNCQTTTGNKPVECSQPESSFKH
20  -CDSSLNR----------------  TAISSSLISFYIPVAIMIVTYT-  RIYRIAQVQIRRISSLERAAEHAQSCRSSAACAPDTSLRASIK---
21  ECIIANP-----------------  AFVVYSSIVSFYVPFIVTLLVYI-  KIYIVLRRRRKRVNTKRSSRAFRAHLRAPLKGNCTHPEDMKLCTVI
22  VCSISNP-----------------  DFVIYSSVVSFYLPFGVTVLVYA-  RIYVVLKQRRRKRILTRQNSQCNSVRPGFPQSTSLPDPAHLELKR
23  VCRLEDR-----------------  DYWYYSSVCSFFLPCPLMLLLYW-  ATFRGLQLRWEVARRAKLHGRAPRPSGPGPPSPTPPAPRLPQPCG
24  DCLVNTSQ----------------  SYTIYSTCGAFYIPSVLLILYG-  RIYRAARNRILNPPSLYGKRFTTAHLITGSAGSSLCSLNSSLHEGH
25  ACTISKDH----------------  GYTIYSTIFAFYIPLLLMLVLYG-  RIFRAARFRIRKTVKKVEKTGADTRHGASPAPQPKKSVNGESGSRN
26  TCVLNDPN----------------  FVLIGSFVA-FFIPTLIMVITYF-  LTIYVLRRQTLMLLRGHTEEELANMSLNFLNCCCKKNGGEEENAPN
27  SCLLADDN----------------  FVLIGSFVA-FFIPLTIMVITYF-  LTIKSLQKFATLCVSDLSTRAKLASFSFLQSSLSSEKLFQRSIHR
28  KCKVQVNE----------------  VYGLVDGLVTFYLPLLIMCITYY-  RIFKVARDOAKRNHISSWKAATI-------------------------

29  ACTFNFSPWTNDPKER--------  INVAVAMLTVRGIIRFIIGFSAPM  SIVAVSYGLIATKIHKQGL-----------------------------
30  LCGCDYSHDKRRER----------  AVAIVRLVLGFLMPLLTLTICYT-  FILLRIWSRRA--------------------------------------
31  TCHDVLNETLLEGYYA--------  YYFSAFSAVFFFVPLIISTVCYVS  IIRCLSSSAVANRSKKSR------------------------------
32  WCFLTLGAESGDVAFG--------  LLFSMLGGLSVGLSFLLNTVSVA-  TLHHYYHGQEAAQQRPR-------------------------------
33  ACYEDMGNNYANWRM---------  LLRILPQSFGFIVPLLIMLYCYGF  TLRTLFKAHM--------------------------------------
34  RCFERYEKGSKPV-----------  LIIHICIVLGFFIVFLLILFCNL-  VIIHTLLRGPVKQQRNA-------------------------------
35  TCMLNATSK--FMEFYQDV-KD    ---WWLFGFYFCMPLVCTAIFYTL  MTCEMLNRRNGSLRIALSEHL---------------------------
36  VCMLNPFQKTAFMQFYKTAAKD    ---WWLFAFYFCLPLAITAIFYTL  MTCEMLRKKSGM-QIALNDHL---------------------------
```

FIGURE 8E(2)

```
     5
37   SCAPYPHSNELHPK--------    IHSMASFLVFYIPLAIISVYYF    IARNLIQSAYNLPVEGNIHVKKQI-------
38   ACIPYPQTDELHPK--------    IHSVLIFLYFLIPLVIISIYYH    IAKTLIRSAHNLPGEYNEHTKKQM-------
39   YCRSFYPEHSIKEWLI------    SLLVSVVLIGFAVPFSSIAVFYFS   LIARAISASSD--------------------
40   VCTPIVDTATVK----------    WIQVNTFMSFLFPMLVISILNT-    VIANKLTVMVHQAAEQGRVCTVGTHNGLEHSTFNMIIEPGRV
41   TCVIVYPSRSWEV---------    FINMLLNLVGFLLPLSIITFCTVR   IMQVLRNNEMKFKFKEVQ-------------
42   SGGYKISRNYYS----------    PIYLMDFGVFYVVPMILATVLYGF   IARILFLNPIPSDPKENSKMWKNDSIHQNKNLNLNA-
43   KCVAWPEDSGGKTLL-------    LYHLVVIALYFLPLAVMHFVAYS-   VIGLTLWRRAVPGHQAHGANLRHL-------
44   VCMIEWPEHPNRTYEK------    AYHICVTVLIYFLPLLVIGYAYT-   VVGITLWASEIPGDSSDRYHEQV--------
45   LCYV-WPEGPKQHF--------    TYHIIVILVCFPLLIMGVTYT--    IVGITLWGGEIPGDTCDKYHEQL--------
46   VCAFHYESQNSTLPV-------    GLGLTKNILGFLFPFLILTSYT-    LIWKTLKKAYEIQKNKP--------------
47   DCRAVI----------------    -IFIAILSFLVFT-PUSVSSTIL-   VVKIRKNTWAS--------------------

48   ICLPMDVETTLSQ---------    -VYILTILILNVVAFLIICACYI-   KIYFAVRNPEIMATN----------------
49   ICLPMDTETPLAL---------    -AYIVFVLTLNIVAFVIVCCCYV-   KIYITVRNPQYNPGD----------------
50   ICLPMDIDSPLSQ---------    -LYVMSLLVLNVLAFVVICGCYT-   HIYLTVRNPNIVSSS----------------

51   SCGIDYYTLKPEVNNE------    SFVIYMFVVHFTIPMIIIFFCYG    QLVFTVKEAAAQQQESATTQ-----------
52   SCGPDVFSGSSYPGVQ------    SYMIVLMVTCCITPLSIIVLCYL-   QVWTAIRAVAKQQKESESTQ-----------
53   SCGPDVFSGSSYPGVQ------    SYMIVLMVTCCIIPLAIIMLCYL-   QVWLAIRAVAKQQKESESTQ-----------
54   SCGPDKYTVGTKYRSE------    SYTWFLFIFCFIVPLSLICFSYT-   QLLRALKAVAAQQQESATTQ-----------

55   FCEPNQVIQLTCSDAFLND---    LVIYFTLVLLATVPLAGIFYSYF-   KIVSSIC------------------------
56   FCDGTPLLKLSCSDTHLNE---    LMILTEGAVVMVTPFVCILISYI-   HITCAVL------------------------
57   FCDISPWIVLSCTDTQVVE---    LVSFGIAFCVILGSCGITLVSYA-   YIITTII------------------------
58   FCELMQLSQLTCSDNFPSH---    LIMNLVPVMLAAISFSGILYSYF-   KIVSSIH------------------------
59   FCDLFVLLKIACSDTYINE---    LMIFIMSTLLIIIPFFLIVMSYA-   RIISSIL------------------------
60   FCDVSPLLNLSCTDMSTAE---    LTDFVIAIFILLGPLSVTGASYM-   AITGAVM------------------------
61   FCDLFVLLKLACSDTYVNE---    LMIHIMEVIIIVIPFVLIVISYA-   KIISSIL------------------------
62   FCDMSTLLKVACSDTHDNE---    LAIFILGGPIVVLPFLLIIVSYA-   RIVSSIF------------------------
63   FCDISALLKLSCSDIYVNE---    LMIYILGGLLIIIPFLLIVMSYV-   RIFFSIL------------------------
64   FCDISPLLKLSCSDTHVNE---    LVIFVMGGLVIVIPPFVLIIVSYA-  RVVASIL------------------------

65   VCCDIFPLIDGTYLM-------    FWIGVTSVLLLFIVYAYMYILW--   KAHSHAVRMIQRGTQKSIIHTSEDGKVQVTRPDQA-
66   LCLDPFPEPADLFWK-------    YLDIATFILLYLLPLFIISVAYA-   RVAKKLWLCNTIGDVTTEQYLALR-------
67   VCFDKFPSDSHRL---------    SYTTLLLVLQYFGPLCFIFICYF-   KIYIRLKRRNNMMDKIRDSKYRSS-------
68   SCSTVLPLYHKH----------    --YILFCTTVFTLLLLSIVILYC-   RIYSLVRTRSRRLTFRKNISKASRS------
69   SCHFRSVVGLD-----------    -YMFFSFITWILIPLVVMCIIYLD   IFYIIRNKLSQNLTGFRETRAFYG-------
70   ACQHLMPEPAQFWLV-------    GFVLYTFLMGFLLPVGAICLCYV-   LIIAKMRHVALKAGWQQRKR-----------
71   ACLNMD----------------    ISLGILLFFLFC-PIMVLPCIAL-   LHVECRARRRQ--------------------
72   TCVLYFVAEEVHTVLL------    SWKVLLTHWGAAPVIMMIWFYA-    FFYSTVQRTSQ--------------------
73   ECVGNFANETSCWFPV------    FLNTKVNICGYLAPIALMAYTN-    RMVRFIINYVG--------------------
74   QCMTDYDYLEVSYPI-------    ILNVELMLGAFVIPLSVISYCYY-   RISRIVAVSQS--------------------
```

FIGURE 8F(1)

|  |  |  |  |
|---|---|---|---|
| 1 | ---------------KEKHLTYQFK | LINYIVFLVCWVFAVVNRIVNGL | NMFPPALNILHTYL------ |
| 2 | ----------------KEVHAAKS | LAIIVGLFALCWLPLHIINCFTFF | ------CPECSHAPLW---- |
| 3 | ----------------KELKIAKS | LALILFLALSWLPLHIINCITLF | ------CPSCRKPSI----- |
| 4 | ( 83)-KGGKPRGKEOLAKRKTFSLVKEKAART | LSAILLAFILTWTPYNIMVLVSTF | ------CKDCVPET------ |
| 5 | (110)-K-IVRRTK-QPAKGKP-PPSREKQVTRT | ILAILLAFIITWAPYNMVLINTF | ------CAPCIPNT------ |
| 6 | (166)-KRFALKTRSQITWKRKMSLVKEKGKAAQT | LSAILLAFIITWTPYNIMVLVNTF | ------CDSCIPKT------ |
| 7 | (113)-K-FASIARNQVRCKRQMLAARERKVTRT | IFAILLAFILTWTPYNWMVLVNTF | ------CQSCIPDT------ |
| 8 | (155)-KGLNPSHQMTKRKRMSLVKERKAAQT | LSAILLAFIITWTPYNIMVLVSTF | ------CDKCVPVT------ |
| 9 | -AAAATAPLANGRAGKRRPSRLVALREGKALKT | LGIIMGVFTLCWLPFFLANVVKAF | ------HRELVPDR------ |
| 10 | -----------------KEHKALKT | LGIIPCTFLCWLPFFIVNIVUVI | ------QDNLIRKE------ |
| 11 | ----------VPACGRPPARLIPIREHRALCT | LGLIMGTFTLCWLPFFIANVLRAL | ------GGPSLVPGP----- |
| 12 | ------------KNKTHFSVRLLKFSREKGKAAKT | LGIVVGCFVLCWLPFFLVMPIGSF | -------FPDFRPSET---- |
| 13 | ------------AKGHNPRSSIAVKLFKFSREKKAAKT | LGIVWGMFILCWLPFFIALPLGSL | -------FSTLKPPDA---- |
| 14 | -(77)-FLSRRRARSSVCRRKVAQAREREKRFTFV | LAVVMGVFVLCWFPFFFIYSLYGI | -------CREACQVPGP--- |
| 15 | -(106)-GRGVGAIGGQWRRAHVTREKRFTFV | LAVVIGVFVLCWFPFFSYSLGAI | -------CPKHCKVPHG--- |
| 16 | -(84)-GRGRSASGLPRRRAGAGGQNREKRFTFV | LAVVIGVFVCWFPFFFTYTLTAV | -------GCSVPRT------ |
| 17 | -(84)-GQGEERAGGAKASWRGRQNREKRFTFV | LAVVIGVFVVCVPFFFFYTLIAV | -------GCPVPYQ------ |
| 18 | -(167)-KKTSGVNQFIEEKQKISLSKERRAART | LGIIMGVFVICVLPFFIMYVILPF | -------CQTCCPTNK---- |
| 19 | ----------------SFKRETKVLKT | LSVITCVFVCCWLPFFILNCILPF | -------CGSGETQPFCIDSN-- |
| 20 | ----------------KETKVLKT | LSVIICVFVCCWLPFFILNCMVPF | ---CSGHPEGPPAGFPCVSET |
| 21 | -(91)-PNGKTRTSLKTHSRRKLSGQKEKGKATQM | LAIVLGVFIICKLPFFITHILNIH | -------CDCNIPV------ |
| 22 | -(47)-SNGRLSTSLKLPLQPRGVPLREGKATQM | VAIVLGAFIVCWLPFFLTHVINTH | -------CQTCHVSPE---- |
| 23 | -(29)-ALPPQTPPQTRRRRAKITGRERKAMRV | LPVVVGAFILCWTPFFVVHITQAL | -------CPACSVPPR---- |
| 24 | -(10)-NHVKJKLADSALERKRISAARERKATKI | LGIILGAFIICWLPFFVVSLVLPI | -------CRDSCWIHPA--- |
| 25 | -(57)-ASFERKNERNAEAKRKHALARERKTVKT | LGIIMGTFILCWLPFFIVALVLPF | -------CESSCHMPTL--- |
| 26 | -NPNPDQKPRRKQKEKRPGTMQAINNEKCASKV | LGIVFFVFLIMWCPFFITNILSVL | -------CGKACNQLMEK-- |
| 27 | ------EPGSYAGRKTWQSISNEQKACKV | LGIVFFLFVWWCPFFITNIMAVI | -------CKESCNENVIGA- |
| 28 | ----------------REHKATVT | LAAVMGAFIICWFPYFTAFVYRGL | -------RGDDAINEV---- |
| 29 | ----------------IKSSRPLRV | LSFVAAAFFLCWSPYQVVALIATV | -RIRELLQGMYKEIGI---- |
| 30 | ----------------TRSTKTLKV | VWAVVASFFIFWLPYQVTGIMMSF | ----LEPSSPTFLLLNK--- |
| 31 | ----------------TNRCFNSTV | ALFLSAAVFCIFIICFGPINVLLI | AHYSFLSHTSTTEAAYF--- |
| 32 | ----------------DSEVEMMAQ | LLGIMVASVCHLPLLVFIAQTVL | -RNPPAMSPAGQLSRTTEKE- |
| 33 | ----------------GQKHRAMRV | IFAVVLIFLLCWLPYNLVLIADTL | MRTQVIQETCERRNHIDR-- |
| 34 | ----------------EVRRRALWM | VCTVIAVFVICFVPHHVQLPWTL | -AELGMVPSSNHQAIND--- |
| 35 | ----------------KQRREVAKT | VFCLVVIFALCWFPLHLSRILKKT | VYDEMDTNRCELLSFLLL-- |
| 36 | ----------------KQRREVAKT | VFCLVLVFALCWLPLHLSRILKLT | LYDQSNPQRCELLSFLLV-- |
| 37 | ----------------ESRKRLAKT | VLVFVGLFAFCWLPNHVIYLYRSY | -HYSEVDTSMLHFV------ |
| 38 | ----------------ETRKRLAKI | VLVFVGCFVFCWFPNHILLYLYRSF | -NYKEIDPSLGTMI----- |

FIGURE 8F(2)

```
39 ----------QEKHSSRKI  IFSYVVVFLVCWLPYHVAVLLDIF  --SILHYIPFTCRLEHALFT---
40 ----------QALRHGVLV  LRAVVIAFVVCWLPYHVRRLMFCY  -ISDEQWTTFLFDFYHY----
41 ----------TEKKATVL   VIAVLGLFVLCWFPFQISTFLDTL  -LRLGVLSGCWNERAVDI---
42 ----------SSRKQVTIN  LAVVVILFALLWNTYRTLVVNSF   -----LSSPFQENWK------
43 ----------QAKKKFVKT  MVLVVVTFAICWLPFHVFLYFILGSF ----QEDIYCHKFIQQ----
44 ----------SAKRKVVKM  MIVVVCTFAICWLPFHVFFLLPYI  ----NPDLYLKKFIQQ----
45 ----------KAKRKVVKM  MIIVVVTFAICWLPYHVYFILTAI  ----YQQLNRMKYIQQ----
46 ----------RKDDIFKI   ILAIVLFFFSWVPHNIFTFMDVL   -IQLGLIRDCKIEDIVDT--
47 ----------HSSKLYIV   IMVTIIIFLIFAMPMRLLYLLYYE  -----YWSTFGN--------

48 ----------KDTKIAKKM  AILIFTDFT-CMAPISFFAISAAF  --------KVPLITVTNSK--
49 ----------KDTKIAKRM  AVLIFTDFI-CMAPISFYALSAIL  --------NKPLITVSNSK--
50 ----------SDTRIAKRM  AMLIFTDFL-CMAPISFFAISASL  --------KVPLITVSKAK--

51 ----------KAEKEVTRM  VIIMVIAFLICWVPYASVAFYIFT  --------HQGSNFGPI----
52 ----------KAEKEVTRM  VVVHVLAFCFCWGPYAFFACFAAA  --------NPGYPFHPL----
53 ----------KAEKEVTRM  VVVMIFAYCVCWGPYTFFACFAAA  --------NPGYAFHPL----
54 ----------KAEREVSRM  VVVHVGSFCVCYVPYAAFAMYMVN  --------NRNHGLDLR----

55 ----------AISSVHGKYK  AFSTCASHLSVVSLFYCTGLGVYL  ------SSAANNSSQASA---
56 ----------RVSSPRGGWK SFSTCGSHIAVVCLFYGTVIAVYF  ------NPSSSHLAGRDM---
57 ----------KIPSARGRHR AFSTCSSHLTVVLIWYGSTIFLHV  ------RTSVESSLDLTK---
58 ----------SISTVQGKYK AFSTCASHLSIVSLFYSTGLGVYV  ------SSAVVQSSHSAA---
59 ----------KVPSTQGICK VFSTCGSHLSVVSLFYGTIIGLYL  ------CPAGNNSTVKEM---
60 ----------RIPSAAGRHK AFSTCASHLTVVIIFYAASIFIYA  ------RPKALSAFTDNK---
61 ----------KVPSTQSIHK VFSTCGSHLSVVSLFYGTIIGLYL  ------CPSGDNFSLKGS---
62 ----------KVPSSQSIHK AFSTCGSHLSVVSLFYGTVIGLYL  ------CPSANNSEVKET---
63 ----------KFPSIQDIYK VFSTCGSHLSVVTLFYGTIFGIYL  ------CPSGNNSTVKEI---
64 ----------KVPSVRGIHK IFSTCGSHLSVVSLFYGTIIGLYL  ------CPSANNSTVKET---

65 ----------RMDIRLAKT  LVLILVLIICWGPLLAINVYDVF   --------GQMNKLIKT----
66 ----------RKKKTTVKM  LVLVVVLFALCCWFPLNCYVLLS-  --------SKAIHTNNA----
67 ----------ETKRINV-M  LLSIVVAFAVCWLPLTIFNIVFDW  --------NHQIIATCNHNL-
68 ----------SENVALLKT  VIIVLSVFIACWAPLFILLLLDVG  --------CKVKTCDILFR--
69 ----------REFKTPKS   LFLVLFLALCWLPLSIINFVSYF   --------NVKIPET------
70 ----------SERKITLM   VMHVMVFVICAMPFYVQLVNVF    ---------AEQDDAT-----
71 ----------RSAKLNHV   VLAIVSVFLV-SSIYLGIDWFLFW  ---------VFQIPAPF----
72 ----------KQRSRTLTF  VSVLLISFVALQTPYVSLMIFNSY  ATTAWPMOCEHLTLRRT----
73 ----------KWHMQTLHV  LLVVVSFASFWFPFNLALFLESI   RLIAGVYNDTLQNVIIF----
74 ----------RHKGRIVRV  LIAWLVFIIFWLPYHLTLFVDTII  KLLKWISSSCEFERSLKR---
```

FIGURE 8G(1)

```
 7    SVSHGFWASVTFIYNNPLM-WRYF    GAKILTVFTFGYFTDVQKKLEKMKNNNPSPYSSSRGTSGATMGGRTTDDVQCSDSDMEQCSLERHPNMV- (63)
 1                                IREFRQTFRKIIRSHVLRREPFKAGGTSARALAAHGSDGEQISLRLNGHPPGVWANGSAPHPERRPNGYT- (50)
 2    LMYLIVLSHTNSVVNPFI-YAYR
 3    LMYIAIFLTHGNSAMNPIV-YAFR    IQKFRVTFLKIWNDHFRCQPTPPVDEDPPEEAPHD

4    LWELGYWLICYNSTINPW-YALC     NKAFRDTFRLLLLCRWDKRRWRKIPKRPGSVHRTPSRQC
 5    VWRIGYWLCYINSTINPAC-YALC    NATFKKTFKHLIMCHYKNIGATR
 6    YWNLGYWLCYINSTVNPVC-YALC    NKTFRTTFKTLLLCQCDKKRKRKQQYQQRQSVIFHKRVPEQAL
 7    VWSIGYWLLCYVNSTINPAC-YALC   NATFKCTFRHLLLCQRYNIGTAR
 8    LWHLGYWLCYINSTVNPIC-YALC    NRTFRKTFKMLLLCRWKKKKVEEKLYWQGNSKLP

9    LFVFFNWLRYANSAFNPII-YCRS    PDFRKAFQGLLCCARRAARRRHATHGDRPRASGCIARPGPPSPGAASDDDDDDVVGATPPARLLEPWAGCN- (25)
10    VYILLNWIGYVNSFNPLI-YCRS     PDFRIAFQELLCLRRSSLKAYGNGYSSNGNTGEQSGYHVEQEKENKLLCEDLPGTEDFVGHQGTVPSDNID- (13)
11    AFLALNWLGYANSAFNPLI-YCRS    PDFRSAFRRLLCRCGRRLPPEPCAAARPALPPSGVPAAESSPAQPRLCQRLDG
12    VFKIAFWLGYINSCINPII-YPCS    SQEFKKAFQNVLRIQCLRRKQSSKHTLGYTLHAPSHVLEGHKDLVRIPVGSAETFYKISKTDGVCEWKIF- (66)
13    VFKVFWLGYFNSCLNPII-YPCS     SKEFKRAFMRILGCQCRGGRRRRRRRRLGACAYTYRPWTRGGSLERSQSRKDSLDDSGSCMSGGQKRTLPSA- (93)
14    LFKFFFWIGYCNSSLNPVI-YTVF    NQDFRPSFKHILFRRRRRGFRQ
15    LFQFFFWIGYCNSSLNPVI-YTVF    NQDFRRAFRRILCRPWTQTAW
16    LFKFFFWFGYCNSSLNPVI-YTIF    NHDFRRAFKKILCRGDRKRIV
17    LFNFFFWFGYCNSSLNPVI-YTIF    NHDFRRAFKKILCRGDRKRIV
18    FKNFITWLGYINSGLNPVI-YTIF    NLDYRRAFKRLLGLN
19    TFDVFVWFGWANSSLNPII-YA-F    NADFRKAFSTLLGCYRLCPATNMAIETVSINUNGAAMFSSHHEPRGSISKECNLVYLIPHAVGSSEDLKKE- (42)
20    TFDVFVWFGWANSSLNPVI-YA-F    NADFQKVFAQLLGCSHFCSRTPVETVNISNELISYNQDIVFHKEIAAAYIHMMPNAVTPGNREVDNDEEEG- (45)
21    LYSAFTWLGYVNSAVNPII-YTTF    NIEFRKAFLKILHC
22    LYSATTWLGYVNSALNPVI-YTTF    NIEFRKAFLKILSC
23    LVSAVTWLSYVNSAINPVI-YTVF    NAEFRNVFRKALRACC
24    LFDFFTWLGYINSLINPII-YTVF    NEEFRQAFQKIVPFRKAS
25    LGAIINWLCVINSLLNPVI-YAYF    NKDFQNAFKKIIKCNFCRQ
26    LLNVFWIGYVCSGINPVI-YTLF     NKIYRRAFSKYLRCDYKPDKKPPVRQIPRVAATALSGRELNVNIYRHTNERVARKANDPEPGIENQVENLE- (16)
27    LLNVFWIGYLSSAVNPLV-YTLF     NKTYRSAFSRYLQCQYKENRKPLQLILVNTIPALAYKSSQLQVGGKKNSQEDAEQTVDDCSMVTLGKQQSE- (17)
28    LEAIVLWLGYANSALNPL-YAAL     NRDFRTGYQQLFCCRIANRNSHKTSLRSNASQLSRTQSREPRQQEEKPLKLQVWSGTEVTAPQGATDR

29    AVDVTSALAFFNSCLNPMI-YVFM    GQDFRERLIHALPASLERALTEDSTQTSDTATNSTLPSAEVALQAK
30    LDSLCVSFAYINCCINPII-YVVA    GQGQFQGRLRKSLPSLLRNVLTEESVVRESKSFTRSTVDTMAQKTQAV
31    AYLLCVCVSSISSCIDPLI-YYYA    SSECQRYVYSILCCKESSDPSSYNSSGQLMASKMDTCSSNLNNSIYKLLT
32    -LLTYLRVATWNQILDPWV-YILF    RRAVLRRLGPRLSTRPRSLSLQPGLTQRSGLQ
33    AIDATEILGILHSCLNPLI-YAFI    GQKFRHGLLKILAIHGLLISKDSLPKDSRPSFVGSSSGHTSTTL
34    AHQVTLCLLSTNCVLDPVI-YCFL    TKKFRKHLSEKLNIMRSSQKCSRVTRDTGTEMAIPINHTPVNPIKN
35    MDYIGINLATMNSCINPIALYFVS    KCKFKNCFQSCLCCCYQSKSIMTSVPMQGTSIQWKNHEQNNHNTERSSHKDSIN
36    LDYIGINMASINSCINPIALYLVS    KRFKNCFQSCLCCWCQTFEEKQSLEEKQSCLKFKANDHGYDNFRSSNKYSSS
37    TSICARLLAPTNSCVNPFALYLLS    KSFRQFNTQLLCCQPGLMNRSHSTGRSTTCMISFKSTNPSATFSLINRNICHEGYV
38    VTLVARVLSFSNSCVNPFALYLLS    ESFRKHFSWQLCCGQKSYPERSTSYLLSSSAVRMISLKSNAKNVVTNSVLINGHSTKQEIAL
39    ALHVTQCLSLVHCCVNPVL-YSFI    NRNYRYEIMKAFIFKYSAKTGLTKLIDASRVSZTEYSALEQNAK
```

FIG. 8G(2)

```
7
40  FYMLTNALFYVSSAINPIL-YNLV    SANFRQVFLSTLACLCPGWRHRRKKRPTFSRKPNSMSSNHAFSTSATRFTLY
41  VRQISSYVAYSNSCLNPLV-YVIV    GKRFRKKSREVYQAICRKGGCMGESVQMENSMGTLRTSISVDRQIHKLQDWAGNKQ
42  -LLKCRICIYLNSAINPVI-YNIM    SQKRFAAFRKLCNCKQKPTEKAANYSVALNYSVIKESDRFSTELEDITVTDTYVSTKVSFDDTCIASEN
43  VYLALFWLAMSSTMYNPII-YCCL    NHRFRSGFRLAFRCCPWVTPKEDKLELTPTTSLSTRVNRCHTKETLFMAGDTAPSEATSGEAGRPQDGSG-(17)
44  VYIASMWLAMSSTMYNPII-YCCL    NDRFRLGFKHAFRCCPFISAGDYEGLEMKSTRYLQT-QSSVYKVSRLETTISTVVGAHEEEPEEGPKATPS-(29)
45  VYLASFWLAMSSTMYNPII-YCCL    NKRFRAGFKRAFRWCPFIQVSSYDELELKTTRFHPTRQSSLYTVSRMESVTVLFDPNDGDPTKSSRKKRAV-(34)
46  AMPITICLAYFQQNLNPLF-YGFL    GKKFKKYFLQLLKYIPPKAKSHNLSTKMSTLSYRPSEQGNSSTKKPAPCIEVE
47  LHHISLLFSTINSSANPFI-YFFV    GSSKKKRFKESLKVVLTRAFKDEMQPRRQKDNC-NTVTVETVV

48  VLLVLFYPI--NSCANPFL-YAIF    TKTFQRDFFIJLSKFOCCKRRADIYRKDFSAYTSNCKKGFTGSNKPSQSTLKLSTLHCQGTALLDKRRYTEC
49  ILLVLFYPL--NSCANPFL-YAIF    TKAFQRDVFILLSKFGICKRQAQAYRGQRVPPKNSTDIQVQKVTHDMRGGALNMEDVVELIENSHLTPKKQ-(12)
50  ILLVLFHPI--NSCANPFL-YAIF    TKNFRRDFFILLSKCGCYEMQAQIYRTETSSTVHNTHPRNGHCSSAPRVTSGSSRYILVPLSHLAQN

51  FMIIPAFFAKSAAIYNPVI-YIIF    NKQFRNCMLQLICCGKNPLGDDEASATVSKTETSQVAPA
52  MAALPAFFAKSATIYNPVI-YVFM    NRQFRNCILQLFGKKVDDGSELSSASKTEVSSVSSVSPA
53  MAALPAYFAKSATIYNPVI-YVFM    NRQFRNCILQLFGKKVDDGSELSSASKTEVSSVSSVSPA
54  LVRIPSFFSKSACIYNPII-YCFM    NKQFQACIMKMVCGKAMIDESDTCSSQKTEVSTVSSTQVGPN

55  --TASVMYTVVTPMVNPFI-YSL-    RNKDVKSVLKKTLCEEVIRSPPSLLHFFLVLCHLPCFIFCY
56  --AAAVMYAVVTPMNPFI-YSL-    RNSDMKAALRKVLAMRFPSKQ
57  --AITVLNTIVTPVLNPFI-YTL-    RNKDVKEALRRTVKGK
58  --SASVMYTVVTPMLNPFI-YSL-    RNKDVKRALERLLEGNCKVHHWTG
59  --VMAMMYTVVTPMINPFI-YSL-    RNRDMKRALIRVICSMITL
60  --LVSVLYAVIVPLFNPII-YCL-    RNQDVKRALRRTLHLAQDQEANTNKGSKIG
61  --AMAMMYTVVTPLMNPFI-YCL-    RNRDMKQALIRVTCSKKISLPW
62  --VMSSLMYTMVPMLNPFI-YSL-    RNRDIKDALEKIMCKKQIPSFL
63  --AMAMLTVVTPMI-NPFI-YSL-    RNRDMKRALIRVICTKISL
64  --VMAMMYTVVTMPLNPFI-YSL-    RNRDMKEALIRVLCKKITFCL

65  VFAFCSMLCLLNSTVNPII-YALR    SKDLRHAFRSMFPSCEGTAQPLDNSMGDSDCLHKHANNTASMHRAAESCIKSTVKIAKVTHSVSTDTSAEAL
66  LYFAFHWFAMSSTCYNPFI-YCWL    NENFRVELKALLSMCQRPPKPEDRLPSPVPSFRVAWTEKSHGRRAPLPNHHLPSSQIQSGKTDLSSVEPVVAHS
67  LFLLCHLTAMISTCVNPIF-YGFL    NKNFQRDLQFFNFCDFRSRDGRTTRL
68  AEYFLV-IAVINSGTNPII-YTLT    NKEMRRAFIRIMSCCKCPSGDSAGKFKRPIIAGMEFSRSKSDNSSHPQKDEGDNPETIMSSGNVNSSS
69  AMCLGILLSHANSMMNPIV-YACK    KKFKETYFVILRACRLCQTSDSLDSNLEQTTE
70  VSQLSVILGYANSCANPIL-YGFL    SDNFKRSFQRILCLSWMDNAAEEPVDYYATALKSRAYSVEDFQPENLESGGVFRNCTCASRISTL
71  PEYVIDLCICINSSAKPIV-YFLA    GRDKSQRLWEPLRVVFQRALRDGAEPGDAASSTPNTVTMEMQCPSGNAS
72  IGTLARVVPHLHCLINPIL-YALL    CHDFLQRMRQCFRGQLIDRAFLRSQQNQRA
73  CLYVGQFIAYVRACLNPGI-YILV    GTCMRKDMWTTLRVFACCCVKQEIPYQDIDI
74  ALILTESLAFCHCCLNPLL-YVFV    GTKFRKNYTVCWPSFASDSFPAMYPGTRA
```

POLYPEPTIDE DERIVED FROM A POPAMINE RECEPTOR, AND COMPOSITIONS AND METHODS THEREOF

The present application is a continuation-in-part of U.S. Ser. No. 07/943,236, filed Sep. 10, 1992, now abandoned, which application is entirely incorporated herein by reference.

FIELD OF THE INVENTION

The present invention relates to compounds, compositions and methods involving synthetic, isolated and/or recombinant G-protein coupled receptor polypeptides that comprise fragments and/or consensus peptides of G-protein coupled receptors.

BACKGROUND OF THE INVENTION

The membrane protein gene superfamily of G-protein coupled receptors (GPRs) has been characterized as having seven putative transmembrane domains. The domains are believed to represent transmembrane α-helices connected by extracellular or cytoplasmic loops. Of the 74 sequenced members of this G-protein receptor superfamily, the shortest sequence of 324 amino acids represents the rat mas oncogene and the longest, of 744 amino acids, represents the human thyroid-stimulating hormone (TSH) receptor. GPRs thus include a wide range of biologically active receptors, such as hormone-, viral-, growth factor- and neuroreceptors.

G-protein coupled receptors have been characterized as including these seven conserved hydrophobic stretches of about 20–30 amino acids, connecting at least 8 divergent hydrophilic loops. The G-protein family of coupled receptors includes dopamine receptors which bind in a noncovalent but high affinity manner to neuroleptic drugs used for treating psychotic and neurological disorders. For example, the dopamine $D_2$ receptor includes these transmembrane domains, two of which (TM III and TM V; see below) have been implicated by site-selective mutagenesis to demonstrate functional, association with $D_2$ ligands.

Transmembrane domains of G-protein coupled receptors are designated TM1, TM2, TM3, TM4, TMS, TM6 and TM7. TM4, TM5, TM6 and TM7 are the most highly conserved and are postulated to provide sequences which impart biological activity to GPRs. Most GPRs have single conserved cysteine residues in each of the first two extracellular loops which form disulfide bonds that are believed to stabilize functional protein structure. TM3 is also implicated in signal transduction.

Phosphorylation and lipidation (palmitylation or farnesylation) of cysteine residues can influence signal transduction of some GPRs. Most GPRs contain potential phosphorylation sites (e.g., serine or theronine residues) within the third cytoplasmic loop and/or the carboxy terminus. For several GPRs, such as the β-adrenoreceptor, phosphorylation by protein kinase A and/or specific receptor kinases mediates receptor desensitization.

Non-limiting examples of GPRs include cAMP receptors, adenosine receptors, β-adrenergic receptors, muscarinic acetylcholine receptors, α-adrenergic receptors, serotonin receptors (5-HT), histamine H2 receptors, thrombin receptors, kinin receptors, follicle stimulating hormone receptors, opsins and rhodopsins, odorant receptors, cytomegalovirus receptor, etc. See e.g., Probst et al DNA and Cell Biology 11:1–20(1992), which is entirely incorporated herein by reference.

The ligand binding sites of GPRs are believed to comprise a hydrophilic socket formed by several GPR transmembrane domains, which socket is surrounded by hydrophobic residues of the GPRs. The hydrophilic side of each GPR transmembrane helix is postulated to face inward and form the polar ligand binding site. TM3 has been implicated in several GPRs as having a ligand binding site, such as including the TM3 aspartate residue. Additionally, TM5 serines, a TM6 asparagine and TM6 or TM7 phenylalanines or tyrosines are also implicated in ligand binding.

GPRs can be intracellularly coupled by heterotrimeric G-proteins to various intracellular enzymes, ion channels and transporters. See, e.g., Johnson et al *Endoc. Rev.* 10:317–331(1989); and Birnbaumer et al Blochem. Biophys. Acta 1031:163–224(1990) which references are incorporated entirely herein by reference. GPR agonist binding catalyzes the exchange of GTP for GDP on the α-subunit of the G-protein. Different G-protein α-subunits preferentially stimulate particular effectors to modulate various biological functions in a cell. Phosphorylation of cytoplasmic residues of GPRs has been identified as an important mechanism for the regulation of G-protein coupling of some GPRs.

As a non-limiting example of a GPR ligand, dopamine (3,4-dihydroxyphenethylamine) is a critical neurotransmitter in the central nervous system (e.g., in the substantial nigra, midbrain, and hypothalamus). Since the elucidation of the ascending mesolimbic and nigrostriatal pathways, these pathways have been found to be critical in the control of both motor initiation (nigrostriatal) behavior and affectire (mesolimbic) behavior. The clinical efficacy of the major neuroleptic antipsychotic medications has been found to correlate with the respective affinities of these agents for the dopamine $D_2$ receptor in the brain. A dopaminergic role in the symptomatology of the major psychoses has thus been hypothesized, although it is unclear if dopamine alone is etiological, (see, e.g., Davis et al. *Am. J. Psych.* 148:1474–1476 (1991)). Nonetheless, this hypothesis has served as a stimulus for current research in this area.

One model for studying possible interactions of G-protein coupled receptors with their ligands has emerged from site-directed mutagenesis and biochemical analysis of the β-adrenergic receptor, as well as from biophysical analysis of the interaction of retinal with opsin.

According to such a model, the binding of a GPR ligand to a G-protein coupled receptor involves multiple interactions between functional groups on the GPR ligand and residues within the hydrophophilic binding site of the receptor.

While a number of the amino acid residues in the dopamine $D_2$ receptor have been postulated to participate in $D_2$ ligand binding, based on results obtained from site-directed mutagenesis studies and photoaffinity labeling studies performed on the β-adrenergic receptor, such studies have failed to specifically determine which residues are actually involved in binding in the $D_2$ system. Sibley et al. *Soc. Neurosci. Abs.* 17:36.10, 324.5, 324.6 (1991).

The clinical use of neuroleptics has provided a means for treating patients suffering from psychotic disorders. Short-term use of neuroleptics is indicated in several types of psychotic disorders, e.g., acute psychotic episodes, regardless of type; exacerbations of schizophrenia; acute manic excitement while deferring use of lithium or awaiting onset of its effects; adjunctive therapy for major depression with prominent psychotic symptoms, or when an antidepressant or ECT alone is not successful; for agitation in delirium, dementia, or severe mental retardation while seeking to identify and treat the primary basis of the problem; in certain chronic, degenerative, or idiopathic neuropsychiatric disorders with dyskinesias, such as Huntington's disease or Gilles de la Tourette's syndrome; or for ballism or hemiballism; childhood psychoses or apparently allied conditions marked by severe agitation or aggressive behavior; miscellaneous medical indications, notably nausea and vomiting, or intractable hiccups.

Additionally, continuous long-term use of neuroleptics is indicated in many psychotic disorders, such as (for more than six months) (i) primary indications such as Schizophrenia, Paranoia[a,b], Childhood psychoses, some degenerative or idiopathic neuropsychiatric disorders (notably, Huntington's disease and Gilles de la Tourette's syndrome); (ii) secondary indications such as extremely unstable manic-depressive or other episodic psychoses (unusual), otherwise unmanageable behavior symptoms in dementia, amentia, or other brain syndromes; and (iii) questionable indications such as chronic characterological disorders with schizoid, "borderline," or neurotic characteristics; substance abuse; or antisocial behavior, recurrent mood disorders. See, e.g., Baldessarini, *Chemotherapy in Psychiatry*, Revised and Enlarged Edition, Harvard University Press, Cambridge, Mass., (1985), the contents of which is entirely incorporated herein by reference.

Neuroleptics are also referred to as neuroplegics, psychoplegics, psycholeptics, antipsychotics and major tranquilizers, but are sometimes distinguished from non-neuroleptic anti-psychotics. Neuroleptics have recently been characterized as an agent that produces sedative or tranquilizing effects, and which also produces motor side effects, such as catalepsy or extrapyramidal symptomatology. Non-limiting representative examples of neuroleptics include phenothiazine derivatives (e.g., chlorpromazine); thioxanthine derivatives (e.g., thiothixene); butyrophenone derivatives e.g., haloperidol); dihydroindolone (e.g., molindone); dibenzoxazepine derivatives (e.g., loxapine); and "atypical" neuroleptics (e.g., sulpiride, remoxipiride pimozide and clozapine). See Berstein Clinical Pharmacology Littleton, Mass. :PSG Publishing (1978); Usdin et al Clinical Pharmacology in Psychiatry New York:Elsevier North-Holland (1981); and Baldessarini, supra, (1985); and , which references are herein entirely incorporated by reference.

The term "atypical neuroleptics" has been used to describe antipsychotic neuroleptics that produce few or no extrapyramidal side effects and which do not cause catalepsy in animals (See, e.g., Picket et al, *Arch. Gen. Psychiatry* 49:345 (May 1992). Alternatively, atypical neuroleptics, such as clozapine, have been described as those neuroleptics which have a higher affinity for $D_4$ and $D_1$ sites than for $D_2$ sites (See, e.g., Davis et al *Amer. J. Psych.* 148:1474, 1476 (November 1991).

The long term use of all known anti-psychotics, such as neuroleptics or non-neuroleptic antipsychotics, has resulted in serious side effects, as present in Table I, such as persistent and poorly reversible motoric dysfunctions (e.g., tardive dyskinesia) in a significant number of patients. These side effects are especially prevalent in geriatric populations, and adequate pharmacological treatment of these debilitating morotic dysfunctions is not currently available. This problem has severely limited the long-term, clinical administration of these agents.

TABLE I

Neurological Side Effects of Neuroleptic-Antipsychotic Drugs

| Reaction | Features | Period of maximum risk | Proposed mechanism | Treatment |
|---|---|---|---|---|
| Acute dystonia | Spasm of muscles of tongue, face, neck, back; may mimic seizures; not hysterical | 1–5 days | Dopamine excess? Acetylcholine excess? | Antiparkinsonism agents are diagnostic and curative (i.m. or i.v., then p.o.) |
| Parkinsonism | Bradykinesia, rigidity, variable tremor, maskfacies, shuffling gait | 5–30 days (rarely persists) | Dopamine blockade | Antiparkinsonism agents (p.o); dopamine agonists risky? |
| Akathisia | Motor restlessness; patient may experience anxiety or agitation | 5–60 days (commonly persists) | Unknown | Reduce dose or change drug low doses of propranolol; antiparkinsonism agents or or benzodiazepines may help |
| Tardive dyskinesia | Oral-facial dyskinesia; choreo-athetosis, sometimes irreversible, rarely progressive | 6–24 months (worse on withdrawal) | Dopamine excess? | Prevention best; treatment unsatisfactory; slow spontaneous remission |
| "Rabbit" syndrome | Perioral tremor (late parkinsonism variant?); usually reversible | Months or years | Unknown | Antiparkinsonism agents; reduce dose of neuroleptic |
| Malignant syndrome | Catatonia, stupor, fever, unstable pulse and blood pressure; myoglobinemia; can be fatal | Weeks | Unknown | Stop neuroleptic; antiparkinsonism agents usually fail; bromocriptine often helps; dantrolene variable; general supportive care crucial |

*There may be an increased risk of hypotension on interacting high doses of propranolol with some antipsychotic agents; clonidine may also be effective at doses of 0.2–0.8 mg/day, but carries a high risk of hypotension (Zubenko et al., Psychiatry Res. 11: 143, 1984).

In addition, clozapine, although apparently capable of producing less motor side effects, can cause irreversible, potentially fatal agranulocytosis in a minority of patients administered the drug. Such serious side effects limit the use of clozapine to patients who are resistant to treatment with other neuroleptics.

Antipsychotics have a variety of significant pharmacological effects, e.g., as presented in the following Tables II and III.

TABLE II

Comparative Pharmacology of Neuroleptics

| Alkaloid Pharmacologic Actions | Phenothiazine Derivative Chlorpromazine | Thioxanthene Derivative Thiothixene | Butyrophenone Derivative Haloperidol |
|---|---|---|---|
| Antipsychotic | Yes++ | Yes++ | Yes++++ |
| Antiemetic | Yes+++ | Not tested | Yes+++ |
| Hypothermia | Yes+ | Yes+ | No |
| Hypotension | Yes++ | Yes+++ | + |
| Parkinsonism | Yes++ | Yes+ | Yes++++ |
| Antiadrenergic | Yes++ | Yes+++ | + |
| Anticholinergic | Yes+ | Yes+ | Negligible |
| Antihistaminic | Yes+ | Negligible | Negligible |
| Releases NE, DA | No | No | No |
| Blocks DA | Yes++ | Yes+ | Yes++++ |
| Blocks NE | Yes++ | Yes+++ | Yes+ |
| Central sympathetic suppressant | Yes++ | Yes+ | Yes+++ |

Chlorpromazine, thiothixene, and haloperidol decrease the functional availability of dopamine (DA) and norepinephrine (NE) by blocking the dopamine receptor sites in the basal ganglia and norepinephrine receptor sites in thalamic and hypothalamic areas. Reserpine simply reduces the concentrations of norepinephrine and dopamine in these areas. Both of these actions result in suppression of central sympathetic activity.
+ → ++++ indicate, from very weak to very strong effects.

TABLE III

Comparative Pharmacology of Antipsychotics

| Drug | Sedation | Adrenergic Blockage | Extrapyramidal Reaction |
|---|---|---|---|
| Chlorpromazine | High | Moderate to high | Moderate |
| Chlorprothixene | High | High | Low to moderate |
| Haloperidol | Low | Low | High |
| Molindone | Moderate | Moderate | Moderate to high |
| Loxapine | High | Low to moderate | High |

See Ebadi, PHARMACOLOGY, Little, Brown and Co., Boston, 61–65 (1985); Cattabeni et al *Adv. Biochem. Psychopharmacology* 24:275 (1980). Baldessarini, supra, which references are herein incorporated entirely by reference.

However, despite the face that thousands of neurolepticor antipsychotic-type compounds have been synthesized and reported in the literature, such compounds which lack serious side effects and which have sufficient pharmacological activity, have not been disclosed.

Alternative to dopamine receptor GPRs, as presented above, other neuroreceptor GPRs are involved in neurological pathologies, and drugs such as neuroreceptor GPR binding agents, presently used for treating these pathologies, also suffer from similar side effects as those of neuroleptics, as presented above.

Other GPRs are also involved in receptor-related pathologies, such as hormone related GPRs involved in endocrine related pathologies, Accordingly, there is a need to provide G-protein coupled receptor binding agents, including neuroreceptor and endocrine receptor GPRs, which do not produce such deleterious and debilitating side effects as those produced by known agents, such as neuroleptics, which can be used for therapy or diagnosis of GPR related pathologies.

Citation of documents herein is not intended as an admission that any of the documents cited herein is pertinent prior art, or an admission that the cited documents are considered material to the patentabilty of the claims of the present application. All statements as to the date or representations as to the contents of these documents are based on the information available to the applicant and does not constitute any admission as to the correctness of the dates or contents of these documents.

SUMMARY OF THE INVENTION

It is therefore an object of the present invention to overcome one or more deficiencies found in the related art.

It is another object of the present invention to provide non-naturally occurring synthetic, isolated and/or recombinant GPR polypeptides which are fragments, consensus fragments and/or sequences having conservative amino acid substitutions, of at least one transmembrane domain of at least one G-protein coupled receptor, which polypeptides have been discovered to have receptor-like functional binding sites of neuroreceptor and endocrine GPRs, such that GPR polypeptides of the present invention may bind GPR ligands, or which may also modulate, quantitatively or qualitatively, GPR ligand binding to GPRs.

In is still another object of the present invention to provide GPR polypeptides and compositions that have only partially helical structures, in contrast to known characterized transmembrane domains of GPRs, such as, but not limited to, GPR transmembrane domains I–VII.

it is yet another object of the present invention to provide synthetic or recombinant GPR polypeptides, conservative substitution derivatives thereof, antibodies, anti-idiotype antibodies, compositions and methods that can be used as potential modulators of G-protein coupled receptor function, by binding to GPR ligands or modulate GPR ligand binding, due to their expected biological properties, which may be used in diagnostic, therapeutic and/or research applications.

It is a further object of the present invention is to provide synthetic, isolated or recombinant polypeptides which are designed to inhibit or mimic various GPRs or fragments thereof, as receptor types and subtypes.

According to one aspect of the present invention, a synthetic or recombinant GPR polypeptide is provided that comprises a GPR amino acid sequence of, e.g., at least 5, 10, 15 or 20 amino acids, substantially corresponding to at least one transmembrane domain, or fragment and/or consensus peptide thereof, of a G-protein coupled receptor, wherein at least 20 amino acids are preferred. In a preferred embodiment, the polypeptide is (a) chemically synthesized and/or (b) obtained from a recombinant host cell or organism which expresses a recombinant nucleic acid encoding a GPR polypeptide, as defined herein.

In another preferred embodiment, the transmembrane domain is selected from at least one of TM1, TM2, TM3, TM4, TM5, TM6 or TM7, corresponding to transmembrane domains I, II, III, IV, V, VI and VII, respectively, of a GPR. In another preferred embodiment, the transmembrane domain is a dopamine receptor transmembrane domain selected from the group consisting of at least one of a $D_1$, $D_2$, $D_3$, $D_4$ and $D_5$ dopamine receptor transmembrane domain. The transmembrane domain, e.g., may be selected from at least one of $D_2$ receptor transmembrane domains III or V. In still another preferred embodiment, the GPR polypeptide amino acid sequence substantially corresponding to an amino acid sequence contained in at least one of FIG. 2 (SEQ ID NO:2), FIG. 3 (SEQ ID NO:3) or FIG. 5 (SEQ ID NO:5).

In another aspect of the present invention, a GPR composition is provided, comprising a GPR polypeptide, or a pharmaceutically acceptable ester, ether, sulfate, carbonate, malate, glucuronide or salt thereof, the composition further comprising a pharmaceutically acceptable carrier and/or diluent.

In still another aspect of the present invention, a method is provided for treating a subject suffering from a disease state involving a qualitative or quantitative pathological abnormality of a GPR protein or a biological molecule functionally associated therewith. Such biological molecule may be a membrane cytoplasmic protein, lipid, carbohydrate, saccharide, nucleoside or nucleotide mono-, di-, or tri-phosphate, an enzyme, a cofactor, a nucleic acid, a neurotransmitter, an ion, a carrier, a cell receptor, or any combination thereof.

In a preferred embodiment, the GPR protein is a dopamine receptor and the abnormality involves a dopamine related pathology, wherein the method comprises administering an effective dopamine receptor modulating amount of a GPR polypeptide of the present invention. In another preferred embodiment, the transmembrane domain is a $D_2$ dopamine receptor domain and the disease state is a psychiatric disorder, such as schizophrenia or schiz affective disorder (see American Psychiatric Association, *Revised Manual of Diagnostic and Statistical Criteria for Psychiatric Disorders (DSM-III-R)*, American Psychiatric Assoc. Press, Washington, DC (1989)).

In another preferred embodiment, the GPR composition is administered as a pharmaceutical composition to provide a GPR polypeptide in an amount ranging from about 0.01 μg to 100 mg/kg, and also preferably, about 10 μg to 10 mg/kg. In another preferred embodiment, the administering is by oraal intravenous, intramuscular, parenteral or topical administration, including mucosal administration to the nasal mucosa or the oral mucosa, by aerosol, nebulizer or drop administration as non-limiting examples.

Other objects of the invention will be apparent to skilled practitioners from the following detailed description and examples relating to the present invention.

BRIEF DESCRIPTION OF THE FIGURES

FIG. 1 is the amino acid sequence of a control peptide (SEQ ID NO:1), which is hydrophobic in its properties, but does not correspond to a known GPR transmembrane domain.

FIG. 2 represents the amino acid sequence of a GPR transmembrane polypeptide, polypeptide II (SEQ ID NO:2), which corresponds to a portion of the dopamine $D_2$ receptor transmembrane segment III.

FIG. 3 represents the amino acid sequence of a transmembrane polypeptide, polypeptide III (SEQ ID NO:3), norresponding to a consensus peptide of the dopamine $D_2$ receptor transmembrane domains I-VII.

FIG. 4 represents the amino acid sequence of a consensus sequence of transmembrane domains that is shortened to be less than the length required to span a lipid bilayer.

FIG. 5 represents a consensus amino acid sequence of transmembrane domain as a consensus peptide between dopamine receptors $D_1$ and $D_2$.

Figure 8C:
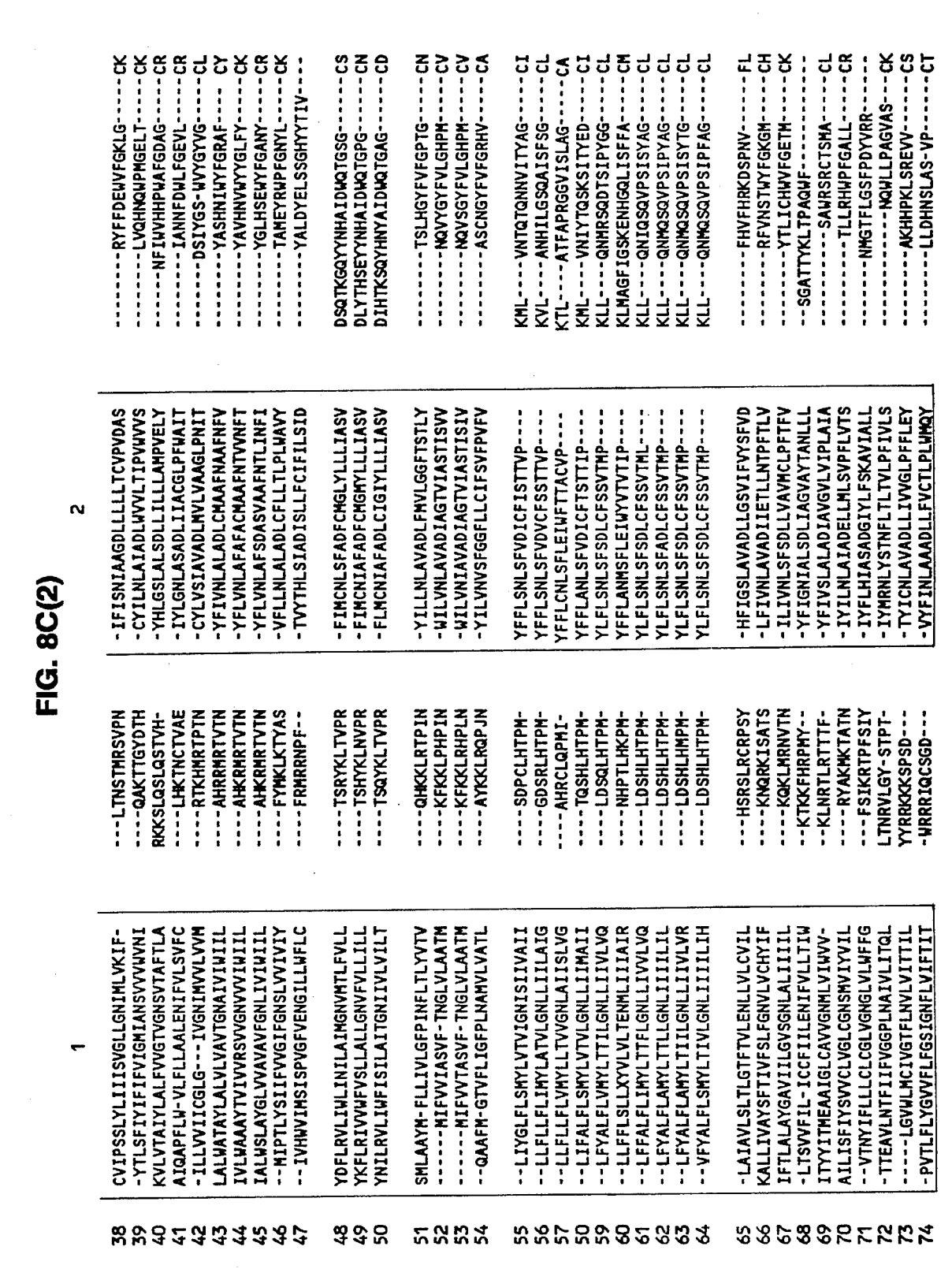

FIG. 8A–G are a comparison listing of amino acid sequences of transmembrane domains and adjacent amino acid sequences of representative GPRs (SEQ ID NOS:6–79).

DETAILED DESCRIPTION OF THE PREFERRED EMBODIMENTS

Figure 6:
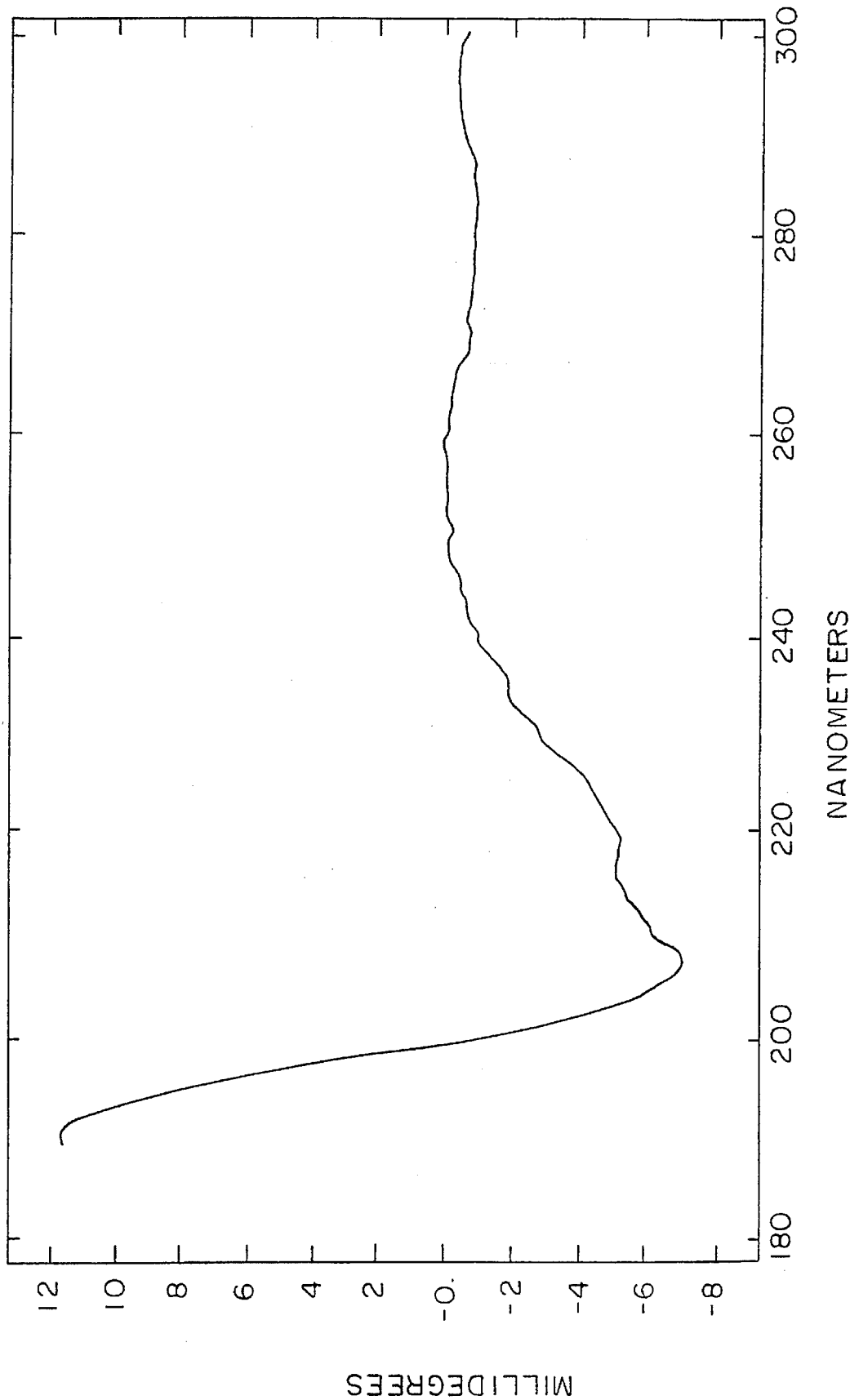
FIG. 6 is a representation of a circular dichroism spectrum of a solution of the consensus polypeptide III (SEQ ID NO: 3) of FIG. 3.

The present invention relates to G-protein coupled receptor (GPR) polypeptides which can be used to mimic naturally occurring or isolated GPRs, or to modulate the binding of GPR ligands to GPRs, such as inhibition or enhancement of binding. GPR polypeptides of the present invention can include GPR transmembrane domain fragments and/or consensus peptides thereof, of at lease 4–10 amino acids in length, and/or corresponding sequences having conservative amino acid substitutions as "substitution peptides", wherein the GPR polypeptide binds a GPR ligand or modulates the binding of a GPR ligand to a GPR in vitro, in vivo or in situ.

GPR polypeptides of the present invention can be synthesized or recombinantly produced, or optionally purified, to provide commercially useful amounts of GPR polypeptides for use in therapeutic, diagnostic or research applications, according to known method steps, see, e.g., Ausubel et al, eds. *Current Protocols in Molecular Biology*, Wiley Interscience, N.Y., (1987, 11992); and Sambrook et al, *Molecular Cloning, A Laboratory Manual*, 2nd edition, Vols. 1–3, Cold Spring Harbor Press, (1989), which references are herein entirely incorporated by reference.

Additionally, GPR polypeptides according to the present invention can be used to generate polyclonal and/or monoclonal antibodies, anti-idiotype antibodies thereto, or fragments thereof, which may used for diagnostic and/or therapeutic applications, according to known method steps, see, e.g., Harlow and Lane, *Antibodies: A Laboratory Manual*, Cold Spring Harbor Press (1988), which is herein entirely incorporated by reference.

GPR polypeptides, anti-GPR antibodies or anti-idiotype antibodies (or fragments thereof) to GPR polypeptides have been unexpectedly discovered to quantitatively or qualitatively modulate G-protein coupled receptors, such that binding of GPR polypeptides or anti-idiotype antibodies (or fragments thereof) to G-protein coupled receptor ligands may be used for diagnostic research or therapeutic applications of the present invention. Such GPR polypeptides, antibodies or anti-idiotype antibodies of the present invention may therefore be used as modulators of G-protein coupled receptors, such as neuroreceptors or endocrine receptors, as non-limiting examples.

Binding of such GPR polypeptides, (including GPR fragments, consensus peptides, substitution derivatives and anti-idiotype antibody fragments) of the present invention may be used to treat symptoms of, and provide diagnosis and treatment for, pathologies related to GPRs. Such pathologies have been found to correlate with symptoms occurring in neurological. viral or endocrine pathologies. $D_2$ receptor-related psychotic disorders, including schizophrenia, now treated with neuroleptics, is a non-limiting example thereof.

The use of synthetic or recombinant GPR polypeptides of the present invention can be preferable to the use of known drugs that bind G-protein coupled receptors, such as neuroleptics that bind or inhibit the biological effect of binding to neuroreceptors as a non-limiting example. Such polypeptides are expected to have significantly less side effects than presently used drugs presently used for inhibiting such receptor binding including neuroleptics, as they would structurally mimic naturally occuring GPRs and/or modulate ligand binding. Thus, GPR polypeptides are expected to have reduced side effects attributable to known foreign compound drugs, with less immunogenicity, and reduced potential for motoric side effects (e.g., extrapyramidal symptoms and/or tardive dyskinesia).

The present invention is also related to the production, by chemical synthesis or recombinant DNA technology, of GPR polypeptides, preferably as small as possible while still retaining sufficiently high affinity or interaction with G-protein coupled receptors to modulate, such as to inhibit or to enhance, binding to such receptors by GPR ligands.

GPR polypeptides of the present invention may include 5– 10 to 50–150 amino acid fragments, consensus sequences or substitution sequences of GPRs, e.g., as presented in FIG. 8A–G (SEQ ID NOS:6–79) including, but not limited to, multiple dopamine receptors, cAMP receptors, adenosine receptors, β-adrenergic receptors, muscarinic acetylcholine receptors, α-adrenergic recepnors, serotonin receptors (5-HT), histamine H2 receptors, thrombin receptors, kinin receptors, follicle stimulating hormone receptors, opsins and rhodopsins, odorant receptors, cytomegalovirus GPRs, adenosine A2 receptors, dopamine receptor, histamine H2 receptors, octopanmine receptors, N-formyl receptors, anaphylatoxin receptors, thromboxane receptors, IL-8 receptors, platelet activating factor receptors, endothelin receptors, bombesin gastrin releasing peptide receptor, neuromedin B preferring bombesin receptors, vasoactive intestinal peptides, neurotensin receptors, bradykinin receptors, thyrotropin-releasing hormone receptors, substance P receptors, neuromedin K receptors, drenal angiotensen II type I receptors, mas oncogene (angiotensin) receptors lutropin-choriogonadotropin receptors, thyrotropin receptors, follicle stimulating hormone receptors, cannabinoid receptors, glucocorticoid-induced receptors, endothelial cell GPRs, testis GPRs, and thoracic aorta GPRs, and homologs thereof having a homology of at least 80% with at least one of transmembrane domains 1–7, as described herein. See, e.g., Probst et al *DNA and Cell Biology* 11:1–20(1992), which is entirely incorporated herein by reference.

Accordingly, a "G-protein coupled receptor polypeptide" or "GPR polypeptide" of the present invention includes polypeptides having a "GPR amino acid sequence" which substantially corresponds to at least one 10 to 50 amino acid fragment and/or consensus sequence of a known GPR or group of GPRs, wherein the GPR polypeptide has homology of at least 80%, such as 81, 82, 83, 84, 85, 86, 87, 88, 89 90 91, 92 93, 94, 95, 96, 97, 98, 99 or 100% homology, while maintaining GPR modulating activity, wherein a GPR polypeptide of the present invention is not naturally occurring or is naturally occurring but is in a purified or isolated form which does not occur in nature. Preferably, a GPR polypeptide of the present invention substantially corresponds to a transmembrane domain of a GPR or group of GPRs as a consensus sequence.

Also preferred are GPR polypeptides wherein the GPR amino acid sequence is 4–10 to 50 amino acids in length, such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140 or 150 amino acids, or any range therein.

An amino acid or nucleic acid sequence of a GPR polypeptide of the present invention is said to "substantially correspond" to another amino acid or nucleic acid sequence, respectively, if the sequence of amino acids or nucleic acid in both molecules provides polypeptides having biological activity that is substantially similar, qualitatively or quantitatively, to the corresponding fragment of at least one GPR transmembrane domain, or which may be synergistic when two or more transmembrane domains, consensus sequences or homologs thereof are present.

Additionally or alternatively, such "substantially corresponding" sequences of GPR polypeptides include conservative amino acid or nucleotide substitutions, or degenerate nucleotide nodon substitutions wherein individual amino acid or nucleotide substitutions are well known in the art.

Alternatively or additionally, substantially corresponding refers to GPR polypeptides having amino acid sequences having at least 80% homology or identity to an amino acid sequence of SEQ ID NO:1, such as 80, 81, 82, 83, 84, 85, 86, 87, 88, 89, 90, 91, 92, 93, 94, 95, 96, 97, 98, 99 or 100% homology or identity.

Accordingly, GPR polypeptides of the present invention, or nucleic acid encoding therefor, include a finite set of substantially corresponding sequences as substituuion peptides or polynucleotides which can be routinely obtained by one of ordinary skill in the art, without undue experimentation, based on the teachings and guidance presented herein. For a detailed description of protein chemistry and structure, see Schulz, G. E. et al., *Principles of Protein Structure,* Springer-Verlag, New York, 1978, and Creighton, T. E., Proteins: *Structure and Molecular Properties,* W. H. Freeman & Co., San Francisco, 1983, which are hereby incorporated by reference. For a presentation of nucleotide sequence substitutions, such as codon preferences, see Ausubel et al, supra, at §§ A.1.1–A.1.24, and Sambrook et al, supra, at Appendices C and D.

Conservative substitutions of a GPR polypeptide of the present invention includes a variant wherein at least one amino acid residue in the polypeptide has been conservatively replaced by a different amino acid. Such substitutions pruferably are made in accordance with the following list as presented in Table IV, which substitutions may be determined by routine experimentation provide modified structural and functional properties of a synthesized polypeptide molecule, while maintaining the receptor binding, inhibiting or mimicking biological activity, as determined by known GPR receptor activity assays.

TABLE IV

| Original Residue | Exemplary Substitution |
| --- | --- |
| Ala | Gly;Ser |
| Arg | Lys |
| Asn | Gln;His |
| Asp | Glu |
| Cys | Ser |
| Gln | Asn |
| Glu | Asp |
| Gly | Ala;Pro |
| His | Asn;Gln |
| Ile | Leu;Val |
| Leu | Ile;Val |
| Lys | Arg;Gln;Glu |
| Met | Leu;Tyr;Ile |
| Phe | Met;Leu;Tyr |
| Ser | Thr |
| Thr | Ser |
| Trp | Tyr |
| Tyr | Trp;Phe |
| Val | Ile;Leu |

Alternatively, another group of substitutions of GPR polypeptides of the present invention are those in which at least one amino acid residue in the protein molecule has been removed and a different residue inserted in its place according to the following Table V. The types of substitutions which may be made in the protein or peptide molecule of the present invention may be based on nalysis of the frequencies of amino acid changes between a homologous protein of different species, such as those presented in Table 1–2 of Schulz et al., .Supra and FIGS. 3–9 of Creighton, supra. Based on such an analysis, alternative conservative substitutions are defined herein as exchanges within one of the following five groups:

TABLE V

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. This however tends to promote the formation of secondary structure other than α-helical. Pro, because of its unusual geometry, tightly constrains the chain. It generally tends to promote β-turn-like structures, although in some cases Cys can be capable of participating in disulfide bond formation which is important in protein folding. Note the Schulz et al. would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and insertions, and substitutions according to the present invention are those which do not produce radical changes in the characteristics of the protein or peptide molecule. "Characteristics" is defined in a non-inclusive manner to define both changes in secondary structure, e.g. α-helix or β-sheet, as well as changes in physiological activity, e.g. in receptor binding assays.

However, when the exact effect of the substitution, deletion, or insertion is to be confirmed one skilled in the art will appreciate that the effect of the substitution or substitutions will be evaluated by routine screening assays, either immunoassays or bioassays to confirm biological activity, such as receptor binding or modulation of ligand binding to the corresponding GPR. See, e.g., Maranges et al., eds., for example, a substituted polypeptide mypically is made by site-specific mutagenesis of the peptide molecule-encoding nucleic acid, expression of the mutant nucleic acid in recombinant cell culture, and, optionally, purification from the cell culture, for example, by immunoaffinity chromatography using a specific antibody on a chemically derivatized column or immobilized membranes or hollow fibers (to absorb the mutant by binding to at least one epitope).

A preferred use of this invention is the production, by chemical or recombinant DNA technology, of GPR polypeptides, preferably as small as possible while still retaining sufficiently high affinity for binding to, or association with, GPRs. By production of GPR polypeptides including smaller fragments or variants of such transmembrane domains, one skilled in the art, using known binding and inhibition assays, can readily identify the GPR polypeptides capable of binding minimizing or modulating G-protein coupled receptors using known methods. Non-limiting examples of fragments of GPRs to be used as GPR polypeptides or as a basis for consensus sequences thereof for GPR polypeptides, are presented in FIGS. 2–5 and FIG. 8A–G, wherein fragments or consensus sequences of 10 to 50 amino acids of at least one sequence of FIGS. 2–5 or corresponding to at least one transmembrane domain or domains 1–7 listed in FIG. 8A–G (SEQ ID NOS:6–79) are encompassed by the present invention, such as at least one transmembrane domain of one or more GPRs, such as a cAMP receptor (1), adenosine receptors (2–3); muscarinic acetylcholine receptors (4–8); human adrenergic receptors (9–11, 14–16, 19–25, 28); adrenergic receptors (9–28); human thrombin receptor (31); endothelin receptors (35–36), bombesin receptors (37– 38), endocrine receptors (48–50), rhodopsin (51) . opsins (52–54), odorant receptors (55–64), and cytomegalovirus GPRs (72–54), as non-limiting examples, wherein ("#") refers to the listed sequences in FIG. 8A–G.

Accordingly, GPR polypeptides may include consensus sequences and/or fragments of at least one of transmembrane domain 1–7 of one or more GPRs as presented in FIGS. 2–5 (SEQ ID NO:2–5) or FIG. 8A–G. (SEQ ID NOS:6–79) or homologs thereof, which GPR polypeptides do not occur naturally, and/or which are provided in an isolated and/or purified form not found in nature.

Consensus peptides of GPR polypeptides of the present invention may include peptides which are distinct from known GPR sequences in critical structural features, but which are derived from consensus sequences of homologous GPR transmembrane domains 1–7, e.g., as presented in FIG. 8A–G (SEQ ID NOS:6–79). Such consensus peptides may be derived by molecular modeling, optionally combined with hydrophobicity analysis and/or fitting to model helices, as non-limiting examples. Such modeling can be accomplished according to known method steps using known modeling algorithms, such as, but not limited to, ECEPP, INSIGHT, DISCOVER, CHEM-DRAW, AMBER, FRODO and CHEM-X. Such algorithms compare transmembrane domains between related G-protein coupled receptors, determine probable energy-miminized structures and define alternative consensus polypeptide fragments.

Such consensus peptides or fragments of GPRs may then be synthesized or produced recombinantly, in order to provide GPR polypepnides according to the present invention which mimic, modulate or inhibit binding of ligands to G-protein coupled receptors. GPR ligands, in the context of the present invention, refer to biological molecules that bind GPRs in vitro, in situ or in vivo, and may include hormones, neurotransmitters, viruses or receptor binding domains, thereof, opsins, rhodopsins, nucleosides, nucleotides, coagulation cascade factors, odorants or pheremones, toxins, colony stimulating factors, platelet activating factors, neuroactive peptides, neurohumors, or any biologically active compounds, such as drugs or synthetic or naturally occurring compounds.

The following non-limiting examples of consensus peptides of GPRs of the present invention are provided by way of guidance and not by way of limitation. In GPR polypeptides of the present invention, one or more, preferably 4–10, Asp and/or Lys residues may additionally be incorporated at the carboxy and/or amino terminal ends in order to provide expected helix forming effects of the helix dipole effect, e.g., as described in Baldwin et al Biochem. 28:2130 (1989); Baldwin et al *Proc. Nat'l Acad. Sci. USA* 84:8898 (1987); and Baldwin et al *Proc. Nat'l Acad. Sci. USA* 86:5286 (1989), which references are entirely incorporated herein by reference.

As a non-limiting example of GPR polypeptide of the present invention, dopamine receptor transmembrane fragments of $D_2$ transmembrane domain (e.g., domain III) as presented in FIG. 2 (SEQ ID NO:2) or a consensus sequence as presented in FIG. 3 (SEQ ID NO:3), e.g., of $D_2$ domains I–VII. Additionally or alternatively a consensus sequence may include less than 20 amino acids, such as 15 amino acids corresponding to a transmembrane domain, such as a $D_2$ receptor domain, as presented in FIG. 4 (SEQ ID NO:4) as polypeptide IV, which is smaller than the length required by spanning an average lipid bilayer of a cell membrane.

However, in the context of the present invention, GPR polypeptides of greater than 15–20 amino acids are preferred such that the GPR polypeptides are able to span the lipid bilayer.

Another non-limiting example of a GPR polypeptide using dopamine receptor transmembrane domains is a consensus sequence of two or more GPR receptors, such as the dopamine $D_1$ and $D_2$ receptors. A non-limiting example of such a consensus GPR polypeptide is presented in FIG. 5 (SEQ ID NO:5).

Additionally, modified amino acids or chemical derivatives of amino acids of consensus or fragments of GPRs proteins, according to the present invention may be provided, which polypeptides contain additional chemical moieties or modified amino acids not normally a part of the protein. Covalent modifications of the peptide are thus included within the scope of the present invention. Such modifications may be introduced into a GPR polypeptide by reacting targeted amino acid residues of the polypeptide with an organic derivatizing agent that is capable of reacting with selected side chains or terminal residues. The following examples of chemical derivatives are provided by way of illustration and not by way of limitation.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole(alkyl)alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of C1—C20.

Acidic amino acids call be substituted with non-carboxylate amino acids while maintaining a negative charge, and derivatives or analogs thereof, such as the non-limiting examples of (phosphono)alanine, glycine, leucine, isoleucine, threonine, or serine; or sulfated (e.g., -$SO_3H$) threonine, serine, tyrosine.

Other substitutions may include unnatural hyroxylated amino acids may made by combining "alkyl" (as defined and exemplified herein) with any natural amino acid. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the GPR polypeptides can be replaced by a ketomethylene moiety, e.g. (—C($=$O)—$CH_2$—) for (—(C$=$O)—NH—). Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

In addition, any amino acid representing a component of the said peptides can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D- amino acid but which can additionally be referred to as the R- or the S-, depending upon its composition and chemical configuration. Such derivatives have the property of greatly increased stability co degradation by enzymes, and therefore are advantageous in the formulation of compounds which may have longer in vivo half lives, when administered by oral, intravenous, intramuscular, intraperitoneal, topical, rectal, intraocular, or other routes.

Additional amino acid modifications of amino acids of GPR polypeptides of to the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-( 5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used;

e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'-N-C-N-R') such as 1-cyclohexyl-3-(2-morpholinyl- (4-ethyl) carbodiimide or 1-ethyl- 3-(4-azonia-4,4- dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

Derivatization with bifunctional agents is useful for cross-linking the peptide to a water-insoluble support matrix or to other macromolecular carriers, according to known method steps. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl- propionate), and bifunctional maleimides such as bis-N-maleimido-1,8-octane. Derivatizing agents such as methyl-3-[(p-azidophenyl)dithio]propioimidateyieldphotoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 (which are herein incorporated entirely by reference), may be employed for protein immobilization.

Other modifications of GPR polypeptides of the present invention may include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties,* W. H. Freeman & Co., San Francisco, pp. 79–86 (1983)), acetylation of the N-terminal amine, methylation of main chain amide residues (or substitution with N-methyl amino acids) and, in some instances, amidation of the C-terminal carboxyl groups, according to known method steps.

Such derivatized moieties may improve the solubility, absorption, permeability across the blood brain barrier biological half life, and the like. Such moieties or modifications of GPR polypeptides may alternatively eliminate or attenuate any possible undesirable side effect of the protein and the like. Moieties capable of mediating such effects are disclosed, for example, in *Remington's Pharmaceutical Sciences,* 16th ed., Mack Publishing Co., Easton, Pa. (1980).

Such chemical derivatives of GPR polypeptides also may provide attachment to solid supports, including but not limited to, agarose, cellulose, hollow fibers, or other polymeric carbohydrates such as agarose, cellulose, such as for purification, generation of antibodies or cloning; or to provide altered physical properties, such as resistance to enzymatic degradation or increased binding affinity or modulation for GPRs, which is desired for therapeutic compositions comprising GPR polypeptides, antibodies thereto or fragments thereof. Such peptide derivatives are well-known in the art, as well as method steps for making such derivatives using carbodiimides active esters of N-hydroxy succinimmide, or mixed anhydrides, as non-limiting examples.

Variation upon consensus peptide sequences of GPR polypeptide of the present invention may also include: the addition of one, two, three, four, or five lysine, arginine or other basic residues added to the —COOH terminal end of the peptide; and/or one, two, three, four, or five glutamate or aspartate or other acidic residues added to the amino terminal end of the peptide, where "acidic" and "basic" are as defined herein. Such modifications are well known to increase the α-helical content of the peptide by the "helix dipole effect". They also can provide enhanced aqueous solubility of the peptide. See, e.g., Baldwin et al., supra.

As another non-limiting example of a GPR polypeptide of the present invention, serotonergic receptors (5-HT) consensus sequences may be determined using presently known 5-HT sequences and include, e.g., as consensus peptides of TM3, TM5 and TM7, respectively:

5-HT consensus (1) DDDDNIWSIFDWIGYLNSISM-VIYTLFKKKK (SEQ ID NO:80)

5-HT consensus (2) DDDDNIWNIFSTIGYLNSISPVSVIM-HIYGKKKK (SEQ ID NO:81)

5-HT consensus (3) DDDDGYSIYDTLVTFAINPVYITVFKKKK (SEQ ID NO:82)

Such non-naturally occurring consensus sequences may also be further modified according to known method steps to provide additional consensus peptides with substituted amino acids to increase or decrease α-helical propensity and/or solubility (e.g., hydrophilicity). As a non-limiting example, 5-HT consensus peptide (1) above may be modified according to the present invention to have increase helical propensity and increased aqueous solubility as follows:

5-HT consensus (4) DDDDNAWSAFDWALYLNSISMAIYTY-AKKKK (SEQ ID 2 10:83), wherein, e.g., smaller, non-polar residues replace either larger, more polar residues (e.g., Ala for Ile or Val) or larger aromatic residues (e.g., Ala for Phe).

Another non-limiting, illustrative example of consensus GPR polypeptides of the present invention are those for adrenergic receptors, are the following:

An example of the consensus GPR polypeptide for domain VII across all presently known adrenergic receptors is as follows:

adrenergic consensus (1) LFSFITWLGYANSSLNPIIYTTF (SEQ

ID NO: 84)

An example of a consensus GPR polypeptide for domain V across all adrenergic receptors is as follows:

adrenergic consensus(2) VYTIYSSSWFFAPSLAIMVITYT (SEQ ID NO :85)

Examples of a consensus GPR polypeptide for domain III across all adrenergic receptors are as follows:

adrenergic consensus (3) IWLTSDIMSTSSILHNLCVISF (SEQ ID NO: 86)

An example of a consensus GPR polypeptide for domains III, V, and VII of all adrenergic receptors is as follows:

adrenergic consensus (4) IWSIFSSDIWGYAINHSSLAIMCPIV-IYTV (SEQ ID NO: 87)

adrenergic consensus(5) IFTIFSSDIAVGYANHSSAAIMPIVIYSV (SEQ ID NO:88), wherein variations and substitutions of amino acids may be made as described herein.

Non-limiting examples of consensus GPR polypeptides for transmembrane domain III across several or many, such as 1–500, or any range or value therein, G-protein receptors are as follows:

TM3-(1) YAIFVLYASAWLSFLNCPFIVTLNI (SEQ N0:96)

TM3-(2) YAIFVLYATAWLSFLNCPFIVTLNI(SEQ ID NO:97)

TM3-(3) YAIFVLYATAWLTFLNCPFIVTLNI(SEQ ID NO:98)

TM3-(4) YAIFVLYASAWLTFLNCPFIVTLNI(SEQ ID NO:99)

TM3-(5) WAIFVLYASAWLSFLNCPFIVTLNI(SEQ ID NO:100)

TM3-(6) WAIFVLYATAWLSFLNCPFIVTLNI (SEQ ID NO: 101)

TM3-(7) WAIFVLYATAWLTFLNCPFIVTLNI(SEQ ID NO:102)

TM3-(8) WAIFVLYASAWLTFLNCPFIVTLNI (SEQ ID NO: 103)

TM3-(9) YAVFVLYASAWLSFLNMPFIVTLNI(SEQ ID NO: 104)

TM3-(10) YAVFVLYATAWLSFLNMPFIVTLNI (SEQ ID NO: 105)

TM3-(11) YAVFVLYATAWLTFLNMPFIVTLNI (SEQ ID NO: 106)

TM3-(12) YAVFVLYASAWLTFLNMPFIVTLNI (SEQ ID NO: 107)

TM3-(13) YAIFVLYASAWLSFLNCVTASIPFIVTLNI (SEQ ID NO: 108)

TM3-(14) YAIFVLYASAWLSFLNCTSSIVVTA-SIVTLNI (SEQ ID NO: 109)

TM3-(15) YAIFVLYASAWLSFLNVTLNICTSSIV (SEQ ID NO: 110)

TM3-(16) YAIFVLYASAWLSFLNTASILNLM-FIVTLNI (SEQ ID NO: 111)

TM3-(17) YAIFVLYASAWLSFLNMASILN-LPFIVTLNI (SEQ ID NO: 112)

TM3-(18) YAIFVLYASAWLSFLNSGILLLAPFIVTLNI (SEQ ID NO: 113)

TM3-(19) YAIFVLYASAWLSFLNMS-GILLLAPFIVTLNI (SEQ ID NO: 114)

TM3-(20) YAIFVLYASAWLSFLNSELS-VYTLTVCPFIVTLNI (SEQ ID NO: 115)

TM3-(21) YAIFVTYASAWLS FLNMSELS-VYTLTVPFIVTLNI (SEQ ID NO: 116)

TM3-(22) YAIFVLYASAWLASELSVYTLTVS-FLNCPFIVTLNI (SEQ ID NO: 117)

TM3-(23) YAIFVLYASAWLASELS-VYTLTVPFIVTLNI (SEQ ID NO: 118)

TM3-(24) YAIFVLYASAWLSFLASELSVYA-SELSSTLTTVNMPFIVTLNI (SEQ ID NO: 119)

TM3-(25) YAIFVLYASAWLSFLNGGEIALWS-LCPFIVTLNI (SEQ ID NO: 120)

TM3-(26) YAIFVLYASAWLSFLNGGEIAL-WSLIVTLNI (SEQ ID NO: 121)

TM3-(27) YAIFVLYASAWLGGEIAL-WSLNCPFIVTLNI (SEQ ID NO: 122)

TM3-(28) YAIFVLYAGGEIALWSLSFLNCPFIVTLNI (SEQ ID NO: 123)

TM3-(29) YAIFVLYASAWLSFFFLLFGYLGN-FLLNCPFIVTLNI (SEQ ID NO: 124)

TM3-(30) YAIFVLYASAWLFFFLLFGYLGNFLL-PFIVTLNI (SEQ ID NO: 125)

TM3-(31) YAIFVLYASAWLSFLNTACFY-VAITASLCFITEIALIPFIVTLNI (SEQ ID NO: 126)

TM3-(32) YAIFVLYASAWLTACFY-VAITASLCFITEIALICPFIVTLNI (SEQ ID NO: 127)

TM3-(33) YAIFVLYATACFYVAITASLCFITEIAL-ISFLNCPFIVTLNI (SEQ ID NO: 128)

TM3-(34) YAITACFYVAITASLCFITE-IALIASAWLSFLNCPFIVTLNI (SEQ ID NO: 129)

TM3-(35) YAIFVLYATACFYVAIITEIALISAWLS-FLNCPFIVTLNI (SEQ ID NO: 130)

TM3-(36) YAIFVLYASAWLSFLNACFYICLFAGVC-FLIPFIVTLNI (SEQ ID NO: 131)

TM3-(37) YAIFVLYASAWNACFYICLFAGVMF-LILSFLNCPFIVTLNI (SEQ ID NO:132)

TM3-(38) YAIFVLYFYICLFAGVCFLIASAWLS-FLNCPFIVTLNI (SEQ ID NO: 133)

TM3-(39) YAIFVLYASVDAVNMFTSAWLS-FLNCPFIVTLNI (SEQ ID NO: 134)

TM3-(40) YAIFSVDAVNMFTVLYASAWLS-FLNCPFIVTLNI (SEQ ID NO: 135)

TM3-(41) YAIFVLYASAWLSVDAVNMFTS-FLNCPFIVTLNI (SEQ ID NO: 136)

TM3-(42) YAIFVLYASAWLSFLNSVDAVNMFT-PFIVTLNI (SEQ ID NO: 137)

TM3-(43) YAIFVLYASAWLSFLNCPFIVSVDAVNM-FTTLNI (SEQ ID NO: 138)

TM3-(44) YAIFVLYASAWLSVDMFTS-FLNCPFIVTLNI (SEQ ID NO: 139)

TM3-(45) YAISVDAVNMFTFVLYASAWLS-FLNCPFIVTLNI (SEQ ID NO: 140)

TM3-(46) YAIFSLSVFSLLAIVLYASAWLS-FLNCPFIVTLNI (SEQ ID NO: 141)

TM3-(47) YAIFVLYASLSVFSLLAISAWLS-FLNCPFIVTLNI (SEQ ID NO: 142 )

TM3-(48) YAIFVLYASAWLSLSVFSLLAIS-FLNCPFIVTLNI (SEQ ID NO: 143 )

TM3-(49) YAIFVLYASAWLSFLSLSVFSLLAIN-CPFIVTLNI (SEQ ID NO: 144 )

TM3-(50) YAIFVLYASAWLSFLNPFSLSVFSLLAI-IVTLNI (SEQ ID NO: 145 l )

TM3-(51) YAIFVLYATAWLTFLNCVTATIPFIVTLNI (SEQ ID NO: 146)

TM3-(52) YAIFVLYATAWLSFLNCTSSIVVTA-TIVTLNI (SEQ ID NO: 147)

TM3-(53) YAIFVLYATAWLSFLNVTLNICTTTIV (SEQ ID NO: 148)

TM3-(54) YAI FVLYATAWLTFLNTATILNLMFIVTLNI ( SEQ ID NO: 149)

TM3-(55) YAIFVLYATAWLSFLNMATILNLPFIVTLNI (SEQ ID NO: 150)

TM3-(56) YAIFVLYATAWLTFLNSGILLLAPFIVTLNI (SEQ ID NO: 151)

TM3-(57) YAIFVLYASAWLTFLNMT-GILLLAPFIVTLNI (SEQ ID NO: 152)

TM3-(58) YAIFVLYASAWLTFLN-TELTVYTLTVCPFIVTLNI (SEQ ID NO: 153)

TM3-(59) YAIFVLYASAWLTFLN-MTELTVYTLTVPFIVTLNI (SEQ ID NO: 154)

TM3-(60) YAIFVLYATAWLATELTVYTLTVT-FLNCPFIVTLNI (SEQ ID NO: 155)

TM3-(61) YAIFVLYASAWLATELS-VYTLTVPFIVTLNI (SEQ ID NO: 156)

TM3-(62) YAIFVLYATAWLSFLATELSVYASELST-TLTTVNMPFILNI ( SEQ ID NO: 157)

TM3-(63) YAIFVLYATAWLSFLNGGEIALWTL-CPFIVTLNI (SEQ ID NO: 158)

TM3-(64) YAIFVLYASAWLTFLNGGEIAL-WTLIVTLNI (SEQ ID NO: 159)

TM3-(65) YAIFVLYASAWLGGEIAL-WTLNCPFIVTLNI (SEQ ID NO: 160)

TM3-(66) YAIFVLYAGGEIALWTLSFLNCPFIVTLNI (SEQ ID NO: 161)

TM3-(67) YAIFVLYATAWLSFFFLLFGYLGN-FLLNCPFIVTLNI (SEQ ID NO: 162)

TM3-(68) YAIFVLYATAWLFFFLLFGYLGNFLL-PFIVTLNI (SEQ ID NO: 163)

TM3-(69) YAIFVLYATAWLTFLNTACFY-VAITASLCFITEIALIPFIVTLNI (SEQ ID NO: 164)

TM3-(70) YAIFVLYATAWLTACFYVAITATL-CFITEIALICPFIVTLNI ( SEQ ID NO: 165)

TM3-(71) YAIFVLYATACFYVAITATLCFITEIAL-ISFLNCPFIVTLNI (SEQ ID NO: 166)

TM3-(72) YAITACFYVAITASLCFITEIALI-ATAWLTFLNCPFIVTLNI (SEQ ID NO: 167)

TM3-(73) YAIFVLYATACFYVAIITEIALITAWLT-FLNCPFIVTLNI (SEQ ID NO. 168)

TM3-(74) YAIFVLYASAWLTFLNACFYICLFAGVC-FLIPFIVTLNI (SEQ ID NO: 169)

TM3-(75) YAIFVLYASAWNACFYICLFAGVMF-LILTFLNCPFIVTLNI (SEQ ID NO: 170)

TM3-(76) YAIFVLYFYICLFAGVCFLIATAWLT-FLNCPFIVTLNI (SEQ ID NO: 171)

TM3-(77) YAIFVLYATVDAVNMFTTAWLT-FLNCPFIVTLNI (SEQ ID NO: 172)

TM3-(78) YAIFTVDAVNMFTVLYATAWLT-FLNCPFIVTLNI (SEQ ID NO: 173)

TM3-(79) YAIFVLYATAWLTVDAVNMFTS-FLNCPFIVTLNI (SEQ ID NO: 174)

TM3-(80) YAIFVLYATAWLSFLNTVDAVgMFT-PFIVTLNI ( SEQ ID NO: 175)

TM3-(81) YAIFVLYASAWLTFLNCPFIVSVDAVNM-FTTLNI ( SEQ ID NO: 176)

TM3-(82) YAIFVLYATAWLSVDMFT-TFLNCPFIVTLNI (SEQ ID NO: 177)

TM3-(83) YAISVDAVNMFTFVLYATAWLS-FLNCPFIVTLNI (SEQ ID NO: 178)

TM3-(84) YAIFVLYASLTVFSLLAISAWLT-FLNCPFIVTLNI (SEQ ID NO: 179)

TM3-(85) YAIFVLYASAWLTLSVFTLLAIS-FLNCPFIVTLNI (SEQ ID NO: 180)

TM3-(86) YAIFVLYASAWLTFLSLSVFTLLAIN-CPFIVTLNI (SEQ ID NO: 181)

TM3-(87) YAIFVLYASAWLTFLNPFSLSVFSLLAI-IVTLNI (SEQ ID NO: 182)

TM3-(88) YAIFVLYASAWLSFLNGGVTASFTAS-VGPFIVTLNI (SEQ ID NO: 183)

TM3-(89) YAIFVLYASAWLSFLNGGVTASFTAS-VGVTLNI (SEQ ID NO: 184)

TM3-(90) YAIFVLLGGVTASFTASVNYASAWLS-FLNCPFIVTLNI (SEQ ID NO: 185)

TM3-(91) YAIFVLYAIFFFLLFSAWLS-FLNCPFIVTLNI (SEQ ID NO: 186)

TM3-(92) YAIFVLYASAWLSFLNCPFIVTLNIIFF-FLLFIVTLNI (SEQ ID NO: 187)

TM3-(93) YAIFVLYASAWIFFFLLFLS-FLNCPFIVTLNI (SEQ ID NO: 188)

TM3-(94) YAIFVLYASAWLFFTVLASELS-VYTLTVSFLNCPFIVTLNI (SEQ ID NO: 189)

TM3-(95) YAIFVLYASAWLSFLFATLGGEIAL-CPFIVTLNI (SEQ ID NO: 190)

TM3-96) YAIFVLYAFATLGGEIkLSAWLS-FLNCPFIVTLNI (SEQ ID NO: 191)

TM3-(97) YAIFFTVLASELSVYTLTVYASAWLS-FLNCPFIVTLNI (SEQ ID NO: 192)

TM3-(98) YAIFFPIAALFAIASAWLSFLNCPFIVTILNI (SEQ ID NO: 193)

TM3-(99) YAIFVLYASAWLSFFPIAALFASIPFIVTLNI (SEQ ID NO: 194)

TM3-(100) YAIFVLYASAWLSFLNCPFFPIAAL-FASILNI (SEQ ID NO: 195)

TM3-(101) YAIFVLYASAWLSLDVLFSTASIMHLS-FLNGGEIALWSLIVTLNI (SEQ ID NO: 196)

TM3-(102) YAIFVLYASLDVLFSTASIMHLIAL-WSLNCPFIVTLNI (SEQ ID NO: 197)

TM3-(103) YAIFVLYAGGEIALWSLSFLNSLDVLFS-TASIMLPFIVTLNI (SEQ ID NO: 198)

TM3-(104) YAIFVLYASAWLSFFDVLFSTASIMLF-GYLGNFLLNCPFIVTLNI (SEQ ID NO: 199)

TM3-(105) YAIFVLYASAWLFFFLLFGYLSLDVLFS-TASIMHLGNFLLPFIVTLNI(SEQ ID NO: 200)

TM3-(106) YAIFVLYASAWLSFLNTACFY-VAITASLSLMHLFITEIALIPFIVTLNI (SEQ ID NO: 201)

TM3-(107) YASLDVLFSTAIMHLSAWLTACFY-VAITASLCFITEIALICPFIVTLNI (SEQ ID NO: 202)

TM3-(108) YAIFVLYATACFYVAITASLS-FLNCPFIVTLNISLDVLFSTASIMHL(SEQ ID NO:203)

TM3-(109) YAITACFYVAITASLCFITE-IALIASAWLSFLNCPFIVTLNI (SEQ ID NO: 204)

TM3-(110) YAIFVLYATACFYSTASILNLIMHL-CAISLVAIITEIALISAWLSFLN(SEQ ID NO:205)

TM3-(111) YAIFVLYASAWLSFLNACFYI-CLFASILNLIMHLGVCFLIPFIVTLNI (SEQ ID NO:206)

TM3-(112) YAIFVLYASAWNASILNLIMHLCFYI-CLFAGVMLILSFLNCPFIVTLNI(SEQ ID NO:207)

TM3-(113) YAI FPFVQCWS IFSLVLIAVVLYFY-IAGVCFLIASAWLS FLNCPFIVTI (SEQ ID NO: 208)

TM3-(114) PFVQCVSITVSIFSLVLIAVYAIFVL-YASVDAVNMFTSAWCPFIVTLNI (SEQ ID NO:209)

TM3-(115) YAIFGDWSSVDAVNMFTVLYASAWLS-FLNCPFIVTLNI (SEQ ID NO:210)

TM3-(116) YAIFVLYAGDWSSAWLSVDAVNMFTS-FLNCPFIVTLNI (SEQ ID NO: 211)

TM3-(117) YAIFVLYASAWLGDWSSFLNSVDAVLG-MFTPFIVTLNI (SEQ ID NO:212)

TM3-(118) YAIFVLYASAWLSFLNCPFIVGDWSSV-DAVNMFTTLNI (SEQ ID NO: 213)

TM3-(119) YAIFVLYASAWLGYLGSVDMFTS-FLNCPFIVTGDWSLNI(SEQ ID NO:214)

TM3-(120) YAISVDAVNMFTFVLYAGYLGSAWLS-FLNCPFIVTLNI (SEQ ID NO:215)

TM3-(121) YAIFSLSVFSLLAIVLAYASAWLGYLGS-FLNCPFIVTLNI (SEQ ID NO: 216)

TM3-(122) YAIFVLYAGYLGAGNMDSLSVFS-LLAISAWLSFLNCPFIVTLNI (SEQ ID NO:217)

TM3-(123) YAIFVLYASAWLSLSVFGNMSLLAIS-FLNCPFIVTLNI (SEQ ID NO:218)

TM3-(124) YAIFVLYASAWLSFLSLSVFGGSLLAIN-CPFIVTLNI (SEQ ID NO: 219)

TM3-(125) YAIFVLYASAWLSFLNPFSLS-VFGSLLAIIVTLNI(SEQ ID NO:220)

TM3-(126) YAIFVLYATAWLT-FLSLANCVTATIPFIVTLNI (SEQ ID NO: 221)

TM3-(127) YAIFVLYATAWLSFLNCTSLASSIVVTA-TIVTLNI (SEQ ID NO: 222)

TM3-(128) YAIFVLYATAWLSFLNVTLNISLACTT-TIV(SEQ ID NO: 223)

TM3-(129) YAIFVLYATAWLTFLNTATILSLANLM-FIVTLNI(SEQ ID NO:224)

TM3-(130) YAIFVLYATAWLSFLNMATILNLPFSV-DAVIVTLNI (SEQ ID NO:225)

Recently discovered G-proteins also can be used according to the presently claimed invention to provide GPR polypeptides of the present invention, based on the teaching and guidance presented herein. Exampled of such GPR polypeptides of the present invention may include, as non-limiting examples, GPR polypeptides corresponding to transmembrane domain III, e.go, as follows:

TM3-(131) ISTMYTVTGRWTLGQVVCDFWLSS-DITCCTASILHLCVIAL (SEQ ID NO: 226)

TM3-(132) ILYGYRWPLPSKLCAVWIYLDVLFSTA-SIMHLCAISL (SEQ ID NO: 227)

TM3-(133) IIYIVMDRWKLGYFLCEVWLSVDMTC-CTCSILHLCVIAL (SEQ ID NO :228)

TM3-(134) IADKTVRVAMGAENDLGYNFRSD-DVCGHCWQWYCSL (SEQ ID NO: 229)

TM3-(135) ILNYWPFGLALCHFVNYSQAVSV-LVSAYTLVAISI (SEQ ID NO:230)

TM3-(136) ILGRWEFGIHLCKLWLTCDVL-CCTSSILNLCAIALD (SEQ ID NO: 231)

TM3-(137) IMASVMHRHCLPLIGICLSSER-HCLVSIFVELGAL (SEQ ID NO:232)

Further non-limiting examples of consensus GPR polypeptides for transmembrane domain III of several or many, such as 1–500, or any range or value therein, more recently discovered G-protein receptors are as follows:

TM3-(138) YAIFVLYASAWLSFLNCPFISILHLCVI-ALVTLNI (SEQ ID NO:233)

TM3-(139) YAIFVLYATAWLSFLNCPFISILNLCA-IALDVTLNI (SEQ ID NO:234)

TM3-(140) YAIFVLYATAWLTFLNCPFISIFVEL-GALVTLNI (SEQ ID NO: 235 )

TM3-(141) YAIFVLYASAWLTFLNCPFISIFVEL-SIMHLCAISLGALVTLNI (SEQ ID NO: 236)

TM3-(142) WAIFVLYAILGRWEFGIHLCKLWLT-SAWLSIMHLCAISLSFLNCPFIVTLNI (SEQ ID NO:237)

TM3-(143) WAIFVLYAILGRWEFGIHLCKLWLT-TAWLSIMHLCAISLSFLNCPFIVTLNI (SEQ ID NO: 238)

TM3-(144) WAIFVLYATAWLTFLNCPFSIMHLCAIS-LIVTLNI (SEQ ID N0:239)

TM3-(145) WAIFVLYASAWLTFLNCPFISIMHL-CAISLVTLNI (SEQ ID NO: 240)

TM3-(146) YAVFVLYASAWLSFLNMSIMHLCAIS-LPFIVTLNI (SEQ ID NO: 241)

TM3-(147) YAVFVLYATAWLSFLBTMPFSILNLCA-IALDVTLNI(SEQ ID NO:242)

TM3-(148) YAVFVLYATAWLSILNLCAIALDTFLN-MPFIVTLNI (SEQ ID NO:243)

TM3-(149) YAVFVLYASILNLCAIALDSAWLTFLN-MPFIVTLNI (SEQ ID NO:244)

TM3-(150) YAFVLYASAWLSFLNCVTA-SIPFCLVSIFVELGALIVTLNI (SEQ ID NO: 245 )

TM3-(151) YAIFVLYASAWLSFLNCLVSIFVEL-GALIVVTASIVTLNI (SEQ ID NO: 246)

TM3-(152) YAIFVLYASAWLSFLNVTLN-CLVSIFVELGALII (SEQ ID NO: 247)

TM3-(153) YAIFVLYASAWLSFLNTASILNLMFI-CLVSIFVELGALVTLNI (SEQ ID NO: 248)

TM3-(154) YAIFVLYASAWLSFLNMASILN-LPFCLVSIFVELGALVTLNI (SEQ ID NO:249)

TM3-(155) YAIFVLYASAWLSFLNILGRWEFGIHL-CKLWLTCDVLCCTSSGILLLAPFIVTLNI (SEQ ID NO:250)

TM3-(156) YAIFVLYASAWLSFLNMILGRWEFGIHL-CKLWLTCDVLCCTSSGILLLAPFIVTLNI (SEQ ID NO:251)

TM3-(157) YAIFVLYASAWLILGRWEFGIHLCKL-WLTCDVLCCTSSFLNSELSVYTLTVCPFIVTLNI (SEQ ID NO: 252 )

TM3-(158) YAIFVLYAILGRWEFGIHLCKLWLTCDV-LCCTSSAWLSFLNMSELSVYTLTVPFIVTLNI (SEQ ID NO:253)

TM3-(159) YAIFVLYASAWLASRWPLPLSVYTLTVS-FLNCPFIVTLNI (SEQ ID NO: 254 )

TM3-(160 ) YAIFVLYASAWLASELILYYWRWPLP-CLHDLVWLCTCSILHLCVIALS-VYTLTVPFIVTLNI (SEQ ID NO:255)

TM3-(161) YAIFVLYASAWLSFLASELSVYA-SELSSTLHDLVWLWLDVFCVIALTTVN-MPFIVTLNI (SEQ ID NO:256)

TM3-(162) YAIFVLYASAWLSFLNGGEIALWS-LCPFIILYYWRWPLPCLHDLVSILHCVIALVTLNI (SEQ ID NO:257)

TM3-(163) YVWLWLDVFCCTCSILHLCVIALFVL-YASAWLSFLNGGEIALWSLIVTLNI (SEQ ID NO: 258)

TM3-(164) YAIFVLYASAWLAIILYYWRWPLPCLH-DLGGEIALWSLNCPFIVTLNI(SEQ ID NO:259)

Non-limiting examples of consensus GPR polypeptides for domain V across several or many, such as 1–500, or any range or value therein, G-protein receptors are as follows:

TM5-(1) CDVFVFVDIMLCTASIFNLCAISVG(SEQ ID NO:260)

TM5-(2) YAIFVLYDIPILCTASIFNLCAISVG(SEQ ID NO:261)

TM5-(3) DYAIFVFVDIFiLMTASIFNLMAISVG(SEQ ID NO:262)

TM5-(4) DYAIFVFVDIMLHTTASTIFNLMATITVG (SEQ ID NO: 263)

TM5-(5) CDVAVVYSSDIMLFYVCTASIFSSNLCAISSVG(SEQ ID NO:264)

TM5-(6) FLFCSLGSFYIPIAVILVDIMLCTASIFNLCAISVG(SEQ ID NO:265)

TM5-(7) YAIFVLYDFLFCSLGSFYIPIAVILIMLCTASIFNLCAISVG (SEQ ID NO: 266)

TM5-(8) DYAIFVFVDIMLMTASIFLFCSLGSFYIPIAVILISVG(SEQ ID NO:267)

TM5-(9) DYAIFVFVDIMLHTTASTIFNLMAFLFCSLGSFYIPIAVILTITVG (SEQ iD NO: 268)

TM5-(10) CDVAVVYSSDIMLFYVCTASIFSSNLFLFCSLGSFYCAISSVG(SEQ ID NO:269)

TM5-(11) CDVFVFVDIMLCTASIFNWYILSSIGSFFAPCLILLVYLLCISVG (SEQ ID NO: 270)

TM5-(12) YAIFVLYDIPILCTASIFNLCAIWYILSSIGSFFAPCLILLVYLSVG (SEQ ID NO: 271)

TM5-(13) DYAIFVFVDIWYILSSIGSFFAPCLILLVYLASIFNLMAISVG (SEQ ID NO:272)

TM5-(14) DYAIWYILSSIGSFFAPCLILLVYLIMLHTTASTIFNLMATITVG (SEQ ID NO: 273 )

TM5-(15) CDVAVVYSSDIMLFYVCWYILSSIGSFFAPCLILLVYLSSNLCAISSVG(SEQ ID NO:274)

TM5-(16) CDVFVFVDIMLCTASIFWYVISSSIGSFFAPCLINHLIrYNLCAISVG (SEQ ID NO:275)

TM5-(17) YAIFVLYDIMLCTASIFNLCAIWINSISSSIGSFFAPCLINHLVYSVG (SEQ ID NO: 276)

TM5-(18) DYAIFVFVWYVISSSIGSFFAPCLINHLVYDIMLMTASIFNLMAISVG (SEQ ID NO:277)

TM5-(19) DYAIFVFVDIMLHTTASTIFWYVISSSIGSFFAPCLINHLVYTVG (SEQ ID NO: 278)

TM5-(20) CDVAVVYSSDIMLFYVCTASIFSWYVISIGSFFAINHLVYNLCAISVG (SEQ ID NO: 279 )

TM5-(21) CDVFVFVDIMLCTASIFNLCAITYAISSSVISFYIPVAILVTYT(SEQ ID NO:280)

TM5-(22) YAIFVLYDIMLCTATYAISSSVISFYIPVAILVTYTSIFNLCAISVG (SEQ ID NO: 281)

TM5-(23) DYAIFVFiVDIMILMTATYAISSSVISFYIPVAILYTISVG(SEQ ID NO:282)

TM5-(24) TYAISSSVISFYIPVATDYAIFVFVDIMLHTTASTIFNLMATITVG (SEQ ID NO: 283 )

TM5-(25) CDVAVVYSSDIMLFYVCTATYAISSSVISFYIPVAILVTYTSSVG(SEQ ID NO:284)

TM5-(26) CDVFVFVDFVIYSSWSFYLPFGIFfVLVYACTASIFNLCAISVG (SEQ ID NO:285)

TM5-(27) YAIFVLYDFVIYSSWSFYLPFGVTVLVYASIFNLCAISVG (SEQ ID NO :286)

TM5-(28) DYAIFVFVDFVIYSSWSFYLPFGVTVLVYATASIFNLMAISVG (SEQ ID NO:287)

TM5-(29) DYAIFVFVDFVIYSSVIZSFYLPFGVTVLVYAHTTASTIFNLMATITVG (SEQ ID NO: 288)

TM5-(30) CDVAVVYSSDFVIYSSWSFYLPFGVTVYVCTASIFSSNLCAISSVG ( SEQ ID NO: 289 )

TM5-(31) CDVFVFVDIMLCTASYTIYSTCGAFYIPSVLLIILYGNLCAISVG (SEQ ID NO: 290)

TM5-(32) YAIFVLYDIMLCTASYTIYSTCGAFYIPSVLLIILYGNLCAI SVG (SEQ ID NO: 291)

TM5-(33) DYAIFVFVDIMLMTASYTIYSTCGAFYIPSVLLIILYGNLMAISVG (SEQ ID NO: 292)

TM5-(34) DYAIFVFVDIMLHTTASYTIYSTCGAFYIPSVLLIILYGMATITVG (SEQ ID NO: 293)

TM5-(35) CDVAVVYSSDIMSYTIYSTCGAFYIPSVLLIILYGIFSSNLCAISSVG (SEQ ID NO: 294)

TMS- (36) CDVFVFFVLIGSFVAVDIMLCTASIFNLCAISVG (SEQ ID NO:295 )

TM5-(37) YAIFVLYFVLIGSFVADIMLCTASIFNLCAISVG (SEQ ID NO: 296)

TM5-(38) DYAIFVFVFVLIGSFVADIMLMTASIFNLMAISVG (SEQ ID NO: 297)

TMS- (39) DYAI FVFVFVLIGSFVADIMLHTTASTIFNLMATITVG ( SEQ ID NO: 298)

TM5-(40) CDVAVVYSSFVLIGSFVADIMLFYVCTASIFSSNLCAISSVG (SEQ ID NO: 299)

TM5-(41) CDVFVFVDIMLCFFIPTLIMVITYFNLCAISVG (SEQ ID NO: 300)

TM5-(42) YAIFVLYDIMLCFFIPTLIMVITYFFNLCAISVG (SEQ ID NO: 301)

TM5-(43) DYAIFVFVDIMLMFFIPTLIMVITYFNLMAISVG (SEQ ID NO: 302)

TM5-(44) DYAIFVFVDIMLHTFFIPTLIMVITYFNIIMATITVG (SEQ ID NO: 303)

TM5-(45) CDVAVVYSSDIMLFYVCFFIPTLIMVITYFSSNLCAISSVG (SEQ ID NO: 304)

TM5-(46) CDVVYGLVDGLVTFYLPLLIMCITYYDIMLCTASIFNLCAI SVG (SEQ ID NO: 305)

TM5-(47) YAIVYGLVDGLVTFYLPLLIMCITYYDIMLCTASIFNLCAISVG (SEQ ID NO: 306)

TM5-(48) DYAIVYGLVDGLVTFYLPLLIMCITYYDIMLMTASIFNLMAISVG (SEQ ID NO: 307)

TM5-(49) DYAIVYGLVDGLVTFYLPLLIMCISSDIMLHTTASTIFNLMATITVG (SEQ ID NO: 308)

TM5-(50) CDVVYDGLVTFYLPLLIMCITYYDIMLFYVCTASIFSSNLCAISSVG (SEQ ID NO: 309)

TM5-(51) CDVFVFVDIMLLVIFLGLVIVIPFVLIIVSYASIFNLCAISVG (SEQ ID NO: 310)

TM5-(52) YAIFVLYDIMLLVIFLGLVIVIPFVLIIVSYAIFNLCAISVG (SEQ ID NO: 311)

TM5-(53) DYAIFVFVDIMLMLVIFLGLVIVIPFVLIIVSYAIFNLMAISVG (SEQ ID NO: 312)

TM5-(54) DYAIFVFVDIMLHTLVIFLGLVIVIPFVLIIVSYAIFNLMATITVG (SEQ ID NO: 313)

TM5-(55) CDVAVVYSSDIMLFLVIFLGLVIVIPFVLIIVSYAIFSSNLCAISSVG (SEQ ID NO: 314)

TM5-(56) CDVFVFVDIMLCTALMIYILGGLIIIIPFLLIVMSYVSIFNLCAISVG (SEQ ID NO: 315)

TM5-(57) YAIFVLYDIMLCTALMIYILGGLIIIIPFLLIVMSYVSIFNLCAISVG (SEQ ID NO:316)

TM5-(58) DYAIFVFVDIMLMTASIFNLMIYILGGLIIIIPFLLIVMSYVLMAISVG (SEQ ID NO: 317)

TM5-(59) DYAI FVFVDIMLHTTASTI LMIYI LGGLI II IPFLLIVMSYVITVG ( SEQ ID NO: 318)

TM5-(60) CDVAVVYSSDIMLFYVCTAYILGGLIP-
FLLIVMTYVS I FTNLCAI S SVG ((SEQ ID NO: 319)

TM5-(61) CDVFVFVDIMLCTASIFNLLMIHI-
MEVIIIVIPFVLIVISYACAISVG ( SEQ ID NO: 320)

TM5-(62) YAIFVLYDIMLCTASIFNLLMIHI-
MEVIIIVIPFVLIVISYACAISVG ( SEQ ID NO: 321)

TM5-(63) DYAIFVFVDIMLMTASIFIIHIEVII-
IVIPFIIVISYAISVG (SEQ ID NO: 322)

TM5-(64) DYAIFVFVDIMLHTTASTILMIHI-
MEVIIIVIPFVLIVISYAITVG (SEQ ID NO: 323)

TM5-(65) CDVAVVYSSDIMLFYVCTASIFLMIHI-
MEVIIIVIPFVLIVISYAAISSVG ( SEQ ID NO: 324)

Non-limiting examples of longer consensus GPR polypeptides for domain V across several or many, such as 1–500, or any value or range therein, G-protein receptors are as follows:

TM1-(1)
TM1NWPALSIWIIINTIGGNILVIMAVSIYTSLDV
MLCTASILNLLISLFVLIGSFVAFFIPL-
TIMVITYF LFNVFFVW IGYVCSSSLGINPVI-
IYTLF (SEQ ID NO: 325)

TM1- (2)
NWPALSIWIIINTIGGNILVIMAVTIYT-
TLDVMLCTATILNLLISLFVLIGT-
FVAFFIPLTIMVITYFLFNVFFVWIGY VCTT-
TLGINPVIIYTLF (SEQ ID NO: 326)

TM1-(3)
NWPALTIWIIIBITIGGNILVI-
MAVSIYTTLDVMLCTATILNLLITLFV-
LIGTFVAFFIPLTIMVITYFLFNVFFVWIGY
VCSTSLGINPVIIYTLF (SEQ ID NO: 327)

TM1- (5)
NWPALTIWIIINTIGGNILVIMAVTIYT-
TLDVMLCTATILNLLITLFVLGT-
FVAFFIPLTIMVITYFLFNVFFVWIGY VCTLG-
INPVIIYTLF (SEQ ID NO: 328)

TM1-(6)
NWKNWSALLTTVVIILTIAGNILVI-
MAVSSLDVMLCTASILNLLISLFVLGS-
FVAFFIPLTIMVITYFLFNVFFVWIGY VCSSS-
LGINPVIIYTLF (SEQ ID NO: 329)

TM1- (7)
ITITVVLAVLILITVAGNVVVCIAVG-
SIYTSLDVMLCTASILNLLISLFVLIGS-
FVAFFIPLTIMVITYFLFNVFFVWIG YVCSSS-
LGINPVIIYTLF (SEQ ID NO: 330)

TM1-(8)
TLTLVCLACLUSLTVFGNVLVIIAVF-
SLDVMLCTASILNLLISLFVLIGS-
FVAFFIPLTIMVITYFLFNVFFVWIGYVCS
SSLGINPVIIYTLF (SEQ ID NO:331)

TM1-(9)
TAAIAAAITFLILFTIFGNALVIIAVL-
SIYTSLDVMLCTASILNLLISLFVLIGS-
FVAFFIPLTIMVITYFLFNVFFVWI GYVCSSS-
LGINPVIIYTLF (SEQ ID NO: 332)

TM1-(10)
AISVGLVLGAFILFAIVGNILVILSVAN-
WPALSIVVIIINTIGGNILVI-
MAVSIYTSLDVMLCTASILNLLISLFVLIGS
FVAFFIPLTIMVITYFLFNVFFVWI-
GYVCSSSLGINPVIIYTLF (SEQ ID NO: 333)

TM1- (ii)
AALAGALLALAVLATVGGNLLVIVA-
IASLDVMLCTASILNLLISLFVLIGS-
FVAFFIPLTIMVITYFLFNVFFVWIGYVC SSS-
LGINPVIIYTLF(SEQ ID NO: 334)

TM1-(12)
TAGDCLIMLIVLLIVAGNVLVIVAISLD-
VMLCTASILNLLISLFVLIGSFVAFFI-
PLTIMVITYFLFNVFFVWIGYVCSS SLGINPVI-
IYTLF (SEQ ID NO: 335)

TM1-(13)
VITIAVVTAVVSLMTIVGNVLVMISF-
SIYTSLDVMLCTASILNLLISLFVLIGS-
FVAFFIILTIMVITYFLFNVFFVWIG YVCSSSLG-
INPVIIYTLF (SEQ ID NO: 336)

TM1(14)
IATVRGSLSLVTVVGNILVML-
SISIYTSLDVMLCTASILNLLISLFV-
LIGSFVAFFIPLTIMVITYFLFNVFFVWIG YVCSSSLG-
INPVIIYTLF (SEQ ID NO: 337)

TM1-(15)
WFIAFLTGILALVTIIGNILVIVSF-
SIYTSLDVMLCTASILNLLISLFVLIGS-
FVAFFIPLTIMVITYFLFNVFFVWIGY VCSSS-
LGINPVIIYTLF (SEQ ID NO: 338)

Non-limiting examples of longer consensus GPR polypeptides for domain V across several or many, such as 1–500, or any value or range therein, G-protein receptors are as follows:

TM3-(165)
NWPALSIVVIIINTIGGNILVIMAF-
FAVWIGYVCSSSLGINPVIIYTLF (SEQ ID NO: 339)

TM3-(166)
NWPALSIWIIINTIGGNILVIMAF-
FACFVLVLTQSSIFSLLAIAIFVLIGS-
FVAFFIPLTIMVITYFLFNVFFVWIGYV CSSS-
LGINPVIIYTLF (SEQ ID NO: 340)

TM3-(167)
NWPALSIWIIINTIGGNILVIMAVM-
VACPVLILTQSSIIALLAIAVSFVAFFI-
PLTIMVITYFLFNVFFVWIGYVCSSS LGINPVI-
IYTLF (SEQ ID NO:341)

TM3-(168)
NWPALSIVVIIINTIGGNILVIMAVLW-
LALDYVASNASVLNLLLISFFFIPLTIM-
VITYFLFNVFFVWIGYVCSSSLGIN PVIIYTLF-
(SEQ ID NO: 342)

TM3-(169)
NWPALSIWIIINTIGGNILVIMAVLYV-
VSNASVMIGLLIISSFVAFFIPLTIMVI-
TYFLFNVFFVWIGYVCSSSLGINPV IIYTLF
(SEQ ID NO: 343)

TM3-(170)
NWPALSIWIIINTIGGNILVIMAVLWI-
AIDYVASNASVLNLLVISFGSFVAFFi-
PLTIMVITYFLFNVFFVWIGYVCSS SLGINPVI-
IYTLF (SEQ ID NO: 344)

TM3-(171)
NWPALSIWIIINTIGGNILVIMAVLFP-
FLQKSSVGITVLNLCALSGSFVAFFIPL-
TIMVITYFLFNVFFVWIGYVCSSS LGINPVI-
IYTLF (SEQ ID NO:345)

TM3-(172)
NWPALSIWIIINTIGGNILVIMAVCI-
TYLQYLGINASSCSITAFTIIGS-
FVAFFIPLTIMVITYFLFNVFFVWIGYVCS
SSLGINPVIIYTLF (SEQ ID NO:346)

TM3-(173)
NWPALSIWIIINTIGGNILVIMAVFHN-
FFPIAKLFASIYSMTAVAGSFVAFFIPL-
TIMVITYFLFNVFFVWGIGYVCSSS LGINPVI-
IYTLF(SEQ ID NO: 347)

TM3-(174)
NWPALSIWIIINTIGGNILVIMAVI-
ASASVSFNLYASVFLLTCLSIGS-
FVAFFIPLTIMVITYFLFNVFFVWIGYVCSS
SLGINPVIIYTLF (SEQ ID NO:348)

As another non-limiting, illustrative example of a GPR polypeptide consensus sequences across each individual or different transmembrane domains of 5-HT receptors may be made, such as for 5-HT, as the following:

5HT consensus(4) KNASALLSVIIINSIGGNVVTAVS (SEQ ID NO:89);

5HT consensus(5) YFLMSLAVTDLWSFVMPVSAL (SEQ ID NO:90);

5HT consensus(6) AITKIAITWAISGVSVPFIPVWG (SEQ ID NO:91); and

5HT consensus(7) LGIIFGTFIIIWLPFFITNLVSPI (SEQ ID NO:92);

Wherein variations and substitutions of amino acids may be made as described herein.

Alternatively, 5-HT consensus sequences may be provided as consensus peptides of the present invention as consensus peptides for individual transmembrane domains, such as 5-HT domains III, V and VII, e.g., as follows:

5-HT consensus (8): IWISLDVLFSTASSIMHLCAISL (SEQ ID NO:93)

3-HT consensus (9): GYTIYSTLVTFYIPSVIMVITYG (SEQ ID NO:94)

5-HT consensus (10): LLNFFNWIGYLNSLINPVIYTLF (SEQ ID NO:95)

This invention is also directed to an antibody which binds an epitope specific for a GPR polypeptide of the present invention and the use of such an antibody to detect the presence of, or measure the quantity or concentration of, the GPR protein in a cell, a cell or tissue extract, a biological fluid, an extract thereof, a solution, or sample, in vitro, in situ, or in vivo.

The term "antibody" is meant to include polyclonal antibodies, monoclonal antibodies (mAbs), chimeric antibodies, anti-idiotypic (anti-Id) antibodies to antibodies specific for GPR polypeptide of the present invention, as well as fragments, consensus polypeptides or chemical derivatives thereof.

Polyclonal antibodies are heterogeneous populations of antibody molecules derived from the sera of animals immunized with an antigen.

A monoclonal antibody contains a substantially homogeneous population of antibodies specific to antigens, which population contains substantially similar epitope binding sites. MAbs may be obtained by methods known to those skilled in the art. See, for example Kohler and Milsrein, *Nature* 256:495–497 (1975); U.S. Pat. No. 4,376,110; Ausubel et al, eds., *Current Protocols in Molecular Biology*, Wiley Interscience, N.Y., (1987, 1992); and Harlow and Lane *Antibodies: A Laboratory Manual* Cold Spring Harbor Laboratory (1988), the contents of which references are incoporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high miters of tabs in vivo or in si tu makes this the presently preferred method of production.

Chimeric antibodies are molecules different portions of which are derived from different animal species, such as those having variable region derived from a murine mAb and a human immunoglobulin constant region, which are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al, *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Cabilly et al., European Patent Application 125023 (published Nov. 14, 1984); Neuberger et al. , *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al. , *J. Immunol.* 137:1066–1074 (1986); Robinson et al., International Patent Publication No. PCT/US86/02269 (published 7 May 1987); Liu et al., *Proc. Natl. Acad. Sci. USA* 84: 3439–3443 (1987); Sun et al. , *Proc. Natl. Acad. Sci. USA* 84:214–218 (1987); Better etal., *Science* 40:1041–1043 (1988); and Harlow and Lane *Antibodies: A Laboratory Manual* Cold Spring Harbor Laboratory (1988)). These references are incorporated entirely herein by reference.

An anti-idiotypic (anti-Id) antibody is an antibody which recognizes unique determinants generally associated with the antigen-binding site of an antibody. An Id antibody carl be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against a GPR polypeptide of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a immunogenic carrier such as keyhole limpet hemocyanin (KLH) or cationized bovine serum albumin and used to immunize additional BALB/c mice. Sera from these mice will contain anti-anti-Id antibodies that have the binding properties of the original mAb specific for a GPR polypeptide epitope.

The anti-IdmAbs thus have their own idiotypic epitopes, or "idiotopes" structurally similar to the epitope being evaluated.

The term "antibody" is also meant to include both intact molecules as well as fragments thereof, such as, fcr example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of a GPR polypeptide according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids. lipids or sugar side chains and have specific three dimentional structural characteristics as well as specific charge characteristics.

An "antigen" is a molecule or a portion of a molecule capable of being bound by an antibody which is additionally capable of inducing an animal to produce antibody capable of binding to an epitope of that antigen. Am antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect a GPR polypeptide in a sample or to detect presence of cells which express a GPR polypeptide of the present invention. This can be accomplished by immunofluorescence techniques employing a fluorescently labeled antibody (see below) coupled with light microscopic, flow cytometric, or fluorometric detection.

The antibodies (of fragments thereof) useful in the present invention may be employed histologically, as in immunofluorescence or immunoelectron microscopy, for in si tu detection of a GPR polypeptide of the present invention. In situ detection may be accomplished by removing a histological specimen from a patient, and providing the a labeled antibody of the present invention to such a specimen. The antibody (or fragment. ) is preferably provided by applying or by overlaying the labeled antibody (or fragment) to a biological sample. Through the use of such a orocedure, it is possible no determine not only the presence of a GPR polypeptide but also its distribution on the examined t. issue. Using the present invention, those of ordinary skill will readily perceive that any of wide variety of histological methods (such as staining procedures) can be modified in order to achieve such in situ detection.

Such assays for a GPR polypepnide of the present invention typically comprise incubating a biological sample, such as a biological fluid, a tissue extract, freshly harvested cells such as lymphocytes or leukocytes, or cells which have been incubated in tissue culture, in the presence of a detectably labeled antibody capable of identifying a GPR polypeptide, and detecting the antibody by any of a number of techniques well-known in the art. See, e.g., Harlow and Lane, supra; Ausubel et al, sunera; and Sambrook et al, The biological sample may be treated with a solid phase support or carrier, such as nitrocellulose, or other solid support or carrier which is capable of immobilizing cells, cell particles or soluble proteins. The support or carrier may then be washed with suitable buffers, followed by treatment with a detectably labeled GPR polypeptide-specific antibody. The solid phase support or carrier may then be washed with the buffer a second time to remove unbound antibody. The amount of bound label on said solid support or carrier may then be detected by known method steps, see, e.g., Harlow, supra; Ausubel, supra; or Sambrook, supra.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrrier configuration may be spherical, as in a bead, or cylindrical, as in the inside surface of a test tube, or the external surface of a rod. Alternatively, the surface may be flat such as a sheet, polymer test strip, etc. Preferred supports or carriers include polystyrene beads. Those skilled in the art will know many other suitable carriers for binding antibody or antigen, or will be able to ascertain the same by use of routine experimentation.

The binding activity of a given lot of anti-GPR polypeptide antibody may be determined according to well known method steps. Those skilled in the art will be able to determine operative and optimal assay conditions for each determination by employing routine experimentation. See, e.g., Harlow, supra.

Other such steps as washing, stirring, shaking, filtering and the like may be added to the assays as is customary or necessary for the particular situation.

One of the ways in which a GPR polypeptide-specific antibody, anti-idiotype antibody or fragment thereof, can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used detectably label. the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose- 6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards. See, Harlow, supra, Ausubel, supra.

Detection may be accomplished using any of a variety of other immunoassays. For example, by radioactivity labeling the antibodies or antibody fragments, it is possible to detect R-PTPase through the use of a radioimmunoassay (RIA). A good description of RIA maybe found in *Laboratory Techniques and Biochemistry in Molecular Biology*, by Work et al., North Holland Publishing Company, N.Y. (1978) with particular reference to the chapter entitled "*An Introduction to Radioimmune Assay and Related Techniques*" by Chard, incorporated entirely by reference herein. The radioactive isotope can be detected by such means as the use of a γ-counter, a scintillation counter or by autoradiography.

It is also possible to label an anti-GPR polypeptide antibody, anti-idiotype antibody or fragment thereof, with a fluorescent compound. When the fluorescently labeled antibody is exposed to light of the proper wave length, its presence can be then be detected due to fluorescence. Among the most commonly used luorescent labelling compounds are fluorescein isothiocyanate, rhodamine, phycoerythrin, phycocyanin, allophycocyanin, o-phthaldehyde and fluorescamine, commercially available, e.g., from Molecular Probes, Inc. (Eugene, Oreg.).

The antibody can also be detectably labeled using fluorescence emitting metals such as $^{152}$EU, or others of the lanthanide series. These metals can be attached to the antibody using such metal chelating groups as diethylenetriamine pentaacetic acid (EDTA).

The antibody also carl be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a hieluminescent compound may be used to label the antibody of the present invention. Bioluminescence is a type of chemiluminescence found in biological systems in which a catalytic protein increases the efficiency of the chemiluminescent reaction. The presence off a bioluminescent protein is determined by detecting the presence of luminescence. Important bioluminescent compounds for purposes of labeling are luciferin, luciferase and aequorin.

An antibody molecule of the present invention may be adapted for utilization in a immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigert, and labeled antibody.

Typical, and preferred, immunometric assays include "forward" assays in which the antibody bound to the solid phase is first contacted with the sample being tested to extract the antigert form the sample by formation of a binary solid phase: antibody-antigen omplex. After a suitable incubation period, the solid support or carrier is washed to remove the residue of the fluid sample, including unreacted arttigon, if any, and then contacted with the solution containing an unknown quantity of labeled antibody (which functions as a "reporter molecule"). After a second incubation period to permit the labeled antibody to complex with the antigert bound to the solid support or carrier through the unlabeled antibody, the solid support or carrier is washed a second time to remove the unreacted labeled antibody.

In another type of "sandwich" assay, which may also be useful with the antigens of the present inventicn, the so-called "simultaneous" and "reverse" assays are used. A "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreated labeled antibody. The determination of labeled antibody associated with a solid support or carrier is then determined as in the "simultaneous" and "forward" assays. See, e.g., for the above-mentioned immunological techniques, Harlow, supra; Ausubel et al, supa; and Sambrook et al, supra. GPR polypeptides of the present invention can be made by chemical synthesis or by recombinant methods, wherein chemical synthesis is preferred.
Synthetic production of transmembrane proteins of the present invention GPR polypeptides, variants and chemical derivatives thereof can be synthesized according to known method steps, including portions of known GPR transmembrane domains, consensus peptides thereof, conservative substitution derivative thereof or functional derivatives thereof.

Chemical polypeptide synthesis is a rapidly evolving area in the art, and methods of solid phase polypeptide synthesis are well-described in the following references, hereby entirely incorporated by reference: (Merrifield, B., *J. Amer. Chem. Soc.* 5:2149–2154 (1963); Merrifield, B., Science 232:341–347 (1986); Wade, J. D. et al., *Biopolymers* 25:S21–S-37 (1986); Fields, G. B., *Int. J. Polypeptide Prot. Res.* 35:161 (1990); MilliGen Report Nos. 2 and 2a, Millipore Corporation, Bedford, Mass., 1987) Ausubel et al, supra, and Sambrook et al, supra.

In general, as is known in the art, such methods involve blocking or protecting reactive functional groues, such as free amino, carboxyl and thio groups. After poiypeptide bond formation, the protective groups are removed ior de-protected). Thus, the addition of each amino acid residue requires several reaction steps lot protecting and deprotecting. Current methods utilize solid phase synthesis, wherein the C-terminal amino acid is covalently linked to an insoluble resin particle large enough to be separated from the fluid phase by filtration. Thus, reactants are removed by washing the resin particles with appropriate solvents using an automated programmed machine. The completed polypeptide chain is cleaved from the resin by a reaction which does not affect polypeptide bonds.

In the more classical method, known as the "tBoc method," the amino group of the amino acid being added to the resin-bound C-terminal amino acid is blocked with tert-butyloxycarbonyl chloride (tBoc). This protected amino acid is reacted with the bound amino acid in the presence of the condensing agent dicyclohexylcarbodiimide, allowing its carboxyl group to form a polypeptide bond the free amino group of the bound amino acid. The amino-blocking group is then removed by acidification with trifluoroacetic acid (TFA); it subsequently decomposes into gaseous carbon dioxide and isobutylene. These steps are repeated cyclically for each additional amino acid residue. A more vigorous treatment with hydrogen fluoride (HF) or trifluoromethanesulfonyl derivatives is common at the end of the synthesis to cleave the benzyl-derived side chain protecting groups and the polypeptide-resin bond.

More recently, the preferred "Fmoc" technique has been introduced as an alternative synthetic approach, offering milder reaction conditions, simpler activation procedures and compatibility with continuous flow techniques. This method was used, e.g., to prepare the peptide sequences disclosed in the present application. Here, the ∝-amino group is protected by the base labile 9-fluorenylmethoxycarbonyl (Fmoc) group. The benzyl side chain protecting groups are replaced by the more acid labile t-butyl derivatives. Repetitive acid treatments are replaced by deprotection with mild base solutions, e.g., 20% piperidine in dimethylformamide (DMF), and the final HF cleavage treatment is eliminated. A TFA solution is used instead to cleave side chain protecting groups and the polypeptide resin linkage simultaneously.

At least three different polypeptide-resin linkage agents can be used: substituted benzyl alcohol derivatives that can be cleaved with 95% TFA to produce a polypeptide acid, methanolic ammonia to produce a polypeptide amide, or 1% TFA to produce a protected polypeptide which can then be used in fragment condensation procedures, as described by Atherton, E. etal., *J. Chem. Sec. Perkin Trans.* 1:538–546 (1981) and Sheppard, R. C. et al., *Int. J. Polypeptide Prot. Res.* 20:451–454 (1982). Furthermore, highly reactive Fmoc amine acids are available as pentafluorophenyl esters or dihydro-oxobenzotriazine esters derivatives, saving the step of activation used in the tBoc method.

Sequences available to use as a basis for polypeptide synthesis can be based on published sequences of G-protein coupled receptors, ligands and/or effectors, wherein the transmembrane or functional domains correspond to sections of hydrophobic or other amine acids of 5 to 100 amine acids, such as 5–10, 10–15, 15–25, 20–25, 23–27, 25–30, 28–35, 20–40, 10–40, 20–30, 30–40, 40–50, 10–80, 20–60 or 25–40 amine acids in length. Recombinant production of GPR polypeptides can be accomplished according to known method steps. Standard reference works setting forth the general principles of recombinant DNA technology include Watson, J. D. et al., *Molecular Biology of the Gone,* Volumes I and II, The Benjamin/Cummings Publishing Company, Inc., publisher, Menlo Park, Calif. (1987); Darnell, J. E. et al., *Molecular Cell Biology,* Scientific American Books, Inc., publisher, New York, N.Y. (1986); Lewin, B. M., Genes III, John Wiley & Sons, publishers, New York, N.Y. (1989); Old, R. W., et al., *Principles of Gene Manipulation: An Introduction to Genetic Engineering,* 2d edition, University of California Press, publisher, Berkeley, Calif. (1981); Ausubel et al, eds. , *Current Protocols in Molecular Biology,* Wiley Interscience, publisher, New York, N.Y. (1987, 1992); and Sambrook et al., *Molecular Cloning: A Laboratory Manual,* Second Edition, Cold Spring Harbor Laboratory, publisher, Cold Spring Harbor, N.Y. (1989), the entire contents of which references are herein incorporated by reference.

A nucleic acid sequence ellcoding a GPR polypeptide of the present invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Ausubel et al, supra, and are well known in the art.

A nucleic acid molecule, such as DNA is said to be capable of expressing" a polypepzide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as GPR polypeptides in recoverable amounts. The precise nature of the regulatory regions needed for gene expression may vary from organism to organism, as is well known in the analogous art. See, e.g., Sambrook, supra and Ausubel supra.

The present invention accordingly encompasses the expression of a GPR polypeptide, in either prokaryotic or eukaryotic cells, although eukaryotic expression is preferred.

Preferred hosts are bacterial or eukaryotic hosts including bacteria, yeast, insects, fungi, bird and mammalian cells either in vivo, or in situ, or host cells of mammalian, insect, bird or yeast origin. It is preferred that the mammalian cell or tissue is of human, primate, hamster, rabbit, rodent, cow, pig, sheep, horse, goat, dog or cat origin, but any other mammalian cell may be used.

Further, by use of, for example, the yeast ubiquitin hydrolase system, in vivo synthesis of ubiquitin-transmembrane polypeptide fusion proteins may be accomplished. The fusion proteins so produced may be processed in vivo or purified and processed in vitro, allowing synthesis of a GPR polypeptide of the present invention with a specified amino terminus sequence. Moreover, problems associated with retention of initiation codon-derived methionine residues in direct yeast (or bacterial) expression may be avoided. Sabin etal., *Bio/Technol.* 7(7): 705–709 (1989); Miller et al., *Bio/Technol.* 7(7): 698–704 (1989).

Any of a series of yeast gene eggression systems incorporating promoter and termination elements from the actively expressed genes coding for glycolytic enzymes produced in large quantities when yeast are grown in mediums rich in glucose can be utilized to obtain GPR polypeptides of the present invention. Known glycolytic genes can also provide very efficient transcriptional control signals. for example, the promoter and terminator signals of the phosphoglycerate kinase gene can be utilized.

Production of GPR polypeptides or functional derivatives thereof in insects can be achieved, for example, by infecting the insect host with a baculovirus engineered to express transmembrane polypeptide by methods known to those of skill. See Ausubel etal, eds. *Current Protocols in Molecular Biology,* Wiley Interscience, §§16.8–16.11 (1987, 1992).

In a preferred embodiment, the introduced nucleotide sequence will be incorporated into a plasmid or vital vector capable of autonomous replication in the recipient host. Any of a wide variety of vectors may be employed for this purpose. See, e.g., Ausubel et al, supra, §§ 1.5, 1.10, 7.1, 7.3, 8.1, 9.6, 9.7, 13.4, 16.2, 16.6, and 16.8–16.11. Pactors of importance in selecting a particular plasmid or vital vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

[Preferred prokaryotic vectors known in the art include plasmids such as those capable of replication in *E. coli* (such as, for example, pBR322, ColE1, pSC101, pACYC 184, πVX). Such plasmids are, for example, disclosed by Maniatis, T., et al. *(Molecular Cloning, A Laboratory Manual,* Second Edition, Cold Spring Harbor Press, Cold Spring Harbor, N.Y. (1989); Ausubel et al, eds., *Current Protocols in Molecular Biology,* Wiley Interscience, New York, N.Y. (1987, 1992)). *Bacillus* plasmids include pC194, pC221, pT127, etc. Such plasmids are disclosed by Gryczan, T. (In: *The Molecular Biology of the Bacilli,* Academic Press, N.Y. (1982), pp. 307–329). Suitable *Streptomyces* plasmids include pIJ101 (Kendall, K. J., et al., *J. Bacteriol.* 169:4177–4183 (1987)) , and streptomyces bacteriophages such as φC31 (Chater, K. F. , et al. , In: *Sixth International Symposium on Actinomycetales Biology*, Akademiai Kaido, Budapest, Hungary (1986), pp. 45–54). Pseudomonas plasmids are reviewed by John, J. F., et al. (Rev. Infect. Dis. 8:693–704 (1986)), and Izaki, K. (*Jpn. J. Bacteriol.* 33:729–742 (1978); and Ausubel et al, supra).

The expressed protein may be isolated and purified in accordance with conventional conditions, such as extraction, precipitamion, chromatography, affinity chromatography, electrophoresis, or the like. Por example, the cells may be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation. Alternatively, thetransmembrane polypeptide or functional derivative thereof may be isolated by the use of anti-transmembrane polypeptide antibodies. Such antibodies may be obtained by well-known methods, some of which are mentioned below. These antibodies may be immobilized on cellulose, agarose, hollow fibers, or cellulose filters by covalent chemical derivatives by methods well known to those skilled in the art.

As discussed herein, GPR poiypeptides of the present invention may be further modified for purposes of drug design, such is for example to reduce immunogenicity, to prevent solubility and/or enhance delivery, or to prevent clearance or degradation.

Appropriate modification of the primary amino acid sequence of GPR polypeptides of the present invention, obtained by mutagenesis or utilizing fragments of other related forms of G-protein transmembrane proteins, as described herein, will allow the creation of molecules which bind G-protein coupled receptors with higher affinity than that exhibited by naturally occurring transmembrane domains. Small polypeptides that are provided according to the present invention which polypeptides maintain G-protein coupled receptor binding inhibition activity, are expected to have two advantages over larger polypeptides. These advantages include (1) greater stability and diffusibility, and (2) less immunogenicity.

Since polypeptides according to the present invention are generally small (10–40, 20–30, 15–25, 30–45 amino acids), cell or tissue sources of G-protein coupled receptors are not required to practice the present invention, since known polypeptide syntheses steps can be used without undue experimentation to provide GPR polypeptides or sequences substantially corresponding thereto.

Pharmaceutical Preparations

Preparations of GPR polypeptides for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

By the term "protection" from infection or disease as used herein is intended "prevention," "suppression" or "treatment." "Prevention" involves administration of a GPR polypeptide, polypeptide derivative, or anti-idiotypic antibody prior to the induction of the disease.

"Suppression" involves administration of the composition prior to the clinical appearance of the disease.

"Treatment" involves administration of the protective composition after the appearance of the disease. It will be understood that in human and veterinary medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis."

At least one GPR polypeptide, antibody or anti-idiotypic antibody of the present invention may be administered by any means that achieve their intended purpose, for example, to treat GPR related pathologies, such as psychotic disorders, including schizophrenia, by inhibition of binding of Dopamine $D_2$ receptors using a GPR polypeptide corresponding to a fragment or consensus portion of a dopamine $D_2$ transmentrane domain; in the form of a pharmaceutical composition.

For example, administration of such a composition may be by various parenteral routes such as subcutaneous, intravenous, intradermal, intramuscular, intraperitoneal, intranasal, transdermal, or buccal routes. Alternatively, or concurrently, ndministration may be by the oral route. Parenteral administration can be by bolus injection or by gradual perfusion over time.

A preferred mode of using a GPR pharmaceutical composition of the present invention is by intravenous or parenteral application.

A typical regimen for preventing, suppressing, or treating G-protein coupled receptor pathologies, such as dopamine receptor related schizophrenia, comprises administration of an effective amount of a GPR polypeptide, consensus sequence, or chemical derivative thereof, administered over a period of one or several days, up to and including between one week and about 24 months.

It is understood that the dosage of a GPR polypeptide of the present invention administered in vivo or in vitro will be dependent upon the age, sex, health, and weight of the recipient, kind of concurrent treatment, if any, frequency of treatment, and the nature of the effect desired. The ranges of effective doses provided below are not intended to limit the inventors and represent preferred dose ranges. However, the most preferred dosage will be tailored to the individual subject, as is understood and determinable by one of skill in the art, without undue experimentation.

The total dose required for each treatment may be administered by multiple doses or in a single dose. a GPR polypeptide or functional a chemical derivative thereof may be administered alone or in conjunction with other therapeutics directed to GPR related pathologies, such as a the dopamine receptor related pathology as a non limiting example, or directed to other symptoms of the disease.

Effective amounts of the a GPR polypeptide or composition, which may also include a functional derivative thereof, or a GPR anti-idiotypic antibody, are from about 0.01 μg to about 100 mg/kg body weight, and preferably from about 10 μg to about 50 mg/kg body weight, such 0.05, 0.07, 0.09, 0.1, 0.5, 0.7, 0.9, 1, 2, 5, 10, 20, 25, 30, 40, 45, or 50 mg/kg.

Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

Pharmaceutical compositions comprising at least one GPR polypeptide of the present invention may include all compositions wherein the GPR polypeptide is contained in an amount effective to achieve its intended purposa. In addition to the GPR polypeptide, a pharmaceutical composition may contain suitable pharmaceutically acceptable carriers, such as comprising excipients and auxiliaries which facilitate processing of the active compounds into preparations which can be used pharmaceutically.

Pharmaceutical compositions include suitable solutions for administration intravenously, subcutaneously, dermally, orally, mucosally, rectally or may by injection or orally, and contain from about 0.01 to 99 percent, preferably from about 20 to 75 percent of active component (i.e. the antibody) together with the excipient. Pharmaceutical compositions for oral administration include tablets and capsules. Compositions which can be administered rectally include suppositories.

EXAMPLE 1

Synthesis of a G-Protein Transmembrane Polypeptide and Consensus Polypeptide

The polypeptides in FIGS. 1–5 were synthesized using the following procedure and include the following characteristics.

Peptide I (SEQ ID NO:I), as shown in FIG. 1, was used as a control for hydrophobic interaction alone as the mechanism of binding and was run in parallel with the test polypeptides described below. Polypeptide II (SEQ ID NO: 2), as shown in FIG. 2, represents a membrane- spanning fragment of transmembrane segment III in the dopamine $D_2$ receptor. This particular fragment was chosen since it has been implicated in the β-adrenergic receptor as having many res idues which are involved in ligand binding interaction. Polypeptide III (SEQ ID NO:3), as shown in FIG. 3, represents the consensus polypeptide which was developed as a model for the dopamine $D_2$ system and polypeptide IV (SEQ ID NO:4), as shown in FIG. 4, is a control for length dependence to show how critical the polypeptide length is in binding studies. Polypeptide V (SEQ ID NO:5), as shown in FIG. 5, is a consensus sequence of transmembrane domains of dopamine receptors $D_1$ and $D_2$.

The above polypeptides I-V (SEQ ID NOS:1–5), as shown in FIGS. 1–5, respectively, were synthesized using solid phase synthesis on a Milligen 9600 polypeptide synthesizer using Fmoc amino acids (provided by Milligen/Biosearch) and PAL polystyrene resin (Milligen/Biosearch). Coupling times were 1 hour and the polypeptides were cleaved by trifluoroacetic acid/phenol/thioanisole/ethanedithiol (82.5:5:5:5:2.5) at room temperature for 2 hours. The filtrate was collected and washed with 2 mL of trifluoroacetic acid (TFA) and 1 mL of dichloromethane (DCM). The filtrate was reduced in vacuo to 2 ml in volume and the resulting polypeptide was precipitated out by the addit ion of water. The polypeptides were then dissolved in 1,1,1,3,3,3-hexafluoro-2-propanol [ (HFIP) Eastman]; lyophilized; and stored at −20° C. until purification. Polypeptides I-V (SEQ ID NOS:1–5), were purified using reverse-phase HPLC using a preparative Vydac C4 column (Vydac) at 60° C. at a flow rate of 6.0 mL/min with a linear gradient of 0–100% B in a 60 min period at a UV detection wavelength of 275 mm.

Due to the highly hydrophobic nature of these polypeptides, methanol was used with 0.1% (W/V) TFA and 0.5% (W/V) HFIP as solvent A and 2-propanol with 0.1% TPA as solvent B, in order to purify these polypeptides. Further purification was performed with an analytical C4 column (Vydac) with an isocratic qradient of 40% B at a flow rate of 1 ml/min. Identity of the polypeptides was confirmed by Fast-atom bombardment mass spectrometry and electrospray mass spectrometry and amino acid analysis. Stock solutions of polypeptides were made in HFIP and stored at −20° −80° C.

Circular Dichroism (CD). Spectra were recorded on an Aviv model 60 DS circular dichroism spectrophotometer at room temperature with a 1 cm by 1 mm cell. The amplitude of the CD signal was calibrated using 10.1% (w/v) solution of d (+)-camphorsulfonic acid (Aldrich) and the wavelength of the CD signal was set using standard absorbance peaks of benzene vapor. Polypeptide ccncentrations were determined in a Cary 210 UV spectrophotomer wwith the absorbance measured at 280 nm. Helical content was estimated using CD signal intensity according to the method of Chen. et al *Biochem.* 13:3350– 13359 (1974). This calculation compares the experimental ellipticity at. 222 nm ( [θ] 222) ( [θ]) to a theoretical [θ]222. The theoretical [θ] 222 is empirically adjusted to account for differences in polypeptide length and is based on experimental CD data from a series of proteins with known crystal structures. Since both the curve shape and magnitude are important in analysis of a CD spectrum for secondary structure contributions, we also considered qualitatively the contributions to the spectral shapes from different secondary structures using reference curves for poly (L-lysine).

FIG. 6 shows a CD spectrum of the consensus polypeptide III (SEQ ID NO: 3) demonstrating that the polypeptide III is only partially helical in a solvent system in which most membrane polypeptides are strongly helical.

Preparation of Small Unilamellar Visicles. Polypeptides were incorporated into DMPC vesicles at lipid:peptide ratio of 147:1 in the followinq manner: polypept ide in HFIP was mixed with dimyrystyroyl-phosphatidylcholine (synthetic) (DMPC) in dry chloroform and dried to a film with a stream of dry nitrogen at 0° C. This residue was then dried further overnight under a vacuum ($1\times10^{-2}$ torr). The residue was then hydrated in 100 mL NaCl and sonicated for a 30-min period under nitrogen at 0° C. The suspension was sedimented for a 30-min at 100,000 q (4° C.) to remove any residual titanium particles and large unilamellar vesicles The supernatant was removed and sedimented once more at 159,000 g for a 45 min period at 4° C. The supernatant in the lower portion was used immediately. This basic procedure has been shown to reliably produce small unilamellar vesicles.

Radioligand Bining Assays. A 0.50 mL volume of 1.00 nM [$^3$H]-spiperone (New England specific activity 21.4 Ci/mol) was added to assay tubes which contained 0.5 mL lipid/peptide supernatant, 0.5 mL Tris buffer pH 7.4 and 0.5 mL of cold drug for a final volume of 2.0 mL. Nonspecific binding was defined in the presence of 1 uM of (+) butaclamol or 1 uM spiperone. Appropriate controls for lipid vesicles containing no polypeptide were also run. Assay tubes were prepared in triplicate and the mixture was incubated for 1 h at 25° C. Incubation was terminated by filtration through filters presoaked in 0.1% polyethyleneimine (w/v, Siqma) for at least 1 h prior to use.

Filters were then washed with 6.0 mL of cold 50 mM Tris-HCl buffer, pH 7.40. For detection of radioactivity, filters were placed in 2.0 mL of scintillation fluid (Scintiverse) and incubated for 24 h. The activity of the tritium was determined in a Beckman LS 7500 liquid scintillation counter. Specific binding of [$^3$H]-spiperone was defined as the difference in binding in the presence and absence of unlabeled (+) butaclamol.

Figure 7:
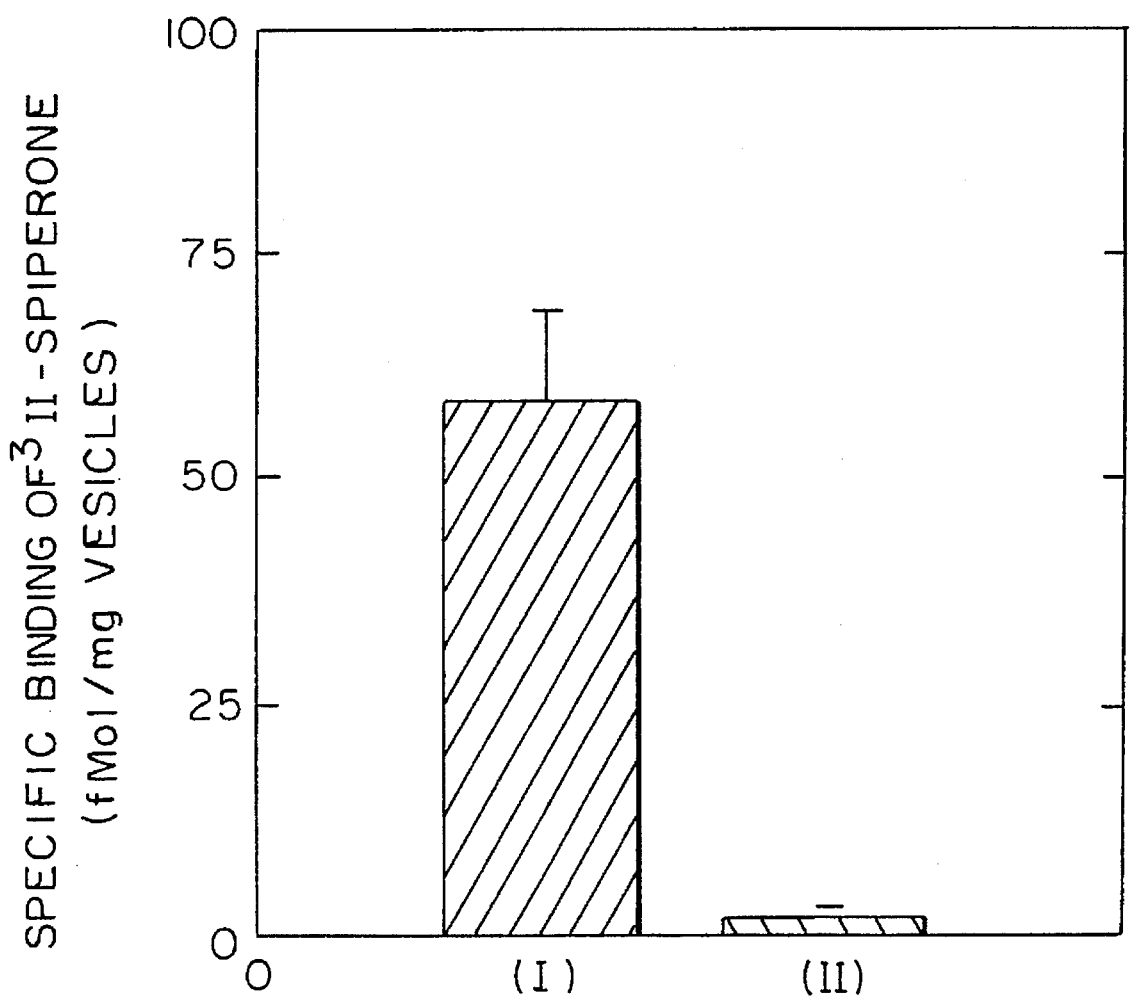
FIG. 7 is a graphical representation of radioligand binding assay data comparing control polypeptide II (SEQ ID NO:1) of FIG. 1, labeled as "II" and consensus polypeptide I (SEQ ID NO: 3 of FIG. 3, labeled as "I".

FIG. 7 shows results of radioligand binding assays comparing polypeptide I (SEQ ID NO:1) as a control unit polypeptide iII (SEQ ID NO:3) according to the present invention. Polypeptide III (SEQ ID NO:3) is shown to unexpectedly provide receptor-like functional binding, as demonstrated by binding to the neuroleptic agent, spiperone, into a stereoselective, concentration-dependent manner.

It has also been demonstrated that as little as 0.1% of a GPR polypeptide according to the present invention is able to form a receptor-like functional binding site. Thus, a GPR polypeptide of the present invention is unexpectedly shown to act both as GPR ligands and GPR binding sites.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entire y incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptations and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

---

What is claimed is:

1. A polypeptide having the amino acid sequence of SEQ ID NO:2.

SEQUENCE LISTING ( 1 ) GENERAL INFORMATION:

( i i i ) NUMBER OF SEQUENCES: 348

( 2 ) INFORMATION FOR SEQ ID NO:1:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Leu  Ser  Leu  Leu  Leu  Ser  Leu  Leu  Ser  Leu  Leu  Leu  Ser  Leu  Leu  Ser
1                   5                        10                       15

Leu  Leu  Leu  Ser  Leu  Tyr  Tyr  Tyr
               20
```

( 2 ) INFORMATION FOR SEQ ID NO:2:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Asp  Asp  Ile  Phe  Val  Thr  Leu  Asp  Val  Leu  Phe  Ser  Thr  Ala  Ser  Ile
1                   5                        10                       15

Leu  Asn  Leu  Ser  Ala  Ile  Ser  Leu  Lys  Lys  Lys
               20                   25
```

( 2 ) INFORMATION FOR SEQ ID NO:3:

( i ) SEQUENCE CHARACTERISTICS:
        ( A ) LENGTH: 26 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:3:

| Asp | Tyr | Ala | Ile | Phe | Val | Leu | Tyr | Ala | Ser | Ala | Trp | Leu | Ser | Phe | Asn |
|---|---|---|---|---|---|---|---|---|---|---|---|---|---|---|---|
| 1 | | | | 5 | | | | | 10 | | | | | 15 | |

| Cys | Pro | Phe | Ile | Val | Thr | Leu | Asn | Ile | Lys |
|---|---|---|---|---|---|---|---|---|---|
| | | | 20 | | | | | 25 | |

(2) INFORMATION FOR SEQ ID NO:4:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

| Lys | Ala | Val | Val | Tyr | Ser | Ser | Ile | Val | Ser | Phe | Tyr | Val | Phe | Ile | Asp |
|---|---|---|---|---|---|---|---|---|---|---|---|---|---|---|---|
| 1 | | | | 5 | | | | | 10 | | | | | 15 | |

(2) INFORMATION FOR SEQ ID NO:5:

(i) SEQUENCE CHARACTERISTICS:
(A) LENGTH: 27 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

| Asp | Cys | Asp | Val | Phe | Val | Phe | Val | Asp | Ile | Met | Leu | Cys | Thr | Ala | Ser |
|---|---|---|---|---|---|---|---|---|---|---|---|---|---|---|---|
| 1 | | | | 5 | | | | | 10 | | | | | 15 | |

| Ile | Phe | Asn | Leu | Cys | Ala | Ile | Ser | Val | Gly | Lys |
|---|---|---|---|---|---|---|---|---|---|---|
| | | | 20 | | | | 25 | | | |

(2) INFORMATION FOR SEQ ID NO:6:

(i) SEQUENCE CHARACTERISTICS:
(A) LENGTH: 317 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:6:

| Ser | Leu | Val | Leu | Leu | Leu | Phe | Ala | Asp | Phe | Ser | Ser | Met | Leu | Gly | Cys |
|---|---|---|---|---|---|---|---|---|---|---|---|---|---|---|---|
| 1 | | | | 5 | | | | | 10 | | | | | 15 | |

| Met | Ala | Val | Leu | Ile | Gly | Phe | Trp | Arg | Leu | Lys | Leu | Leu | Arg | Asn | His |
|---|---|---|---|---|---|---|---|---|---|---|---|---|---|---|---|
| | | | 20 | | | | 25 | | | | | 30 | | | |

| Val | Thr | Lys | Val | Ile | Ala | Cys | Phe | Cys | Ala | Thr | Ser | Phe | Cys | Lys | Asp |
|---|---|---|---|---|---|---|---|---|---|---|---|---|---|---|---|
| | | 35 | | | | | 40 | | | | | 45 | | | |

| Phe | Pro | Ser | Thr | Ile | Leu | Thr | Leu | Thr | Asn | Thr | Ala | Val | Asn | Gly | Gly |
|---|---|---|---|---|---|---|---|---|---|---|---|---|---|---|---|
| | 50 | | | | | 55 | | | | | 60 | | | | |

| Phe | Pro | Cys | Tyr | Leu | Tyr | Ala | Ile | Val | Ile | Thr | Tyr | Gly | Ser | Phe | Ala |
|---|---|---|---|---|---|---|---|---|---|---|---|---|---|---|---|
| 65 | | | | | 70 | | | | | 75 | | | | | 80 |

| Cys | Trp | Leu | Trp | Thr | Leu | Ile | Cys | Leu | Ala | Ile | Ser | Ile | Tyr | Met | Leu |
|---|---|---|---|---|---|---|---|---|---|---|---|---|---|---|---|
| | | | | 85 | | | | | 90 | | | | | 95 | |

| Ile | Val | Lys | Arg | Glu | Pro | Glu | Pro | Glu | Leu | Phe | Glu | Lys | Tyr | Tyr | Tyr |

100                          105                           110

Leu   Leu   Cys   Trp   Gly   Leu   Pro   Leu   Ile   Ser   Thr   Ile   Gly   Leu   Lys   Asn
                          115                         120                         125

Thr   Val   Gln   Phe   Val   Gly   Asn   Trp   Cys   Trp   Ile   Gly   Val   Ser   Phe   Thr
                    130                         135                         140

Gly   Tyr   Arg   Phe   Gly   Leu   Phe   Tyr   Pro   Phe   Leu   Phe   Ile   Trp   Ala   Ile
        145                           150                         155                         160

Ser   Ala   Val   Leu   Val   Gly   Leu   Thr   Ser   Arg   Tyr   Thr   Tyr   Trp   Ile   His
                                165                         170                         175

Asn   Gly   Val   Ser   Asp   Asn   Lys   Glu   Lys   His   Leu   Thr   Tyr   Gln   Phe   Lys
                          180                         185                         190

Leu   Ile   Asn   Tyr   Ile   Ile   Val   Phe   Leu   Val   Cys   Trp   Val   Phe   Ala   Val
                    195                         200                         205

Val   Asn   Arg   Ile   Val   Asn   Gly   Leu   Asn   Trp   Pro   Pro   Ala   Leu   Asn   Ile
                    210                         215                         220

Leu   His   Thr   Tyr   Leu   Ser   Val   Ser   His   Gly   Phe   Trp   Ala   Ser   Val   Thr
        225                           230                         235                         240

Phe   Ile   Tyr   Asn   Asn   Pro   Leu   Met   Trp   Arg   Tyr   Phe   Gly   Ala   Lys   Ile
                                245                         250                         255

Leu   Thr   Val   Phe   Thr   Phe   Phe   Gly   Tyr   Phe   Thr   Asp   Val   Gln   Lys   Lys
                          260                         265                         270

Leu   Glu   Lys   Asn   Leu   Ser   Pro   Tyr   Ser   Ser   Ser   Arg   Gly   Thr   Ser   Gly
                    275                         280                         285

Lys   Thr   Met   Leu   Gly   His   Pro   Thr   Gly   Asp   Asp   Val   Gln   Cys   Ser   Ser
                    290                         295                         300

Asp   Leu   Gln   Cys   Ser   Leu   Glu   Arg   His   Pro   Asn   Met   Val
        305                           310                         315

( 2 ) INFORMATION FOR SEQ ID NO:7:

( i ) SEQUENCE CHARACTERISTICS:
        ( A ) LENGTH: 349 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Val   Tyr   Ile   Thr   Val   Glu   Leu   Ala   Ile   Ala   Val   Leu   Ala   Thr   Leu   Gly
        1                 5                           10                          15

Asn   Val   Leu   Val   Cys   Trp   Ala   Val   Trp   Leu   Asn   Ser   Asn   Leu   Asn   Val
                          20                          25                          30

Thr   Asn   Tyr   Phe   Val   Val   Ser   Leu   Ala   Ala   Ala   Asp   Ile   Ala   Val   Gly
                    35                          40                          45

Val   Ile   Ala   Ile   Pro   Phe   Ala   Ile   Thr   Ile   Ser   Thr   Gly   Phe   Cys   Ala
                    50                          55                          60

Ala   Cys   His   Asn   Cys   Leu   Phe   Phe   Ala   Cys   Phe   Val   Leu   Val   Leu   Thr
        65                          70                          75                          80

Gln   Ser   Ser   Ile   Phe   Ser   Leu   Leu   Ala   Ile   Ala   Ile   Asp   Arg   Tyr   Ile
                                85                          90                          95

Ala   Ile   Arg   Ile   Pro   Leu   Arg   Tyr   Asn   Gly   Leu   Val   Thr   Gly   Thr   Arg
                          100                         105                         110

Ala   Lys   Gly   Ile   Ile   Ala   Val   Cys   Trp   Val   Leu   Ser   Phe   Ala   Ile   Gly
                    115                         120                         125

Leu   Thr   Pro   Met   Leu   Gly   Trp   Asn   Asn   Cys   Ser   Gln   Pro   Lys   Glu   Gly
                    130                         135                         140

```
Arg  Asn  Tyr  Ser  Gln  Gly  Cys  Gly  Glu  Gly  Gln  Val  Ala  Cys  Leu  Phe
145                      150                      155                      160

Glu  Asp  Val  Val  Pro  Met  Asn  Tyr  Met  Val  Tyr  Tyr  Asn  Phe  Phe  Ala
                    165                      170                      175

Phe  Val  Leu  Val  Pro  Leu  Leu  Leu  Val  Tyr  Leu  Arg  Ile  Phe  Leu  Ala
               180                      185                      190

Ala  Arg  Arg  Gln  Leu  Lys  Gln  Met  Glu  Ser  Gln  Pro  Leu  Pro  Gly  Glu
          195                      200                      205

Arg  Ala  Arg  Ser  Thr  Leu  Gln  Lys  Glu  Val  His  Ala  Ala  Lys  Ser  Ala
     210                      215                      220

Ile  Ile  Val  Gly  Leu  Phe  Ala  Leu  Cys  Trp  Leu  Pro  Leu  His  Ile  Ile
225                      230                      235                      240

Asn  Cys  Phe  Thr  Phe  Phe  Cys  Pro  Glu  Cys  Ser  His  Ala  Pro  Leu  Trp
                    245                      250                      255

Leu  Met  Tyr  Leu  Thr  Ile  Val  Leu  Ser  His  Thr  Asn  Ser  Trp  Asn  Pro
               260                      265                      270

Phe  Ile  Tyr  Ala  Tyr  Arg  Ile  Arg  Glu  Phe  Arg  Gln  Thr  Phe  Arg  Lys
          275                      280                      285

Ile  Ile  Arg  Ser  His  Val  Leu  Arg  Arg  Arg  Glu  Pro  Phe  Lys  Ala  Gly
     290                      295                      300

Gly  Thr  Ser  Ala  Arg  Ala  Leu  Ala  Ala  His  Gly  Ser  Asp  Gly  Glu  Gln
305                      310                      315                      320

Ile  Ser  Leu  Arg  Leu  Asn  Gly  His  Pro  Pro  Gly  Val  Trp  Ala  Asn  Gly
                    325                      330                      335

Ser  Ala  Pro  His  Pro  Glu  Arg  Arg  Pro  Asn  Gly  Tyr  Thr
               340                      345
```

( 2 ) INFORMATION FOR SEQ ID NO:8:

( i ) SEQUENCE CHARACTERISTICS:
( A ) LENGTH: 314 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

```
Ala  Tyr  Ile  Gly  Ile  Glu  Val  Leu  Ile  Ala  Leu  Val  Ser  Val  Pro  Gly
1                   5                        10                       15

Trp  Leu  Val  Ile  Trp  Ala  Val  Lys  Val  Asn  Gln  Ala  Leu  Arg  Asp  Ala
               20                       25                       30

Thr  Phe  Cys  Phe  Ile  Val  Ser  Ile  Ala  Val  Ala  Asp  Val  Ala  Val  Gly
          35                       40                       45

Ala  Leu  Val  Ile  Pro  Leu  Ala  Ile  Leu  Ile  Asn  Ile  Gly  Pro  Arg  Thr
     50                       55                       60

Tyr  Phe  His  Thr  Cys  Leu  Met  Val  Ala  Cys  Pro  Val  Leu  Ile  Leu  Thr
65                       70                       75                       80

Gln  Ser  Ser  Ile  Ile  Ala  Leu  Leu  Ala  Ile  Ala  Val  Asp  Arg  Tyr  Leu
                    85                       90                       95

Arg  Val  Lys  Ile  Pro  Leu  Arg  Tyr  Lys  Thr  Val  Val  Thr  Pro  Arg  Arg
               100                      105                      110

Ala  Ala  Val  Ala  Ile  Ala  Gly  Cys  Trp  Ile  Leu  Ser  Phe  Val  Val  Gly
          115                      120                      125

Leu  Thr  Pro  Leu  Phe  Gly  Trp  Asn  Arg  Leu  Gly  Glu  Ala  Gln  Arg  Ala
     130                      135                      140
```

```
Trp  Ala  Ala  Asn  Gly  Ser  Gly  Gly  Glu  Pro  Val  Ile  Lys  Cys  Glu  Phe
145                      150                      155                      160

Glu  Lys  Val  Ile  Ser  Met  Glu  Tyr  Met  Val  Tyr  Phe  Asn  Phe  Phe  Val
                    165                      170                      175

Trp  Val  Leu  Pro  Pro  Leu  Leu  Leu  Met  Val  Leu  Ile  Tyr  Leu  Glu  Val
               180                      185                      190

Phe  Tyr  Leu  Ile  Arg  Arg  Gln  Leu  Gly  Lys  Lys  Val  Ser  Ala  Ser  Ser
          195                      200                      205

Gly  Asp  Pro  Gln  Lys  Tyr  Tyr  Gly  Lys  Glu  Leu  Lys  Ile  Ala  Lys  Ser
     210                      215                      220

Leu  Ala  Leu  Ile  Leu  Phe  Leu  Phe  Ala  Leu  Ser  Trp  Leu  Pro  Leu  His
225                      230                      235                      240

Ile  Ile  Asn  Cys  Ile  Thr  Leu  Phe  Cys  Pro  Ser  Cys  Arg  Lys  Pro  Ser
                    245                      250                      255

Ile  Leu  Met  Tyr  Ile  Ala  Ile  Phe  Leu  Thr  His  Gly  Asn  Ser  Ala  Met
               260                      265                      270

Pro  Ile  Val  Tyr  Ala  Phe  Arg  Ile  Gln  Lys  Phe  Arg  Val  Thr  Phe  Leu
          275                      280                      285

Lys  Ile  Trp  Asn  Asp  His  Phe  Arg  Cys  Gln  Pro  Thr  Pro  Pro  Val  Asp
     290                      295                      300

Glu  Asp  Pro  Pro  Glu  Glu  Ala  Pro  His  Asp
305                      310
```

(2) INFORMATION FOR SEQ ID NO:9:

(i) SEQUENCE CHARACTERISTICS:
        (A) LENGTH: 342 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Val  Ala  Phe  Ile  Gly  Ile  Thr  Thr  Gly  Leu  Leu  Ser  Ile  Ala  Thr  Val
1                   5                        10                       15

Thr  Gly  Asn  Leu  Leu  Val  Leu  Ile  Ser  Phe  Lys  Val  Asn  Thr  Glu  Leu
               20                       25                       30

Lys  Thr  Val  Asn  Asn  Tyr  Phe  Leu  Leu  Ser  Ile  Ala  Cys  Ala  Asp  Leu
          35                       40                       45

Ile  Ile  Gly  Thr  Phe  Ser  Met  Leu  Tyr  Leu  Met  His  Trp  Ala  Leu
     50                       55                       60

Gly  Thr  Leu  Ala  Cys  Asp  Leu  Trp  Leu  Ala  Leu  Asp  Tyr  Val  Ala  Ser
65                       70                       75                       80

Asn  Ala  Ser  Val  Leu  Asn  Leu  Leu  Leu  Ile  Ser  Phe  Asp  Arg  Tyr  Phe
                    85                       90                       95

Ser  Val  Thr  Arg  Pro  Leu  Ser  Tyr  Arg  Ala  Lys  Arg  Thr  Pro  Arg  Arg
               100                      105                      110

Ala  Ala  Ile  Met  Ile  Gly  Ile  Ala  Trp  Leu  Val  Ser  Phe  Val  Leu  Trp
          115                      120                      125

Ala  Pro  Ala  Ile  Leu  Phe  Trp  Gln  Tyr  Leu  Val  Gly  Glu  Arg  Thr  Met
     130                      135                      140

Leu  Ala  Gly  Gln  Cys  Tyr  Ile  Gln  Phe  Leu  Ser  Gln  Pro  Ile  Ile  Thr
145                      150                      155                      160

Phe  Gly  Thr  Ala  Met  Ala  Ala  Phe  Tyr  Met  Pro  Val  Thr  Val  Met  Thr
                    165                      170                      175

Leu  Tyr  Trp  Arg  Ile  Tyr  Arg  Phe  Thr  Glu  Asn  Arg  Ala  Arg  Glu  Leu
```

```
                           180                     185                     190
      Gln  Gly  Ser  Glu  Thr  Pro  Gly  Lys  Gly  Gly  Gly  Ser  Ser  Ser  Ser
                195                     200                     205

Glu  Arg  Ser  Gln  Pro  Gly  Ala  Glu  Gly  Ser  Pro  Glu  Thr  Pro  Lys  Gly
           210                     215                     220

Gln  Lys  Pro  Arg  Gly  Lys  Glu  Leu  Ala  Lys  Arg  Lys  Thr  Phe  Ser  Leu
      225                     230                     235                          240

Val  Lys  Glu  Lys  Lys  Ala  Ala  Arg  Thr  Leu  Ser  Ala  Ile  Leu  Leu  Ala
                          245                     250                          255

Phe  Ile  Leu  Thr  Trp  Thr  Pro  Tyr  Asn  Ile  Met  Val  Leu  Val  Ser  Thr
                     260                     265                     270

Phe  Cys  Lys  Asp  Cys  Val  Pro  Glu  Thr  Leu  Trp  Glu  Leu  Gly  Tyr  Trp
                275                     280                     285

Leu  Ile  Cys  Tyr  Val  Asn  Ser  Thr  Ile  Asn  Pro  Trp  Tyr  Ala  Leu  Cys
           290                     295                     300

Asn  Lys  Ala  Phe  Arg  Asp  Thr  Phe  Arg  Leu  Leu  Leu  Leu  Cys  Trp  Asp
      305                     310                     315                          320

Lys  Arg  Arg  Trp  Arg  Lys  Ile  Pro  Lys  Arg  Pro  Gly  Ser  Val  His  Arg
                          325                     330                          335

Thr  Pro  Ser  Arg  Gln  Cys
                          340
```

( 2 ) INFORMATION FOR SEQ ID NO:10:

( i ) SEQUENCE CHARACTERISTICS:
        ( A ) LENGTH: 317 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
      Val  Val  Phe  Ile  Val  Leu  Val  Ala  Gly  Ser  Leu  Ser  Leu  Val  Thr  Ile
      1              5                    10                         15

Ile  Gly  Asn  Ile  Leu  Val  Met  Val  Ser  Ile  Lys  Val  Asn  Arg  His  Tyr
                     20                     25                     30

Phe  Leu  Phe  Ser  Ile  Ala  Cys  Ala  Asp  Leu  Ile  Ile  Gly  Val  Phe  Ser
                35                     40                         45

Met  Asn  Leu  Tyr  Thr  Leu  Tyr  Thr  Val  Ile  Gly  Tyr  Trp  Pro  Leu  Gly
           50                     55                     60

Pro  Val  Val  Cys  Asp  Leu  Tyr  Val  Val  Ser  Asn  Ala  Ser  Val  Met  Asn
      65                     70                     75                          80

Leu  Leu  Ile  Ile  Ser  Phe  Asp  Arg  Tyr  Phe  Cys  Val  Thr  Lys  Pro  Leu
                          85                     90                          95

Thr  Tyr  Pro  Val  Lys  Arg  Thr  Thr  Lys  Met  Ala  Gly  Met  Met  Ile  Ala
                     100                    105                    110

Ala  Ala  Trp  Val  Leu  Ser  Phe  Ile  Leu  Trp  Ala  Pro  Ala  Ile  Leu  Phe
                115                    120                    125

Trp  Gln  Phe  Ile  Val  Gly  Val  Arg  Thr  Val  Glu  Asp  Gly  Glu  Cys  Tyr
           130                    135                    140

Ile  Gln  Phe  Phe  Ser  Asn  Pro  Ala  Val  Thr  Phe  Gly  Thr  Ala  Ile  Ala
      145                    150                    155                         160

Ala  Phe  Tyr  Leu  Pro  Val  Ile  Ile  Met  Ile  Val  Leu  Tyr  Trp  His  Ile
                          165                    170                         175

Ser  Arg  Ala  Ser  Lys  Ser  Arg  Ile  Lys  Lys  Asp  Lys  Lys  Glu  Pro  Val
                     180                    185                    190
```

| | | | | | | | | | | | | | | |
|---|---|---|---|---|---|---|---|---|---|---|---|---|---|---|
|Ala|Asn|Gln<br>195|Asp|Pro|Val|Ser|Pro<br>200|Ser|Leu|Val|Gln|Gly<br>205|Arg|Ile|Val|
|Lys|Pro<br>210|Leu|Ser|Ser|Asp|Asp<br>215|Lys|Ile|Val|Arg|Arg<br>220|Thr|Lys|Gln|Pro|
|Ala<br>225|Lys|Lys|Lys|Pro|Pro<br>230|Pro|Ser|Arg|Glu|Lys<br>235|Lys|Val|Thr|Arg|Thr<br>240|
|Ile|Ala|Ile|Leu|Leu<br>245|Ala|Phe|Ile|Ile|Thr<br>250|Trp|Ala|Pro|Tyr|Asn<br>255|Val|
|Met|Val|Leu|Ile<br>260|Asn|Thr|Phe|Cys|Ala<br>265|Pro|Cys|Ile|Pro|Asn<br>270|Thr|Val|
|Trp|Arg|Ile<br>275|Gly|Tyr|Trp|Leu|Cys<br>280|Tyr|Ile|Asn|Ser|Thr<br>285|Ile|Asn|Pro|
|Ala|Cys<br>290|Tyr|Ala|Leu|Cys|Asn<br>295|Ala|Thr|Phe|Lys|Lys<br>300|Thr|Phe|Lys|His|
|Leu<br>305|Ile|Met|Cys|His|Tyr<br>310|Lys|Asn|Ile|Gly|Ala<br>315|Thr|Arg| | | |

( 2 ) INFORMATION FOR SEQ ID NO:11:

( i ) SEQUENCE CHARACTERISTICS:
        ( A ) LENGTH: 355 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

| | | | | | | | | | | | | | | |
|---|---|---|---|---|---|---|---|---|---|---|---|---|---|---|
|Trp<br>1|Phe|Ile|Ala|Phe<br>5|Leu|Thr|Gly|Ile|Leu<br>10|Ala|Leu|Val|Thr|Ile<br>15|Ile|
|Gly|Asn|Ile|Leu<br>20|Val|Ile|Val|Ser|Phe<br>25|Lys|Val|Asn|Lys|Gln<br>30|Leu|Lys|
|Thr|Val|Asn<br>35|Asn|Tyr|Phe|Leu|Leu<br>40|Ser|Leu|Ala|Cys|Ala<br>45|Asp|Leu|Ile|
|Ile|Gly<br>50|Val|Ile|Ser|Met|Asn<br>55|Leu|Phe|Thr|Thr|Tyr<br>60|Ile|Ile|Met|Asn|
|Arg<br>65|Trp|Ala|Leu|Gly|Asn<br>70|Thr|Ala|Cys|Asp|Leu<br>75|Trp|Ile|Ala|Ile|Asp<br>80|
|Tyr|Val|Ala|Ser|Asn<br>85|Ala|Ser|Val|Leu|Asn<br>90|Leu|Leu|Val|Ile|Ser|Phe<br>95|
|Asp|Arg|Tyr|Phe<br>100|Ser|Ile|Thr|Arg|Pro<br>105|Leu|Thr|Tyr|Arg|Ala<br>110|Lys|Arg|
|Thr|Thr|Lys<br>115|Arg|Ala|Gly|Val|Met<br>120|Ile|Gly|Leu|Ala|Trp<br>125|Val|Ile|Ser|
|Phe|Val<br>130|Leu|Trp|Ala|Pro|Ala<br>135|Ile|Leu|Phe|Trp|Gln<br>140|Tyr|Phe|Val|Gly|
|Lys<br>145|Arg|Thr|Val|Pro|Pro<br>150|Gly|Glu|Cys|Phe|Ile<br>155|Gln|Phe|Leu|Ser|Glu<br>160|
|Pro|Thr|Ile|Thr|Phe<br>165|Gly|Thr|Ala|Ile|Ala<br>170|Ala|Phe|Tyr|Met|Pro<br>175|Val|
|Thr|Ile|Met|Arg<br>180|Ile|Leu|Tyr|Trp|Arg<br>185|Ile|Tyr|Lys|Glu|Thr<br>190|Glu|Lys|
|Arg|Thr|Lys<br>195|Glu|Leu|Ala|Gly|Leu<br>200|Gln|Ala|Ser|Gly|Thr<br>205|Glu|Ala|Glu|
|Thr|Glu<br>210|Asn|Phe|Val|His|Pro<br>215|Thr|Gly|Ser|Ser|Arg<br>220|Ser|Cys|Ser|Ser|

```
Tyr  Glu  Leu  Gln  Gln  Gln  Lys  Arg  Phe  Ala  Leu  Lys  Thr  Arg  Ser  Gln
225                      230                     235                          240

Ile  Thr  Lys  Arg  Lys  Leu  Leu  Val  Lys  Glu  Lys  Lys  Ala  Ala  Gln  Thr
                    245                     250                          255

Leu  Ser  Ala  Ile  Leu  Leu  Ala  Phe  Ile  Ile  Thr  Trp  Thr  Pro  Tyr  Asn
                260                     265                     270

Ile  Met  Val  Leu  Val  Asn  Thr  Phe  Cys  Asp  Ser  Cys  Ile  Pro  Lys  Thr
          275                     280                     285

Tyr  Trp  Asn  Leu  Gly  Gly  Tyr  Trp  Leu  Cys  Tyr  Ile  Asn  Ser  Thr  Val
          290                285                     300

Asn  Pro  Val  Cys  Tyr  Ala  Leu  Cys  Asn  Lys  Thr  Phe  Arg  Thr  Thr  Phe
305                     310                     315                          320

Lys  Thr  Leu  Leu  Leu  Cys  Gln  Cys  Asp  Lys  Arg  Lys  Arg  Arg  Lys  Gln
                325                     330                          335

Gln  Tyr  Gln  Gln  Arg  Gln  Ser  Val  Ile  Phe  His  Lys  Arg  Val  Pro  Glu
                340                     345                     350

Gln  Ala  Leu
          355
```

( 2 ) INFORMATION FOR SEQ ID NO:12:

( i ) SEQUENCE CHARACTERISTICS:
        ( A ) LENGTH: 333 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Met  Val  Phe  Ile  Ala  Thr  Val  Arg  Gly  Ser  Leu  Ser  Leu  Val  Thr  Val
1                   5                       10                          15

Val  Gly  Asn  Ile  Leu  Val  Met  Leu  Ser  Ile  Lys  Val  Asn  Arg  Gln  Leu
               20                      25                      30

Gln  Thr  Val  Asn  Asn  Tyr  Phe  Leu  Phe  Ser  Ile  Ala  Cys  Ala  Asp  Leu
          35                      40                      45

Ile  Ile  Gly  Ala  Phe  Ser  Met  Asn  Leu  Tyr  Thr  Val  Tyr  Ile  Ile  Lys
     50                      55                      60

Gly  Tyr  Trp  Pro  Leu  Gly  Ala  Trp  Cys  Asp  Leu  Trp  Leu  Ala  Leu  Asp
65                      70                      75                           80

Tyr  Val  Val  Ser  Asn  Ala  Ser  Val  Met  Leu  Leu  Ile  Ile  Ser  Phe  Asp
                85                      90                           95

Arg  Tyr  Phe  Cys  Val  Thr  Lys  Pro  Leu  Thr  Tyr  Pro  Ala  Arg  Arg  Thr
               100                     105                     110

Thr  Lys  Met  Ala  Gly  Ile  Met  Ile  Ala  Ala  Ala  Trp  Val  Leu  Ser  Phe
          115                     120                     125

Val  Leu  Trp  Ala  Pro  Ala  Ile  Leu  Phe  Trp  Gln  Phe  Val  Val  Gly  Lys
     130                     135                     140

Arg  Thr  Val  Pro  Asp  Asn  Gln  Cys  Phe  Ile  Gln  Phe  Leu  Ser  Asn  Pro
145                     150                     155                          160

Ala  Val  Thr  Phe  Gly  Thr  Ala  Ile  Ala  Ala  Phe  Tyr  Leu  Pro  Val  Val
               165                     170                     175

Ile  Met  Ile  Val  Leu  Tyr  Ile  His  Ile  Ser  Leu  Ala  Ser  Arg  Ser  Arg
               180                     185                     190

Val  His  Lys  His  Arg  Pro  Glu  Gly  Pro  Lys  Glu  Lys  Lys  Ala  Lys  Thr
          195                     200                     205

Ile  Ala  Phe  Leu  Lys  Ser  Pro  Ile  Met  Gln  Ser  Val  Lys  Lys  Pro  Pro
```

|     |     |     | 210 |     |     |     |     | 215 |     |     |     |     | 220 |     |     |
| --- | --- | --- | --- | --- | --- | --- | --- | --- | --- | --- | --- | --- | --- | --- | --- |
| Pro | Gly | Glu | Ala | Lys | Phe | Ala | Ser | Ile | Ala | Arg | Asn | Gln | Val | Arg | Lys |
| 225 |     |     |     |     | 230 |     |     |     |     | 235 |     |     |     |     | 240 |
| Lys | Arg | Gln | Leu | Ala | Ala | Arg | Glu | Arg | Lys | Val | Thr | Arg | Thr | Ile | Phe |
|     |     |     |     | 245 |     |     |     |     | 250 |     |     |     |     | 255 |     |
| Ala | Ile | Leu | Leu | Ala | Phe | Ile | Leu | Thr | Trp | Thr | Pro | Tyr | Asn | Val | Met |
|     |     |     |     | 260 |     |     |     |     | 265 |     |     |     |     | 270 |     |
| Val | Leu | Val | Asn | Thr | Phe | Cys | Gln | Ser | Cys | Ile | Pro | Asp | Thr | Val | Trp |
|     |     |     | 275 |     |     |     |     | 280 |     |     |     |     | 285 |     |     |
| Ser | Ile | Gly | Tyr | Trp | Leu | Ile | Cys | Tyr | Val | Asn | Ser | Thr | Ile | Asn | Pro |
|     |     |     | 290 |     |     |     | 295 |     |     |     |     | 300 |     |     |     |
| Ala | Cys | Tyr | Ala | Leu | Cys | Asn | Ala | Thr | Phe | Lys | Lys | Thr | Phe | Arg | His |
| 305 |     |     |     |     | 310 |     |     |     |     | 315 |     |     |     |     | 320 |
| Leu | Leu | Leu | Cys | Gln | Arg | Tyr | Asn | Ile | Gly | Thr | Ala | Arg |     |     |     |
|     |     |     |     | 325 |     |     |     |     | 330 |     |     |     |     |     |     |

( 2 ) INFORMATION FOR SEQ ID NO:13:

( i ) SEQUENCE CHARACTERISTICS:
        ( A ) LENGTH: 348 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

| Val | Ile | Thr | Ile | Ala | Val | Val | Thr | Ala | Val | Val | Ser | Leu | Met | Thr | Ile |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Val | Gly | Asn | Val | Leu | Val | Met | Ile | Ser | Phe | Lys | Val | Asn | Ser | Gln | Leu |
|     |     |     | 20  |     |     |     |     | 25  |     |     |     |     | 30  |     |     |
| Lys | Thr | Val | Asn | Asn | Tyr | Tyr | Leu | Leu | Ser | Ile | Ala | Cys | Ala | Asp | Leu |
|     |     | 35  |     |     |     |     | 40  |     |     |     |     | 45  |     |     |     |
| Ile | Ile | Gly | Ile | Phe | Ser | Met | Asn | Leu | Tyr | Thr | Thr | Tyr | Ile | Leu | Ile |
|     | 50  |     |     |     |     | 55  |     |     |     |     | 60  |     |     |     |     |
| Met | Gly | Arg | Trp | Ala | Leu | Gly | Ser | Leu | Ala | Cys | Asp | Leu | Trp | Leu | Ala |
| 65  |     |     |     |     | 70  |     |     |     |     | 75  |     |     |     |     | 80  |
| Ile | Asp | Tyr | Val | Ala | Ser | Asn | Ala | Ser | Val | Leu | Asn | Leu | Leu | Val | Ile |
|     |     |     |     | 85  |     |     |     |     | 90  |     |     |     |     | 95  |     |
| Ser | Phe | Asp | Arg | Tyr | Phe | Ser | Ile | Thr | Arg | Pro | Leu | Thr | Tyr | Arg | Ala |
|     |     |     | 100 |     |     |     |     | 105 |     |     |     |     | 110 |     |     |
| Lys | Arg | Thr | Pro | Lys | Arg | Ala | Gly | Ile | Met | Ile | Gly | Ile | Ala | Trp | Leu |
|     |     | 115 |     |     |     |     | 120 |     |     |     |     | 125 |     |     |     |
| Ile | Ser | Phe | Ile | Leu | Trp | Ala | Pro | Ala | Ile | Leu | Cys | Trp | Gln | Tyr | Leu |
|     | 130 |     |     |     |     | 135 |     |     |     |     | 140 |     |     |     |     |
| Val | Gly | Lys | Arg | Thr | Val | Pro | Ile | Asp | Glu | Cys | Gln | Ile | Gln | Phe | Leu |
| 145 |     |     |     |     | 150 |     |     |     |     | 155 |     |     |     |     | 160 |
| Ser | Glu | Pro | Thr | Ile | Thr | Phe | Gly | Thr | Ala | Ile | Ala | Ala | Phe | Tyr | Ile |
|     |     |     |     | 165 |     |     |     |     | 170 |     |     |     |     | 175 |     |
| Pro | Val | Ser | Ile | Met | Arg | Ile | Leu | Tyr | Cys | Arg | Ile | Tyr | Arg | Glu | Thr |
|     |     |     | 180 |     |     |     |     | 185 |     |     |     |     | 190 |     |     |
| Glu | Lys | Arg | Thr | Lys | Asp | Leu | Ala | Asp | Leu | Gln | Gly | Ser | Asp | Ser | Val |
|     |     | 195 |     |     |     |     | 200 |     |     |     |     | 205 |     |     |     |
| Tyr | Lys | Ala | Glu | Lys | Arg | Lys | Pro | Ala | His | Arg | Ala | Leu | Phe | Arg | Ser |
|     | 210 |     |     |     |     | 215 |     |     |     |     | 220 |     |     |     |     |
| Cys | Leu | Arg | Cys | Pro | Arg | Pro | Thr | Lys | Gly | Leu | Asn | Pro | Asn | Pro | Ser |
| 225 |     |     |     |     | 230 |     |     |     |     | 235 |     |     |     |     | 240 |

```
His Gln Met Thr Lys Arg Lys Arg Met Ser Leu Val Lys Glu Arg Lys
                245                 250                 255

Ala Ala Gln Thr Leu Ser Ala Ile Leu Leu Ala Phe Ile Ile Thr Trp
                260                 265                 270

Thr Pro Tyr Asn Ile Met Val Leu Val Ser Thr Phe Cys Asp Lys Cys
            275                 280                 285

Val Pro Val Thr Leu Trp His Leu Gly Tyr Trp Leu Cys Tyr Ile Asn
        290                 295                 300

Ser Thr Val Asn Pro Ile Cys Tyr Ala Leu Cys Asn Arg Thr Phe Arg
305                 310                 315                 320

Lys Thr Phe Ile Met Leu Leu Cys Arg Trp Lys Lys Lys Lys Val Glu
                325                 330                 335

Glu Lys Leu Tyr Trp Gln Gly Asn Ser Lys Leu Pro
            340                 345
```

( 2 ) INFORMATION FOR SEQ ID NO:14:

( i ) SEQUENCE CHARACTERISTICS:
        ( A ) LENGTH: 377 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Thr Ala Gly Asp Cys Leu Ile Met Leu Ile Val Leu Leu Ile Val Ala
1               5                   10                  15

Gly Asn Val Leu Val Ile Val Ala Ile Ala Lys Thr Pro Arg Leu Gln
                20                  25                  30

Thr Leu Thr Asn Leu Phe Ile Met Ser Ile Ala Ser Ala Asp Leu Val
            35                  40                  45

Met Leu Leu Val Val Pro Phe Cys Ala Thr Leu Val Val Trp Gly
        50                  55                  60

Arg Trp Glu Tyr Gly Ser Phe Phe Cys Glu Leu Trp Thr Ser Val Asp
65                  70                  75                  80

Val Leu Cys Val Thr Ala Ser Ile Glu Thr Leu Cys Val Ile Ala Leu
                85                  90                  95

Asp Arg Tyr Leu Ala Ile Thr Ser Pro Phe Arg Tyr Gln Ser Leu Leu
                100                 105                 110

Thr Arg Ala Arg Ala Arg Gly Leu Val Cys Thr Val Trp Ala Ile Ser
            115                 120                 125

Ala Leu Val Ser Phe Leu Pro Ile Leu Leu Ser Asp Glu Ala Arg Arg
        130                 135                 140

Cys Tyr Asn Asp Pro Lys Cys Cys Asp Phe Val Thr Asn Arg Ala Tyr
145                 150                 155                 160

Ala Ile Ala Ser Ser Val Val Ser Phe Tyr Val Pro Leu Cys Ile Met
                165                 170                 175

Phe Val Tyr Leu Arg Val Phe Arg Glu Ala Gln Lys Gln Val Lys Lys
                180                 185                 190

Ile Asp Ser Cys Glu Arg Arg Phe Leu Gly Gly Pro Ala Arg Pro Pro
            195                 200                 205

Ser Pro Ser Pro Ser Pro Val Pro Ala Pro Ala Pro Pro Gly Pro Pro
        210                 215                 220

Arg Pro Ala Ala Ala Ala Ala Thr Ala Pro Leu Ala Asn Gly Arg Ala
225                 230                 235                 240
```

|   |   |   |   |   |   |   |   |   |   |   |   |   |   |   |
|---|---|---|---|---|---|---|---|---|---|---|---|---|---|---|
| Gly | Lys | Arg | Arg | Pro 245 | Ser | Arg | Leu | Val | Ala 250 | Leu | Arg | Glu | Gln | Lys 255 | Ala |
| Leu | Lys | Thr | Leu 260 | Gly | Ile | Ile | Met | Gly 265 | Val | Phe | Thr | Leu 270 | Cys | Trp | Leu |
| Pro | Phe | Phe 275 | His | Arg | Glu | Leu | Val 280 | Pro | Asp | Arg | Leu 285 | Phe | Val | Phe | Phe |
| Asn | Trp 290 | Leu | Arg | Tyr | Ala | Asn 295 | Ser | Ala | Phe | Asn | Pro 300 | Ile | Ile | Tyr | Cys |
| Arg 305 | Ser | Pro | Asp | Phe | Arg 310 | Lys | Ala | Phe | Gln | Gly 315 | Leu | Leu | Cys | Cys | Ala 320 |
| Arg | Arg | Ala | Ala | Arg 325 | Arg | Arg | His | Ala | Thr 330 | His | Gly | Asp | Arg | Pro 335 | Arg |
| Ala | Ser | Gly | Cys 340 | Ile | Ala | Arg | Pro | Gly 345 | Pro | Pro | Ser | Pro 350 | Gly | Ala | Ala |
| Ser | Asp | Asp 355 | Asp | Asp | Asp | Val | Val 360 | Gly | Ala | Thr | Pro 365 | Pro | Ala | Arg |
| Leu | Leu 370 | Glu | Pro | Trp | Ala | Gly 375 | Cys | Asn |

(2) INFORMATION FOR SEQ ID NO:15:

(i) SEQUENCE CHARACTERISTICS:
(A) LENGTH: 362 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:15:

|   |   |   |   |   |   |   |   |   |   |   |   |   |   |   |   |
|---|---|---|---|---|---|---|---|---|---|---|---|---|---|---|---|
| Val 1 | Val | Gly | Ile | Val 5 | Met | Ser | Leu | Ile | Val 10 | Leu | Ala | Ile | Val | Phe 15 | Gly |
| Asn | Val | Leu | Val 20 | Ile | Thr | Ala | Ile | Ala 25 | Lys | Phe | Glu | Arg | Leu 30 | Gln | Thr |
| Val | Thr | Asn 35 | Tyr | Phe | Ile | Thr | Ser 40 | Ile | Ala | Cys | Ala | Asp 45 | Leu | Val | Met |
| Gly | Leu 50 | Ala | Val | Val | Pro | Phe 55 | Gly | Ala | Ala | His | Ile 60 | Leu | Met | Lys | Met |
| Trp 65 | Thr | Phe | Gly | Asn | Phe 70 | Trp | Cys | Glu | Phe | Trp 75 | Thr | Ser | Ile | Asp | Val 80 |
| Leu | Cys | Val | Thr | Ala 85 | Ser | Ile | Glu | Thr | Leu 90 | Cys | Val | Ile | Ala | Val 95 | Asp |
| Arg | Tyr | Phe | Ala 100 | Ile | Thr | Ser | Pro | Phe 105 | Lys | Tyr | Gln | Ser | Leu 110 | Leu | Thr |
| Lys | Asn | Lys 115 | Ala | Arg | Val | Ile | Ile 120 | Ile | Met | Val | Trp | Ile 125 | Val | Ser | Gly |
| Leu | Thr 130 | Ser | Phe | Leu | Pro | Ile 135 | Leu | Tyr | Arg | Ala | Thr 140 | His | Gln | Glu | Ala |
| Ile 145 | Asn | Cys | Tyr | Ala | Asn 150 | Glu | Thr | Cys | Cys | Asp 155 | Phe | Phe | Thr | Asn | Gln 160 |
| Ala | Tyr | Ala | Ala | Ser 165 | Ser | Ala | Val | Ser | Phe 170 | Tyr | Val | Pro | Leu 175 | Val | Ile |
| Met | Val | Phe | Val 180 | Tyr | Ser | Arg | Val | Phe 185 | Gln | Glu | Ala | Lys | Arg 190 | Gln | Leu |
| Gln | Lys | Ile 195 | Asp | Lys | Ser | Glu | Gly 200 | Arg | Phe | Ile | Phe | Val 205 | Gln | Asn | Leu |
| Ser | Gln | Val | Glu | Gln | Asp | Gly | Arg | Thr | Gly | His | Gly | Leu | Arg | Arg | Ser |

|     |     |     |     |     |     |     |     |     |     |     |     |     |     |     |
| --- | --- | --- | --- | --- | --- | --- | --- | --- | --- | --- | --- | --- | --- | --- |
|     |     |     |     |     | 210 |     |     |     | 215 |     |     |     | 220 |     |
| Ser 225 | Lys | Phe | Cys | Leu | Lys 230 | Glu | His | Lys | Ala | Leu 235 | Lys | Thr | Leu | Gly | Ile 240 |
| Ile | Pro | Cys | Thr | Phe 245 | Thr | Leu | Cys | Trp | Leu 250 | Pro | Phe | Phe | Ile | Val 255 | Asn |
| Ile | Val | Val | Ile 260 | Gln | Asp | Asn | Leu | Ile 265 | Arg | Lys | Glu | Val | Tyr 270 | Ile | Leu |
| Leu | Asn | Trp 275 | Ile | Gly | Tyr | Val | Asn 280 | Ser | Gly | Phe | Asn | Pro 285 | Leu | Ile | Tyr |
| Cys | Arg 290 | Ser | Pro | Asp | Phe | Arg 295 | Ile | Ala | Phe | Gln | Glu 300 | Leu | Leu | Cys | Leu |
| Arg 305 | Arg | Ser | Ser | Leu | Lys 310 | Ala | Tyr | Gly | Asn | Gly 315 | Tyr | Ser | Ser | Asn | Gly 320 |
| Asn | Thr | Gly | Glu | Gln 325 | Ser | Gly | Tyr | His | Val 330 | Glu | Gln | Glu | Lys | Glu 335 | Asn |
| Lys | Leu | Leu | Cys 340 | Glu | Asp | Leu | Pro | Gly 345 | Thr | Glu | Asp | Phe | Val 350 | Gly | His |
| Gln | Gly | Thr 355 | Val | Pro | Ser | Asp | Asn 360 | Ile | Asp |     |     |     |     |     |     |

( 2 ) INFORMATION FOR SEQ ID NO:16:

( i ) SEQUENCE CHARACTERISTICS:
( A ) LENGTH: 362 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:16:

|     |     |     |     |     |     |     |     |     |     |     |     |     |     |     |
| --- | --- | --- | --- | --- | --- | --- | --- | --- | --- | --- | --- | --- | --- | --- |
| Ala 1 | Ala | Leu | Ala | Gly 5 | Ala | Leu | Leu | Ala | Leu 10 | Ala | Val | Leu | Ala | Thr 15 | Val |
| Gly | Gly | Asn | Leu 20 | Leu | Val | Ile | Val | Ala 25 | Ile | Ala | Trp | Thr | Pro 30 | Arg | Leu |
| Gln | Thr | Met 35 | Thr | Asn | Val | Phe | Val 40 | Thr | Ser | Leu | Ala | Ala 45 | Ala | Asp | Leu |
| Asp | Leu 50 | Leu | Val | Val | Pro | Pro 55 | Ala | Ala | Thr | Leu | Ala 60 | Leu | Thr | Gly | His |
| Trp 65 | Pro | Leu | Gly | Ala | Thr 70 | Gly | Cys | Glu | Leu | Trp 75 | Thr | Ser | Val | Asp | Val 80 |
| Leu | Cys | Val | Thr | Ala 85 | Ser | Ile | Glu | Thr | Leu 90 | Cys | Ala | Ile | Ala | Val 95 | Asp |
| Arg | Tyr | Leu | Ala 100 | Val | Thr | Asn | Pro | Leu 105 | Arg | Tyr | Gly | Ala | Leu 110 | Val | Thr |
| Lys | Arg | Cys 115 | Ala | Arg | Thr | Ala | Trp 120 | Leu | Val | Trp | Val | Val 125 | Ser | Ala | Ala |
| Val | Ser | Phe 130 | Ala | Pro | Ile | Met | Ser 135 | Gln | Trp | Trp | Arg | Val 140 | Gly | Ala | Asp |
| Ala 145 | Glu | Ala | Gln | Arg | Cys 150 | His | Ser | Asn | Pro | Arg 155 | Cys | Cys | Ala | Phe | Ala 160 |
| Ser | Asn | Met | Pro | Tyr 165 | Ala | Val | Leu | Leu | Ser 170 | Ser | Ser | Val | Ser | Phe 175 | Tyr |
| Leu | Pro | Leu | Leu 180 | Leu | Phe | Val | Tyr | Ala 185 | Arg | Val | Phe | Trp | Ala 190 | Thr | Arg |
| Gln | Leu | Arg 195 | Leu | Leu | Arg | Gly | Glu 200 | Leu | Gly | Arg | Phe | Pro 205 | Pro | Glu | Glu |

Ser Pro Pro Ala Pro Ser Arg Ser Leu Ala Pro Ala Pro Val Gly Thr
    210             215             220

Gly Ala Pro Pro Glu Gly Val Pro Ala Cys Gly Arg Pro Pro Ala Arg
225             230             235                         240

Leu Ile Pro Ile Arg Glu His Arg Ala Leu Cys Thr Leu Gly Leu Ile
            245             250             255

Met Gly Thr Phe Thr Leu Cys Trp Leu Pro Phe Phe Ile Ala Asn Val
            260             265             270

Leu Arg Ala Leu Gly Gly Pro Ser Leu Val Pro Gly Pro Ala Phe Leu
        275             280             285

Ala Leu Asn Trp Leu Ile Gly Tyr Ala Asn Ser Ala Phe Asn Pro Leu
290             295             300

Ile Tyr Cys Arg Ser Pro Asp Phe Arg Ser Ala Phe Arg Arg Leu Leu
305             310             315                         320

Cys Arg Cys Gly Arg Arg Leu Pro Pro Glu Pro Cys Ala Ala Ala Arg
                325             330             335

Pro Ala Leu Phe Pro Ser Gly Val Pro Ala Ala Glu Ser Ser Pro Ala
            340             345             350

Gln Pro Arg Leu Cys Gln Arg Leu Asp Gly
        355             360

( 2 ) INFORMATION FOR SEQ ID NO:17:

( i ) SEQUENCE CHARACTERISTICS:
( A ) LENGTH: 375 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:17:

Ala Ile Leu Leu Gly Val Ile Leu Gly Gly Leu Ile Leu Phe Gly Val
1               5                   10              15

Leu Gly Asn Ile Leu Val Ile Leu Ser Val Ala Cys His Arg His Leu
            20              25              30

His Ser Val Thr His Tyr Tyr Ile Val Asn Leu Ala Val Ala Asp Leu
        35              40              45

Leu Leu Thr Ser Thr Val Leu Pro Phe Ser Ala Ile Phe Glu Ile Leu
50              55              60

Gly Tyr Trp Lys Phe Gly Arg Val Phe Cys Asn Val Trp Ala Ala Val
65              70              75              80

Asp Val Leu Cys Cys Thr Ala Ser Ile Met Leu Leu Cys Ile Ile Ser
            85              90              95

Ile Asp Arg Tyr Ile Gly Val Ser Tyr Pro Leu Arg Tyr Pro Thr Ile
        100             105             110

Val Thr Gln Lys Arg Gly Leu Met Ala Leu Leu Cys Val Trp Ala Leu
        115             120             125

Ser Leu Val Ile Ser Ile Gly Pro Leu Phe Gly Trp Arg Gln Pro Ala
    130             135             140

Pro Glu Asp Glu Thr Ile Cys Gln Ile Asn Glu Glu Pro Gly Tyr Val
145             150             155             160

Leu Phe Ser Ala Leu Gly Ser Phe Tyr Val Pro Leu Thr Ile Ile Leu
            165             170             175

Val Met Tyr Cys Arg Val Tyr Val Val Ala Lys Arg Glu Ser Arg Gly
        180             185             190

| | | | | | | | | | | | | | | |
|---|---|---|---|---|---|---|---|---|---|---|---|---|---|---|
| Leu | Lys | Ser<br>195 | Gly | Leu | Lys | Thr | Asp<br>200 | Lys | Ser | Asp | Ser<br>205 | Glu | Gln | Val | Thr |
| Leu | Arg<br>210 | Ile | His | Arg | Lys | Asn<br>215 | Ala | Gln | Val | Gly | Gly<br>220 | Ser | Gly | Val | Thr |
| Ser<br>225 | Ala | Lys | Asn | Lys | Thr<br>230 | His | Phe | Ser | Val | Arg<br>235 | Leu | Leu | Lys | Phe | Ser<br>240 |
| Arg | Glu | Lys | Lys | Ala<br>245 | Ala | Lys | Thr | Leu | Gly<br>250 | Ile | Val | Val | Gly | Cys<br>255 | Phe |
| Val | Leu | Cys | Trp<br>260 | Leu | Pro | Phe | Phe | Leu<br>265 | Val | Met | Pro | Ile | Gly<br>270 | Ser | Phe |
| Phe | Pro | Asp<br>275 | Phe | Arg | Pro | Ser | Glu<br>280 | Thr | Val | Phe | Lys | Ile<br>285 | Ala | Phe | Trp |
| Leu | Gly<br>290 | Tyr | Ile | Asn | Ser | Cys<br>295 | Ile | Asn | Pro | Ile | Ile<br>300 | Tyr | Pro | Cys | Ser |
| Ser<br>305 | Gln | Glu | Phe | Lys | Lys<br>310 | Ala | Phe | Gln | Asn | Val<br>315 | Leu | Arg | Ile | Gln | Cys<br>320 |
| Leu | Arg | Arg | Lys | Gln<br>325 | Ser | Ser | Lys | His | Thr<br>330 | Leu | Gly | Tyr | Thr | Leu<br>335 | His |
| Ala | Pro | Ser | His<br>340 | Val | Leu | Glu | Gly | Gln<br>345 | His | Lys | Asp | Leu | Val<br>350 | Arg | Ile |
| Pro | Val | Gly<br>355 | Ser | Ala | Glu | Thr | Phe<br>360 | Tyr | Lys | Ile | Ser | Lys<br>365 | Thr | Asp | Gly |
| Val | Cys<br>370 | Glu | Trp | Lys | Ile | Phe<br>375 | | | | | | | | | |

( 2 ) INFORMATION FOR SEQ ID NO:18:

( i ) SEQUENCE CHARACTERISTICS:
        ( A ) LENGTH: 370 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

| | | | | | | | | | | | | | | | |
|---|---|---|---|---|---|---|---|---|---|---|---|---|---|---|---|
| Ala<br>1 | Ile | Ser | Val | Gly<br>5 | Leu | Val | Leu | Gly | Ala<br>10 | Phe | Ile | Leu | Phe | Ala<br>15 | Ile |
| Val | Gly | Asn | Ile<br>20 | Leu | Val | Ile | Leu | Ser<br>25 | Val | Ala | Cys | Asn | Arg<br>30 | His | Leu |
| Arg | Thr | Pro<br>35 | Thr | Asn | Tyr | Phe | Ile<br>40 | Val | Asn | Ile | Ala | Ile<br>45 | Ala | Asp | Leu |
| Leu | Leu<br>50 | Ser | Phe | Thr | Val | Leu<br>55 | Pro | Phe | Ser | Ala | Thr<br>60 | Leu | Glu | Val | Leu |
| Gly<br>65 | Tyr | Trp | Val | Leu | Gly<br>70 | Arg | Ile | Phe | Cys | Asp<br>75 | Ile | Trp | Ala | Ala | Val<br>80 |
| Asp | Val | Leu | Cys | Cys<br>85 | Thr | Ala | Ser | Ile | Leu<br>90 | Ser | Leu | Cys | Ala | Ile<br>95 | Ser |
| Ile | Asp | Arg | Tyr<br>100 | Ile | Gly | Val | Arg | Tyr<br>105 | Ser | Leu | Gln | Tyr | Pro<br>110 | Thr | Leu |
| Val | Thr | Arg<br>115 | Arg | Tyr | Ala | Ile | Ile<br>120 | Ala | Leu | Leu | Ser | Val<br>125 | Trp | Val | Leu |
| Ser | Thr<br>130 | Val | Ile | Ser | Ile | Gly<br>135 | Pro | Leu | Leu | Gly | Trp<br>140 | Lys | Glu | Pro | Ala |
| Pro<br>145 | Asn | Asp | Asp | Lys | Glu<br>150 | Cys | Val | Thr | Glu | Glu<br>155 | Pro | Phe | Leu | Phe | Cys<br>160 |
| Ser | Leu | Gly | Ser | Phe | Tyr | Ile | Pro | Ile | Ala | Val | Ile | Leu | Val | Met | Tyr |

|  | 165 |  |  |  |  | 170 |  |  |  |  | 175 |  |  |
|---|---|---|---|---|---|---|---|---|---|---|---|---|---|
| Cys | Arg | Val | Tyr<br>180 | Ile | Val | Ala | Lys | Arg<br>185 | Thr | Thr | Lys | Asn<br>190 | Leu | Glu | Ala |
| Gly | Val | Met<br>195 | Lys | Glu | Met | Ser | Asn<br>200 | Ser | Lys | Phe | Leu | Thr<br>205 | Leu | Arg | Ile |
| His | Trp<br>210 | Ser | Lys | Asn | Phe | His<br>215 | Glu | Asp | Thr | Leu | Ser<br>220 | Ser | Thr | Lys | Ala |
| Lys<br>225 | Gly | His | Asn | Pro | Arg<br>230 | Ser | Ser | Ile | Ala | Val<br>235 | Lys | Leu | Phe | Lys | Phe<br>240 |
| Ser | Arg | Glu | Lys | Lys<br>245 | Ala | Ala | Lys | Thr | Leu<br>250 | Gly | Ile | Val | Val | Gly<br>255 | Trp |
| Ile | Leu | Cys | Trp<br>260 | Leu | Pro | Phe | Phe | Ile<br>265 | Ala | Leu | Pro | Leu | Gly<br>270 | Ser | Leu |
| Phe | Ser | Thr<br>275 | Leu | Lys | Pro | Pro | Asp<br>280 | Ala | Val | Phe | Lys | Trp<br>285 | Phe | Trp | Leu |
| Gly | Tyr<br>290 | Phe | Asn | Ser | Cys | Leu<br>295 | Asn | Pro | Ile | Ile | Tyr<br>300 | Pro | Cys | Ser | Ser |
| Lys<br>305 | Glu | Phe | Lys | Arg | Ala<br>310 | Leu | Leu | Gly | Cys | Gln<br>315 | Cys | Arg | Gly | Gly | Arg<br>320 |
| Arg | Arg | Arg | Arg | Arg<br>325 | Arg | Arg | Leu | Ala | Cys<br>330 | Ala | Tyr | Thr | Tyr | Arg<br>335 | Pro |
| Trp | Thr | Arg | Gly<br>340 | Gly | Ser | Leu | Glu | Arg<br>345 | Ser | Gln | Ser | Arg | Lys<br>350 | Asp | Ser |
| Ile | Asp | Asp<br>355 | Ser | Gly | Ser | Cys | Met<br>360 | Ser | Gly | Gln | Lys | Arg<br>365 | Thr | Leu | Pro |
| Ser | Ala<br>370 | | | | | | | | | | | | | | |

( 2 ) INFORMATION FOR SEQ ID NO:19:

( i ) SEQUENCE CHARACTERISTICS:
        ( A ) LENGTH: 330 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

| Val<br>1 | Ala | Gly | Leu | Ala<br>5 | Ala | Val | Val | Gly | Phe<br>10 | Leu | Ile | Val | Phe | Thr<br>15 | Val |
|---|---|---|---|---|---|---|---|---|---|---|---|---|---|---|---|
| Val | Gly | Asn | Val<br>20 | Leu | Val | Val | Ile | Ala<br>25 | Val | Leu | Thr | Ser | Arg<br>30 | Ala | Leu |
| Arg | Ala | Pro | Gln<br>35 | Asn | Leu | Phe | Leu | Val<br>40 | Ser | Ile | Ala | Ser | Ala<br>45 | Asp | Ile |
| Leu | Val<br>50 | Ala | Thr | Leu | Val | Met<br>55 | Pro | Phe | Ser | Leu | Ala<br>60 | Asn | Glu | Ile | Met |
| Tyr<br>65 | Trp | Tyr | Phe | Gly | Gln<br>70 | Val | Trp | Cys | Gly | Val<br>75 | Tyr | Leu | Ala | Ile | Asp<br>80 |
| Val | Leu | Phe | Cys | Thr<br>85 | Ser | Ser | Ile | Val | His<br>90 | Leu | Cys | Ala | Ile | Ser<br>95 | Leu |
| Asp | Arg | Tyr | Trp<br>100 | Ser | Val | Thr | Gln | Ala<br>105 | Val | Glu | Tyr | Asn | Leu<br>110 | Lys | Arg |
| Thr | Pro | Arg | Arg<br>115 | Val | Lys | Ala | Thr | Ile<br>120 | Val | Ala | Val | Trp | Leu<br>125 | Ile | Ser |
| Ala | Val<br>130 | Ile | Ser | Phe | Pro | Pro<br>135 | Leu | Val | Ser | Leu | Tyr<br>140 | Arg | Gln | Pro | Asp |

| Gly | Ala | Ala | Tyr | Pro | Gln | Cys | Gly | Leu | Asn | Asp | Glu | Thr | Trp | Tyr | Ile |
| --- | --- | --- | --- | --- | --- | --- | --- | --- | --- | --- | --- | --- | --- | --- | --- |
| 145 | | | | 150 | | | | | 155 | | | | | | 160 |
| Leu | Ser | Ser | Cys | Ile | Gly | Ser | Phe | Phe | Ala | Pro | Cys | Leu | Ile | Tyr | Leu |
| | | | | 165 | | | | | 170 | | | | | 175 | |
| Leu | Val | Tyr | Ala | Arg | Ile | Tyr | Arg | Val | Ala | Lys | Arg | Arg | Thr | Arg | Thr |
| | | | 180 | | | | | 185 | | | | | 190 | | |
| Leu | Ser | Glu | Lys | Arg | Ala | Pro | Val | Gly | Pro | Asp | Gly | Ala | Ser | Pro | Thr |
| | | | 195 | | | | 200 | | | | | 205 | | | |
| Thr | Glu | Asn | Gly | Leu | Gly | Ala | Ala | Ala | Gly | Glu | Ala | Arg | Thr | Gly | Thr |
| | | 210 | | | | | 215 | | | | | 220 | | | |
| Ala | Arg | Phe | Leu | Ser | Arg | Arg | Arg | Ala | Arg | Ser | Ser | Val | Cys | Arg |
| 225 | | | | | 230 | | | | 235 | | | | | 240 |
| Arg | Lys | Val | Ala | Gln | Ala | Arg | Glu | Lys | Arg | Phe | Thr | Phe | Val | Leu | Ala |
| | | | | 245 | | | | | 250 | | | | | 255 | |
| Leu | Val | Phe | Val | Leu | Cys | Trp | Phe | Pro | Phe | Phe | Phe | Ile | Tyr | Ser | Leu |
| | | | 260 | | | | | 265 | | | | | 270 | | |
| Tyr | Gly | Ile | Cys | Arg | Glu | Ala | Cys | Gln | Val | Pro | Gly | Pro | Leu | Phe | Lys |
| | | 275 | | | | | 280 | | | | | 285 | | | |
| Phe | Phe | Phe | Trp | Ile | Gly | Tyr | Cys | Asn | Ser | Ser | Leu | Asn | Pro | Val | Ile |
| | 290 | | | | | 295 | | | | | 300 | | | | |
| Tyr | Thr | Val | Phe | Asn | Gln | Asp | Phe | Arg | Pro | Ser | Phe | Lys | His | Ile | Leu |
| 305 | | | | | 310 | | | | | 315 | | | | | 320 |
| Phe | Arg | Arg | Arg | Arg | Arg | Gly | Phe | Arg | Gln |
| | | | | 325 | | | | | 330 |

( 2 ) INFORMATION FOR SEQ ID NO:20:

( i ) SEQUENCE CHARACTERISTICS:
( A ) LENGTH: 330 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:20:

| Thr | Ala | Ala | Ile | Ala | Ala | Ala | Ile | Thr | Phe | Leu | Ile | Leu | Phe | Thr | Ile |
| --- | --- | --- | --- | --- | --- | --- | --- | --- | --- | --- | --- | --- | --- | --- | --- |
| 1 | | | | 5 | | | | | 10 | | | | | 15 | |
| Phe | Gly | Asn | Ala | Leu | Val | Ile | Ile | Ala | Val | Leu | Thr | Ser | Arg | Ser | Leu |
| | | | 20 | | | | | 25 | | | | | 30 | | |
| Arg | Ala | Pro | Gln | Asn | Leu | Phe | Leu | Val | Ser | Ile | Ala | Ala | Ala | Asp | Ile |
| | | 35 | | | | | 40 | | | | | 45 | | | |
| Leu | Val | Ala | Thr | Leu | Ile | Ile | Pro | Phe | Ser | Leu | Ala | Asn | Glu | Leu | Leu |
| | 50 | | | | | 55 | | | | | 60 | | | | |
| Gly | Tyr | Trp | Tyr | Phe | Arg | Arg | Thr | Trp | Cys | Glu | Val | Tyr | Leu | Ala | Leu |
| 65 | | | | | 70 | | | | | 75 | | | | | 80 |
| Asp | Val | Leu | Phe | Cys | Thr | Ser | Ser | Ile | Val | His | Leu | Cys | Ala | Ile | Ser |
| | | | | 85 | | | | | 90 | | | | | 95 | |
| Leu | Asp | Arg | Tyr | Trp | Ala | Val | Ser | Arg | Ala | Leu | Glu | Tyr | Asn | Ser | Lys |
| | | | | 100 | | | | | 105 | | | | | 110 | |
| Arg | Thr | Pro | Arg | Arg | Ile | Lys | Cys | Ile | Ile | Leu | Thr | Val | Trp | Leu | Ile |
| | | | 115 | | | | | 120 | | | | | 125 | | |
| Ala | Ala | Val | Ile | Ser | Leu | Pro | Pro | Leu | Ile | Tyr | Lys | Gly | Asp | Gln | Gly |
| | | | 130 | | | | 135 | | | | | 140 | | | |
| Pro | Gln | Pro | Arg | Gly | Arg | Pro | Gln | Cys | Lys | Leu | Asn | Gln | Glu | Ala | Trp |
| 145 | | | | | 150 | | | | | 155 | | | | | 160 |

```
Tyr Ile Leu Ser Ser Ile Gly Ser Phe Phe Ala Pro Cys Leu Ile Leu
                165                 170                 175

Leu Val Tyr Leu Arg Ile Tyr Leu Ile Ala Lys Arg Ser Asn Arg Arg
            180                 185             190

Gly Pro Arg Ala Lys Cys Gly Pro Gly Gln Gly Glu Ser Lys Gln Pro
        195                 200             205

Arg Pro Asp His Gly Gly Ala Ile Ala Ser Ala Lys Leu Pro Ala Ile
    210                 215             220

Ala Ser Gly Arg Gly Val Gly Ala Ile Gly Gly Gln Trp Trp Arg Arg
225                 230             235                     240

Arg Ala His Val Thr Arg Glu Lys Arg Phe Thr Phe Val Leu Ala Val
            245             250             255

Val Ile Gly Val Phe Val Leu Cys Trp Phe Pro Phe Phe Ser Tyr
            260             265             270

Ser Leu Gly Ala Ile Cys Pro Lys His Cys Lys Val Pro His Gly Leu
        275             280             285

Phe Gln Phe Phe Phe Trp Ile Gly Tyr Cys Asn Ser Ser Leu Asn Pro
    290             295             300

Val Ile Tyr Thr Ile Phe Asn Gln Asp Phe Arg Met Phe Arg Arg Ile
305             310             315                     320

Leu Cys Arg Pro Trp Thr Gln Thr Ala Trp
            325             330
```

(2) INFORMATION FOR SEQ ID NO:21:

(i) SEQUENCE CHARACTERISTICS:
       (A) LENGTH: 330 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:21:

```
Thr Leu Thr Leu Val Cys Ile Ala Cys Leu Ser Leu Thr Val Phe Gly
1               5                   10                  15

Asn Val Leu Val Ile Ile Ala Val Phe Thr Ser Arg Ala Leu Lys Ala
            20                  25              30

Pro Gln Asn Leu Phe Leu Val Ser Ile Ala Ser Ala Asp Ile Leu Val
        35              40              45

Ala Thr Leu Val Ile Pro Phe Ser Leu Ala Asn Glu Val Asn Gly Tyr
    50              55              60

Trp Tyr Phe Gly Lys Trp Cys Glu Ile Tyr Leu Ala Leu Asp Val Leu
65              70              75                      80

Phe Cys Thr Ser Ser Ile Val His Leu Cys Ala Ile Ser Leu Asp Arg
            85              90              95

Tyr Trp Ser Ile Thr Gln Ala Ile Glu Tyr Asn Leu Lys Arg Thr Pro
            100             105             110

Arg Arg Ile Lys Ala Ile Ile Ile Thr Val Trp Val Ile Ser Ala Val
        115             120             125

Ile Ser Phe Pro Pro Leu Ile Ser Ile Glu Lys Lys Gly Gly Gly Gly
    130             135             140

Gly Pro Gln Pro Ala Glu Pro Arg Cys Glu Ile Asn Asp Gln Lys Trp
145             150             155                     160

Tyr Val Ile Ser Ser Cys Ile Gly Ser Phe Phe Ala Pro Cys Leu Ile
            165             170             175

Trp Leu Val Tyr Val Arg Ile Tyr Gln Ile Ala Lys Arg Arg Thr Arg
```

|     |     |            |     |     |     |     |     |     |     |     |            |     |     |     |
|-----|-----|------------|-----|-----|-----|-----|-----|-----|-----|-----|------------|-----|-----|-----|
|     |     |            |     |     | 180 |     |     |     | 185 |     |            |     | 190 |     |
| Val | Pro | Pro<br>195 | Ser | Arg | Arg | Asp | Pro<br>200 | Asp | Ala | Val | Ala<br>205 | Ala | Pro | Pro | Gly |
| Gly | Thr<br>210 | Glu | Arg | Arg | Pro | Asn<br>215 | Gly | Leu | Gly | Pro | Glu<br>220 | Arg | Ser | Ala | Gly |
| Pro<br>225 | Gly | Gly | Gly | Arg | Gly<br>230 | Arg | Ser | Ala | Ser | Gly<br>235 | Leu | Pro | Arg | Arg | Arg<br>240 |
| Ala | Gly | Ala | Gly | Gly<br>245 | Gln | Asn | Arg | Glu | Lys<br>250 | Arg | Phe | Thr | Phe | Val<br>255 | Ile |
| Ala | Val | Val | Ile<br>260 | Gly | Val | Phe | Val | Val<br>265 | Cys | Trp | Phe | Pro<br>270 | Phe | Phe | Phe |
| Thr | Tyr | Thr<br>275 | Leu | Thr | Ala | Val | Leu<br>280 | Cys | Ser | Val | Pro<br>285 | Arg | Thr | Leu | Phe |
| Lys | Phe<br>290 | Phe | Phe | Trp | Phe | Gly<br>295 | Tyr | Cys | Asn | Ser | Ser<br>300 | Leu | Asn | Pro | Val |
| Ile<br>305 | Tyr | Thr | Ile | Phe | Asn<br>310 | His | Asp | Phe | Arg | Arg<br>315 | Ala | Phe | Lys | Lys | Ile<br>320 |
| Leu | Cys | Arg | Gly | Asp<br>325 | Arg | Lys | Arg | Ile | Val<br>330 |

( 2 ) INFORMATION FOR SEQ ID NO:22:

( i ) SEQUENCE CHARACTERISTICS:
        ( A ) LENGTH: 334 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

| Thr<br>1 | Leu | Thr | Leu | Val<br>5 | Cys | Ile | Ala | Gly | Leu<br>10 | Ile | Met | Leu | Phe | Thr<br>15 | Val |
|----|----|----|----|----|----|----|----|----|----|----|----|----|----|----|----|
| Phe | Gly | Asn | Val<br>20 | Leu | Val | Ile | Ile | Ala<br>25 | Val | Phe | Thr | Ser | Arg<br>30 | Ala | Leu |
| Lys | Ala | Pro<br>35 | Gln | Asn | Leu | Phe | Leu<br>40 | Val | Ser | Ile | Ala | Ser<br>45 | Ala | Asp | Ile |
| Leu | Val<br>50 | Ala | Thr | Leu | Val | Ile<br>55 | Pro | Phe | Ser | Leu | Ala<br>60 | Asn | Glu | Val | Met |
| Tyr<br>65 | Trp | Tyr | Phe | Gly | Lys<br>70 | Val | Trp | Cys | Glu | Ile<br>75 | Tyr | Leu | Ala | Ile<br>80 | Asp |
| Val | Leu | Phe | Cys | Thr<br>85 | Ser | Ser | Ile | Val | His<br>90 | Leu | Cys | Ala | Ile<br>95 | Ser | Leu |
| Asp | Arg | Tyr | Trp<br>100 | Ser | Ile | Thr | Gln | Ala<br>105 | Ile | Glu | Tyr | Asn | Leu<br>110 | Lys | Arg |
| Thr | Pro | Arg<br>115 | Arg | Ile | Lys | Ala | Ile<br>120 | Ile | Val | Thr | Val | Trp<br>125 | Val | Ile | Ser |
| Ala | Val<br>130 | Ile | Ser | Phe | Pro | Pro<br>135 | Leu | Leu | Ile | Ser | Ile<br>140 | Glu | Lys | Lys | Gly |
| Ala<br>145 | Gly | Gly | Gly | Gln | Gln<br>150 | Pro | Ala | Glu | Pro | Ser<br>155 | Cys | Lys | Ile | Asn | Asp<br>160 |
| Gln | Lys | Trp | Tyr | Val<br>165 | Ile | Ser | Ser | Ser | Ile<br>170 | Gly | Ser | Phe | Phe | Ala<br>175 | Pro |
| Cys | Leu | Ile | Asn<br>180 | His | Leu | Val | Tyr | Val<br>185 | Arg | Ile | Tyr | Gln | Ile<br>190 | Ala | Lys |
| Arg | Arg | Thr<br>195 | Arg | Val | Pro | Pro | Ser<br>200 | Arg | Arg | Gly | Pro | Asp<br>205 | Ala | Cys | Ser |

```
Ala  Pro  Pro  Gly  Gly  Ala  Asp  Arg  Arg  Pro  Asn  Ala  Val  Gly  Pro  Glu
     210                 215                      220

Arg  Gly  Ala  Gly  Thr  Ala  Gly  Gly  Gln  Gly  Glu  Glu  Arg  Ala  Gly  Gly
225                      230                 235                           240

Ala  Lys  Ala  Ser  Arg  Trp  Arg  Gly  Arg  Gln  Asn  Arg  Glu  Lys  Arg  Phe
               245                      250                           255

Thr  Phe  Val  Ile  Ala  Val  Val  Ile  Gly  Val  Phe  Val  Val  Cys  Trp  Phe
               260                 265                      270

Pro  Phe  Phe  Phe  Thr  Tyr  Thr  Leu  Ile  Ala  Val  Gly  Cys  Pro  Val  Pro
          275                      280                 285

Tyr  Gln  Leu  Phe  Asn  Phe  Phe  Phe  Trp  Phe  Gly  Tyr  Cys  Asn  Ser  Ser
     290                      295                      300

Leu  Asn  Pro  Val  Ile  Tyr  Thr  Ile  Phe  Asn  His  Asp  Phe  Arg  Arg  Ala
305                      310                      315                      320

Phe  Lys  Lys  Ile  Leu  Cys  Arg  Gly  Asp  Arg  Lys  Arg  Ile  Val
               325                      330
```

(2) INFORMATION FOR SEQ ID NO:23:

(i) SEQUENCE CHARACTERISTICS:
        (A) LENGTH: 321 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Leu  Leu  Thr  Ala  Leu  Val  Leu  Ser  Val  Ile  Val  Leu  Thr  Ile  Ile
1               5                    10                       15

Gly  Asn  Ile  Leu  Val  Ile  Leu  Ser  Val  Phe  Thr  Tyr  Lys  Pro  Leu  Arg
               20                      25                       30

Ile  Val  Gln  Asn  Phe  Phe  Ile  Val  Ser  Ile  Ala  Val  Ala  Asp  Leu  Thr
               35                      40                       45

Val  Ala  Leu  Leu  Val  Leu  Pro  Phe  Trp  Ala  Tyr  Ser  Ile  Leu  Gly  Arg
     50                      55                       60

Trp  Glu  Phe  Gly  Ile  His  Leu  Cys  Lys  Leu  Trp  Leu  Thr  Cys  Asp  Val
65                       70                      75                       80

Leu  Cys  Cys  Thr  Ser  Ser  Ile  Leu  Asn  Leu  Cys  Ala  Ile  Ala  Leu  Asp
                    85                      90                       95

Arg  Tyr  Trp  Ala  Ile  Thr  Asp  Pro  Ile  Asn  Tyr  Ala  Gln  Lys  Arg  Thr
               100                     105                      110

Val  Gly  Arg  Val  Leu  Leu  Leu  Ile  Ser  Gly  Val  Trp  Leu  Leu  Ser  Leu
          115                     120                      125

Leu  Ile  Ser  Ser  Pro  Pro  Leu  Ile  Gly  Trp  Asn  Asp  Trp  Pro  Asp  Glu
     130                     135                      140

Phe  Thr  Ser  Ala  Thr  Pro  Cys  Glu  Leu  Thr  Ser  Gln  Arg  Ile  Gly  Tyr
145                     150                      155                      160

Val  Ile  Tyr  Ser  Ser  Leu  Gly  Ser  Phe  Phe  Ile  Pro  Ile  Ala  Ile  Met
                    165                     170                      175

Arg  Ile  Val  Tyr  Ile  Glu  Ile  Phe  Val  Ala  Thr  Arg  Arg  Arg  Leu  Arg
               180                     185                      190

Glu  Arg  Ala  Arg  Ala  Asn  Lys  Ile  Asn  Thr  Ile  Ala  Leu  Lys  Ser  Thr
          195                     200                      205

Glu  Leu  Glu  Pro  Met  Ala  Asn  Ser  Ser  Pro  Val  Ala  Ala  Ser  Asn  Ser
     210                     215                      220
```

```
Gly Ser Lys Lys Lys Thr Ser Gly Val Asn Gln Phe Ile Glu Glu Lys
225                 230                 235                 240

Gln Lys Ile Ser Leu Ser Lys Glu Arg Arg Ala Ala Arg Thr Leu Gly
                245                 250                 255

Ile Ile Met Val Phe Val Ile Cys Trp Leu Pro Phe Phe Ile Met Tyr
            260                 265                 270

Val Ile Leu Pro Phe Cys Cys Pro Thr Asn Lys Phe Lys Asn Phe Ile
            275                 280                 285

Thr Trp Leu Gly Tyr Ile Asn Ser Gly Leu Asn Pro Val Ile Tyr Thr
    290                 295                 300

Ile Phe Asn Leu Asp Tyr Arg Arg Ala Phe Lys Arg Leu Leu Gly Leu
305                 310                 315                 320

Asn
```

(2) INFORMATION FOR SEQ ID NO:24:

(i) SEQUENCE CHARACTERISTICS:
  (A) LENGTH: 373 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:24:

```
Arg Ile Leu Thr Ala Cys Phe Leu Ser Leu Leu Ile Leu Ser Thr Leu
1               5                   10                  15

Leu Gly Asn Thr Leu Val Cys Ala Ala Val Ile Arg Phe Arg His Leu
                20                  25                  30

Arg Ser Lys Val Thr Asn Phe Phe Val Ile Ser Leu Ala Val Ser Asp
            35                  40                  45

Leu Leu Val Ala Val Leu Leu Trp Lys Ala Val Ala Glu Ile Ala Gly
    50                  55                  60

Phe Trp Pro Phe Gly Ser Phe Cys Asn Ile Trp Val Ala Phe Asp Ile
65                  70                  75                  80

Met Cys Ser Thr Ala Ser Ile Leu Asn Leu Cys Val Ile Ser Val Asp
                85                  90                  95

Arg Tyr Trp Ala Ile Ser Ser Pro Phe Arg Tyr Glu Arg Lys Lys Arg
            100                 105                 110

Pro Lys Ala Ala Phe Ile Leu Ile Ser Val Ala Trp Thr Leu Ser Val
        115                 120                 125

Leu Ile Ser Phe Ile Pro Val Gln Leu Ser Trp His Lys Ala Lys Pro
    130                 135                 140

Thr Ser Pro Ser Asp Gly Met Ala Thr Ser Leu Ala Glu Thr Ile Asp
145                 150                 155                 160

Asn Cys Asp Ser Ser Leu Ser Arg Thr Tyr Ala Ile Ser Ser Ser Val
                165                 170                 175

Ile Ser Phe Tyr Ile Pro Val Ala Ile Leu Val Thr Tyr Thr Arg Ile
            180                 185                 190

Tyr Arg Ile Ala Gln Lys Gln Ile Arg Arg Ile Ala Ala Leu Glu Arg
        195                 200                 205

Ala Ala Val His Ala Lys Asn Cys Gln Gly Asn Lys Pro Val Glu Cys
210                 215                 220

Ser Gln Pro Glu Ser Ser Phe Met Ser Phe Lys Arg Glu Thr Lys Val
225                 230                 235                 240

Leu Lys Thr Leu Ser Val Ile Thr Cys Val Phe Val Cys Cys Trp Leu
                245                 250                 255
```

```
    Pro  Phe  Phe  Ile  Leu  Asn  Cys  Ile  Leu  Pro  Phe  Cys  Gly  Ser  Gly  Glu
                   260                      265                     270

Thr  Gln  Pro  Phe  Cys  Thr  Asp  Ser  Asn  Thr  Phe  Asp  Val  Phe  Val  Trp
              275                      280                     285

Phe  Gly  Trp  Ala  Asn  Ser  Ser  Leu  Asn  Pro  Ile  Ile  Tyr  Ala  Phe  Asn
         290                      295                     300

Ala  Asp  Phe  Arg  Lys  Ala  Phe  Ser  Thr  Leu  Leu  Gly  Cys  Tyr  Arg  Leu
    305                 310                      315                          320

Cys  Pro  Ala  Thr  Asn  Met  Ala  Ile  Glu  Thr  Val  Ser  Ile  Asn  Asn  Gly
                        325                      330                     335

Ala  Ala  Met  Phe  Ser  Ser  His  His  Glu  Pro  Arg  Gly  Ser  Ile  Ser  Lys
                   340                      345                     350

Glu  Cys  Asn  Leu  Val  Tyr  Leu  Ile  Pro  His  Ala  Val  Gly  Ser  Ser  Glu
              355                      360                     365

Asp  Leu  Lys  Lys  Glu
         370
```

(2) INFORMATION FOR SEQ ID NO:25:

(i) SEQUENCE CHARACTERISTICS:
    (A) LENGTH: 360 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:25:

```
    Gln  Trp  Thr  Ala  Cys  Leu  Leu  Thr  Leu  Leu  Ile  Ile  Trp  Thr  Leu  Leu
    1              5                        10                      15

Gly  Asn  Val  Leu  Val  Cys  Ala  Ala  Ile  Val  Arg  Ser  Arg  His  Leu  Leu
                   20                      25                      30

Val  Phe  Ile  Val  Ser  Ile  Ala  Val  Ser  Asp  Leu  Phe  Val  Ala  Leu  Leu
              35                       40                      45

Val  Asn  Thr  Trp  Lys  Ala  Tyr  Ala  Glu  Val  Ala  Gly  Tyr  Trp  Pro  Phe
         50                      55                      60

Gly  Ala  Phe  Cys  Asp  Val  Trp  Val  Ala  Phe  Asp  Ile  Met  Cys  Ser  Thr
    65                  70                      75                           80

Ala  Ser  Ile  Leu  Asn  Leu  Cys  Val  Ile  Ser  Val  Asp  Arg  Tyr  Trp  Ala
                        85                      90                      95

Ile  Ser  Arg  Pro  Phe  Arg  Tyr  Lys  Ala  Leu  Val  Met  Val  Gly  Ile  Ala
                   100                      105                     110

Trp  Thr  Leu  Ser  Ile  Leu  Ile  Ser  Phe  Ile  Pro  Val  Gln  Ile  Asn  Trp
              115                      120                     125

Asn  Arg  Asp  Gln  Ala  Ala  Ser  Trp  Gly  Gly  Leu  Asp  Leu  Pro  Asn  Asn
         130                      135                     140

Ile  Asp  Cys  Asp  Ser  Ser  Leu  Asn  Arg  Thr  Tyr  Ala  Ile  Ser  Ser  Ser
    145                 150                      155                          160

Leu  Ile  Ser  Phe  Tyr  Ile  Pro  Val  Ala  Ile  Leu  Val  Thr  Tyr  Thr  Arg
                   165                      170                     175

Ile  Tyr  Arg  Ile  Ala  Gln  Val  Gln  Ile  Arg  Arg  Ile  Ser  Ser  Leu  Glu
                   180                      185                     190

Arg  Ala  Ala  Glu  His  Ala  Gln  Ser  Cys  Arg  Ser  Ser  Ala  Ala  Cys  Ala
              195                      200                     205

Pro  Asp  Thr  Ser  Leu  Arg  Ala  Ser  Ile  Lys  Lys  Glu  Thr  Lys  Val  Leu
         210                      215                     220
```

| | | | | | | | | | | | | | | |
|---|---|---|---|---|---|---|---|---|---|---|---|---|---|---|
| Lys 225 | Thr | Leu | Ser | Val | Ile 230 | Ile | Cys | Val | Phe | Cys 235 | Cys | Trp | Leu | Pro 240 |
| Phe | Phe | Ile | Leu | Asn 245 | Cys | Met | Val | Pro | Phe 250 | Cys | Ser | Gly | His | Pro 255 | Glu |
| Gly | Pro | Pro | Ala 260 | Gly | Phe | Pro | Cys | Val 265 | Ser | Glu | Thr | Thr | Phe 270 | Asp | Val |
| Phe | Val | Trp 275 | Phe | Gly | Trp | Ala | Asn 280 | Ser | Ser | Leu | Asn | Pro 285 | Val | Ile | Tyr |
| Ala | Phe 290 | Asn | Ala | Asp | Phe | Gln 295 | Lys | Val | Phe | Ala | Gln 300 | Leu | Leu | Cys | Ser |
| His 305 | Phe | Cys | Ser | Arg | Thr 310 | Pro | Val | Glu | Thr | Val 315 | Asn | Ile | Ser | Asn | Glu 320 |
| Leu | Ile | Ser | Tyr | Asn 325 | Gln | Asp | Ile | Val | Phe 330 | His | Lys | Glu | Ile | Ala 335 | Ala |
| Ala | Tyr | Ile | His 340 | Met | Met | Pro | Asn | Ala 345 | Val | Thr | Pro | Gly | Asn 350 | Arg | Glu |
| Val | Asp | Asn 355 | Asp | Glu | Glu | Glu | Gly 360 | | | | | | | | |

( 2 ) INFORMATION FOR SEQ ID NO:26:

( i ) SEQUENCE CHARACTERISTICS:
        ( A ) LENGTH: 314 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

| | | | | | | | | | | | | | | |
|---|---|---|---|---|---|---|---|---|---|---|---|---|---|---|
| Tyr 1 | Asn | Tyr | Tyr | Ala 5 | Thr | Leu | Leu | Thr | Leu 10 | Leu | Ile | Ala | Val | Ile 15 | Val |
| Phe | Gly | Asn | Val 20 | Leu | Val | Cys | Met | Ala 25 | Val | Ser | Arg | Glu | Lys 30 | Ala | Leu |
| Gln | Thr | Met 35 | Asn | Tyr | Leu | Ile | Val 40 | Ser | Ile | Ala | Val | Ala 45 | Asp | Leu | Leu |
| Val | Ala 50 | Thr | Leu | Val | Trp | Trp 55 | Trp | Tyr | Leu | Glu | Val 60 | Val | Gly | Glu | Trp |
| Lys 65 | Phe | Ser | Arg | Ile | His 70 | Cys | Asp | Ile | Phe | Val 75 | Thr | Leu | Asp | Ile | Thr 80 |
| Ala | Ser | Ile | Leu | Asn 85 | Leu | Cys | Ala | Ile | Ser 90 | Ile | Asp | Arg | Tyr | Thr 95 | Ala |
| Val | Ala | Met | Pro 100 | Met | Leu | Tyr | Asn | Thr 105 | Arg | Tyr | Ser | Ser | Lys 110 | Arg | Arg |
| Val | Thr | Val 115 | Met | Ile | Ser | Ile | Val 120 | Trp | Val | Leu | Ser | Phe 125 | Thr | Ile | Ser |
| Cys | Pro 130 | Leu | Leu | Phe | Gly | Leu 135 | Asn | Asn | Ala | Asp | Gln 140 | Asn | Glu | Cys | Ile |
| Ile | Ala 145 | Asn | Pro | Ala | Phe | Val 150 | Val | Tyr | Ser | Ser | Ile 155 | Val | Ser | Phe | Tyr 160 |
| Val | Pro | Phe | Ile | Val 165 | Thr | Leu | Leu | Val | Tyr 170 | Ile | Lys | Ile | Tyr | Ile 175 | Val |
| Leu | Arg | Arg | Arg 180 | Arg | Lys | Arg | Val | Asn 185 | Thr | Lys | Arg | Ser | Ser 190 | Arg | Ala |
| Phe | Arg | Ala 195 | His | Leu | Arg | Ala | Pro 200 | Leu | Lys | Gly | Asn | Cys 205 | Thr | His | Pro |
| Glu | Asp | Met | Lys | Leu | Cys | Thr | Val | Ile | Pro | Asn | Gly | Lys | Thr | Arg | Thr |

|     |     |     |     |     | 210 |     |     |     |     | 215 |     |     |     |     | 220 |     |     |     |     |
| --- | --- | --- | --- | --- | --- | --- | --- | --- | --- | --- | --- | --- | --- | --- | --- | --- | --- | --- | --- |
| Ser | Leu | Lys | Thr | Met | Ser | Arg | Arg | Lys | Leu | Ser | Gln | Gln | Lys | Glu | Lys |
| 225 |     |     |     | 230 |     |     |     |     | 235 |     |     |     |     |     | 240 |
| Lys | Ala | Thr | Gln | Met | Ile | Ala | Ile | Val | Leu | Gly | Val | Phe | Ile | Ile | Cys |
|     |     |     |     | 245 |     |     |     |     | 250 |     |     |     |     | 255 |     |
| Lys | Leu | Pro | Phe | Phe | Ile | Thr | His | Ile | Leu | Asn | Ile | His | Cys | Asp | Cys |
|     |     |     | 260 |     |     |     |     | 265 |     |     |     | 270 |     |     |     |
| Asn | Ile | Pro | Pro | Val | Leu | Tyr | Ser | Ala | Phe | Thr | Trp | Leu | Gly | Tyr | Val |
|     |     | 275 |     |     |     |     | 280 |     |     |     |     | 285 |     |     |     |
| Asn | Ser | Ala | Val | Asn | Pro | Ile | Ile | Tyr | Thr | Thr | Phe | Asn | Ile | Glu | Phe |
|     | 290 |     |     |     |     | 295 |     |     |     |     | 300 |     |     |     |     |
| Arg | Lys | Ala | Phe | Leu | Lys | Ile | Leu | His | Cys |
| 305 |     |     |     |     | 310 |     |     |     |     |

(2) INFORMATION FOR SEQ ID NO:27:

(i) SEQUENCE CHARACTERISTICS:
      (A) LENGTH: 317 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:27:

| Ala | Tyr | Tyr | Ala | Leu | Ser | Tyr | Cys | Ala | Leu | Ile | Leu | Ala | Ile | Val | Phe |
| --- | --- | --- | --- | --- | --- | --- | --- | --- | --- | --- | --- | --- | --- | --- | --- |
| 1 |   |   |   | 5 |   |   |   |   | 10 |   |   |   |   | 15 |   |
| Gly | Asn | Gly | Leu | Val | Cys | Met | Ala | Val | Leu | Arg | Glu | Lys | Ala | Leu | Gln |
|   |   |   | 20 |   |   |   | 25 |   |   |   |   | 30 |   |   |   |
| Thr | Thr | Thr | Asn | Tyr | Leu | Val | Val | Ser | Leu | Ala | Val | Ala | Asp | Leu | Leu |
|   |   | 35 |   |   |   |   | 40 |   |   |   |   | 45 |   |   |   |
| Val | Ala | Thr | Leu | Val | Trp | Trp | Val | Val | Tyr | Leu | Glu | Val | Thr | Gly | Gly |
|   | 50 |   |   |   |   | 55 |   |   |   |   | 60 |   |   |   |   |
| Val | Trp | Asn | Phe | Ser | Arg | Ile | Cys | Cys | Asp | Val | Phe | Val | Thr | Leu | Asp |
| 65 |   |   |   |   | 70 |   |   |   |   | 75 |   |   |   |   | 80 |
| Val | Met | Met | Thr | Ala | Ser | Ile | Leu | Asn | Leu | Cys | Ala | Ile | Ser | Ile | Asp |
|   |   |   |   | 85 |   |   |   |   | 90 |   |   |   |   | 95 |   |
| Arg | Tyr | Thr | Ala | Val | His | Tyr | Gln | His | Gly | Thr | Gly | Gln | Ser | Ser | Cys |
|   |   |   | 100 |   |   |   |   | 105 |   |   |   |   | 110 |   |   |
| Arg | Arg | Val | Ala | Ile | Met | Ile | Thr | Ala | Val | Trp | Val | Leu | Ala | Phe | Ala |
|   |   | 115 |   |   |   |   | 120 |   |   |   |   | 125 |   |   |   |
| Val | Ser | Cys | Pro | Leu | Leu | Phe | Gly | Phe | Asn | Thr | Gly | Asp | Pro | Thr | Val |
|   | 130 |   |   |   |   | 135 |   |   |   |   | 140 |   |   |   |   |
| Cys | Ser | Ile | Ser | Asn | Pro | Asp | Phe | Val | Ile | Tyr | Ser | Ser | Val | Val | Ser |
| 145 |   |   |   |   | 150 |   |   |   |   | 155 |   |   |   |   | 160 |
| Phe | Tyr | Leu | Pro | Phe | Gly | Val | Thr | Val | Leu | Val | Tyr | Ala | Arg | Ile | Tyr |
|   |   |   |   | 165 |   |   |   |   | 170 |   |   |   |   | 175 |   |
| Val | Val | Leu | Lys | Gln | Arg | Arg | Arg | Lys | Arg | Ile | Leu | Thr | Arg | Gln | Asn |
|   |   |   | 180 |   |   |   |   | 185 |   |   |   |   | 190 |   |   |
| Ser | Gln | Cys | Asn | Ser | Val | Arg | Pro | Gly | Phe | Pro | Gln | Gln | Ser | Thr | Ser |
|   |   | 195 |   |   |   |   | 200 |   |   |   |   | 205 |   |   |   |
| Leu | Pro | Asp | Pro | Ala | His | Leu | Glu | Leu | Lys | Arg | Ser | Asn | Gly | Arg | Leu |
|   | 210 |   |   |   |   | 215 |   |   |   |   | 220 |   |   |   |   |
| Ser | Thr | Ser | Leu | Lys | Leu | Pro | Leu | Gln | Pro | Arg | Gly | Val | Pro | Leu | Arg |
| 225 |   |   |   |   | 230 |   |   |   |   | 235 |   |   |   |   | 240 |
| Glu | Lys | Lys | Ala | Thr | Gln | Met | Val | Ala | Ile | Val | Leu | Gly | Ala | Phe | Ile |
|   |   |   |   | 245 |   |   |   |   | 250 |   |   |   |   | 255 |   |

```
Val Cys Trp Leu Pro Phe Phe Leu Thr His Val Ile Asn Thr His Cys
            260                 265                 270

Gln Thr Cys His Val Ser Pro Glu Leu Tyr Ser Ala Thr Thr Trp Leu
        275                 280                 285

Gly Tyr Val Asn Ser Ala Leu Asn Pro Val Ile Tyr Thr Thr Phe Asn
        290                 295                 300

Ile Glu Phe Arg Lys Ala Phe Leu Lys Ile Leu Ser Cys
305                 310                 315
```

(2) INFORMATION FOR SEQ ID NO:28:

(i) SEQUENCE CHARACTERISTICS:
        (A) LENGTH: 315 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Gly Ala Ala Ala Leu Val Gly Gly Val Leu Leu Ile Cys Ala Val Leu
1               5                   10                  15

Ala Gly Asn Ser Leu Val Cys Val Ser Val Ala Thr Glu Arg Ala Leu
            20                  25                  30

Gln Thr Pro Thr Asn Ser Phe Ile Val Ser Leu Ala Ala Ala Asp Leu
        35                  40                  45

Leu Leu Ala Leu Leu Val Leu Pro Leu Phe Val Tyr Ser Glu Val Gln
50                  55                  60

Gly Ala Ala Trp Leu Leu Ser Pro Arg Leu Cys Asp Val Met Leu Cys
65                  70                  75                  80

Thr Ala Ser Ile Phe Asn Leu Cys Ala Ile Ser Val Asp Arg Phe Val
                85                  90                  95

Ala Val Ala Val Pro Leu Arg Tyr Asn Arg Gln Gly Gly Ser Arg Arg
            100                 105                 110

Gln Leu Leu Leu Ile Gly Ala Thr Trp Leu Leu Ser Ala Ala Val Ala
        115                 120                 125

Ala Pro Val Leu Cys Gly Leu Asn Asp Val Arg Gly Arg Asp Pro Ala
        130                 135                 140

Val Cys Arg Leu Glu Asp Arg Asp Tyr Val Val Tyr Ser Ser Val Cys
145                 150                 155                 160

Ser Phe Phe Leu Pro Cys Pro Leu Leu Tyr Trp Ala Thr Phe Arg Gly
                165                 170                 175

Leu Gln Leu Val Ala Arg Arg Ala Lys Leu His Gly Arg Ala Pro Arg
            180                 185                 190

Arg Pro Ser Gly Pro Gly Pro Pro Ser Pro Thr Pro Pro Ala Pro Arg
        195                 200                 205

Leu Pro Gln Asp Pro Cys Gly Ala Leu Pro Pro Gln Thr Pro Pro Gln
        210                 215                 220

Thr Arg Arg Arg Arg Arg Ala Lys Ile Thr Gly Arg Glu Arg Lys Ala
225                 230                 235                 240

Met Arg Val Leu Pro Val Val Val Gly Ala Phe Ile Leu Cys Trp Thr
                245                 250                 255

Pro Phe Phe Val Val His Ile Thr Gln Ala Leu Cys Pro Ala Cys Ser
            260                 265                 270

Val Pro Pro Arg Leu Val Ser Ala Val Thr Trp Leu Ser Tyr Val Asn
        275                 280                 285
```

| | | | | | | | | | | | | | | |
|---|---|---|---|---|---|---|---|---|---|---|---|---|---|---|
| Ser | Ala | Ile | Asn | Pro | Val | Ile | Tyr | Thr | Val | Phe | Asn | Ala | Glu | Phe | Arg |
| | | | | 290 | | | 295 | | | | | 300 | | | |
| Asn | Val | Phe | Arg | Lys | Ala | Leu | Arg | Ala | Cys | Cys | | | | | |
| 305 | | | | | 310 | | | | | 315 | | | | | |

(2) INFORMATION FOR SEQ ID NO:29:

(i) SEQUENCE CHARACTERISTICS:
        (A) LENGTH: 327 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

| | | | | | | | | | | | | | | |
|---|---|---|---|---|---|---|---|---|---|---|---|---|---|---|
| Lys | Ile | Ser | Leu | Ala | Val | Val | Leu | Ser | Val | Ile | Thr | Leu | Ala | Thr | Val |
| 1 | | | | 5 | | | | 10 | | | | | 15 | | |
| Leu | Ser | Asn | Ala | Phe | Val | Leu | Thr | Arg | Ile | Leu | Leu | Thr | Arg | Lys | Leu |
| | | | 20 | | | | 25 | | | | | 30 | | | |
| His | Thr | Pro | Ala | Asn | Tyr | Leu | Ile | Gly | Ser | Ile | Ala | Thr | Thr | Asp | Leu |
| | | 35 | | | | 40 | | | | | 45 | | | | |
| Leu | Val | Ser | Ile | Leu | Val | Trp | Ile | Ser | Ile | Ala | Tyr | Thr | Ile | Thr | His |
| | 50 | | | | 55 | | | | | 60 | | | | | |
| Thr | Trp | Asn | Phe | Gly | Gln | Ile | Leu | Cys | Asp | Ile | Trp | Leu | Ser | Ser | Asp |
| 65 | | | | | 70 | | | | 75 | | | | | 80 | |
| Ile | Thr | Cys | Cys | Thr | Ala | Ser | Ile | Leu | His | Leu | Cys | Val | Ile | Ala | Leu |
| | | | 85 | | | | | 90 | | | | | 95 | | |
| Asp | Arg | Tyr | Trp | Ala | Ile | Thr | Asp | Ala | Leu | Glu | Tyr | Ser | Lys | Arg | Arg |
| | | | 100 | | | | | 105 | | | | 110 | | | |
| Thr | Ala | Gly | His | Ala | Ala | Thr | Met | Ile | Ala | Ile | Val | Trp | Ala | Ile | Ser |
| | | 115 | | | | | 120 | | | | | 125 | | | |
| Ile | Cys | Ile | Ser | Ile | Pro | Pro | Leu | Phe | Trp | Arg | Ala | Lys | Ala | Gln | Glu |
| | 130 | | | | | 135 | | | | | 140 | | | | |
| Glu | Met | Ser | Asp | Cys | Leu | Val | Asn | Thr | Ser | Gln | Ser | Tyr | Thr | Ile | Tyr |
| 145 | | | | | 150 | | | | | 155 | | | | | 160 |
| Ser | Thr | Cys | Gly | Ala | Phe | Tyr | Ile | Pro | Ser | Val | Leu | Leu | Ile | Ile | Leu |
| | | | | 165 | | | | | 170 | | | | | 175 | |
| Tyr | Gly | Arg | Ile | Tyr | Arg | Ala | Ala | Arg | Asn | Arg | Ile | Leu | Asn | Pro | Pro |
| | | | 180 | | | | | 185 | | | | | 190 | | |
| Ser | Leu | Tyr | Gly | Lys | Arg | Phe | Thr | Thr | Ala | His | Leu | Ile | Thr | Gly | Ser |
| | | | 195 | | | | | 200 | | | | | 205 | | |
| Ala | Gly | Ser | Ser | Leu | Cys | Ser | Leu | Asn | Ser | Ser | Leu | His | Glu | Gly | His |
| | 210 | | | | | 215 | | | | | 220 | | | | |
| Asn | His | Val | Lys | Ile | Lys | Leu | Ala | Asp | Ser | Ala | Leu | Glu | Arg | Lys | Arg |
| 225 | | | | | 230 | | | | | 235 | | | | | 240 |
| Ile | Ser | Ala | Ala | Arg | Glu | Arg | Lys | Ala | Thr | Lys | Ile | Leu | Gly | Ile | Ile |
| | | | | 245 | | | | | 250 | | | | | 255 | |
| Leu | Gly | Ala | Phe | Ile | Ile | Cys | Trp | Leu | Pro | Phe | Phe | Val | Val | Ser | Leu |
| | | | 260 | | | | | 265 | | | | | 270 | | |
| Val | Leu | Pro | Ile | Cys | Arg | Asp | Ser | Cys | Trp | Ile | His | Pro | Ala | Leu | Phe |
| | | 275 | | | | | 280 | | | | | 285 | | | |
| Asp | Phe | Phe | Thr | Trp | Leu | Gly | Tyr | Ile | Asn | Ser | Leu | Ile | Asn | Pro | Ile |
| | | 290 | | | | | 295 | | | | | 300 | | | |
| Ile | Tyr | Thr | Val | Phe | Asn | Glu | Glu | Phe | Arg | Gln | Ala | Phe | Gln | Lys | Ile |
| 305 | | | | | 310 | | | | | 315 | | | | | 320 |
| Val | Pro | Phe | Arg | Lys | Ala | Ser | | | | | | | | | |

(2) INFORMATION FOR SEQ ID NO:30:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Val Ile Thr Ser Leu Leu Leu Gly Thr Leu Ile Phe Cys Ala Val Leu
 1               5                  10                  15
Gly Asn Ala Cys Val Val Ala Ala Ile Ala Leu Glu Arg Ser Leu Gln
             20                  25                  30
Asn Val Ala Asn Tyr Leu Ile Gly Ser Leu Ala Val Arg Asp Leu Met
             35                  40                  45
Val Ser Val Leu Val Leu Pro Met Ala Ala Leu Tyr Gln Val Leu Asn
 50                  55                  60
Lys Trp Thr Leu Gly Gln Val Thr Cys Asp Leu Phe Ile Ala Leu Asp
 65                  70                  75                  80
Val Leu Cys Cys Thr Ser Ser Ile Leu His Leu Cys Ala Ile Ala Leu
             85                  90                  95
Asp Arg Tyr Trp Ala Ile Thr Asp Pro Ile Asp Tyr Val Asn Lys Arg
            100                 105                 110
Thr Pro Arg Pro Arg Ala Leu Ile Ser Leu Thr Trp Leu Ile Gly Phe
            115                 120                 125
Leu Ile Ser Ile Pro Pro Met Leu Gly Trp Arg Thr Pro Glu Asp Arg
            130                 135                 140
Ser Asp Pro Asp Ala Cys Thr Ile Ser Lys Asp His Gly Tyr Thr Ile
145                 150                 155                 160
Tyr Ser Thr Ile Phe Ala Phe Tyr Ile Pro Leu Leu Leu Met Leu Val
                165                 170                 175
Leu Tyr Gly Arg Ile Phe Arg Ala Ala Arg Phe Arg Ile Arg Lys Thr
            180                 185                 190
Val Lys Lys Val Glu Lys Thr Gly Ala Asp Thr Arg His Gly Ala Ser
            195                 200                 205
Pro Ala Pro Gln Pro Lys Lys Ser Val Asn Gly Glu Ser Gly Ser Arg
210                 215                 220
Asn Ala Ser Phe Glu Arg Lys Asn Glu Arg Asn Ala Phe Ala Lys Leu
225                 230                 235                 240
Leu Ala Arg Glu Arg Lys Thr Val Lys Thr Leu Gly Ile Ile Met Thr
                245                 250                 255
Phe Ile Leu Cys Trp Leu Pro Phe Phe Ile Val Ala Leu Val Leu Pro
            260                 265                 270
Phe Cys Glu Ser Ser Cys His Met Pro Thr Leu Ile Arg Ala Ile Ile
            275                 280                 285
Asn Trp Leu Cys Val Ile Asn Ser Leu Leu Asn Pro Val Ile Tyr Ala
            290                 295                 300
Tyr Phe Asn Lys Asp Phe Gln Asn Ala Phe Lys Lys Ile Ile Lys Cys
305                 310                 315                 320
Asn Phe Cys Arg Gln
            325
```

(2) INFORMATION FOR SEQ ID NO:31:

( i ) SEQUENCE CHARACTERISTICS:
   ( A ) LENGTH: 385 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:31:

```
Gln Asn Trp Pro Ala Leu Ser Ile Val Val Ile Ile Ile Asn Thr Ile
1               5                   10                  15

Gly Gly Asn Ile Leu Val Ile Met Ala Val Ser Lys Lys Leu His Asn
            20                  25                  30

Ala Thr Asn Tyr Phe Leu Met Ser Ile Ala Ile Ala Asp Met Leu Val
        35                  40                  45

Gly Phe Leu Val Trp Leu Ser Leu Leu Ala Ile Leu Tyr Asp Tyr Val
    50                  55                  60

Trp Pro Leu Pro Arg Tyr Leu Cys Pro Val Trp Ile Ser Leu Asp Val
65              70                  75                  80

Leu Phe Ser Thr Ala Ser Ile Met His Leu Cys Ala Ile Ser Leu Asp
                85                  90                  95

Arg Tyr Val Ala Ile Arg Asn Pro Ile Glu His Ser Arg Phe Ser Arg
            100                 105                 110

Thr Lys Ala Ile Met Lys Ile Ala Ile Val Trp Ala Ile Ser Ile Gly
        115                 120                 125

Val Ser Val Pro Ile Pro Val Ile Gly Leu Arg Asp Glu Ser Lys Val
    130                 135                 140

Phe Val Asn Asn Thr Thr Ile Cys Val Leu Asn Asp Pro Asn Phe Val
145                 150                 155                 160

Leu Ile Gly Ser Phe Val Ala Phe Phe Ile Pro Thr Leu Ile Met Val
                165                 170                 175

Ile Thr Tyr Phe Leu Thr Ile Tyr Val Leu Arg Arg Gln Thr Leu Met
            180                 185                 190

Leu Leu Arg Gly His Thr Glu Glu Glu Ile Ala Met Ser Leu Asn Phe
        195                 200                 205

Leu Asn Cys Cys Cys Lys Lys Asn Gly Gly Glu Glu Asn Ala Pro
210                 215                 220

Asn Asn Pro Asn Pro Asp Gln Lys Pro Arg Arg Lys Lys Lys Glu Lys
225                 230                 235                 240

Arg Pro Arg Gly Thr Met Gln Ala Ile Asn Asn Glu Lys Lys Ala Ser
            245                 250                 255

Lys Val Leu Gly Ile Val Phe Phe Val Phe Leu Ile Met Trp Cys Pro
        260                 265                 270

Phe Phe Ile Thr Asn Ile Leu Ser Val Leu Cys Gly Lys Ala Cys Asn
    275                 280                 285

Gln Cys Lys Leu Leu Asn Val Phe Val Trp Ile Gly Tyr Val Cys Ser
290                 295                 300

Gly Ile Asn Pro Val Ile Tyr Thr Leu Phe Asn Lys Ile Tyr Arg Arg
305                 310                 315                 320

Ala Phe Ser Lys Tyr Leu Arg Cys Asp Tyr Lys Pro Asp Lys Lys Pro
            325                 330                 335

Pro Val Arg Gln Ile Pro Arg Val Ala Ala Thr Ala Leu Ser Gly Arg
        340                 345                 350

Glu Leu Asn Val Asn Ile Tyr Arg His Thr Asn Glu Arg Val Ala Arg
    355                 360                 365
```

| | | | | | | | | | | | | | | |
|---|---|---|---|---|---|---|---|---|---|---|---|---|---|---|
|Lys|Ala|Asn|Asp|Pro|Glu|Pro|Gly|Ile|Glu|Asn|Gln|Val|Glu|Asn|Leu|
| |370| | | |375| | | | |380| | | | |

Glu

385

( 2 ) INFORMATION FOR SEQ ID NO:32:

( i ) SEQUENCE CHARACTERISTICS:
( A ) LENGTH: 379 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:32:

| | | | | | | | | | | | | | | |
|---|---|---|---|---|---|---|---|---|---|---|---|---|---|---|
|Lys|Asn|Trp|Ser|Ala|Leu|Leu|Thr|Thr|Val|Ile|Ile|Leu|Thr|Ile|
|1| | | |5| | | | |10| | | | |15|
|Ala|Gly|Asn|Ile|Leu|Val|Ile|Met|Ala|Val|Ser|Leu|Glu|Lys|Lys|Leu|
| | | |20| | | | |25| | | | |30| | |
|Gln|Asn|Ala|Thr|Asn|Tyr|Phe|Leu|Met|Ser|Leu|Ala|Ile|Ala|Asp|Met|
| | |35| | | | |40| | | | |45| | | |
|Leu|Leu|Gly|Phe|Leu|Val|Trp|Val|Ser|Asn|Glu|Thr|Ile|Leu|Tyr|Gly|
| |50| | | | |55| | | | |60| | | | |
|Tyr|Arg|Trp|Pro|Leu|Pro|Ser|Lys|Leu|Cys|Ala|Ile|Trp|Ile|Tyr|Leu|
|65| | | | |70| | | | |75| | | | |80|
|Asp|Val|Leu|Phe|Ser|Thr|Ala|Ser|Ile|Met|His|Leu|Cys|Ala|Ile|Ser|
| | | | |85| | | | |90| | | | |95| |
|Leu|Asp|Arg|Tyr|Val|Ala|Ile|Gln|Asn|Pro|Ile|His|His|Ser|Arg|Phe|
| | | |100| | | | |105| | | | |110| | |
|Asn|Ser|Arg|Thr|Lys|Ala|Phe|Leu|Lys|Ile|Ile|Ala|Val|Trp|Thr|Ile|
| | |115| | | | |120| | | | |125| | | |
|Ser|Val|Gly|Ile|Ser|Met|Pro|Ile|Pro|Val|Phe|Gly|Leu|Gln|Asp|Asp|
| |130| | | | |135| | | | |140| | | | |
|Ser|Lys|Val|Phe|Lys|Glu|Gly|Ser|Cys|Leu|Leu|Ala|Asp|Asp|Asn|Phe|
|145| | | | |150| | | | |155| | | | |160|
|Val|Leu|Ile|Gly|Ser|Phe|Val|Ala|Phe|Phe|Ile|Pro|Leu|Thr|Ile|Met|
| | | | |165| | | | |170| | | | |175| |
|Val|Ile|Thr|Tyr|Phe|Leu|Thr|Ile|Lys|Ser|Leu|Arg|Gln|Lys|Phe|Ala|
| | | |180| | | | |185| | | | |190| | |
|Thr|Leu|Cys|Val|Ser|Asp|Leu|Ser|Thr|Arg|Ala|Lys|Leu|Ala|Ser|Phe|
| | |195| | | | |200| | | | |205| | | |
|Ser|Phe|Leu|Pro|Gln|Ser|Ser|Leu|Ser|Ser|Glu|Lys|Leu|Phe|Gln|Arg|
| |210| | | | |215| | | | |220| | | | |
|Ser|Ile|His|Arg|Glu|Pro|Gly|Ser|Tyr|Ala|Gly|Arg|Lys|Thr|Met|Gln|
|225| | | | |230| | | | |235| | | | |240|
|Ser|Ile|Ser|Asn|Glu|Gln|Lys|Ala|Cys|Lys|Val|Leu|Gly|Ile|Val|Phe|
| | | | |245| | | | |250| | | | |255| |
|Phe|Leu|Phe|Val|Val|Met|Trp|Cys|Pro|Phe|Phe|Ile|Thr|Asn|Ile|Met|
| | | |260| | | | |265| | | | |270| | |
|Val|Ile|Cys|Lys|Glu|Ser|Cys|Asn|Glu|Asn|Val|Ile|Gly|Ala|Leu|Leu|
| | |275| | | | |280| | | | |285| | | |
|Asn|Val|Phe|Val|Trp|Ile|Gly|Tyr|Leu|Ser|Ser|Ala|Val|Asn|Pro|Leu|
| |290| | | | |295| | | | |300| | | | |
|Val|Tyr|Thr|Leu|Phe|Asn|Lys|Thr|Tyr|Arg|Ser|Ala|Phe|Ser|Arg|Tyr|
|305| | | | |310| | | | |315| | | | |320|

|     |     |     |     |     |     |     |     |     |     |     |     |     |     |     |
|-----|-----|-----|-----|-----|-----|-----|-----|-----|-----|-----|-----|-----|-----|-----|
| Leu | Gln | Cys | Gln | Tyr<br>325 | Lys | Glu | Asn | Arg | Lys<br>330 | Pro | Leu | Leu | Ile | Leu<br>335 | Val |
| Asn | Thr | Ile | Pro<br>340 | Ala | Leu | Ala | Tyr | Lys<br>345 | Ser | Ser | Gln | Leu | Gln<br>350 | Val | Gly |
| Gln | Lys | Lys<br>355 | Asn | Ser | Gln | Glu | Asp<br>360 | Ala | Glu | Gln | Thr | Val<br>365 | Asp | Asp | Cys |
| Ser | Met<br>370 | Val | Thr | Leu | Gly | Lys<br>375 | Gln | Gln | Ser | Glu |     |     |     |     |     |

( 2 ) INFORMATION FOR SEQ ID NO:33:

( i ) SEQUENCE CHARACTERISTICS:
        ( A ) LENGTH: 337 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

|     |     |     |     |     |     |     |     |     |     |     |     |     |     |     |     |
|-----|-----|-----|-----|-----|-----|-----|-----|-----|-----|-----|-----|-----|-----|-----|-----|
| Ile<br>1 | Thr | Ile | Thr | Val<br>5 | Val | Leu | Ala | Val | Leu<br>10 | Ile | Leu | Ile | Thr | Val<br>15 | Ala |
| Gly | Asn | Val | Val<br>20 | Val | Cys | Ile | Ala | Val<br>25 | Gly | Ile | Asn | Arg | Arg<br>30 | Leu | Arg |
| Asn | Leu | Thr<br>35 | Asn | Cys | Phe | Ile | Val<br>40 | Ser | Leu | Ala | Ile | Thr<br>45 | Asp | Leu | Leu |
| Leu | Gly<br>50 | Leu | Leu | Val | Leu | Pro<br>55 | Phe | Ser | Ala | Ile | Tyr<br>60 | Gln | Leu | Ser | Cys |
| Lys<br>65 | Trp | Ser | Phe | Gly | Lys<br>70 | Val | Phe | Cys | Asn | Ile<br>75 | Tyr | Thr | Ser | Leu | Asp<br>80 |
| Val | Met | Leu | Cys | Thr<br>85 | Ala | Ser | Ile | Leu | Asn<br>90 | Leu | Leu | Ile | Ser | Leu<br>95 | Asp |
| Arg | Tyr | Cys | Ala<br>100 | Val | Met | Asp | Pro | Leu<br>105 | Arg | Tyr | Pro | Val | Leu<br>110 | Val | Arg |
| Pro | Val | Arg<br>115 | Val | Ala | Ile | Ser | Leu<br>120 | Val | Leu | Ile | Trp | Val<br>125 | Ile | Ser | Ile |
| Thr | Leu<br>130 | Ser | Phe | Leu | Ser | Ile<br>135 | His | Leu | Gly | Trp | Asn<br>140 | Ser | Arg | Asn | Glu |
| Thr<br>145 | Ser | Lys | Gly | Asn | His<br>150 | Thr | Thr | Ser | Lys | Cys<br>155 | Lys | Val | Gln | Val | Asn<br>160 |
| Glu | Val | Tyr | Gly | Leu<br>165 | Val | Asp | Gly | Leu | Val<br>170 | Thr | Phe | Tyr | Leu | Pro<br>175 | Leu |
| Leu | Ile | Met | Cys<br>180 | Ile | Thr | Tyr | Tyr | Arg<br>185 | Ile | Phe | Lys | Val | Ala<br>190 | Arg | Asp |
| Ala | Lys | Arg<br>195 | Asn | His | Ile | Ser | Ser<br>200 | Trp | Lys | Ala | Ala | Thr<br>205 | Ile | Arg | Glu |
| His | Lys<br>210 | Ala | Thr | Val | Thr | Ile<br>215 | Ala | Ala | Val | Met | Ala<br>220 | Phe | Ile | Ile | Cys |
| Trp<br>225 | Phe | Pro | Tyr | Phe | Thr<br>230 | Ala | Phe | Val | Tyr | Arg<br>235 | Gly | Leu | Arg | Gly | Asp<br>240 |
| Asp | Ala | Ile | Asn | Glu<br>245 | Val | Leu | Glu | Ala | Ile<br>250 | Val | Leu | Trp | Leu | Gly<br>255 | Tyr |
| Ala | Asn | Ser | Ala<br>260 | Leu | Asn | Pro | Ile | Leu<br>265 | Tyr | Ala | Ala | Leu | Asn<br>270 | Arg | Asp |
| Phe | Arg | Thr<br>275 | Gly | Tyr | Gln | Gln | Leu<br>280 | Phe | Cys | Cys | Arg | Ile<br>285 | Ala | Asn | Arg |
| Asn | Ser | His | Lys | Thr | Ser | Leu | Arg | Ser | Asn | Ala | Ser | Gln | Leu | Ser | Arg |

|         |         |         |         | 290     |         |         |         | 295     |         |         |         | 300     |         |         |
|---------|---------|---------|---------|---------|---------|---------|---------|---------|---------|---------|---------|---------|---------|---------|
| Thr     | Gln     | Ser     | Arg     | Glu     | Pro     | Arg     | Gln     | Gln     | Glu     | Glu     | Lys     | Pro     | Leu     | Lys     | Leu
| 305     |         |         |         |         | 310     |         |         |         |         | 315     |         |         |         |         | 320
| Gln     | Val     | Trp     | Ser     | Gly     | Thr     | Glu     | Val     | Thr     | Ala     | Pro     | Gln     | Gly     | Ala     | Thr     | Asp
|         |         |         |         | 325     |         |         |         |         | 330     |         |         |         |         | 335     |
| Arg     |         |         |         |         |         |         |         |         |         |         |         |         |         |         |

( 2 ) INFORMATION FOR SEQ ID NO:34:

( i ) SEQUENCE CHARACTERISTICS:
        ( A ) LENGTH: 315 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:34:

| Ile | Ile | Thr | Tyr | Leu | Val | Phe | Ala | Val | Arg | Phe | Val | Leu | Gly | Val | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gly | Asn | Gly | Leu | Val | Ile | Trp | Val | Ala | Gly | Phe | Arg | Met | Thr | His | Thr |
|     |     |     | 20  |     |     |     |     | 25  |     |     |     | 30  |     |     |     |
| Val | Thr | Thr | Ile | Ser | Tyr | Leu | Asn | Leu | Ala | Val | Ala | Asp | Phe | Cys | Phe |
|     |     | 35  |     |     |     |     | 40  |     |     |     |     | 45  |     |     |     |
| Thr | Ser | Thr | Leu | Pro | Phe | Phe | Met | Val | Arg | Leu | Gly | His | Trp | Pro | Phe |
|     | 50  |     |     |     |     | 55  |     |     |     |     | 60  |     |     |     |     |
| Gly | Trp | Phe | Leu | Cys | Lys | Phe | Leu | Phe | Thr | Ile | Val | Asp | Ile | Asn | Leu |
| 65  |     |     |     |     | 70  |     |     |     |     | 75  |     |     |     |     | 80  |
| Phe | Gly | Ser | Val | Phe | Leu | Ile | Ala | Leu | Ile | Ala | Leu | Asp | Arg | Cys | Val |
|     |     |     |     | 85  |     |     |     |     | 90  |     |     |     |     | 95  |     |
| Cys | Val | Leu | His | Pro | Val | Trp | Thr | Gln | Asn | His | Arg | Thr | Val | Ser | Leu |
|     |     |     | 100 |     |     |     |     | 105 |     |     |     |     | 110 |     |     |
| Ala | Lys | Lys | Val | Ile | Ile | Gly | Pro | Trp | Val | Met | Ala | Leu | Leu | Leu | Thr |
|     |     | 115 |     |     |     |     | 120 |     |     |     |     | 125 |     |     |     |
| Leu | Pro | Val | Ile | Ile | Arg | Val | Thr | Ile | Val | Pro | Gly | Lys | Thr | Gly | Thr |
|     | 130 |     |     |     |     | 135 |     |     |     |     | 140 |     |     |     |     |
| Val | Ala | Cys | Thr | Phe | Asn | Phe | Ser | Pro | Trp | Thr | Asn | Asp | Pro | Lys | Glu |
| 145 |     |     |     |     | 150 |     |     |     |     | 155 |     |     |     |     | 160 |
| Arg | Ile | Asn | Val | Ala | Val | Ala | Met | Leu | Thr | Val | Arg | Gly | Ile | Ile | Arg |
|     |     |     |     | 165 |     |     |     |     | 170 |     |     |     |     | 175 |     |
| Phe | Ile | Ile | Gly | Phe | Ser | Ala | Pro | Met | Ser | Ile | Val | Ala | Val | Ser | Tyr |
|     |     |     | 180 |     |     |     |     | 185 |     |     |     |     | 190 |     |     |
| Gly | Leu | Ile | Ala | Thr | Lys | Ile | Ile | Lys | Ser | Ser | Arg | Pro | Leu | Arg | Val |
|     |     | 195 |     |     |     |     | 200 |     |     |     |     | 205 |     |     |     |
| Leu | Ser | Phe | Val | Ala | Ala | Ala | Phe | Phe | Leu | Cys | Trp | Ser | Pro | Tyr | Gln |
|     | 210 |     |     |     |     | 215 |     |     |     |     | 220 |     |     |     |     |
| Val | Val | Ala | Leu | Ile | Ala | Thr | Val | Arg | Ile | Arg | Glu | Leu | Leu | Gln | Gly |
| 225 |     |     |     |     | 230 |     |     |     |     | 235 |     |     |     |     | 240 |
| Met | Tyr | Lys | Glu | Ile | Gly | Ile | Ala | Val | Asp | Val | Thr | Ser | Ala | Ile | Ala |
|     |     |     |     | 245 |     |     |     |     | 250 |     |     |     |     | 255 |     |
| Phe | Phe | Asn | Ser | Cys | Leu | Asn | Pro | Leu | Tyr | Val | Phe | Met | Gly | Gln | Asp |
|     |     |     | 260 |     |     |     |     | 265 |     |     |     |     | 270 |     |     |
| Phe | Arg | Glu | Arg | Leu | Ile | His | Ala | Leu | Pro | Ala | Ser | Leu | Glu | Arg | Ala |
|     |     | 275 |     |     |     |     | 280 |     |     |     |     | 285 |     |     |     |
| Leu | Thr | Glu | Asp | Ser | Thr | Gln | Thr | Ser | Asp | Thr | Ala | Thr | Asn | Ser | Thr |
|     | 290 |     |     |     |     | 295 |     |     |     |     | 300 |     |     |     |     |

5,508,384

-continued

```
Leu  Pro  Ser  Ala  Glu  Val  Ala  Leu  Gln  Ala  Lys
305            310                 315
```

( 2 ) INFORMATION FOR SEQ ID NO:35:

( i ) SEQUENCE CHARACTERISTICS:
        ( A ) LENGTH: 304 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:35:

```
Asp  Ile  Leu  Ala  Leu  Val  Ile  Phe  Ala  Val  Val  Phe  Leu  Val  Gly  Val
1              5                      10                     15

Leu  Gly  Asn  Ala  Leu  Val  Val  Trp  Val  Thr  Ala  Phe  Glu  Ala  Lys  Arg
              20                      25                     30

Thr  Ile  Asn  Ala  Ile  Trp  Phe  Leu  Asn  Ile  Ala  Val  Ala  Asp  Phe  Leu
              35                      40                     45

Ser  Cys  Leu  Ala  Leu  Pro  Ile  Leu  Phe  Thr  Ser  Ile  Val  Gln  His  His
     50                      55                     60

His  Trp  Pro  Phe  Gly  Gly  Ala  Ala  Cys  Ser  Ile  Leu  Pro  Ser  Leu  Ile
65                      70                     75                          80

Leu  Leu  Asn  Met  Tyr  Ala  Ser  Ile  Leu  Leu  Leu  Ala  Thr  Ile  Ser  Ala
                    85                      90                     95

Asp  Arg  Phe  Leu  Leu  Val  Phe  Lys  Pro  Ile  Trp  Cys  Gln  Asn  Phe  Arg
               100                     105                    110

Gly  Ala  Gly  Leu  Ala  Trp  Ile  Ala  Cys  Ala  Val  Ala  Trp  Gly  Ile  Ala
               115                     120                    125

Leu  Leu  Leu  Thr  Ile  Pro  Ser  Phe  Leu  Tyr  Arg  Val  Val  Arg  Glu  Glu
     130                     135                    140

Tyr  Phe  Pro  Pro  Lys  Val  Leu  Cys  Gly  Cys  Asp  Tyr  Ser  His  Asp  Lys
145                     150                    155                         160

Arg  Arg  Glu  Arg  Ala  Val  Ala  Ile  Val  Arg  Leu  Val  Leu  Gly  Phe  Leu
               165                     170                    175

Trp  Pro  Leu  Leu  Thr  Leu  Thr  Ile  Cys  Tyr  Thr  Thr  Arg  Ser  Thr  Lys
               180                     185                    190

Thr  Leu  Lys  Val  Val  Val  Ala  Val  Val  Ala  Ser  Phe  Phe  Ile  Phe  Trp
          195                     200                    205

Leu  Pro  Tyr  Gln  Val  Thr  Gly  Ile  Met  Met  Ser  Phe  Leu  Glu  Pro  Ser
     210                     215                    220

Ser  Pro  Thr  Phe  Leu  Leu  Leu  Asn  Lys  Leu  Asp  Ser  Leu  Cys  Val  Ser
225                     230                    235                         240

Phe  Ala  Tyr  Ile  Asn  Cys  Cys  Ile  Asn  Pro  Ile  Ile  Tyr  Val  Val  Ala
               245                     250                    255

Gly  Gln  Gly  Gln  Phe  Gln  Gly  Arg  Leu  Arg  Lys  Ser  Leu  Pro  Ser  Leu
               260                     265                    270

Leu  Arg  Asn  Val  Leu  Thr  Glu  Glu  Ser  Val  Val  Arg  Glu  Ser  Lys  Ser
          275                     280                    285

Phe  Thr  Arg  Ser  Thr  Val  Asp  Thr  Met  Ala  Gln  Lys  Thr  Gln  Ala  Val
     290                     295                    300
```

( 2 ) INFORMATION FOR SEQ ID NO:36:

( i ) SEQUENCE CHARACTERISTICS:
        ( A ) LENGTH: 322 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:36:

| Thr | Leu | Phe | Val | Pro | Ser | Val | Tyr | Thr | Gly | Val | Phe | Val | Val | Ser | Leu |
|---|---|---|---|---|---|---|---|---|---|---|---|---|---|---|---|
| 1 | | | | 5 | | | | | 10 | | | | | 15 | |

| Pro | Leu | Asn | Ile | Met | Ala | Ile | Val | Val | Phe | Ile | Leu | Lys | Met | Lys | Val |
|---|---|---|---|---|---|---|---|---|---|---|---|---|---|---|---|
| | | | 20 | | | | | 25 | | | | | 30 | | |

| Lys | Lys | Pro | Ala | Val | His | Ile | Ala | Thr | Ala | Asp | Val | Leu | Phe | Val | Ser |
|---|---|---|---|---|---|---|---|---|---|---|---|---|---|---|---|
| | | 35 | | | | | 40 | | | | | 45 | | | |

| Val | Leu | Pro | Phe | Lys | Ile | Ser | Tyr | Tyr | Phe | Ser | Gly | Ser | Asp | Trp | Gln |
|---|---|---|---|---|---|---|---|---|---|---|---|---|---|---|---|
| | 50 | | | | | 55 | | | | | 60 | | | | |

| Phe | Gly | Ser | Glu | Leu | Cys | Arg | Phe | Val | Thr | Ala | Ala | Phe | Tyr | Cys | Asn |
|---|---|---|---|---|---|---|---|---|---|---|---|---|---|---|---|
| 65 | | | | | 70 | | | | | 75 | | | | | 80 |

| Met | Tyr | Ala | Ser | Ile | Leu | Leu | Ile | Ser | Ile | Asp | Arg | Phe | Ile | Ala | Val |
|---|---|---|---|---|---|---|---|---|---|---|---|---|---|---|---|
| | | | | 85 | | | | | 90 | | | | | 95 | |

| Val | Tyr | Pro | Met | Gln | Ser | Leu | Ser | Trp | Arg | Thr | Leu | Gly | Arg | Ala | Ser |
|---|---|---|---|---|---|---|---|---|---|---|---|---|---|---|---|
| | | | 100 | | | | | 105 | | | | | 110 | | |

| Phe | Thr | Cys | Ile | Ala | Ile | Trp | Ala | Ile | Ala | Ile | Ala | Gly | Val | Pro | Leu |
|---|---|---|---|---|---|---|---|---|---|---|---|---|---|---|---|
| | | 115 | | | | | 120 | | | | | 125 | | | |

| Val | Leu | Lys | Glu | Gln | Thr | Ile | Gln | Val | Pro | Gly | Leu | Asn | Ile | Thr | Thr |
|---|---|---|---|---|---|---|---|---|---|---|---|---|---|---|---|
| | 130 | | | | | 135 | | | | | 140 | | | | |

| Ile | Cys | His | Asp | Val | Leu | Asn | Glu | Thr | Leu | Leu | Glu | Gly | Tyr | Tyr | Ala |
|---|---|---|---|---|---|---|---|---|---|---|---|---|---|---|---|
| 145 | | | | | 150 | | | | | 155 | | | | | 160 |

| Tyr | Tyr | Phe | Ser | Ala | Phe | Ser | Ala | Val | Phe | Phe | Val | Pro | Leu | Ile |
|---|---|---|---|---|---|---|---|---|---|---|---|---|---|---|
| | | | | 165 | | | | | 170 | | | | | 175 |

| Ile | Ser | Thr | Val | Cys | Tyr | Val | Ser | Ile | Ile | Arg | Cys | Leu | Ser | Ser | Ser |
|---|---|---|---|---|---|---|---|---|---|---|---|---|---|---|---|
| | | | 180 | | | | | 185 | | | | | 190 | | |

| Ala | Val | Ala | Asn | Arg | Ser | Lys | Lys | Ser | Arg | Thr | Asn | Arg | Cys | Phe | Asn |
|---|---|---|---|---|---|---|---|---|---|---|---|---|---|---|---|
| | | 195 | | | | | 200 | | | | | 205 | | | |

| Ser | Thr | Val | Ala | Leu | Phe | Leu | Ser | Ala | Ala | Val | Phe | Cys | Ile | Phe | Ile |
|---|---|---|---|---|---|---|---|---|---|---|---|---|---|---|---|
| | 210 | | | | | 215 | | | | | 220 | | | | |

| Ile | Cys | Phe | Gly | Pro | Thr | Trp | Leu | Leu | Ile | Ala | His | Tyr | Ser | Phe | Leu |
|---|---|---|---|---|---|---|---|---|---|---|---|---|---|---|---|
| 225 | | | | | 230 | | | | | 235 | | | | | 240 |

| Ser | His | Thr | Ser | Thr | Thr | Glu | Ala | Ala | Tyr | Phe | Ala | Tyr | Leu | Leu | Cys |
|---|---|---|---|---|---|---|---|---|---|---|---|---|---|---|---|
| | | | | 245 | | | | | 250 | | | | | 255 | |

| Val | Cys | Val | Ser | Ser | Ile | Ser | Ser | Cys | Ile | Asp | Pro | Leu | Ile | Tyr | Tyr |
|---|---|---|---|---|---|---|---|---|---|---|---|---|---|---|---|
| | | | 260 | | | | | 265 | | | | | 270 | | |

| Tyr | Ala | Ser | Ser | Glu | Cys | Gln | Arg | Tyr | Val | Tyr | Ser | Ile | Leu | Cys | Cys |
|---|---|---|---|---|---|---|---|---|---|---|---|---|---|---|---|
| | | 275 | | | | | 280 | | | | | 285 | | | |

| Lys | Glu | Ser | Ser | Asp | Pro | Ser | Ser | Tyr | Asn | Ser | Ser | Gly | Gln | Leu | Met |
|---|---|---|---|---|---|---|---|---|---|---|---|---|---|---|---|
| | 290 | | | | | 295 | | | | | 300 | | | | |

| Ser | Leu | Thr | Cys | Ser | Ser | Asn | Leu | Asn | Asn | Ser | Ile | Tyr | Lys | Lys | Leu |
|---|---|---|---|---|---|---|---|---|---|---|---|---|---|---|---|
| 305 | | | | | 310 | | | | | 315 | | | | | 320 |

| Leu | Thr |
|---|---|
| | |

(2) INFORMATION FOR SEQ ID NO:37:

(i) SEQUENCE CHARACTERISTICS:
      (A) LENGTH: 311 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:37:

| Tyr | Ile | Asn | Thr | Val | Ile | Ser | Cys | Thr | Ile | Phe | Ile | Val | Gly | Trp | Gly |
|---|---|---|---|---|---|---|---|---|---|---|---|---|---|---|---|
| 1 | | | | 5 | | | | | 10 | | | | | 15 | |

| Asn | Ala | Thr | Leu | Leu | Arg | Ile | Ile | Tyr | Gln | Asn | Lys | Cys | Met | Arg | Asn |
|---|---|---|---|---|---|---|---|---|---|---|---|---|---|---|---|
| | | | 20 | | | | | 25 | | | | | 30 | | |

| Gly | Pro | Asn | Ala | Leu | Ile | Ala | Ser | Ile | Ala | Leu | Gly | Asp | Leu | Ile | Tyr |
|---|---|---|---|---|---|---|---|---|---|---|---|---|---|---|---|
| | | | 35 | | | | | 40 | | | | | 45 | | |

| Val | Val | Ile | Asp | Leu | Pro | Ile | Asn | Val | Pro | Lys | Leu | Ile | Ala | Gly | Arg |
|---|---|---|---|---|---|---|---|---|---|---|---|---|---|---|---|
| | 50 | | | | | 55 | | | | | 60 | | | | |

| Trp | Pro | Phe | Glu | Gln | Asn | Asp | Phe | Gly | Val | Phe | Cys | Lys | Phe | Met | Gly |
|---|---|---|---|---|---|---|---|---|---|---|---|---|---|---|---|
| 65 | | | | | 70 | | | | | 75 | | | | | 80 |

| Val | Val | Met | Ile | Phe | Phe | Gly | Leu | Ser | Pro | Leu | Leu | Leu | Gly | Ala | Ala |
|---|---|---|---|---|---|---|---|---|---|---|---|---|---|---|---|
| | | | | 85 | | | | | 90 | | | | | 95 | |

| Met | Ala | Ser | Glu | Arg | Tyr | Leu | Gly | Ile | Thr | Arg | Pro | Phe | Ser | Arg | Pro |
|---|---|---|---|---|---|---|---|---|---|---|---|---|---|---|---|
| | | | 100 | | | | | 105 | | | | | 110 | | |

| Ala | Val | Ala | Ser | Gln | Arg | Arg | Ala | Trp | Ala | Thr | Val | Gly | Leu | Val | Trp |
|---|---|---|---|---|---|---|---|---|---|---|---|---|---|---|---|
| | | | 115 | | | | | 120 | | | | | 125 | | |

| Ala | Ala | Ala | Leu | Ala | Leu | Gly | Leu | Leu | Pro | Leu | Leu | Gly | Val | Gly | Arg |
|---|---|---|---|---|---|---|---|---|---|---|---|---|---|---|---|
| | 130 | | | | | 135 | | | | | 140 | | | | |

| Tyr | Thr | Val | Gln | Tyr | Pro | Gly | Ser | Trp | Cys | Phe | Leu | Thr | Leu | Gly | Ala |
|---|---|---|---|---|---|---|---|---|---|---|---|---|---|---|---|
| 145 | | | | | 150 | | | | | 155 | | | | | 160 |

| Glu | Ser | Gly | Asp | Val | Ala | Phe | Gly | Leu | Leu | Phe | Ser | Gly | Leu | Ser | Val |
|---|---|---|---|---|---|---|---|---|---|---|---|---|---|---|---|
| | | | | 165 | | | | | 170 | | | | | 175 | |

| Gly | Leu | Ser | Phe | Leu | Leu | Asn | Thr | Val | Ser | Val | Ala | Thr | Leu | His | His |
|---|---|---|---|---|---|---|---|---|---|---|---|---|---|---|---|
| | | | 180 | | | | | 185 | | | | | 190 | | |

| Val | Tyr | His | Gly | Gln | Glu | Ala | Ala | Gln | Gln | Arg | Pro | Arg | Asp | Ser | Glu |
|---|---|---|---|---|---|---|---|---|---|---|---|---|---|---|---|
| | | 195 | | | | | 200 | | | | | 205 | | | |

| Val | Glu | Met | Met | Ala | Gln | Leu | Leu | Gly | Ile | Met | Val | Val | Ala | Ser | Val |
|---|---|---|---|---|---|---|---|---|---|---|---|---|---|---|---|
| | 210 | | | | | 215 | | | | | 220 | | | | |

| Cys | Trp | Leu | Pro | Leu | Leu | Val | Phe | Ile | Ala | Gln | Thr | Val | Leu | Arg | Asn |
|---|---|---|---|---|---|---|---|---|---|---|---|---|---|---|---|
| 225 | | | | | 230 | | | | | 235 | | | | | 240 |

| Pro | Pro | Ala | Met | Ser | Pro | Ala | Gly | Gln | Leu | Ser | Arg | Thr | Thr | Glu | Lys |
|---|---|---|---|---|---|---|---|---|---|---|---|---|---|---|---|
| | | | | 245 | | | | | 250 | | | | | 255 | |

| Glu | Leu | Leu | Ile | Tyr | Leu | Arg | Val | Ala | Thr | Trp | Asn | Gln | Ile | Leu | Asp |
|---|---|---|---|---|---|---|---|---|---|---|---|---|---|---|---|
| | | | 260 | | | | | 265 | | | | | 270 | | |

| Pro | Trp | Val | Tyr | Ile | Leu | Phe | Arg | Arg | Ala | Val | Leu | Arg | Arg | Leu | Gln |
|---|---|---|---|---|---|---|---|---|---|---|---|---|---|---|---|
| | | 275 | | | | | 280 | | | | | 285 | | | |

| Pro | Arg | Leu | Ser | Thr | Arg | Pro | Arg | Ser | Leu | Ser | Leu | Gln | Pro | Gln | Leu |
|---|---|---|---|---|---|---|---|---|---|---|---|---|---|---|---|
| | 290 | | | | | 295 | | | | | 300 | | | | |

| Thr | Gln | Arg | Ser | Gly | Leu | Gln |
|---|---|---|---|---|---|---|
| 305 | | | | | 310 | |

(2) INFORMATION FOR SEQ ID NO:38:

(i) SEQUENCE CHARACTERISTICS:
       (A) LENGTH: 312 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:38:

| Lys | Tyr | Phe | Val | Val | Ile | Ile | Tyr | Ala | Leu | Val | Phe | Leu | Leu | Ser | Leu |
|---|---|---|---|---|---|---|---|---|---|---|---|---|---|---|---|
| 1 | | | | 5 | | | | | 10 | | | | | 15 | |

| Leu | Gly | Asn | Ser | Leu | Val | Met | Leu | Val | Ile | Leu | Tyr | Ser | Arg | Gly | Val |
|---|---|---|---|---|---|---|---|---|---|---|---|---|---|---|---|
| | | | 20 | | | | | 25 | | | | | 30 | | |

```
Arg  Ser  Val  Thr  Ile  Val  Tyr  Leu  Leu  Asn  Ile  Ala  Ile  Ala  Asp  Leu
          35                       40                      45

Leu  Phe  Ala  Leu  Thr  Leu  Pro  Ile  Trp  Ala  Ala  Ser  Lys  Val  Asn  Gly
     50                       55                      60

Trp  Ile  Phe  Gly  Thr  Phe  Leu  Cys  Lys  Trp  Ser  Leu  Leu  Lys  Glu  Val
65                       70                      75                           80

Asn  Phe  Tyr  Ser  Gly  Ile  Leu  Leu  Leu  Ala  Cys  Ile  Ser  Val  Asp  Arg
               85                       90                           95

Tyr  Leu  Ala  Ile  Val  Arg  Ala  Thr  Arg  Thr  Leu  Thr  Gln  Lys  Arg  His
               100                      105                      110

Leu  Val  Lys  Phe  Ile  Cys  Leu  Ser  Ile  Trp  Gly  Leu  Ser  Leu  Leu  Leu
          115                      120                      125

Ala  Leu  Pro  Val  Leu  Leu  Phe  Arg  Arg  Thr  Val  Tyr  Ser  Ser  Asn  Val
     130                      135                      140

Ser  Pro  Ala  Cys  Tyr  Glu  Asp  Met  Gly  Asn  Asn  Tyr  Ala  Asn  Trp  Arg
145                      150                      155                          160

Met  Leu  Leu  Pro  Ile  Leu  Pro  Gln  Ser  Phe  Gly  Phe  Ile  Val  Pro  Leu
               165                      170                           175

Leu  Ile  Met  Leu  Tyr  Cys  Tyr  Gly  Phe  Thr  Leu  Arg  Thr  Leu  Phe  Lys
               180                      185                      190

Ala  Ile  Met  Gly  Gln  Lys  His  Arg  Ala  Met  Arg  Val  Ile  Phe  Ala  Val
          195                      200                      205

Val  Leu  Ile  Phe  Leu  Leu  Cys  Trp  Leu  Pro  Tyr  Asn  Leu  Val  Leu  Ile
     210                      215                      220

Ala  Asp  Thr  Leu  Met  Arg  Thr  Gln  Val  Ile  Gln  Glu  Thr  Cys  Glu  Arg
225                      230                      235                          240

Arg  Asn  His  Ile  Asp  Arg  Ala  Ile  Asp  Ala  Thr  Glu  Ile  Leu  Gly  Ile
               245                      250                           255

Leu  His  Ser  Cys  Leu  Asn  Pro  Leu  Ile  Tyr  Ala  Phe  Ile  Gly  Gln  Lys
               260                      265                      270

Phe  Arg  His  Gly  Leu  Leu  Lys  Ile  Leu  Ala  Ile  His  Gly  Leu  Ile  Ser
          275                      280                      285

Lys  Asp  Ser  Leu  Pro  Lys  Asp  Ser  Arg  Pro  Ser  Phe  Val  Gly  Ser  Ser
     290                      295                      300

Ser  Gly  His  Thr  Ser  Thr  Thr  Leu
305                      310
```

(2) INFORMATION FOR SEQ ID NO:39:

(i) SEQUENCE CHARACTERISTICS:
        (A) LENGTH: 326 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
Leu  Phe  Pro  Ile  Val  Tyr  Ser  Ile  Ile  Phe  Val  Leu  Gly  Ile  Ile  Ala
1                   5                      10                           15

Asn  Gly  Tyr  Val  Leu  Trp  Val  Phe  Ala  Arg  Leu  Tyr  Pro  Ser  Lys  Lys
               20                      25                      30

Asn  Glu  Ile  Lys  Ile  Phe  Met  Val  Asn  Leu  Thr  Val  Ala  Asp  Leu  Leu
          35                       40                      45

Phe  Leu  Ile  Thr  Leu  Pro  Leu  Trp  Ile  Val  Tyr  Tyr  Ser  Asn  Gln  Gly
     50                       55                      60

Asn  Trp  Phe  Leu  Pro  Lys  Phe  Leu  Cys  Asn  Leu  Ala  Gly  Cys  Leu  Phe
```

```
        65                          70                          75                          80
    Phe  Ile  Asn  Thr  Tyr  Cys  Ser  Val  Ala  Phe  Leu  Gly  Val  Ile  Thr  Tyr
                        85                       90                       95

Asn  Arg  Phe  Gln  Ala  Val  Lys  Tyr  Pro  Ile  Lys  Thr  Ala  Gln  Ala  Thr
                        100                      105                      110

Thr  Arg  Lys  Arg  Gly  Ile  Ala  Leu  Ser  Leu  Val  Ile  Trp  Val  Ala  Ile
                        115                      120                      125

Val  Ala  Ala  Ala  Ser  Tyr  Phe  Val  Met  Met  Asp  Ser  Thr  Asn  Val
         130                      135                      140

Val  Ser  Asn  Lys  Ala  Gly  Ser  Gly  Asn  Ile  Thr  Arg  Cys  Phe  Glu  Arg
    145                      150                      155                           160

Tyr  Glu  Lys  Gly  Ser  Lys  Pro  Val  Leu  Ile  Ile  His  Ile  Cys  Ile  Val
                        165                      170                           175

Leu  Gly  Phe  Phe  Ile  Val  Phe  Leu  Leu  Ile  Leu  Phe  Cys  Asn  Leu  Val
                        180                      185                      190

Ile  Ile  His  Thr  Leu  Leu  Arg  Gly  Pro  Val  Lys  Gln  Gln  Arg  Asn  Ala
              195                      200                      205

Glu  Val  Arg  Arg  Arg  Ala  Leu  Trp  Met  Val  Cys  Thr  Val  Ile  Ala  Val
         210                      215                      220

Phe  Val  Ile  Cys  Phe  Val  Pro  His  His  Met  Val  Gln  Leu  Pro  Trp  Thr
    225                      230                      235                           240

Leu  Ala  Glu  Leu  Gly  Met  Trp  Pro  Ser  Ser  Asn  His  Gln  Ala  Ile  Asn
                        245                      250                      255

Asp  Ala  His  Gln  Val  Thr  Leu  Cys  Leu  Leu  Ser  Thr  Asn  Cys  Val  Leu
                   260                      265                      270

Asp  Pro  Val  Ile  Tyr  Cys  Phe  Leu  Thr  Lys  Lys  Phe  Arg  Lys  His  Leu
                   275                      280                      285

Ser  Glu  Lys  Leu  Asn  Ile  Met  Arg  Ser  Ser  Gln  Lys  Cys  Ser  Arg  Val
         290                      295                      300

Thr  Arg  Asp  Thr  Gly  Thr  Glu  Met  Ala  Ile  Pro  Ile  Asn  His  Thr  Pro
    305                      310                      315                           320

Val  Asn  Pro  Ile  Lys  Asn
                        325
```

( 2 ) INFORMATION FOR SEQ ID NO:40:

( i ) SEQUENCE CHARACTERISTICS:
         ( A ) LENGTH: 333 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:40:

```
    Tyr  Ile  Asn  Thr  Ile  Val  Ser  Cys  Leu  Val  Phe  Val  Leu  Gly  Ile  Ile
    1                   5                        10                           15

Gly  Asn  Ser  Thr  Leu  Leu  Arg  Ile  Ile  Tyr  Lys  Asn  Lys  Cys  Met  Arg
                        20                       25                       30

Asn  Gly  Pro  Asn  Ile  Leu  Ile  Ala  Ser  Ile  Ala  Leu  Gly  Asp  Leu  Leu
                   35                       40                       45

His  Ile  Ile  Ile  Asp  Ile  Pro  Ile  Met  Ala  Tyr  Lys  Leu  Ile  Ala  Gly
              50                       55                       60

Asp  Trp  Pro  Phe  Ala  Cys  Lys  Leu  Phe  Pro  Phe  Leu  Gln  Lys  Ser  Ser
    65                       70                       75                            80

Val  Gly  Ile  Thr  Val  Leu  Asn  Leu  Cys  Ala  Leu  Ser  Val  Asp  Arg  Tyr
                        85                       90                       95
```

```
Arg  Ala  Val  Ala  Ser  Trp  Ser  Arg  Val  Gln  Gly  Ile  Gly  Ile  Pro  Leu
               100                      105                     110

Val  Thr  Ala  Ile  Glu  Ile  Val  Ser  Ile  Trp  Ile  Leu  Ser  Phe  Ile  Leu
               115                      120                     125

Ala  Ile  Pro  Glu  Ala  Ile  Gly  Phe  Trp  Met  Val  Pro  Phe  Glu  Tyr  Lys
          130                      135                140

Gly  Ala  Gln  His  Arg  Thr  Cys  Met  Leu  Asn  Ala  Thr  Ser  Lys  Leu  Phe
145                           150                155                          160

Tyr  Gln  Asp  Val  Lys  Asp  Trp  Trp  Leu  Phe  Gly  Phe  Tyr  Phe  Leu  Leu
               165                      170                     175

Val  Cys  Thr  Ala  Ile  Phe  Tyr  Thr  Leu  Met  Thr  Cys  Glu  Met  Leu  Asn
               180                      185                     190

Arg  Arg  Asn  Gly  Ser  Leu  Arg  Ile  Ala  Leu  Ser  Glu  His  Leu  Lys  Gln
          195                      200                     205

Arg  Arg  Glu  Val  Ala  Lys  Thr  Val  Phe  Cys  Leu  Val  Val  Ile  Phe  Ala
          210                      215                     220

Leu  Cys  Trp  Phe  Pro  Leu  His  Leu  Ser  Arg  Ile  Leu  Lys  Lys  Thr  Val
225                      230                235                          240

Tyr  Asp  Glu  Met  Asp  Thr  Asn  Arg  Cys  Glu  Leu  Leu  Ser  Phe  Leu  Leu
               245                      250                     255

Leu  Met  Tyr  Ile  Gly  Ile  Asn  Thr  Ala  Thr  Met  Ser  Cys  Ile  Asn  Pro
               260                      265                     270

Ile  Ala  Leu  Tyr  Phe  Val  Ser  Lys  Lys  Phe  Lys  Asn  Cys  Phe  Gln  Ser
          275                      280                     285

Cys  Leu  Cys  Cys  Cys  Cys  Tyr  Gln  Ser  Lys  Ser  Ile  Met  Thr  Ser  Val
          290                      295                     300

Pro  Met  Gln  Gly  Thr  Ser  Ile  Gln  Trp  Lys  Asn  His  Glu  Gln  Asn  Asn
305                      310                     315                          320

His  Asn  Thr  Glu  Arg  Ser  Ser  His  Lys  Asp  Ser  Ile  Asn
               325                      330
```

( 2 ) INFORMATION FOR SEQ ID NO:41:

( i ) SEQUENCE CHARACTERISTICS:
        ( A ) LENGTH: 350 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:41:

```
Leu  Ile  Ala  Ser  Pro  Trp  Phe  Ala  Ala  Ser  Phe  Cys  Val  Val  Gly  Leu
1                   5                   10                      15

Ala  Ser  Asn  Leu  Leu  Ala  Leu  Ser  Val  Leu  Ala  Gly  Ala  Arg  Gln  Ser
               20                       25                      30

Ser  Ser  His  Thr  Arg  Ser  Ser  Phe  Leu  Thr  Phe  Leu  Cys  Gly  Leu  Val
          35                       40                      45

Leu  Thr  Leu  Asp  Phe  Leu  Gly  Leu  Leu  Val  Thr  Gly  Thr  Ile  Val  Val
     50                       55                      60

Ser  Gln  His  Ala  Ala  Leu  Phe  Glu  Trp  His  Ala  Val  Asp  Pro  Gly  Cys
65                       70                      75                           80

Arg  Leu  Cys  Arg  Leu  Val  Pro  Phe  Ile  Gln  Lys  Ala  Ser  Val  Gly  Ile
               85                       90                      95

Thr  Val  Leu  Ser  Leu  Cys  Ala  Leu  Ser  Ile  Asp  Arg  Tyr  Arg  Ala  Val
               100                      105                     110
```

```
Ala  Ser  Trp  Ser  Arg  Ile  Lys  Gly  Ile  Gly  Val  Pro  Lys  Trp  Thr  Ala
          115                      120                     125

Val  Glu  Ile  Val  Leu  Ile  Trp  Val  Val  Ser  Val  Val  Leu  Ala  Val  Pro
          130                      135                     140

Glu  Ala  Ile  Gly  Phe  Asp  Thr  Thr  Ser  Asp  Tyr  Lys  Gly  Lys  Pro  Leu
145                           150                     155                     160

Arg  Val  Cys  Met  Leu  Asn  Pro  Phe  Gln  Lys  Thr  Ala  Phe  Met  Phe  Tyr
               165                      170                     175

Lys  Thr  Ala  Ala  Lys  Asp  Trp  Trp  Leu  Phe  Ala  Phe  Tyr  Phe  Cys  Leu
               180                      185                     190

Pro  Leu  Ala  Ile  Thr  Ala  Ile  Phe  Tyr  Thr  Leu  Met  Thr  Cys  Glu  Met
               195                      200                     205

Leu  Arg  Lys  Lys  Ser  Gly  Met  Gln  Ile  Ala  Leu  Asn  Asp  His  Leu  Lys
     210                      215                     220

Gln  Arg  Arg  Glu  Val  Ala  Lys  Thr  Val  Phe  Cys  Leu  Val  Leu  Val  Phe
225                           230                     235                     240

Ala  Leu  Cys  Trp  Leu  Pro  Leu  His  Leu  Ser  Arg  Ile  Leu  Lys  Leu  Thr
                    245                     250                     255

Leu  Tyr  Asp  Gln  Ser  Asn  Pro  Gln  Arg  Cys  Glu  Leu  Leu  Ser  Phe  Leu
               260                      265                     270

Leu  Val  Leu  Asp  Tyr  Ile  Gly  Ile  Asn  Met  Ala  Ser  Ile  Asn  Ser  Cys
          275                      280                     285

Ile  Asn  Pro  Ile  Ala  Leu  Tyr  Leu  Val  Ser  Lys  Arg  Phe  Lys  Asn  Cys
     290                      295                     300

Phe  Lys  Ser  Cys  Leu  Cys  Cys  Trp  Cys  Gln  Thr  Phe  Glu  Glu  Lys  Gln
305                           310                     315                     320

Ser  Leu  Glu  Glu  Lys  Gln  Ser  Cys  Leu  Lys  Phe  Lys  Ala  Asn  Asp  His
                    325                     330                     335

Gly  Tyr  Asp  Asn  Phe  Arg  Ser  Ser  Asn  Lys  Tyr  Ser  Ser  Ser
               340                      345                     350
```

( 2 ) INFORMATION FOR SEQ ID NO:42:

( i ) SEQUENCE CHARACTERISTICS:
        ( A ) LENGTH: 328 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:42:

```
Ile  Tyr  Val  Ile  Pro  Ala  Val  Tyr  Gly  Leu  Ile  Ile  Val  Ile  Gly  Leu
1                   5                        10                      15

Ile  Gly  Asn  Ile  Thr  Leu  Ile  Lys  Ile  Phe  Cys  Thr  Val  Lys  Ser  Leu
               20                       25                      30

Asn  Leu  Phe  Ile  Ser  Ser  Ile  Ala  Leu  Gly  Asp  Leu  Leu  Leu  Leu  Val
          35                       40                      45

Thr  Ile  Cys  Ala  Pro  Val  Asp  Ala  Ser  Lys  Tyr  Ile  Ala  Asp  Arg  Trp
     50                       55                      60

Leu  Phe  Gly  Arg  Ile  Gly  Cys  Lys  Leu  Ile  Pro  Phe  Ile  Gln  Leu  Thr
65                       70                      75                           80

Ser  Val  Gly  Val  Ser  Val  Phe  Thr  Leu  Thr  Ala  Leu  Ser  Ala  Asp  Arg
                    85                       90                      95

Tyr  Lys  Ala  Ile  Val  Arg  Pro  Thr  Cys  Ile  Gln  Ala  Ser  Leu  Ile  Cys
               100                      105                     110

Leu  Lys  Ala  Ala  Leu  Ile  Trp  Ile  Val  Ser  Leu  Leu  Ala  Ile  Pro  Glu
```

115                                   120                                   125
       Ala  Val  Phe  Ser  Asp  Leu  His  Pro  Phe  His  Val  Lys  Asp  Thr  Asn  Gln
            130                           135                           140

Thr  Phe  Ile  Ser  Cys  Ala  Pro  Tyr  Pro  His  Ser  Asn  Glu  Leu  His  Pro
       145                           150                           155                           160

Lys  Ile  His  Ser  Met  Ala  Ser  Phe  Leu  Val  Phe  Tyr  Val  Ile  Pro  Leu
                                165                           170                           175

Ala  Ile  Ile  Ser  Val  Tyr  Tyr  Tyr  Phe  Ile  Ala  Arg  Asn  Leu  Ile  Gln
                           180                           185                           190

Ser  Ala  Tyr  Asn  Leu  Pro  Val  Glu  Gly  Asn  Ile  His  Val  Lys  Lys  Gln
                 195                           200                           205

Ile  Glu  Ser  Arg  Lys  Arg  Leu  Ala  Lys  Thr  Val  Leu  Val  Phe  Val  Gly
            210                           215                           220

Leu  Phe  Ala  Phe  Cys  Trp  Leu  Pro  Asn  His  Val  Ile  Tyr  Leu  Tyr  Arg
       225                           230                           235                           240

Ser  Tyr  His  Tyr  Ser  Glu  Val  Asp  Thr  Ser  Met  Leu  His  Phe  Val  Thr
                           245                           250                           255

Ser  Ile  Cys  Ala  Arg  Leu  Leu  Ala  Pro  Thr  Asn  Ser  Cys  Val  Asn  Pro
                      260                           265                           270

Phe  Ala  Leu  Tyr  Leu  Leu  Ser  Lys  Ser  Phe  Arg  Gln  Phe  Asn  Thr  Gln
                 275                           280                           285

Leu  Leu  Cys  Cys  Gln  Pro  Gly  Leu  Ser  His  Ser  Thr  Gly  Arg  Ser  Leu
            290                           295                           300

Ser  Phe  Lys  Ser  Thr  Asn  Pro  Ser  Ala  Thr  Phe  Ser  Leu  Ile  Asn  Arg
       305                           310                           315                           320

Asn  Ile  Cys  His  Glu  Gly  Tyr  Val
                           325

( 2 ) INFORMATION FOR SEQ ID NO:43:

( i ) SEQUENCE CHARACTERISTICS:
        ( A ) LENGTH: 345 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:43:

Cys  Val  Ile  Pro  Ser  Ser  Leu  Tyr  Leu  Ile  Ile  Ile  Ser  Val  Gly  Leu
       1                 5                            10                           15

Leu  Gly  Asn  Ile  Met  Leu  Val  Lys  Ile  Phe  Leu  Thr  Asn  Ser  Thr  Met
                           20                           25                           30

Arg  Ser  Val  Pro  Asn  Ile  Phe  Ile  Ser  Asn  Ile  Ala  Ala  Gly  Asp  Leu
                      35                           40                           45

Leu  Leu  Leu  Leu  Thr  Cys  Val  Pro  Val  Asp  Ala  Ser  Arg  Tyr  Phe  Phe
            50                           55                           60

Asp  Glu  Trp  Val  Phe  Gly  Lys  Leu  Ile  Gly  Cys  Lys  Leu  Ile  Pro  Ala
       65                           70                           75                           80

Ile  Gln  Leu  Thr  Ser  Val  Gly  Val  Ser  Val  Pro  Thr  Leu  Thr  Ala  Leu
                           85                           90                           95

Ser  Ala  Asp  Arg  Tyr  Arg  Ala  Ile  Val  Asn  Pro  Met  Asp  Met  Thr  Ser
                      100                           105                           110

Gly  Val  Val  Leu  Trp  Thr  Ser  Val  Ala  Val  Gly  Ile  Trp  Val  Val  Ser
                 115                           120                           125

Val  Leu  Leu  Ala  Val  Pro  Glu  Ala  Val  Phe  Ser  Glu  Val  Ala  Arg  Ile
            130                           135                           140

```
Gly  Ser  Ser  Asp  Asn  Ser  Ser  Phe  Thr  Ala  Cys  Ile  Pro  Tyr  Pro  Gln
145                 150                      155                      160

Thr  Asp  Glu  Leu  His  Pro  Lys  Ile  His  Ser  Val  Leu  Ile  Phe  Leu  Val
                    165                      170                 175

Tyr  Phe  Leu  Ile  Pro  Leu  Val  Ile  Ile  Ser  Ile  Tyr  Tyr  Tyr  His  Ile
               180                 185                           190

Ala  Lys  Thr  Leu  Ile  Arg  Ser  Ala  His  Asn  Leu  Pro  Gly  Glu  Tyr  Asn
          195                      200                      205

Glu  His  Thr  Lys  Lys  Gln  Met  Glu  Thr  Arg  Lys  Arg  Leu  Ala  Lys  Ile
     210                      215                      220

Val  Leu  Val  Phe  Val  Gly  Cys  Phe  Val  Phe  Cys  Trp  Phe  Pro  Asn  His
225                      230                      235                      240

Ile  Leu  Tyr  Leu  Tyr  Arg  Ser  Phe  Asn  Tyr  Lys  Glu  Ile  Asp  Pro  Ser
                    245                      250                      255

Leu  Gly  Thr  Cys  Val  Thr  Leu  Val  Ala  Arg  Val  Leu  Ser  Phe  Ser  Asn
               260                      265                      270

Ser  Cys  Val  Asn  Pro  Phe  Ala  Leu  Tyr  Leu  Leu  Ser  Glu  Ser  Phe  Arg
          275                      280                      285

Lys  His  Phe  Ser  Asn  Gln  Leu  Cys  Cys  Gly  Gln  Lys  Ser  Tyr  Pro  Glu
     290                      295                      300

Arg  Ser  Thr  Ser  Tyr  Leu  Leu  Ser  Ser  Ser  Ala  Val  Trp  Arg  Ser  Leu
305                      310                      315                      320

Lys  Ser  Asn  Ala  Lys  Asn  Val  Val  Thr  Asn  Ser  Val  Leu  Ile  Asn  Gly
                    325                      330                      335

His  Ser  Thr  Lys  Gln  Glu  Ile  Ala  Leu
               340                      345
```

( 2 ) INFORMATION FOR SEQ ID NO:44:

( i ) SEQUENCE CHARACTERISTICS:
        ( A ) LENGTH: 316 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:44:

```
Tyr  Thr  Leu  Ser  Phe  Ile  Tyr  Ile  Phe  Ile  Phe  Val  Ile  Cys  Glx  Leu
1                   5                        10                      15

Leu  Ala  Asn  Ser  Val  Val  Trp  Val  Asn  Ile  Gln  Ala  Lys  Thr  Thr
                    20                   25                      30

Gly  Tyr  Asp  Thr  His  Cys  Tyr  Ile  Leu  Asn  Leu  Ala  Ile  Ala  Asp  Leu
          35                        40                      45

Trp  Trp  Leu  Thr  Ile  Pro  Val  Trp  Trp  Ser  Leu  Val  Gln  His  Asn  Gln
50                       55                        60

Trp  Pro  Met  Gly  Glu  Leu  Thr  Cys  Lys  Val  Thr  His  Leu  Ile  Phe  Ser
65                       70                        75                      80

Ile  Asn  Leu  Phe  Ser  Gly  Ile  Phe  Phe  Leu  Thr  Cys  Met  Ser  Val  Asp
                    85                        90                      95

Arg  Tyr  Leu  Ser  Ile  Thr  Tyr  Phe  Thr  Asn  Thr  Pro  Ser  Ser  Arg  Lys
               100                       105                      110

Lys  Met  Val  Arg  Arg  Ala  Val  Cys  Ile  Leu  Val  Trp  Leu  Leu  Ala  Phe
          115                       120                      125

Cys  Val  Ser  Leu  Pro  Asp  Thr  Tyr  Tyr  Leu  Lys  Thr  Val  Thr  Ser  Ala
130                       135                      140
```

```
Ser  Asn  Asn  Glu  Thr  Tyr  Cys  Arg  Ser  Phe  Tyr  Pro  Glu  His  Ser  Ile
145            150                      155                      160

Lys  Glu  Trp  Leu  Ile  Ser  Leu  Leu  Val  Ser  Val  Val  Leu  Ile  Gly  Phe
               165                      170                      175

Ala  Val  Pro  Phe  Ser  Ile  Ile  Ala  Val  Phe  Tyr  Phe  Ser  Leu  Ile  Ala
               180                      185                      190

Arg  Ala  Ile  Ser  Ala  Ser  Ser  Asp  Gln  Glu  Lys  His  Ser  Ser  Arg  Lys
               195                      200                      205

Ile  Ile  Phe  Ser  Tyr  Val  Val  Val  Phe  Leu  Val  Cys  Trp  Leu  Pro  Tyr
          210                      215                      220

His  Val  Ala  Val  Leu  Leu  Asp  Ile  Phe  Ser  Ile  Leu  His  Tyr  Ile  Pro
225                      230                      235                      240

Phe  Thr  Cys  Arg  Leu  Glu  His  Ala  Leu  Phe  Thr  Ala  Leu  His  Val  Thr
               245                      250                      255

Gln  Cys  Leu  Ser  Leu  Val  His  Cys  Cys  Val  Asn  Pro  Val  Leu  Tyr  Ser
               260                      265                      270

Phe  Ile  Asn  Arg  Asn  Tyr  Arg  Tyr  Glu  Ile  Asn  Trp  Ile  Phe  Lys  Tyr
          275                      280                      285

Ser  Ala  Lys  Thr  Gly  Leu  Thr  Lys  Leu  Ile  Asp  Ala  Ser  Arg  Val  Ser
     290                      295                      300

Glx  Thr  Glu  Tyr  Ser  Ala  Leu  Glu  Gln  Asn  Ala  Lys
305                      310                      315
```

( 2 ) INFORMATION FOR SEQ ID NO:45:

( i ) SEQUENCE CHARACTERISTICS:
        ( A ) LENGTH: 353 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:45:

```
Lys  Val  Leu  Val  Thr  Ala  Ile  Tyr  Leu  Ala  Leu  Phe  Val  Val  Gly  Thr
1              5                        10                      15

Val  Gly  Asn  Ser  Val  Thr  Ala  Phe  Thr  Leu  Ala  Arg  Lys  Lys  Ser  Leu
               20                      25                      30

Gln  Ser  Leu  Gln  Ser  Thr  Val  His  Tyr  His  Leu  Ser  Ser  Leu  Ala  Leu
               35                      40                      45

Ser  Asp  Leu  Leu  Ile  Leu  Leu  Trp  Val  Glu  Leu  Tyr  Asn  Phe  Ile  Trp
     50                      55                      60

His  His  Pro  Trp  Ala  Phe  Gly  Asp  Ala  Gly  Cys  Arg  Gly  Tyr  Tyr  Phe
65                       70                      75                       80

Leu  Arg  Asp  Ala  Cys  Thr  Tyr  Ala  Thr  Ala  Leu  Asn  Val  Ala  Ser  Leu
               85                      90                      95

Ser  Val  Glu  Arg  Tyr  Leu  Ala  Ile  Cys  His  Pro  Phe  Lys  Ala  Lys  Thr
               100                     105                     110

Leu  Met  Ser  Arg  Ser  Arg  Thr  Lys  Lys  Phe  Ile  Ser  Ala  Ile  Trp  Leu
               115                     120                     125

Ala  Ser  Ala  Leu  Leu  Ala  Ile  Pro  Met  Leu  Phe  Thr  Leu  Gly  Leu  Gln
     130                     135                     140

Asn  Arg  Ser  Gly  Asp  Gly  Thr  His  Pro  Gly  Gly  Leu  Val  Cys  Thr  Pro
145                     150                     155                     160

Ile  Val  Asp  Thr  Ala  Thr  Val  Lys  Val  Val  Ile  Gln  Val  Asn  Thr  Phe
               165                     170                     175

Met  Ser  Phe  Leu  Phe  Pro  Met  Leu  Val  Ile  Ser  Ile  Leu  Asn  Thr  Val
```

|   |     |     |     |     |     | 180 |     |     |     |     | 185 |     |     |     |     | 190 |     |
|---|-----|-----|-----|-----|-----|-----|-----|-----|-----|-----|-----|-----|-----|-----|-----|-----|-----|

```
              180                              185                              190
    Ile  Ala  Asn  Lys  Leu  Thr  Val  Met  Val  His  Gln  Ala  Ala  Glu  Gln  Gly
              195                    200                    205
    Arg  Val  Cys  Thr  Val  Gly  Thr  His  Asn  Gly  Leu  Glu  His  Ser  Thr  Phe
    210                         215                    220
    Asn  Met  Arg  Ile  Glu  Pro  Gly  Arg  Val  Gln  Ala  Leu  Arg  His  Gly  Val
    225                    230                    235                              240
    Leu  Val  Leu  Arg  Ala  Val  Val  Ile  Ala  Phe  Val  Val  Cys  Trp  Leu  Pro
                        245                    250                    255
    Tyr  Leu  Cys  Tyr  Ile  Ser  Asp  Glu  Gln  Trp  Arg  Thr  Phe  Leu  Phe  Asp
                   260                    265                    270
    Phe  Tyr  His  Tyr  Phe  Tyr  Met  Leu  Thr  Asn  Ala  Leu  Phe  Tyr  Val  Ser
              275                    280                    285
    Ser  Ala  Ile  Asn  Pro  Ile  Leu  Tyr  Asn  Leu  Val  Ser  Ala  Asn  Phe  Arg
         290                    295                    300
    Gln  Val  Phe  Leu  Ser  Thr  Leu  Ala  Cys  Leu  Phe  Cys  Pro  Gly  Trp  Pro
    305                    310                    315                              320
    Leu  Ile  Arg  Arg  Lys  Lys  Arg  Pro  Thr  Phe  Ser  Arg  Lys  Pro  Asn  Ser
                        325                    330                    335
    Met  Ser  Ser  Asn  His  Ala  Phe  Ser  Thr  Ser  Ala  Thr  Arg  Phe  Thr  Leu
                   340                    345                    350
    Tyr
```

( 2 ) INFORMATION FOR SEQ ID NO:46:

( i ) SEQUENCE CHARACTERISTICS:
( A ) LENGTH: 316 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:46:

```
    Ala  Ile  Gln  Ala  Pro  Phe  Leu  Trp  Val  Leu  Phe  Leu  Leu  Ala  Ala  Leu
    1                   5                        10                        15
    Glu  Asn  Ile  Phe  Val  Leu  Ser  Val  Phe  Cys  Leu  His  Lys  Thr  Asn  Cys
                   20                        25                        30
    Thr  Val  Ala  Glu  Ile  Tyr  Leu  Gly  Asn  Ile  Ala  Ser  Ala  Asp  Leu  Ile
                   35                        40                        45
    Ile  Ala  Cys  Gly  Leu  Pro  Phe  Trp  Ala  Ile  Thr  Ile  Ala  Asn  Asn  Phe
         50                        55                        60
    Asp  Trp  Leu  Phe  Gly  Glu  Val  Leu  Cys  Arg  Val  Val  Asn  Leu  Tyr  Met
    65                        70                        75                        80
    Asn  Leu  Tyr  Ser  Ser  Ile  Cys  Phe  Leu  Val  Ser  Ile  Asp  Arg  Tyr  Leu
                        85                        90                        95
    Ala  Leu  Val  Lys  Thr  Met  Ser  Asn  Leu  Arg  Trp  Ala  Lys  Leu  Tyr  Ser
                   100                       105                       110
    Leu  Val  Ile  Trp  Ser  Cys  Thr  Leu  Leu  Leu  Ser  Ser  Pro  Met  Leu  Val
                   115                       120                       125
    Phe  Arg  Thr  Met  Tyr  Arg  Glu  Glu  Gly  His  Asn  Val  Thr  Cys  Val  Ile
         130                       135                       140
    Val  Tyr  Pro  Ser  Arg  Ser  Trp  Glu  Val  Phe  Leu  Leu  Asn  Leu  Val  Gly
    145                       150                       155                       160
    Phe  Leu  Leu  Pro  Leu  Ser  Ile  Ile  Thr  Phe  Cys  Thr  Val  Arg  Ile  Met
                        165                       170                       175
```

|  |  |  |  |  |  |  |  |  |  |  |  |  |  |  |
|---|---|---|---|---|---|---|---|---|---|---|---|---|---|---|
| Val | Leu | Arg | Asn<br>180 | Asn | Glu | Met | Lys | Lys<br>185 | Phe | Lys | Glu | Val | Gln<br>190 | Thr | Glu |
| Lys | Lys | Ala<br>195 | Thr | Val | Leu | Val | Ile<br>200 | Ala | Val | Leu | Gly | Leu<br>205 | Phe | Val | Leu |
| Cys | Trp<br>210 | Phe | Pro | Phe | Gln | Ile<br>215 | Ser | Thr | Phe | Leu | Asp<br>220 | Thr | Leu | Leu | Arg |
| Leu<br>225 | Gly | Val | Leu | Ser | Gly<br>230 | Cys | Trp | Asn | Glu | Arg<br>235 | Ala | Val | Asp | Ile | Val<br>240 |
| Arg | Gln | Ile | Ser | Ser<br>245 | Tyr | Val | Ala | Tyr | Ser<br>250 | Asn | Ser | Cys | Leu | Asn<br>255 | Pro |
| Leu | Val | Tyr | Val<br>260 | Ile | Val | Gly | Lys | Arg<br>265 | Phe | Arg | Lys | Lys | Ser<br>270 | Arg | Glu |
| Val | Tyr | Gln<br>275 | Ala | Ile | Cys | Arg | Lys<br>280 | Gly | Gly | Cys | Met | Gly<br>285 | Glu | Ser | Val |
| Leu | Asn<br>290 | Ser | Met | Gly | Thr | Leu<br>295 | Arg | Thr | Ser | Ile | Ser<br>300 | Val | Asp | Arg | Gln |
| Ile<br>305 | His | Lys | Leu | Gln | Asp<br>310 | Trp | Ala | Gly | Asn | Lys<br>315 | Gln |  |  |  |  |

(2) INFORMATION FOR SEQ ID NO:47:

(i) SEQUENCE CHARACTERISTICS:
    (A) LENGTH: 347 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:47:

|  |  |  |  |  |  |  |  |  |  |  |  |  |  |  |
|---|---|---|---|---|---|---|---|---|---|---|---|---|---|---|
| Ile<br>1 | Leu | Leu | Val | Val<br>5 | Ile | Ile | Cys | Gly | Leu<br>10 | Gly | Ile | Val | Gly | Asn<br>15 | Ile |
| Met | Val | Val | Leu<br>20 | Val | Val | Met | Arg | Thr<br>25 | Thr | Pro | Thr | Asn | Cys<br>30 | Tyr | Leu |
| Val | Ser | Ile<br>35 | Ala | Val | Ala | Asp | Leu<br>40 | Met | Val | Leu | Val | Ala<br>45 | Ala | Gly | Leu |
| Pro | Asn<br>50 | Ile | Thr | Asp | Ser | Ile<br>55 | Tyr | Gly | Ser | Trp | Val<br>60 | Tyr | Gly | Tyr | Val |
| Gly<br>65 | Cys | Leu | Cys | Ile | Thr<br>70 | Tyr | Leu | Gln | Tyr | Leu<br>75 | Gly | Ile | Asn | Ala | Ser<br>80 |
| Ser | Cys | Ser | Ile | Thr<br>85 | Ala | Phe | Thr | Ile | Glu<br>90 | Arg | Tyr | Ile | Ala | Ile<br>95 | Cys |
| His | Pro | Ile | Lys<br>100 | Ala | Gln | Phe | Leu | Cys<br>105 | Thr | Phe | Ser | Arg | Ala<br>110 | Lys | Lys |
| Ile | Ile | Ile<br>115 | Phe | Val | Trp | Ala | Phe<br>120 | Thr | Ser | Ile | Tyr | Leu<br>125 | Phe | Leu | Leu |
| Asp | Ile<br>130 | Asn | Ile | Ser | Thr | Tyr<br>135 | Lys | Asn | Ala | Val | Val<br>140 | Val | Ser | Cys | Gly |
| Tyr<br>145 | Lys | Ile | Ser | Arg | Asn<br>150 | Tyr | Tyr | Ser | Pro | Ile<br>155 | Tyr | Leu | Met | Asp | Phe<br>160 |
| Gly | Val | Phe | Tyr | Val<br>165 | Val | Pro | Leu | Ile | Ala<br>170 | Thr | Val | Leu | Tyr | Gly<br>175 | Phe |
| Ile | Ala | Arg | Ile<br>180 | Leu | Phe | Leu | Asn | Pro<br>185 | Ile | Pro | Ser | Asp | Pro<br>190 | Lys | Glu |
| Asn | Ser | Lys<br>195 | Met | Trp | Lys | Asn | Asp<br>200 | Ser | Ile | His | Gln | Asn<br>205 | Lys | Asn | Leu |
| Asn | Leu | Asn | Ala | Ser | Ser | Arg | Lys | Gln | Val | Thr | Ile | Asn | Leu | Ala | Val |

```
              210                      215                      220
Val  Val  Ile  Leu  Phe  Ala  Leu  Leu  Trp  Asn  Thr  Tyr  Arg  Thr  Leu  Val
225                      230                      235                      240

Val  Val  Asn  Ser  Phe  Leu  Ser  Ser  Pro  Phe  Gln  Glu  Asn  Trp  Lys  Leu
                    245                      250                      255

Leu  Lys  Cys  Arg  Ile  Cys  Ile  Tyr  Leu  Asn  Ser  Ala  Ile  Asn  Pro  Val
               260                      265                      270

Ile  Tyr  Asn  Ile  Met  Ser  Gln  Lys  Arg  Phe  Ala  Ala  Phe  Arg  Lys  Leu
          275                      280                      285

Cys  Asn  Cys  Lys  Gln  Lys  Pro  Thr  Glu  Lys  Ala  Ala  Asn  Tyr  Ser  Val
          290                      295                      300

Ala  Leu  Asn  Tyr  Ser  Val  Ile  Lys  Glu  Ser  Asp  Arg  Phe  Ser  Thr  Glu
305                      310                      315                      320

Leu  Glu  Asp  Ile  Thr  Val  Thr  Asp  Thr  Tyr  Val  Ser  Thr  Thr  Lys  Val
                    325                      330                      335

Ser  Phe  Asp  Asp  Thr  Cys  Ile  Ala  Ser  Glu  Asn
                    340                      345
```

( 2 ) INFORMATION FOR SEQ ID NO:48:

( i ) SEQUENCE CHARACTERISTICS:
        ( A ) LENGTH: 341 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:48:

```
Leu  Ala  Leu  Trp  Ala  Thr  Ala  Tyr  Leu  Ala  Leu  Val  Leu  Val  Ala  Val
1                   5                        10                       15

Thr  Gly  Asn  Ala  Ile  Val  Ile  Trp  Ile  Ile  Leu  Ala  His  Arg  Arg  Met
               20                       25                       30

Arg  Thr  Val  Thr  Asn  Tyr  Phe  Ile  Val  Asn  Ile  Ala  Leu  Ala  Asp  Leu
          35                       40                       45

Leu  Asn  Ala  Ala  Phe  Asn  Phe  Val  Tyr  Ala  Ser  His  Asn  Ile  Trp  Tyr
     50                       55                       60

Phe  Gly  Arg  Ala  Phe  Cys  Tyr  Phe  Gln  Asn  Leu  Phe  Pro  Ile  Thr  Ala
65                       70                       75                       80

Met  Phe  Val  Ser  Ile  Tyr  Ser  Met  Thr  Ala  Ile  Ala  Ala  Asp  Arg  Tyr
               85                       90                       95

Met  Ala  Ile  Val  His  Pro  Phe  Gln  Pro  Arg  Leu  Ser  Ala  Pro  Ser  Thr
               100                      105                      110

Lys  Ala  Val  Ile  Ala  Gly  Ile  Trp  Leu  Val  Ala  Ile  Lys  Leu  Ala  Phe
          115                      120                      125

Pro  Gln  Cys  Phe  Tyr  Ser  Thr  Val  Thr  Met  Gln  Gly  Ala  Thr  Lys  Cys
     130                      135                      140

Val  Val  Ala  Trp  Pro  Glu  Asp  Ser  Gly  Lys  Thr  Leu  Leu  Leu  Tyr  
145                      150                      155                      160

His  Leu  Val  Val  Ile  Ala  Leu  Ile  Tyr  Phe  Leu  Pro  Ile  Ala  Leu  Ala
                    165                      170                      175

Tyr  Ser  Val  Ile  Gly  Leu  Thr  Leu  Trp  Arg  Arg  Ala  Val  Pro  Gly  His
               180                      185                      190

Gln  Ala  His  Gly  Ala  Asn  Leu  Arg  His  Leu  Gln  Ala  Lys  Lys  Lys  Phe
          195                      200                      205

Val  Lys  Thr  Met  Val  Leu  Val  Val  Val  Thr  Phe  Ala  Ile  Cys  Trp  Leu
     210                      215                      220
```

```
Pro  Tyr  His  Leu  Tyr  Phe  Ile  Leu  Gly  Ser  Phe  Gln  Glu  Asp  Ile  Tyr
225                 230                      235                          240

Cys  His  Lys  Phe  Ile  Gln  Gln  Val  Tyr  Leu  Ala  Leu  Phe  Trp  Leu  Ala
               245                      250                     255

Met  Ser  Ser  Thr  Met  Tyr  Asn  Pro  Ile  Tyr  Cys  Cys  Leu  Asn  His
               260                 265                     270

Arg  Phe  Arg  Ser  Gly  Phe  Arg  Leu  Ala  Phe  Arg  Cys  Cys  Pro  Trp  Val
          275                      280                     285

Thr  Pro  Thr  Lys  Glu  Asp  Lys  Leu  Glu  Leu  Thr  Pro  Thr  Thr  Ser  Leu
     290                 295                      300

Ser  Thr  Arg  Val  Asn  Arg  Cys  His  Thr  Lys  Glu  Thr  Leu  Phe  Met  Ala
305                      310                 315                          320

Gly  Asp  Thr  Ala  Pro  Ser  Glu  Ala  Thr  Ser  Gly  Glu  Ala  Gly  Arg  Pro
                    325                      330                     335

Gln  Asp  Gly  Ser  Gly
                    340
```

( 2 ) INFORMATION FOR SEQ ID NO:49:

( i ) SEQUENCE CHARACTERISTICS:
        ( A ) LENGTH: 340 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

```
Ile  Val  Leu  Trp  Ala  Ala  Tyr  Thr  Val  Ile  Val  Val  Arg  Ser  Val
1                   5                      10                      15

Val  Gly  Asn  Val  Val  Ile  Trp  Ile  Ile  Leu  Ala  His  Lys  Arg  Met
               20                 25                      30

Arg  Thr  Val  Thr  Asn  Tyr  Phe  Leu  Val  Asn  Ile  Ala  Phe  Ala  Phe  Ala
          35                      40                      45

Leu  Asn  Thr  Trp  Asn  Phe  Thr  Tyr  Ala  Val  His  Asn  Val  Trp  Tyr  Tyr
     50                      55                      60

Gly  Leu  Phe  Tyr  Cys  Lys  Phe  His  Asn  Phe  Phe  Pro  Ile  Ala  Ala  Leu
65                       70                     75                            80

Phe  Ala  Ser  Ile  Tyr  Ser  Met  Thr  Ala  Val  Ala  Phe  Asp  Arg  Tyr  Leu
               85                      90                          95

Ile  Ile  His  Pro  Leu  Gln  Pro  Arg  Leu  Ser  Ala  Thr  Ala  Thr  Lys  Val
               100                 105                     110

Val  Ile  Phe  Val  Ile  Trp  Val  Ile  Ala  Leu  Leu  Leu  Ala  Ser  Pro  Gln
          115                 120                      125

Gly  Tyr  Tyr  Ser  Thr  Thr  Glu  Leu  Ser  Arg  Val  Val  Cys  Met  Ile  Glu
     130                 135                      140

Trp  Pro  Glu  His  Pro  Asn  Arg  Thr  Tyr  Glu  Lys  Ala  Tyr  His  Ile  Cys
145                      150                      155                     160

Val  Thr  Val  Leu  Ile  Tyr  Phe  Leu  Pro  Leu  Leu  Val  Ile  Gly  Tyr  Ala
               165                      170                     175

Tyr  Thr  Val  Val  Gly  Ile  Thr  Leu  Trp  Ala  Ser  Glu  Ile  Pro  Gly  Asp
          180                      185                     190

Ser  Ser  Asp  Arg  Tyr  His  Glu  Gln  Val  Ser  Ala  Lys  Arg  Lys  Val  Val
          195                 200                      205

Lys  Met  Ile  Cys  Val  Val  Val  Cys  Thr  Phe  Ala  Ile  Cys  Trp  Leu  Pro
     210                 215                      220
```

```
        Phe  His  Val  Phe  Phe  Leu  Leu  Pro  Tyr  Ile  Asn  Pro  Asp  Leu  Tyr  Leu
        225                 230                      235                      240

Lys  Lys  Phe  Ile  Gln  Gln  Val  Tyr  Ile  Ala  Ser  Met  Trp  Leu  Ala  Met
                            245                      250                      255

Ser  Ser  Thr  Met  Tyr  Asn  Pro  Ile  Ile  Tyr  Cys  Cys  Leu  Asn  Asp  Arg
                       260                      265                      270

Phe  Arg  Leu  Gly  Phe  Lys  His  Ala  Phe  Arg  Cys  Cys  Pro  Phe  Ile  Ser
                       275                      280                      285

Ala  Gly  Asp  Tyr  Glu  Gly  Leu  Glu  Met  Ile  Lys  Ser  Thr  Arg  Tyr  Leu
                  290                      295                      300

Gln  Thr  Leu  Ser  Ser  Val  Tyr  Lys  Val  Ser  Arg  Leu  Glu  Thr  Thr  Ile
        305                      310                      315                      320

Ser  Thr  Val  Val  Gly  Ala  His  Glu  Glu  Glu  Pro  Glu  Glu  Gly  Pro  Lys
                            325                      330                      335

Ala  Thr  Pro  Ser
                       340
```

( 2 ) INFORMATION FOR SEQ ID NO:50:

( i ) SEQUENCE CHARACTERISTICS:
        ( A ) LENGTH: 336 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:50:

```
        Ile  Ala  Leu  Trp  Ser  Leu  Ala  Tyr  Gly  Leu  Val  Val  Ala  Val  Ala  Val
        1                  5                        10                       15

Phe  Gly  Asn  Leu  Ile  Val  Ile  Trp  Ile  Ile  Leu  Ala  His  Lys  Arg  Met
                       20                       25                       30

Arg  Thr  Val  Thr  Asn  Tyr  Phe  Leu  Val  Asn  Leu  Ala  Phe  Ser  Asp  Ala
                       35                       40                       45

Ser  Val  Ala  Ala  Phe  Asn  Thr  Leu  Ile  Asn  Phe  Ile  Tyr  Gly  Leu  His
                  50                       55                       60

Ser  Glu  Trp  Tyr  Phe  Gly  Ala  Asn  Tyr  Cys  Arg  Phe  Gln  Asn  Phe  Phe
        65                       70                       75                       80

Pro  Ile  Thr  Ala  Val  Phe  Ala  Ser  Ile  Tyr  Ser  Met  Ala  Ile  Ala  Val
                            85                       90                       95

Asp  Arg  Tyr  Met  Ala  Ile  Ile  Asp  Pro  Leu  Lys  Pro  Arg  Leu  Ser  Ala
                       100                      105                      110

Thr  Ala  Thr  Lys  Ile  Val  Ile  Gly  Ser  Ile  Trp  Ile  Leu  Ala  Phe  Leu
                       115                      120                      125

Leu  Ala  Phe  Pro  Gln  Cys  Leu  Tyr  Ser  Lys  Ile  Leu  Gly  Arg  Thr  Leu
                  130                      135                      140

Cys  Tyr  Val  Trp  Pro  Glu  Gly  Pro  Lys  Gln  His  Phe  Thr  Tyr  His  Ile
        145                      150                      155                      160

Ile  Val  Ile  Ile  Leu  Val  Tyr  Cys  Phe  Pro  Leu  Leu  Ile  Leu  Thr  Tyr
                            165                      170                      175

Thr  Ile  Val  Gly  Ile  Thr  Leu  Trp  Gly  Gly  Glu  Ile  Pro  Gly  Asp  Thr
                       180                      185                      190

Cys  Asp  Lys  Tyr  His  Glu  Gln  Leu  Lys  Ala  Lys  Arg  Lys  Val  Val  Met
                       195                      200                      205

Asn  Ile  Val  Val  Val  Thr  Phe  Ala  Ile  Cys  Trp  Leu  Pro  Tyr  His  Val
                  210                      215                      220

Tyr  Phe  Ile  Leu  Thr  Ala  Ile  Tyr  Gln  Gln  Leu  Asn  Arg  Trp  Lys  Tyr
```

|  | 225 |  |  |  | 230 |  |  |  | 235 |  |  |  | 240 |
|---|---|---|---|---|---|---|---|---|---|---|---|---|---|

Ile Gln Gln Val Tyr Leu Ala Ser Phe Trp Leu Ala Met Ser Ser Thr
                245                 250                 255

Met Tyr Asn Pro Ile Ile Tyr Cys Cys Leu Asn Lys Arg Phe Arg Ala
            260             265                 270

Gly Phe Lys Arg Ala Phe Arg Trp Cys Pro Phe Ile Gln Val Ser Ser
        275             280                 285

Tyr Asp Glu Leu Glu Leu Lys Thr Thr Arg Phe His Pro Thr Arg Gln
    290                 295                 300

Ser Ser Leu Tyr Thr Val Ser Phe Met Ser Val Thr Val Leu Phe Asp
305             310                 315                 320

Pro Asn Asp Gly Asp Pro Thr Lys Ser Ser Arg Lys Lys Arg Ala Val
            325                 330                 335

( 2 ) INFORMATION FOR SEQ ID NO:51:

( i ) SEQUENCE CHARACTERISTICS:
        ( A ) LENGTH: 325 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:51:

Met Ile Pro Thr Leu Tyr Ser Ile Ile Phe Val Val Gly Ile Phe Gly
1               5                   10                  15

Asn Ser Leu Val Val Ile Val Ile Tyr Phe Tyr Met Lys Leu Lys Thr
            20                  25                  30

Tyr Ala Ser Val Phe Leu Leu Asn Leu Ala Leu Ala Asp Leu Cys Phe
        35                  40                  45

Leu Leu Thr Leu Pro Leu Trp Ala Val Tyr Thr Leu Tyr Arg Trp Pro
    50                  55                  60

Phe Gly Asn Tyr Leu Cys Lys Ile Ala Ser Ala Ser Val Ser Phe Asn
65                  70                  75                  80

Leu Tyr Ala Ser Val Phe Leu Leu Thr Cys Leu Ser Ile Asp Arg Tyr
            85                  90                  95

Leu Ala Ile Val His Pro Met Lys Ser Arg Leu Arg Arg Leu Val Ala
            100                 105                 110

Lys Val Thr Cys Ile Ile Ile Trp Leu Leu Ala Gly Ile Ala Ser Leu
            115                 120                 125

Pro Thr Ile Ile His Arg Asn Phe Phe Ile Glu Asn Thr Asn Ile Thr
        130                 135                 140

Val Cys Ala Phe His Tyr Glu Ser Gln Asn Ser Thr Leu Pro Val Gly
145                 150                 155                 160

Leu Gly Leu Thr Lys Asn Ile Leu Gly Phe Leu Phe Pro Phe Leu Ile
            165                 170                 175

Ile Leu Thr Ser Tyr Thr Leu Ile Trp Lys Thr Leu Lys Lys Ala Tyr
            180                 185                 190

Glu Ile Gln Lys Asn Lys Pro Arg Lys Asp Asp Ile Phe Lys Ile Ile
        195                 200                 205

Ile Ala Ile Val Leu Phe Phe Phe Phe Ser Trp Val Pro His Asn Ile
    210                 215                 220

Phe Thr Phe Met Val Leu Ile Gln Leu Gly Leu Ile Arg Asp Cys Lys
225                 230                 235                 240

Ile Glu Asp Ile Val Asp Thr Ala Met Pro Ile Thr Ile Cys Leu Ala
            245                 250                 255

```
Tyr Phe Gln Gln Asn Leu Asn Pro Leu Phe Tyr Gly Phe Leu Gly Lys
            260                 265                 270

Lys Phe Lys Lys Tyr Phe Leu His Ala Leu Leu Lys Tyr Ile Pro Pro
        275                 280                 285

Lys Ala Lys Ser His Ser Asn Leu Ser Thr Lys Met Ser Thr Leu Ser
        290                 295                 300

Tyr Arg Pro Ser Glu Gln Gly Asn Ser Ser Thr Lys Lys Pro Ala Pro
305                 310                 315                 320

Cys Ile Glu Val Glu
                325
```

(2) INFORMATION FOR SEQ ID NO:52:

(i) SEQUENCE CHARACTERISTICS:
    (A) LENGTH: 282 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:52:

```
Ile Val His Trp Val Ile Met Ser Ile Ser Pro Val Gly Phe Val Glu
1               5                   10                  15

Asn Gly Ile Leu Leu Trp Phe Leu Cys Phe Phe Thr Val Tyr Thr His
            20                  25                  30

Leu Ser Ile Ala Asp Ile Ser Leu Leu Phe Cys Ile Phe Ile Leu Ser
            35                  40                  45

Ile Asp Tyr Ala Leu Asp Tyr Glu Leu Ser Ser Gly His Tyr Tyr Thr
        50                  55                  60

Ile Val Thr Leu Ser Val Thr Phe Leu Phe Gly Tyr Asn Thr Gly Leu
65                  70                  75                  80

Tyr Leu Leu Thr Ala Ile Ser Val Glu Arg Cys Leu Ser Val Leu Tyr
                85                  90                  95

Pro Ile Trp Tyr Arg Cys His Arg Pro Lys Tyr Gln Ser Ala Leu Val
            100                 105                 110

Cys Ala Leu Leu Trp Ala Leu Ser Cys Leu Val Thr Thr Met Tyr Val
            115                 120                 125

Met Cys Ile Asp Arg Phe Glu Glu Ser His Ser Arg Asn Asp Cys Arg
        130                 135                 140

Ala Val Ile Ile Phe Ile Ala Ile Leu Ser Phe Leu Val Phe Thr Pro
145                 150                 155                 160

Ser Val Ser Ser Thr Ile Leu Val Val Lys Ile Arg Lys Asn Thr Trp
                165                 170                 175

Ala Ser His Ser Ser Lys Leu Tyr Ile Val Ile Met Val Thr Ile Ile
            180                 185                 190

Ile Phe Leu Ile Phe Ala Met Pro Met Arg Leu Leu Tyr Leu Leu Tyr
            195                 200                 205

Tyr Glu Tyr Trp Ser Thr Phe Gly Asn Leu His His Ile Ser Leu Leu
        210                 215                 220

Phe Ser Thr Ile Asn Ser Ser Ala Asn Pro Phe Ile Tyr Phe Phe Val
225                 230                 235                 240

Gly Ser Ser Lys Lys Lys Arg Phe Lys Glu Ser Leu Lys Val Val Leu
                245                 250                 255

Thr Arg Ala Phe Lys Asp Glu Met Gln Pro Arg Arg Gln Lys Asp Asn
            260                 265                 270
```

Cys Asn Thr Val Thr Val Glu Thr Val Val
    275             280

(2) INFORMATION FOR SEQ ID NO:53:

(i) SEQUENCE CHARACTERISTICS:
    (A) LENGTH: 332 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:53:

Tyr Asp Phe Leu Arg Val Leu Ile Trp Leu Ile Asn Ile Leu Ala Ile
1               5                   10                  15
Met Gly Asn Val Met Thr Leu Phe Val Leu Leu Thr Ser Arg Tyr Lys
            20                  25                  30
Leu Thr Val Pro Arg Phe Ile Met Asn Leu Ser Phe Ala Asp Phe Cys
        35                  40                  45
Met Leu Tyr Leu Leu Leu Ile Ala Ser Val Asp Ser Gln Thr Lys Gly
    50                  55                  60
Gln Tyr Tyr Asn His Ala Ile Asp Trp Gln Thr Gly Ser Gly Cys Ser
65                  70                  75                  80
Thr Ala Gly Phe Phe Thr Val Leu Ala Ser Glu Leu Ser Val Tyr Thr
                85                  90                  95
Leu Thr Val Ile Thr Leu Glu Arg Trp His Thr Ile Thr Tyr Ala Ile
                100                 105                 110
His Ile Asp Gln Lys Leu Arg Leu Arg His Ala Ile Leu Ile Met Leu
        115                 120                 125
Gly Gly Trp Leu Phe Ser Ser Leu Ile Ala Met Leu Pro Leu Val Cys
    130                 135                 140
Val Ser Asn Tyr Met Lys Val Ser Ile Cys Leu Pro Met Val Glu Thr
145                 150                 155                 160
Thr Leu Ser Gln Val Tyr Ile Leu Thr Ile Leu Ile Leu Asn Val Val
                165                 170                 175
Ala Phe Leu Ile Ile Cys Ala Cys Tyr Ile Lys Ile Tyr Phe Ala Val
                180                 185                 190
Arg Asn Pro Glu Ile Met Ala Thr Asn Lys Asp Thr Lys Ile Ala Leu
            195                 200                 205
Ala Ile Leu Ile Phe Thr Asp Phe Thr Cys Met Pro Ile Ser Phe Phe
210                 215                 220
Ala Ile Ser Ala Ala Phe Lys Val Pro Leu Ile Val Thr Asn Ser Lys
225                 230                 235                 240
Val Leu Leu Val Leu Phe Tyr Pro Ile Asn Ser Cys Ala Asn Pro Phe
                245                 250                 255
Leu Tyr Ala Ile Phe Thr Lys Thr Phe Gln Arg Asp Phe Phe Ile Leu
            260                 265                 270
Ser Lys Phe Cys Cys Lys Arg Arg Ala Asp Ile Tyr Arg Arg Lys Asp
        275                 280                 285
Phe Ser Ala Tyr Thr Ser Asn Cys Lys Lys Gly Phe Thr Gly Ser Asn
    290                 295                 300
Lys Pro Ser Gln Ser Thr Leu Lys Leu Ser Thr Leu His Cys Gln Gly
305                 310                 315                 320
Thr Ala Leu Leu Asp Lys Arg Arg Tyr Thr Glu Cys
                325                 330

( 2 ) INFORMATION FOR SEQ ID NO:54:

( i ) SEQUENCE CHARACTERISTICS:
    ( A ) LENGTH: 336 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:54:

| | | | | | | | | | | | | | | |
|---|---|---|---|---|---|---|---|---|---|---|---|---|---|---|
| Tyr | Lys | Phe | Leu | Arg | Ile | Val | Val | Trp | Phe | Val | Ser | Leu | Leu | Ala | Leu |
| 1 | | | | 5 | | | | | 10 | | | | | 15 | |
| Leu | Gly | Asn | Val | Phe | Val | Leu | Leu | Ile | Leu | Leu | Thr | Ser | His | Tyr | Lys |
| | | | 20 | | | | | 25 | | | | | 30 | | |
| Leu | Asn | Val | Pro | Arg | Phe | Ile | Met | Asn | Ile | Ala | Phe | Ala | Asp | Phe | Cys |
| | | | 35 | | | | | 40 | | | | | 45 | | |
| Met | Met | Tyr | Leu | Leu | Leu | Ile | Ala | Ser | Val | Asp | Leu | Tyr | Thr | His | Ser |
| | | 50 | | | | | 55 | | | | | 60 | | | |
| Glu | Tyr | Tyr | Asn | His | Ala | Ile | Asp | Trp | Gln | Thr | Gly | Pro | Gly | Cys | Asn |
| 65 | | | | | 70 | | | | | 75 | | | | | 80 |
| Thr | Ala | Gly | Phe | Phe | Thr | Val | Phe | Ala | Ser | Glu | Leu | Ser | Val | Tyr | Thr |
| | | | | 85 | | | | | 90 | | | | | 95 | |
| Leu | Thr | Val | Ile | Thr | Leu | Glu | Arg | Trp | Tyr | Ala | Ile | Thr | Phe | Ala | Met |
| | | | | 100 | | | | | 105 | | | | | 110 | |
| Arg | Leu | Asp | Arg | Lys | Ile | Arg | Leu | Arg | His | Ala | Cys | Ala | Ile | Met | Val |
| | | | 115 | | | | | 120 | | | | | 125 | | |
| Gly | Gly | Trp | Val | Cys | Cys | Phe | Leu | Leu | Ala | Leu | Leu | Pro | Leu | Val | Gly |
| | | 130 | | | | | 135 | | | | | 140 | | | |
| Ile | Ser | Ser | Tyr | Ala | Lys | Val | Ser | Ile | Cys | Leu | Pro | Met | Thr | Glu | Thr |
| 145 | | | | | 150 | | | | | 155 | | | | | 160 |
| Pro | Leu | Ala | Leu | Ala | Tyr | Ile | Val | Phe | Val | Leu | Thr | Leu | Asn | Ile | Val |
| | | | | 165 | | | | | 170 | | | | | 175 | |
| Ala | Phe | Val | Ile | Val | Cys | Cys | Cys | Tyr | Val | Lys | Ile | Tyr | Ile | Thr | Val |
| | | | 180 | | | | | 185 | | | | | 190 | | |
| Arg | Asn | Pro | Gln | Tyr | Asn | Pro | Gly | Asp | Lys | Asp | Thr | Lys | Ile | Ala | Lys |
| | | 195 | | | | | 200 | | | | | 205 | | | |
| Arg | Met | Ala | Val | Leu | Ile | Phe | Thr | Asp | Phe | Ile | Cys | Met | Ala | Pro | Ile |
| | 210 | | | | | 215 | | | | | 220 | | | | |
| Ser | Phe | Tyr | Ala | Leu | Ser | Ala | Ile | Leu | Asn | Lys | Pro | Leu | Ile | Thr | Val |
| 225 | | | | | 230 | | | | | 235 | | | | | 240 |
| Ser | Asn | Ser | Lys | Ile | Leu | Leu | Val | Leu | Phe | Tyr | Pro | Leu | Asn | Ser | Cys |
| | | | | 245 | | | | | 250 | | | | | 255 | |
| Ala | Asn | Pro | Phe | Leu | Tyr | Ala | Ile | Phe | Thr | Lys | Ala | Phe | Gln | Arg | Asp |
| | | | 260 | | | | | 265 | | | | | 270 | | |
| Val | Phe | Ile | Leu | Leu | Ser | Lys | Phe | Gly | Ile | Cys | Lys | Arg | Gln | Ala | Gln |
| | | 275 | | | | | 280 | | | | | 285 | | | |
| Ala | Tyr | Arg | Gly | Gln | Arg | Val | Pro | Pro | Lys | Asn | Ser | Thr | Asp | Ile | Gln |
| | 290 | | | | | 295 | | | | | 300 | | | | |
| Val | Gln | Lys | Val | Thr | His | Asp | Met | Arg | Gln | Gly | Ala | Leu | Asn | Met | Glu |
| 305 | | | | | 310 | | | | | 315 | | | | | 320 |
| Asp | Val | Val | Glu | Leu | Ile | Glu | Asn | Ser | His | Leu | Thr | Pro | Lys | Lys | Gln |
| | | | | 325 | | | | | 330 | | | | | 335 | |

( 2 ) INFORMATION FOR SEQ ID NO:55:

( i ) SEQUENCE CHARACTERISTICS:
    ( A ) LENGTH: 327 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:55:

| Tyr | Asn | Ile | Leu | Arg | Val | Leu | Ile | Trp | Phe | Ile | Ser | Ile | Leu | Ala | Ile |
|---|---|---|---|---|---|---|---|---|---|---|---|---|---|---|---|
| 1 | | | | 5 | | | | | 10 | | | | | 15 | |
| Thr | Gly | Asn | Ile | Ile | Val | Leu | Val | Ile | Leu | Thr | Thr | Ser | Gln | Tyr | Lys |
| | | | 20 | | | | | 25 | | | | | 30 | | |
| Leu | Thr | Val | Pro | Arg | Phe | Leu | Met | Asn | Ile | Ala | Phe | Ala | Asp | Leu | Cys |
| | | 35 | | | | | 40 | | | | | 45 | | | |
| Ile | Gly | Ile | Tyr | Leu | Leu | Leu | Ile | Ala | Ser | Val | Asp | Ile | His | Thr | Lys |
| | 50 | | | | | 55 | | | | | 60 | | | | |
| Ser | Gln | Tyr | His | Asn | Tyr | Ala | Ile | Asp | Trp | Gln | Arg | Gly | Ala | Gly | Cys |
| 65 | | | | | 70 | | | | | 75 | | | | | 80 |
| Asp | Ala | Ala | Gly | Phe | Phe | Thr | Val | Phe | Ala | Ser | Glu | Leu | Ser | Val | Tyr |
| | | | | 85 | | | | | 90 | | | | | 95 | |
| Thr | Leu | Thr | Ala | Ile | Thr | Leu | Glu | Arg | Trp | His | Thr | Ile | Thr | His | Ile |
| | | | 100 | | | | | 105 | | | | | 110 | | |
| Met | Gln | Ile | Asp | Cys | Lys | Val | Gln | Leu | Arg | His | Ala | Ala | Ser | Val | Met |
| | | 115 | | | | | 120 | | | | | 125 | | | |
| Val | Met | Gly | Trp | Ile | Phe | Ala | Phe | Ala | Ala | Ala | Leu | Phe | Pro | Ile | Phe |
| | 130 | | | | | 135 | | | | | 140 | | | | |
| Gly | Ile | Ser | Ser | Tyr | Met | Lys | Val | Ser | Ile | Cys | Leu | Pro | Leu | Ile | Asp |
| 145 | | | | | 150 | | | | | 155 | | | | | 160 |
| Ser | Pro | Leu | Ser | Gln | Leu | Tyr | Val | Met | Ser | Leu | Leu | Val | Leu | Asn | Val |
| | | | | 165 | | | | | 170 | | | | | 175 | |
| Leu | Ala | Phe | Val | Val | Ile | Cys | Gly | Cys | Tyr | Thr | His | Ile | Tyr | Leu | Thr |
| | | | 180 | | | | | 185 | | | | | 190 | | |
| Val | Arg | Asn | Pro | Asn | Ile | Val | Ser | Ser | Ser | Ser | Asp | Thr | Arg | Ile | Ala |
| | | 195 | | | | | 200 | | | | | 205 | | | |
| Lys | Arg | Met | Leu | Ile | Phe | Thr | Asp | Phe | Leu | Leu | Pro | Ile | Ser | Phe | Phe |
| 210 | | | | | 215 | | | | | 220 | | | | | |
| Ala | Ile | Ser | Ala | Ser | Leu | Lys | Val | Pro | Leu | Ile | Thr | Val | Ser | Lys | Ala |
| 225 | | | | | 230 | | | | | 235 | | | | | 240 |
| Lys | Ile | Leu | Leu | Val | Leu | Phe | His | Pro | Ile | Asn | Ser | Cys | Ala | Asn | Pro |
| | | | | 245 | | | | | 250 | | | | | 255 | |
| Phe | Leu | Tyr | Ala | Ile | Phe | Thr | Lys | Asn | Phe | Arg | Arg | Asp | Phe | Phe | Ile |
| | | | 260 | | | | | 265 | | | | | 270 | | |
| Leu | Leu | Ser | Lys | Cys | Gly | Cys | Tyr | Glu | Met | Gln | Ala | Gln | Ile | Tyr | Arg |
| | | 275 | | | | | 280 | | | | | 285 | | | |
| Thr | Glu | Thr | Ser | Ser | Thr | Val | His | Asn | Thr | His | Pro | Arg | Asn | Gly | His |
| | 290 | | | | | 295 | | | | | 300 | | | | |
| Cys | Ser | Ser | Ala | Pro | Arg | Val | Thr | Ser | Gly | Ser | Ser | Arg | Tyr | Ile | Leu |
| 305 | | | | | 310 | | | | | 315 | | | | | 320 |
| Val | Pro | Leu | Ser | Leu | Gln | Asn | | | | | | | | | |
| | | | | 325 | | | | | | | | | | | |

(2) INFORMATION FOR SEQ ID NO:56:

(i) SEQUENCE CHARACTERISTICS:
(A) LENGTH: 309 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:56:

```
Ser Met Leu Ala Ala Tyr Met Phe Leu Leu Ile Val Leu Gly Phe Pro
  1               5                  10                 15

Ile Asn Phe Leu Thr Leu Tyr Val Thr Val Gln His Lys Lys Leu Arg
                20                 25                 30

Thr Pro Ile Asn Tyr Ile Leu Leu Asn Leu Ala Val Ala Asp Leu Phe
         35                 40                 45

Met Val Leu Gly Gly Phe Thr Ser Thr Leu Tyr Thr Ser Leu His Gly
     50                 55                 60

Tyr Phe Val Phe Gly Pro Thr Gly Cys Asn Leu Glu Gly Phe Phe Ala
 65             70                 75                     80

Thr Leu Gly Gly Glu Ile Ala Leu Trp Ser Leu Trp Leu Ala Ile Glu
                85                 90                 95

Arg Tyr Val Val Val Cys Lys Pro Met Ser Asn Phe Arg Phe Gly Glu
            100                105                110

Asn His Ala Ile Met Gly Val Ala Phe Thr Trp Val Met Ala Leu Ala
        115            120                125

Cys Ala Ala Pro Pro Ile Ala Gly Trp Ser Arg Tyr Ile Pro Glu Gly
    130                135                140

Leu Gln Cys Ser Cys Gly Ile Asp Tyr Tyr Thr Leu Lys Pro Glu Val
145                150                155                160

Asn Asn Glu Ser Phe Val Ile Tyr Met Phe Val Val His Phe Thr Ile
            165                170                175

Pro Leu Ile Ile Phe Phe Cys Tyr Gly Gln Leu Val Phe Thr Val Lys
            180                185                190

Glu Ala Ala Ala Gln Gln Gln Glu Ser Ala Thr Thr Gln Lys Ala Glu
        195                200                205

Lys Glu Val Thr Arg Met Val Ile Ile Met Val Ile Ala Phe Leu Ile
    210                215                220

Cys Trp Val Pro Tyr Ala Ser Val Ala Phe Tyr Ile Phe Thr His Gln
225                230                235                240

Gly Ser Asn Phe Gly Pro Ile Phe Met Arg Ile Pro Ala Phe Phe Ala
                245                250                255

Lys Ser Ala Ala Ile Tyr Asn Pro Val Ile Tyr Ile Ile Phe Asn Lys
            260                265                270

Gln Phe Arg Asn Cys Met Leu Gln Leu Ile Cys Cys Gly Lys Asn Pro
        275                280                285

Leu Gly Asp Asp Glu Ala Ser Ala Thr Val Ser Lys Arg Glu Thr Ser
    290                295                300

Gln Val Ala Pro Ala
305
```

(2) INFORMATION FOR SEQ ID NO:57:

(i) SEQUENCE CHARACTERISTICS:
(A) LENGTH: 297 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:57:

```
Met Ile Phe Val Val Ile Ala Ser Val Phe Thr Asn Gly Leu Val Leu
  1               5                  10                 15
```

```
Ala Ala Thr Met Lys Phe Lys Lys Leu Pro His Pro Ile Asn Trp Ile
         20              25                  30

Leu Val Asn Leu Ala Val Ala Asp Ile Ala Gly Thr Val Ile Ala Ser
         35              40                  45

Thr Ile Ser Val Val Asn Gln Val Tyr Gly Tyr Phe Val Leu Gly His
         50              55                  60

Pro Met Cys Val Leu Glu Gly Tyr Thr Val Ser Leu Cys Gly Ile Thr
 65                   70              75                      80

Gly Leu Trp Ser Leu Ala Ile Ile Ser Trp Glu Arg Trp Met Val Val
                 85              90                  95

Cys Lys Pro Phe Gly Asn Val Arg Phe Asp Ala Lys Ile Ala Ile Val
             100             105                 110

Gly Ile Ala Phe Ser Trp Ile Trp Ala Ala Val Trp Thr Ala Pro Pro
         115             120                 125

Ile Phe Gly Trp Ser Arg Tyr Trp Pro His Gly Leu Lys Thr Ser Cys
     130             135                 140

Gly Pro Asp Val Phe Ser Gly Ser Ser Tyr Pro Gly Val Gln Ser Leu
145                 150             155                     160

Leu Cys Ile Thr Pro Leu Ser Ile Ile Val Leu Cys Tyr Leu Gln Val
             165                 170                 175

Trp Thr Ala Ile Arg Ala Val Ala Lys Gln Gln Lys Glu Ser Glu Ser
             180             185                 190

Thr Gln Lys Ala Glu Lys Glu Val Thr Arg Met Trp Val Met Val Leu
         195             200                 205

Ala Phe Cys Phe Cys Trp Gly Pro Tyr Ala Phe Phe Ala Cys Phe Ala
         210             215                 220

Ala Ala Asn Pro Gly Tyr Pro Phe His Pro Leu Met Ala Ala Leu Pro
225             230             235                         240

Ala Phe Phe Ala Lys Ser Ala Thr Ile Tyr Asn Pro Val Ile Tyr Val
             245             250                 255

Phe Met Asn Arg Gln Phe Arg Asn Cys Ile Leu Gln Leu Phe Gly Lys
             260             265                 270

Lys Val Asp Asp Gly Ser Glu Leu Ser Ser Ala Ser Lys Thr Glu Val
             275             280             285

Ser Ser Val Ser Ser Val Ser Pro Ala
         290             295
```

(2) INFORMATION FOR SEQ ID NO:58:

(i) SEQUENCE CHARACTERISTICS:
        (A) LENGTH: 297 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

```
Arg Cys Phe Val Val Thr Ala Ser Val Phe Thr Asn Gly Leu Val Leu
 1               5                  10                  15

Ala Ala Thr Met Lys Phe Lys Lys Leu Arg His Pro Leu Asn Trp Ile
         20              25                  30

Leu Val Asn Ile Ala Val Ala Asp Ile Ala Gly Thr Val Ile Ala Ser
         35              40                  45

Thr Ile Ser Ile Val Asn Gln Val Ser Gly Tyr Phe Val Leu Gly His
         50              55                  60

Pro Met Cys Val Leu Glu Gly Tyr Thr Val Ser Leu Cys Gly Ile Thr
```

```
 65                  70                  75                  80

Gly Leu Trp Ser Leu Ala Ile Ile Ser Trp Glu Arg Trp Leu Trp Cys
                85                  90                  95

Lys Pro Phe Gly Asn Val Arg Phe Asp Ala Lys Ile Ala Ile Val Gly
            100                 105                 110

Ile Ala Phe Ser Trp Ile Trp Ser Ala Val Trp Thr Ala Pro Pro Ile
            115                 120                 125

Phe Gly Trp Ser Arg Tyr Trp Pro His Gly Leu Lys Thr Ser Cys Gly
    130                 135                 140

Pro Asp Val Phe Ser Gly Ser Ser Tyr Pro Gly Val Gln Ser Leu Val
145                 150                 155                 160

Ile Met Val Thr Cys Cys Ile Ile Pro Ile Ala Ile Ile Leu Cys Tyr
                165                 170                 175

Leu Gln Val Trp Leu Ala Ile Arg Ala Val Ala Lys Gln Gln Lys Glu
            180                 185                 190

Ser Glu Ser Thr Gln Lys Ala Glu Lys Glu Val Thr Arg Met Leu Phe
            195                 200                 205

Ala Tyr Cys Val Cys Trp Gly Pro Tyr Thr Phe Phe Ala Cys Phe Ala
    210                 215                 220

Ala Ala Asn Pro Gly Tyr Ala Phe His Pro Leu Met Ala Ala Leu Pro
225                 230                 235                 240

Ala Tyr Phe Ala Lys Ser Ala Thr Ile Tyr Asn Pro Val Ile Tyr Val
                245                 250                 255

Phe Met Asn Arg Gln Phe Arg Asn Cys Ile Leu Gln Leu Phe Gly Lys
            260                 265                 270

Lys Val Asp Asp Gly Ser Glu Leu Ser Ser Ala Ser Lys Thr Glu Val
            275                 280                 285

Ser Ser Val Ser Ser Val Ser Pro Ala
290                 295
```

( 2 ) INFORMATION FOR SEQ ID NO:59:

( i ) SEQUENCE CHARACTERISTICS:
( A ) LENGTH: 305 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:59:

```
Gln Ala Ala Phe Met Gly Thr Val Phe Leu Ile Gly Phe Pro Leu Leu
1               5                   10                  15

Val Ala Thr Leu Ala Tyr Lys Lys Leu Arg Gln Pro Asn Tyr Ile Leu
            20                  25                  30

Val Asn Val Ser Phe Gly Gly Phe Leu Leu Cys Ile Phe Ser Val Phe
            35                  40                  45

Pro Val Phe Val Ala Ser Cys Asn Gly Tyr Phe Val Phe Gly Arg His
    50                  55                  60

Val Cys Ala Leu Glu Gly Phe Leu Gly Thr Val Ala Gly Leu Val Thr
65                  70                  75                  80

Gly Trp Ser Leu Ala Phe Leu Ala Phe Glu Arg Tyr Ile Val Ile Cys
                85                  90                  95

Lys Pro Phe Gly Asn Phe Arg Phe Ser Ser Lys His Ala Leu Thr Val
            100                 105                 110

Val Ile Ala Thr Trp Thr Ile Gly Ile Gly Val Ser Ile Pro Pro Phe
            115                 120                 125
```

```
Phe  Gly  Trp  Ser  Arg  Phe  Ile  Pro  Glu  Gly  Leu  Gln  Cys  Ser  Cys  Gly
     130                 135                 140

Pro  Asp  Lys  Tyr  Thr  Val  Gly  Thr  Lys  Tyr  Arg  Ser  Glu  Ser  Tyr  Thr
145                      150                 155                           160

Trp  Phe  Leu  Phe  Ile  Phe  Cys  Phe  Ile  Val  Pro  Leu  Ser  Leu  Ile  Cys
                    165                 170                           175

Phe  Ser  Tyr  Thr  Gln  Leu  Leu  Arg  Ala  Leu  Lys  Ala  Val  Ala  Ala  Gln
               180                 185                      190

Gln  Gln  Glu  Ser  Ala  Thr  Thr  Gln  Lys  Ala  Glu  Arg  Glu  Val  Ser  Arg
          195                      200                 205

Met  Val  Val  Met  Val  Gly  Ser  Phe  Cys  Val  Cys  Tyr  Val  Pro  Tyr
     210                 215                 220

Ala  Ala  Phe  Ala  Met  Tyr  Met  Val  Asn  Asn  Arg  Asn  His  Gly  Leu  Asp
225                      230                 235                           240

Leu  Arg  Leu  Val  Arg  Ile  Pro  Ser  Phe  Phe  Ser  Lys  Ser  Ala  Cys  Ile
                    245                 250                      255

Tyr  Asn  Pro  Ile  Ile  Tyr  Cys  Phe  Met  Asn  Lys  Gln  Phe  Gln  Ala  Cys
               260                 265                      270

Ile  Met  Met  Val  Cys  Gly  Lys  Ala  Met  Met  Glu  Ser  Asp  Thr  Cys  Ser
          275                      280                 285

Ser  Gln  Lys  Thr  Glu  Val  Ser  Thr  Val  Ser  Ser  Thr  Gln  Val  Gly  Pro
     290                      295                 300

Asn
305
```

( 2 ) INFORMATION FOR SEQ ID NO:60:

( i ) SEQUENCE CHARACTERISTICS:
( A ) LENGTH: 293 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:60:

```
Leu  Ile  Tyr  Gly  Leu  Phe  Leu  Ser  Met  Tyr  Leu  Val  Thr  Val  Ile  Gly
1                    5                   10                           15

Asn  Ile  Ser  Ile  Ile  Val  Ala  Ile  Ile  Ser  Asp  Pro  Cys  Leu  His  Thr
               20                  25                      30

Pro  Met  Tyr  Phe  Phe  Leu  Ser  Asn  Leu  Ser  Phe  Val  Asp  Ile  Cys  Phe
          35                  40                  45

Ile  Ser  Thr  Thr  Val  Pro  Val  Asn  Thr  Gln  Thr  Gln  Asn  Asn  Val  Ile
     50                  55                  60

Thr  Tyr  Ala  Gly  Cys  Ile  Thr  Gln  Ile  Tyr  Phe  Phe  Leu  Leu  Phe  Val
65                       70                  75                           80

Glu  Leu  Asp  Asn  Phe  Leu  Leu  Thr  Ile  Met  Ala  Tyr  Asp  Arg  Tyr  Val
                    85                  90                       95

Ala  Ile  Cys  His  Pro  Met  His  Tyr  Thr  Val  Ile  Met  Asn  Tyr  Lys  Leu
               100                 105                     110

Cys  Gly  Phe  Leu  Val  Leu  Val  Ser  Trp  Ile  Val  Ser  Val  Leu  His  Ala
          115                 120                 125

Leu  Phe  Gln  Ser  Leu  Ala  Leu  Pro  Phe  Cys  Thr  His  Leu  Glu  Ile  Pro
     130                 135                 140

His  Tyr  Phe  Cys  Glu  Pro  Asn  Gln  Val  Ile  Gln  Leu  Thr  Cys  Ser  Asp
145                 150                 155                           160
```

```
Ala  Phe  Leu  Asn  Asp  Leu  Val  Ile  Tyr  Phe  Thr  Leu  Val  Leu  Leu  Ala
               165                 170                          175

Thr  Val  Pro  Ile  Ala  Gly  Ile  Phe  Tyr  Ser  Tyr  Phe  Ala  Ile  Ser  Ser
               180                 185                          190

Val  His  Gly  Lys  Tyr  Lys  Ala  Phe  Ser  Thr  Cys  Ala  Ser  His  Leu  Ser
          195                      200                          205

Val  Val  Ser  Leu  Phe  Tyr  Cys  Thr  Gly  Leu  Gly  Val  Tyr  Leu  Ser  Ser
     210                 215                          220

Ala  Ala  Asn  Asn  Ser  Leu  Ser  Ala  Thr  Ala  Ser  Val  Met  Tyr  Thr  Val
225                      230                      235                          240

Val  Thr  Pro  Met  Val  Asn  Pro  Phe  Ile  Tyr  Ser  Leu  Arg  Asn  Lys  Asp
               245                      250                          255

Val  Lys  Ser  Val  Leu  Lys  Lys  Thr  Leu  Cys  Glu  Glu  Val  Ile  Arg  Ser
               260                      265                     270

Pro  Pro  Ser  Leu  Leu  His  Phe  Phe  Leu  Val  Leu  Cys  His  Leu  Pro  Cys
               275                      280                     285

Phe  Ile  Phe  Cys  Tyr
          290
```

(2) INFORMATION FOR SEQ ID NO:61:

(i) SEQUENCE CHARACTERISTICS:
        (A) LENGTH: 284 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

```
Leu  Leu  Phe  Leu  Leu  Phe  Leu  Ile  Met  Tyr  Leu  Ala  Thr  Val  Leu  Gly
1                   5                    10                          15

Asn  Leu  Leu  Ile  Ile  Leu  Ala  Ile  Gly  Gly  Asp  Ser  Arg  Leu  His  Thr
               20                       25                          30

Pro  Met  Tyr  Phe  Phe  Leu  Ser  Asn  Leu  Ser  Phe  Val  Asp  Val  Cys  Phe
               35                       40                          45

Ser  Ser  Thr  Thr  Val  Pro  Lys  Val  Leu  Ala  Asn  His  Ile  Leu  Gly  Ser
     50                      55                       60

Gln  Ala  Ile  Ser  Phe  Ser  Gly  Cys  Leu  Thr  Gln  Leu  Tyr  Phe  Leu  Ala
65                       70                       75                          80

Val  Phe  Gly  Asn  Met  Asp  Asn  Phe  Leu  Leu  Ala  Val  Met  Ser  Tyr  Asp
                    85                      90                           95

Arg  Tyr  Val  Ala  Ile  Cys  His  Pro  Leu  His  Tyr  Thr  Thr  Ile  Arg  Gln
               100                      105                         110

Leu  Cys  Val  Leu  Leu  Val  Val  Gly  Ser  Trp  Val  Val  Ala  Asn  Met  Asn
          115                      120                         125

Cys  Leu  Leu  His  Ile  Leu  Ile  Met  Ala  Arg  Lys  Ser  Phe  Cys  Ala  Asp
     130                      135                         140

Leu  Pro  His  Phe  Phe  Cys  Asp  Gly  Thr  Pro  Leu  Leu  Lys  Leu  Ser  Cys
145                      150                      155                         160

Ser  Asp  Thr  His  Leu  Asn  Glu  Leu  Met  Ile  Leu  Thr  Glu  Gly  Ala  Val
                    165                      170                         175

Val  Met  Val  Thr  Pro  Phe  Val  Cys  Ile  Leu  Ile  Ser  Tyr  Ile  His  Ile
               180                      185                         190

Thr  Cys  Ala  Val  Leu  Arg  Val  Ser  Ser  Pro  Arg  Gly  Gly  Trp  Lys  Ser
          195                      200                      205

Phe  Ser  Thr  Cys  Gly  Ser  His  Ile  Ala  Val  Val  Cys  Leu  Phe  Tyr  Gly
```

|       |       |       |       | 210   |       |       |       |       | 215   |       |       |       |       | 220   |
|-------|-------|-------|-------|-------|-------|-------|-------|-------|-------|-------|-------|-------|-------|-------|
| Thr   | Val   | Ile   | Ala   | Val   | Tyr   | Phe   | Asn   | Pro   | Ser   | Ser   | His   | Leu   | Ala   | Gly   |
| 225   |       |       |       |       | 230   |       |       |       |       | 235   |       |       |       | 240   |
| Arg   | Asp   | Met   | Ala   | Ala   | Ala   | Val   | Met   | Tyr   | Ala   | Val   | Val   | Thr   | Pro   | Met   | Ile   |
|       |       |       |       | 245   |       |       |       |       | 250   |       |       |       |       | 255   |
| Asn   | Pro   | Phe   | Ile   | Tyr   | Ser   | Leu   | Arg   | Asn   | Ser   | Asp   | Met   | Lys   | Ala   | Ala   | Leu   |
|       |       |       | 260   |       |       |       |       | 265   |       |       |       | 270   |       |       |
| Arg   | Lys   | Val   | Leu   | Ala   | Met   | Arg   | Phe   | Pro   | Ser   | Lys   | Gln   |
|       |       | 275   |       |       |       |       | 280   |

( 2 ) INFORMATION FOR SEQ ID NO:62:

( i ) SEQUENCE CHARACTERISTICS:
      ( A ) LENGTH: 277 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:62:

| Leu | Leu | Phe | Leu | Leu | Phe | Leu | Val | Met | Tyr | Leu | Leu | Thr | Val | Val | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |
| Asn | Leu | Ala | Ile | Ile | Ser | Leu | Val | Gly | Ala | His | Arg | Cys | Leu | Gln | Pro |
|     |     |     | 20  |     |     |     |     | 25  |     |     |     | 30  |     |     |
| His | Thr | Pro | Met | Tyr | Phe | Phe | Leu | Cys | Asn | Leu | Ser | Phe | Leu | Glu | Ile |
|     |     | 35  |     |     |     |     | 40  |     |     |     |     | 45  |     |     |
| Trp | Phe | Thr | Thr | Ala | Cys | Val | Pro | Lys | Thr | Leu | Ala | Thr | Phe | Ala | Pro |
|     | 50  |     |     |     |     | 55  |     |     |     |     | 60  |     |     |     |
| Arg | Gly | Gly | Val | Ile | Ser | Leu | Ala | Gly | Cys | Ala | Thr | Lys | Tyr | Phe | Val |
| 65  |     |     |     |     | 70  |     |     |     |     | 75  |     |     |     |     | 80  |
| Phe | Ser | Leu | Gly | Cys | Thr | Glu | Tyr | Phe | Leu | Leu | Ala | Val | Met | Ala | Tyr |
|     |     |     |     | 85  |     |     |     |     | 90  |     |     |     |     | 95  |     |
| Asp | Arg | Tyr | Leu | Ala | Ile | Cys | Leu | Pro | Leu | Arg | Tyr | Gly | Gly | Ile | Met |
|     |     |     | 100 |     |     |     |     | 105 |     |     |     |     | 110 |     |
| Arg | Pro | Gly | Ile | Ala | Met | Arg | Leu | Ala | Leu | Gly | Ser | Trp | Leu | Cys | Gly |
|     |     | 115 |     |     |     |     | 120 |     |     |     |     | 125 |     |     |
| Phe | Ser | Ala | Ile | Thr | Val | Pro | Ala | Thr | Leu | Ile | Ala | Arg | Leu | Ser | Phe |
|     | 130 |     |     |     |     | 135 |     |     |     |     | 140 |     |     |     |
| Cys | Gly | Ser | Arg | Val | Ile | Asn | His | Phe | Phe | Cys | Asp | Ile | Ser | Pro | Trp |
| 145 |     |     |     |     | 150 |     |     |     |     | 155 |     |     |     |     | 160 |
| Ile | Val | Leu | Ser | Cys | Thr | Asp | Thr | Gln | Val | Val | Glu | Leu | Val | Ser | Phe |
|     |     |     |     | 165 |     |     |     |     | 170 |     |     |     |     | 175 |     |
| Gly | Ile | Ala | Phe | Cys | Val | Ile | Leu | Gly | Ser | Cys | Gly | Ile | Thr | Leu | Val |
|     |     |     | 180 |     |     |     |     | 185 |     |     |     |     | 190 |     |
| Ser | Tyr | Ala | Lys | Ile | Pro | Ser | Ala | Arg | Gly | Arg | His | Arg | Ala | Phe | Ser |
|     |     | 195 |     |     |     |     | 200 |     |     |     |     | 205 |     |     |
| Thr | Cys | Ser | Ser | His | Leu | Thr | Val | Val | Leu | Ile | Trp | Tyr | Gly | Ser | Thr |
|     | 210 |     |     |     |     | 215 |     |     |     |     | 220 |     |     |     |
| Ile | Phe | Leu | His | Val | Arg | Thr | Ser | Val | Glu | Ser | Ser | Leu | Asp | Leu | Thr |
| 225 |     |     |     |     | 230 |     |     |     |     | 235 |     |     |     |     | 240 |
| Lys | Ala | Ile | Thr | Val | Leu | Asn | Thr | Ile | Val | Thr | Pro | Val | Leu | Asn | Pro |
|     |     |     | 245 |     |     |     |     | 250 |     |     |     | 255 |     |     |
| Phe | Ile | Tyr | Thr | Leu | Arg | Asn | Lys | Asp | Val | Lys | Glu | Ala | Leu | Arg | Arg |
|     |     |     | 260 |     |     |     |     | 265 |     |     |     | 270 |     |     |
| Thr | Val | Lys | Gly | Lys |
|     |     | 275 |     |     |

( 2 ) INFORMATION FOR SEQ ID NO:63:

( i ) SEQUENCE CHARACTERISTICS:
        ( A ) LENGTH: 273 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:63:

| Leu | Ile | Phe | Ala | Leu | Phe | Leu | Ser | Met | Tyr | Leu | Val | Thr | Val | Leu | Gly |
|---|---|---|---|---|---|---|---|---|---|---|---|---|---|---|---|
| 1 | | | | 5 | | | | | 10 | | | | | 15 | |
| Asn | Leu | Leu | Ile | Ile | Met | Ala | Ile | Ile | Thr | Gln | Ser | His | Leu | His | Thr |
| | | | 20 | | | | | 25 | | | | | 30 | | |
| Pro | Met | Tyr | Phe | Phe | Leu | Ser | Phe | Val | Asp | Ile | Cys | Phe | Thr | Ser | Thr |
| | | 35 | | | | | 40 | | | | | 45 | | | |
| Thr | Ile | Pro | Leu | Val | Asn | Ile | Tyr | Thr | Gln | Ser | Lys | Ser | Ile | Thr | Tyr |
| | | 50 | | | | 55 | | | | | 60 | | | | |
| Glu | Asp | Cys | Ile | Ser | Leu | Val | Phe | Ala | Glu | Leu | Gly | Asn | Phe | Leu | Leu |
| 65 | | | | | 70 | | | | | 75 | | | | | 80 |
| Ala | Val | Met | Ala | Tyr | Asp | Arg | Tyr | Val | Ala | Xaa | Cys | His | Pro | Leu | Cys |
| | | | | 85 | | | | | 90 | | | | | 95 | |
| Tyr | Thr | Val | Ile | Val | Asn | His | Arg | Leu | Cys | Ile | Leu | Leu | Leu | Leu | Leu |
| | | | 100 | | | | | 105 | | | | | 110 | | |
| Ser | Trp | Val | Ile | Ser | Ile | Phe | Arg | Ala | Phe | Ile | Gln | Ser | Leu | Ile | Val |
| | | 115 | | | | | 120 | | | | | 125 | | | |
| Leu | Gln | Leu | Thr | Phe | Cys | Gly | Asp | Val | Lys | Ile | Pro | His | Phe | Phe | Cys |
| | 130 | | | | | 135 | | | | | 140 | | | | |
| Glu | Leu | Asn | Gln | Leu | Ser | Gln | Leu | Thr | Cys | Ser | Asp | Asn | Phe | Pro | Ser |
| 145 | | | | | 150 | | | | | 155 | | | | | 160 |
| His | Leu | Ile | Met | Asn | Leu | Val | Pro | Val | Met | Leu | Ala | Ala | Ile | Ser | Phe |
| | | | | 165 | | | | | 170 | | | | | 175 | |
| Ser | Gly | Ile | Leu | Tyr | Ser | Tyr | Phe | Ser | Ile | Ser | Thr | Val | Gln | Gly | Lys |
| | | | 180 | | | | | 185 | | | | | 190 | | |
| Tyr | Lys | Ala | Phe | Ser | Thr | Cys | Ala | Ser | His | Leu | Ser | Ile | Val | Ser | Leu |
| | | 195 | | | | | 200 | | | | | 205 | | | |
| Phe | Tyr | Ser | Thr | Gly | Leu | Gly | Val | Tyr | Val | Ser | Ser | Ala | Val | Val | Gln |
| | 210 | | | | | 215 | | | | | 220 | | | | |
| Ser | Ser | His | Ser | Ala | Ala | Ser | Ala | Ser | Val | Met | Tyr | Thr | Val | Val | Pro |
| 225 | | | | | 230 | | | | | 235 | | | | | 240 |
| Met | Leu | Asn | Pro | Phe | Ile | Tyr | Ser | Leu | Arg | Asn | Lys | Asp | Val | Lys | Arg |
| | | | | 245 | | | | | 250 | | | | | 255 | |
| Ala | Leu | Glu | Arg | Leu | Leu | Glu | Gly | Asn | Cys | Lys | Val | His | His | Trp | Thr |
| | | | 260 | | | | | 265 | | | | | 270 | | |
| Gly | | | | | | | | | | | | | | | |

( 2 ) INFORMATION FOR SEQ ID NO:64:

( i ) SEQUENCE CHARACTERISTICS:
        ( A ) LENGTH: 269 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:64:

| Leu | Phe | Tyr | Ala | Leu | Phe | Leu | Val | Met | Tyr | Leu | Thr | Thr | Ile | Leu | Gly |
| 1 | | | | 5 | | | | | 10 | | | | | 15 | |

| Asn | Leu | Leu | Ile | Ile | Val | Leu | Val | Gln | Leu | Asp | Ser | Gln | Leu | His | Thr |
| | | | 20 | | | | | 25 | | | | | 30 | | |

| Pro | Met | Tyr | Leu | Phe | Leu | Ser | Asn | Leu | Ser | Phe | Ser | Asp | Leu | Cys | Phe |
| | | 35 | | | | | 40 | | | | | 45 | | | |

| Ser | Ser | Leu | Lys | Leu | Leu | Gln | Asn | Met | Arg | Ser | Gln | Asp | Thr | Ser | Ile |
| | 50 | | | | | 55 | | | | | 60 | | | | |

| Pro | Tyr | Gly | Gly | Cys | Leu | Ala | Gln | Thr | Tyr | Phe | Phe | Met | Val | Phe | Gly |
| 65 | | | | | 70 | | | | 75 | | | | | | 80 |

| Asp | Leu | Ser | Phe | Leu | Leu | Val | Ala | Met | Ala | Tyr | Asp | Arg | Tyr | Val | Ala |
| | | | | 85 | | | | | 90 | | | | | 95 | |

| Ile | Cys | Phe | Leu | Pro | His | Tyr | Thr | Ser | Ile | Met | Ser | Pro | Lys | Leu | Cys |
| | | | 100 | | | | | 105 | | | | | 110 | | |

| Thr | Cys | Leu | Val | Leu | Leu | Leu | Trp | Met | Leu | Thr | Thr | Ser | His | Met | Met |
| | | | 115 | | | | | 120 | | | | | 125 | | |

| Thr | Leu | Leu | Ala | Ala | Arg | Leu | Ser | Phe | Cys | Glu | Asn | Asn | Trp | Leu | Asn |
| | 130 | | | | | 135 | | | | | 140 | | | | |

| Phe | Phe | Cys | Asp | Leu | Phe | Val | Leu | Leu | Lys | Ile | Ala | Cys | Ser | Asp | Thr |
| 145 | | | | | 150 | | | | | 155 | | | | | 160 |

| Tyr | Ile | Asn | Glu | Leu | Phe | Ile | Met | Ser | Thr | Leu | Leu | Ile | Ile | Ile | Pro |
| | | | | 165 | | | | | 170 | | | | | 175 | |

| Phe | Phe | Leu | Ile | Val | Met | Ser | Tyr | Ala | Lys | Val | Pro | Ser | Thr | Gln | Gly |
| | | | 180 | | | | | 185 | | | | | 190 | | |

| Ile | Cys | Lys | Val | Phe | Ser | Thr | Cys | Gly | Ser | His | Leu | Ser | Val | Val | Ser |
| | | 195 | | | | | 200 | | | | | 205 | | | |

| Leu | Phe | Tyr | Gly | Thr | Ile | Ile | Gly | Leu | Tyr | Leu | Cys | Pro | Ala | Gly | Asn |
| | 210 | | | | | 215 | | | | | 220 | | | | |

| Asn | Ser | Thr | Val | Lys | Glu | Met | Val | Met | Ala | Met | Met | Tyr | Thr | Val | Val |
| 225 | | | | | 230 | | | | | 235 | | | | | 240 |

| Thr | Pro | Met | Ile | Asn | Pro | Phe | Ile | Tyr | Ser | Leu | Arg | Asn | Arg | Asp | Leu |
| | | | | 245 | | | | | 250 | | | | | 255 | |

| Arg | Ala | Leu | Ile | Arg | Val | Ile | Cys | Ser | Met | Ile | Thr | Leu |
| | | | 260 | | | | | 265 | | | | |

( 2 ) INFORMATION FOR SEQ ID NO:65:

( i ) SEQUENCE CHARACTERISTICS:
        ( A ) LENGTH: 286 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:65:

| Leu | Leu | Phe | Phe | Leu | Ser | Leu | Leu | Xaa | Tyr | Val | Leu | Val | Leu | Thr | Glu |
| 1 | | | | 5 | | | | | 10 | | | | | 15 | |

| Asn | Met | Leu | Ile | Ile | Ile | Ala | Ile | Arg | Asn | His | Pro | Thr | Leu | His | Lys |
| | | | 20 | | | | | 25 | | | | | 30 | | |

| Pro | Met | Tyr | Phe | Phe | Leu | Phe | Leu | Glu | Ile | Trp | Tyr | Val | Thr | Val | Thr |
| | | 35 | | | | | 40 | | | | | 45 | | | |

| Ile | Pro | Lys | Leu | Met | Gly | Phe | Ile | Gly | Ser | Lys | Glu | Asn | His | Gly | Gln |
| | 50 | | | | | 55 | | | | | 60 | | | | |

| Leu | Ile | Ser | Phe | Phe | Ala | Cys | Met | Thr | Gln | Leu | Tyr | Phe | Phe | Leu | Gly |
| 65 | | | | | 70 | | | | | 75 | | | | | | 80 |

| Leu | Gly | Cys | Thr | Glu | Cys | Val | Leu | Leu | Ala | Val | Met | Ala | Tyr | Asp | Arg |

|     |     |     |     | 85  |     |     |     | 90  |     |     |     | 95  |     |     |
| --- | --- | --- | --- | --- | --- | --- | --- | --- | --- | --- | --- | --- | --- | --- |
| Tyr | Val | Ala | Ile | Cys | His | Pro | Leu | His | Tyr | Pro | Val | Ile | Val | Ser | Ser |
|     |     |     | 100 |     |     |     |     | 105 |     |     |     | 110 |     |     |
| Arg | Ile | Glx | Val | Leu | Gly | Ser | Trp | Ala | Gly | Gly | Phe | Gly | Ile | Ser | Met |
|     |     | 115 |     |     |     |     | 120 |     |     |     |     | 125 |     |     |
| Val | Lys | Val | Phe | Leu | Ile | Ser | Arg | Leu | Ser | Tyr | Cys | Gly | Pro | Asn | Thr |
|     |     | 130 |     |     |     | 135 |     |     |     |     | 140 |     |     |     |
| Ile | Asn | His | Phe | Phe | Cys | Asp | Val | Ser | Pro | Leu | Leu | Asn | Leu | Ser | Cys |
| 145 |     |     |     |     | 150 |     |     |     |     | 155 |     |     |     |     | 160 |
| Thr | Asp | Met | Ser | Thr | Ala | Glu | Leu | Thr | Asp | Phe | Val | Ile | Ala | Ile | Phe |
|     |     |     |     | 165 |     |     |     |     | 170 |     |     |     |     | 175 |     |
| Ile | Leu | Leu | Gly | Pro | Leu | Ser | Val | Thr | Gly | Ala | Ser | Tyr | Met | Arg | Ile |
|     |     |     | 180 |     |     |     |     | 185 |     |     |     |     | 190 |     |     |
| Pro | Ser | Ala | Ala | Gly | Arg | His | Lys | Ala | Phe | Ser | Thr | Cys | Ala | Ser | His |
|     |     | 195 |     |     |     |     | 200 |     |     |     |     | 205 |     |     |     |
| Leu | Thr | Val | Val | Ile | Ile | Phe | Tyr | Ala | Ala | Ser | Ile | Phe | Ile | Tyr | Ala |
|     | 210 |     |     |     |     | 215 |     |     |     |     | 220 |     |     |     |     |
| Arg | Pro | Lys | Ala | Leu | Ser | Ala | Phe | Thr | Asp | Asn | Lys | Leu | Val | Ser | Val |
| 225 |     |     |     |     | 230 |     |     |     |     | 235 |     |     |     |     | 240 |
| Leu | Tyr | Ala | Val | Ile | Val | Pro | Leu | Phe | Asn | Pro | Ile | Ile | Tyr | Cys | Leu |
|     |     |     |     | 245 |     |     |     |     | 250 |     |     |     |     | 255 |     |
| Arg | Asn | Gln | Asp | Val | Lys | Arg | Ala | Leu | Arg | Arg | Thr | Leu | His | Leu | Ala |
|     |     |     | 260 |     |     |     |     | 265 |     |     |     |     | 270 |     |     |
| Gln | Asp | Gln | Glu | Ala | Asn | Thr | Asn | Lys | Gly | Ser | Lys | Ile | Gly |     |     |
|     |     | 275 |     |     |     |     | 280 |     |     |     |     | 285 |     |     |

( 2 ) INFORMATION FOR SEQ ID NO:66:

( i ) SEQUENCE CHARACTERISTICS:
      ( A ) LENGTH: 275 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:66:

| Leu | Phe | Phe | Ala | Leu | Phe | Leu | Ile | Met | Tyr | Leu | Thr | Thr | Phe | Leu | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Asn | Leu | Leu | Ile | Val | Val | Leu | Val | Gln | Leu | Asp | Ser | His | Leu | His | Thr |
|     |     |     | 20  |     |     |     |     | 25  |     |     |     |     | 30  |     |     |
| Pro | Met | Tyr | Leu | Phe | Leu | Ser | Asn | Leu | Ser | Phe | Ser | Asp | Leu | Cys | Phe |
|     |     | 35  |     |     |     |     | 40  |     |     |     |     | 45  |     |     |     |
| Ser | Ser | Val | Thr | Met | Leu | Lys | Leu | Leu | Gln | Asn | Ile | Gln | Ser | Gln | Val |
|     | 50  |     |     |     |     | 55  |     |     |     |     | 60  |     |     |     |     |
| Pro | Ser | Ile | Ser | Tyr | Ala | Gly | Cys | Leu | Trp | Ile | Phe | Phe | Phe | Leu | Leu |
| 65  |     |     |     |     | 70  |     |     |     |     | 75  |     |     |     |     | 80  |
| Phe | Gly | Tyr | Leu | Gly | Asn | Phe | Leu | Leu | Val | Ala | Met | Ala | Tyr | Asp | Arg |
|     |     |     |     | 85  |     |     |     |     | 90  |     |     |     |     | 95  |     |
| Tyr | Val | Ala | Ile | Cys | Phe | Pro | Leu | His | Tyr | Thr | Asn | Ile | Met | Ser | His |
|     |     |     | 100 |     |     |     |     | 105 |     |     |     | 110 |     |     |     |
| Lys | Leu | Cys | Thr | Cys | Leu | Leu | Leu | Val | Phe | Trp | Ile | Met | Arg | Ser | Ser |
|     |     | 115 |     |     |     |     | 120 |     |     |     |     | 125 |     |     |     |
| His | Ala | Met | Met | Ile | Thr | Leu | Ile | Ala | Ala | Arg | Leu | Ser | Phe | Cys | Glu |
|     |     | 130 |     |     |     | 135 |     |     |     |     | 140 |     |     |     |     |
| Asn | Asn | Val | Leu | Leu | Asn | Phe | Phe | Cys | Asp | Leu | Phe | Val | Leu | Leu | Lys |
| 145 |     |     |     |     | 150 |     |     |     |     | 155 |     |     |     |     | 160 |

```
Leu Ala Cys Ser Asp Thr Tyr Val Asn Glu Leu Met Ile His Ile Met
                165                 170                 175
Glu Val Ile Ile Ile Val Ile Pro Phe Val Leu Ile Val Ile Ser Tyr
            180                 185                 190
Ala Lys Val Pro Ser Thr Gln Ser Ile His Lys Val Phe Ser Thr Cys
        195                 200                 205
Gly Ser His Leu Ser Val Val Ser Leu Phe Tyr Gly Thr Ile Ile Gly
        210                 215                 220
Leu Tyr Leu Cys Pro Ser Gly Asp Asn Phe Ser Leu Lys Gly Ser Leu
225                 230                 235                 240
Thr Val Val Thr Pro Ile Met Pro Phe Ile Tyr Ser Leu Arg Asn Arg
                245                 250                 255
Asp Met Lys Gln Ala Leu Ile Arg Val Thr Cys Ser Lys Lys Ile Ser
                260                 265                 270
Leu Pro Trp
        275
```

(2) INFORMATION FOR SEQ ID NO:67:

(i) SEQUENCE CHARACTERISTICS:
        (A) LENGTH: 284 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

```
Leu Phe Tyr Ala Leu Phe Leu Ala Met Tyr Leu Thr Thr Leu Leu Gly
1               5                   10                  15
Asn Leu Ile Ile Ile Ile Leu Ile Leu Leu Asp Ser His Leu His Thr
            20                  25                  30
Pro Met Tyr Leu Phe Leu Ser Asn Leu Ser Phe Ala Asp Leu Cys Phe
        35                  40                  45
Ser Ser Leu Lys Leu Leu Gln Asn Met Gln Ser Gln Val Pro Ser Ile
    50                  55                  60
Pro Tyr Ala Gly Cys Leu Ala Gln Ile Tyr Phe Phe Leu Phe Phe Gly
65                  70                  75                  80
Asp Leu Gly Asn Phe Leu Leu Val Ala Met Ala Tyr Asp Arg Tyr Val
                85                  90                  95
Ala Ile Cys Phe Pro Leu His Tyr Met Ser Ile Met Ser Pro Lys Ile
                100                 105                 110
Glx Val Ser Leu Val Val Leu Ser Trp Val Leu Thr Thr Phe His Ala
            115                 120                 125
Met Leu His Thr Leu Ile Met Ala Arg Leu Ser Phe Cys Glu Asp Ser
        130                 135                 140
Val Ile Pro His Tyr Phe Cys Asp Met Ser Thr Leu Leu Lys Val Ala
145                 150                 155                 160
Cys Ser Asp Thr His Asp Asn Glu Leu Ala Ile Phe Ile Leu Gly Gly
                165                 170                 175
Pro Ile Val Val Leu Pro Phe Leu Leu Ile Ile Val Ser Tyr Ala Arg
                180                 185                 190
Ile Val Ser Ser Ile Phe Lys Val Pro Ser Ser Gln Ser Ile His Lys
            195                 200                 205
Ala Phe Ser Thr Cys Gly Ser His Leu Ser Val Val Ser Leu Phe Tyr
        210                 215                 220
```

```
Gly Thr Val Ile Gly Leu Tyr Leu Cys Pro Ser Ala Asn Asn Ser Glu
225                 230                 235                 240

Val Lys Glu Thr Val Met Ser Ile Tyr Thr Met Val Pro Met Leu Asn
                245                 250                 255

Pro Phe Ile Tyr Ser Leu Arg Asn Arg Asp Ile Lys Asp Ala Leu Glu
            260                 265                 270

Lys Ile Met Cys Lys Lys Gln Ile Pro Ser Phe Leu
            275                 280
```

( 2 ) INFORMATION FOR SEQ ID NO:68:

( i ) SEQUENCE CHARACTERISTICS:
        ( A ) LENGTH: 277 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:68:

```
Leu Phe Tyr Ala Leu Phe Leu Ala Met Tyr Leu Thr Ile Ile Leu Gly
1               5                   10                  15

Asn Leu Leu Ile Ile Val Leu Val Arg Leu Asp Ser His Leu His Met
            20                  25                  30

Tyr Leu Phe Leu Ser Asn Leu Ser Phe Ser Asp Leu Cys Phe Ser Ser
        35                  40                  45

Val Thr Trp Lys Leu Leu Gln Asn Met Gln Ser Gln Val Pro Ser Ile
    50                  55                  60

Ser Tyr Thr Gly Cys Leu Thr Gln Leu Tyr Phe Phe Met Val Phe Gly
65                  70                  75                  80

Asp Trp Ser Phe Leu Leu Val Val Met Ala Tyr Asp Arg Tyr Val Ala
                85                  90                  95

Ile Cys Phe Pro Leu Arg Tyr Thr Thr Ile Met Ser Thr Lys Phe Cys
            100                 105                 110

Ala Ser Leu Val Leu Leu Leu Trp Met Leu Thr Met Arg His Ala Leu
            115                 120                 125

Leu His Thr Leu Leu Ile Ala Arg Leu Ser Phe Cys Glu Asp Ser Val
        130                 135                 140

Ile Leu His Phe Phe Cys Asp Ile Ser Ala Leu Leu Lys Leu Ser Cys
145                 150                 155                 160

Ser Asp Ile Tyr Val Asn Glu Leu Met Ile Tyr Ile Leu Gly Gly Leu
            165                 170                 175

Ile Ile Ile Ile Pro Phe Leu Leu Ile Val Met Ser Tyr Val Arg Ile
            180                 185                 190

Phe Phe Ser Ile Leu Lys Phe Pro Ser Ile Gln Asp Ile Tyr Lys Val
        195                 200                 205

Phe Ser Thr Cys Gly Ser His Leu Ser Val Val Thr Leu Phe Tyr Gly
    210                 215                 220

Thr Ile Phe Gly Ile Tyr Leu Cys Pro Ser Gly Asn Asn Ser Thr Val
225                 230                 235                 240

Lys Glu Ile Leu Thr Val Val Thr Pro Met Ile Asn Pro Phe Ile Tyr
            245                 250                 255

Ser Leu Arg Asn Arg Asp Trp Arg Ala Leu Ile Arg Val Ile Cys Thr
            260                 265                 270

Lys Lys Ile Ser Leu
            275
```

5,508,384

161 162

-continued ( 2 ) INFORMATION FOR SEQ ID NO:69:

( i ) SEQUENCE CHARACTERISTICS:
        ( A ) LENGTH: 274 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:69:

```
Val Phe Tyr Ala Leu Phe Leu Ser Met Tyr Leu Thr Ile Val Leu Gly
 1               5                  10                  15

Asn Leu Ile Ile Ile Ile Leu Ile His Leu Asp Ser His Leu His Thr
            20                  25                  30

Pro Met Tyr Leu Phe Leu Ser Asn Leu Ser Phe Ser Asp Leu Cys Phe
         35                  40                  45

Ser Ser Leu Lys Leu Leu Gln Asn Met Gln Ser Gln Val Pro Ser Ile
     50                  55                  60

Pro Phe Ala Gly Cys Leu Thr Gln Leu Tyr Phe Tyr Leu Tyr Phe Ala
 65              70                  75                  80

Asp Leu Glu Ser Phe Leu Leu Val Ala Met Ala Tyr Asp Arg Tyr Val
                 85                  90                  95

Ala Ile Cys Phe Pro Leu His Tyr Met Ser Ile Met Ser Pro Lys Leu
            100                 105                 110

Cys Val Ser Leu Trp Leu Ser Trp Val Leu Thr Thr Phe His Ala Met
            115                 120                 125

Leu His Thr Leu Ile Met Ala Arg Leu Ser Phe Cys Ala Asp Leu Pro
    130                 135                 140

His Phe Phe Cys Asp Ile Ser Pro Leu Leu Lys Leu Ser Cys Ser Asp
145                 150                 155                 160

Thr His Val Asn Glu Leu Val Ile Phe Leu Gly Leu Val Ile Val Ile
                165                 170                 175

Pro Phe Val Leu Ile Ile Val Ser Tyr Ala Arg Val Val Ala Ser Ile
            180                 185                 190

Leu Lys Val Pro Ser Val Arg Gly Ile His Lys Ile Phe Ser Thr Cys
        195                 200                 205

Gly Ser His Leu Ser Val Val Ser Leu Phe Tyr Gly Thr Ile Ile Gly
    210                 215                 220

Leu Tyr Leu Cys Pro Ser Ala Asn Asn Ser Thr Val Lys Glu Thr Leu
225                 230                 235                 240

Thr Val Val Thr Pro Leu Pro Phe Ile Tyr Ser Leu Arg Asn Arg Asp
                245                 250                 255

Met Lys Glu Ala Leu Ile Arg Val Leu Cys Lys Lys Lys Ile Thr Phe
            260                 265                 270

Cys Leu
```

( 2 ) INFORMATION FOR SEQ ID NO:70:

( i ) SEQUENCE CHARACTERISTICS:
        ( A ) LENGTH: 345 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:70:

```
Leu Ala Ile Ala Val Leu Ser Leu Thr Leu Leu Gly Thr Phe Thr Val
 1               5                  10                  15
```

| | | | | | | | | | | | | | | |
|---|---|---|---|---|---|---|---|---|---|---|---|---|---|---|
| Leu | Glu | Asn | Leu | Leu | Val | Leu | Cys | Val | Ile | Leu | His | Ser | Arg | Ser | Leu |
| | | | 20 | | | | 25 | | | | | 30 | | | |
| Arg | Cys | Arg | Pro | Ser | Tyr | His | Phe | Ile | Gly | Ser | Leu | Ala | Val | Ala | Asp |
| | | 35 | | | | | 40 | | | | | 45 | | | |
| Leu | Leu | Gly | Ser | Val | Ile | Phe | Val | Tyr | Ser | Phe | Val | Asp | Phe | His | Val |
| | 50 | | | | | 55 | | | | | 60 | | | | |
| Phe | His | Arg | Lys | Asp | Ser | Pro | Asn | Val | Phe | Leu | Phe | Lys | Leu | Gly | Gly |
| 65 | | | | | 70 | | | | | 75 | | | | | 80 |
| Val | Thr | Ala | Ser | Phe | Thr | Ala | Ser | Val | Gly | Ser | Leu | Phe | Leu | Thr | Ala |
| | | | | 85 | | | | | 90 | | | | | 95 | |
| Ile | Asp | Arg | Tyr | Ile | Ser | Ile | His | Pro | Pro | Ile | Ala | Tyr | Lys | Arg | Ile |
| | | | 100 | | | | | 105 | | | | | 110 | | |
| Val | Arg | Arg | Pro | Lys | Ala | Val | Val | Ala | Phe | Cys | Leu | Met | Thr | Ile | Ala |
| | | 115 | | | | | 120 | | | | | 125 | | | |
| Ile | Val | Ile | Ala | Val | Leu | Pro | Leu | Leu | Gly | Trp | Asn | Cys | Lys | Lys | Leu |
| | 130 | | | | | 135 | | | | | 140 | | | | |
| Gln | Ser | Val | Cys | Cys | Asp | Ile | Phe | Pro | Leu | Ile | Asp | Gly | Thr | Tyr | Leu |
| 145 | | | | | 150 | | | | | 155 | | | | | 160 |
| Met | Phe | Trp | Ile | Gly | Val | Thr | Ser | Val | Leu | Leu | Leu | Phe | Ile | Val | Tyr |
| | | | | 165 | | | | | 170 | | | | | 175 | |
| Ala | Tyr | Met | Tyr | Ile | Leu | Trp | Lys | Ala | His | Ser | His | Ala | Val | Arg | Ala |
| | | | 180 | | | | | 185 | | | | | 190 | | |
| Gln | Arg | Gly | Thr | Gln | Lys | Ser | Ile | Ile | Ile | His | Thr | Ser | Glu | Asp | Gly |
| | | 195 | | | | | 200 | | | | | 205 | | | |
| Lys | Val | Gln | Val | Thr | Arg | Pro | Asp | Gln | Ala | Arg | Met | Asp | Ile | Arg | Leu |
| | 210 | | | | | 215 | | | | | 220 | | | | |
| Ala | Lys | Thr | Leu | Val | Leu | Ile | Leu | Val | Val | Leu | Ile | Ile | Cys | Trp | Gly |
| 225 | | | | | 230 | | | | | 235 | | | | | 240 |
| Pro | Leu | Leu | Ala | Ile | Met | Val | Tyr | Asp | Val | Phe | Gly | Leu | Leu | Ile | Lys |
| | | | | 245 | | | | | 250 | | | | | 255 | |
| Thr | Val | Phe | Ala | Phe | Cys | Ser | Leu | Leu | Ile | Asn | Ser | Thr | Val | Asn | Pro |
| | | | 260 | | | | | 265 | | | | | 270 | | |
| Ile | Ile | Tyr | Ala | Leu | Arg | Ser | Lys | Asp | Leu | Arg | His | Ala | Phe | Arg | Ser |
| | | 275 | | | | | 280 | | | | | 285 | | | |
| Trp | Pro | Ser | Cys | Glu | Gly | Thr | Ala | Gln | Pro | Leu | Asp | Asn | Ser | Met | Gly |
| | 290 | | | | | 295 | | | | | 300 | | | | |
| Asp | Ser | Asp | Cys | Leu | His | Lys | His | Ala | Asn | Asn | Thr | Ala | Ser | Met | His |
| 305 | | | | | 310 | | | | | 315 | | | | | 320 |
| Arg | Ala | Ala | Glu | Ser | Cys | Ile | Lys | Ser | Thr | Val | Lys | Leu | Ala | Leu | Val |
| | | | | 325 | | | | | 330 | | | | | 335 | |
| Ser | Thr | Asp | Thr | Ser | Ala | Glu | Ala | Leu | | | | | | | |
| | | | 340 | | | | | 345 | | | | | | | |

( 2 ) INFORMATION FOR SEQ ID NO:71:

( i ) SEQUENCE CHARACTERISTICS:
        ( A ) LENGTH: 349 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:71:

| | | | | | | | | | | | | | | |
|---|---|---|---|---|---|---|---|---|---|---|---|---|---|---|
| Lys | Ala | Leu | Leu | Ile | Val | Ala | Tyr | Ser | Phe | Thr | Ile | Val | Phe | Ser | Leu |
| 1 | | | | 5 | | | | | 10 | | | | | 15 | |

|     |     |     |     |     |     |     |     |     |     |     |     |     |     |     |
|-----|-----|-----|-----|-----|-----|-----|-----|-----|-----|-----|-----|-----|-----|-----|
| Phe | Gly | Asn | Val 20 | Leu | Val | Cys | His | Tyr 25 | Ile | Phe | Lys | Asn | Gln 30 | Arg | Lys |
| Ile | Ser | Ala 35 | Thr | Ser | Leu | Phe | Ile 40 | Val | Asn | Leu | Ala | Val 45 | Ala | Asp | Ile |
| Ile | Glu 50 | Thr | Leu | Leu | Asn | Thr | Pro 55 | Phe | Thr | Leu | Val 60 | Arg | Phe | Val | Asn |
| Ser 65 | Thr | Trp | Tyr | Phe | Gly 70 | Lys | Gly | Met | Leu | His 75 | Val | Ser | Arg | Phe | Ala 80 |
| Gln | Tyr | Cys | Ser | Leu 85 | His | Val | Ser | Ala | Leu 90 | Ile | Leu | Thr | Ala | Ile 95 | Ala |
| Val | Asp | Arg | His 100 | Gln | Val | Ile | Met | Pro 105 | Leu | Lys | Pro | Arg | Ile 110 | Ser | Ile |
| Thr | Lys | Gly 115 | Val | Ile | Tyr | Ile | Ala 120 | Val | Ile | Trp | Val | Met 125 | Thr | Phe | Phe |
| Ser | Leu 130 | Pro | His | Ala | Ile | Cys 135 | Gln | Lys | Leu | Phe | Thr 140 | Phe | Lys | Tyr | Ser |
| Glu 145 | Asp | Ile | Val | Arg | Ser 150 | Leu | Cys | Leu | Asp | Pro 155 | Phe | Pro | Glu | Pro | Ala 160 |
| Asp | Leu | Phe | Trp | Lys 165 | Tyr | Leu | Asp | Ile | Ala 170 | Thr | Phe | Ile | Leu | Leu 175 | Tyr |
| Leu | Leu | Pro | Leu 180 | Phe | Ile | Ile | Ser | Val 185 | Ala | Tyr | Ala | Arg | Val 190 | Ala | Lys |
| Lys | Leu | Trp 195 | Leu | Cys | Asn | Thr | Ile 200 | Gly | Asp | Val | Thr | Thr 205 | Glu | Gln | Tyr |
| Leu | Ala 210 | Leu | Arg | Arg | Lys | Lys 215 | Lys | Thr | Thr | Val | Lys 220 | Met | Leu | Val | Leu |
| Val 225 | Val | Val | Leu | Phe | Ala 230 | Leu | Cys | Trp | Phe | Pro 235 | Leu | Asn | Cys | Tyr | Val 240 |
| Leu | Leu | Leu | Ser | Ser 245 | Lys | Ala | Ile | His | Thr 250 | Asn | Asn | Ala | Leu | Tyr 255 | Phe |
| Ala | Phe | His | Trp 260 | Phe | Ala | Met | Ser | Ser 265 | Thr | Cys | Tyr | Asn | Pro 270 | Phe | Ile |
| Tyr | Cys | Trp 275 | Leu | Asn | Glu | Asn | Phe 280 | Arg | Val | Glu | Leu | Lys 285 | Ala | Leu | Leu |
| Ser | Met 290 | Gln | Pro | Pro | Pro | Lys 295 | Pro | Glu | Asp | Arg | Leu 300 | Pro | Ser | Pro | Val |
| Pro 305 | Ser | Phe | Arg | Val | Ala 310 | Trp | Thr | Glu | Lys | Ser 315 | His | Gly | Arg | Arg | Ala 320 |
| Pro | Leu | Pro | Asn | His 325 | His | Leu | Pro | Ser | Ser 330 | Gln | Ile | Gln | Ser 335 | Gly | Lys |
| Thr | Asp | Leu | Ser 340 | Ser | Val | Glu | Pro | Val 345 | Val | Ala | Met | Ser |     |     |     |

( 2 ) INFORMATION FOR SEQ ID NO:72:

( i ) SEQUENCE CHARACTERISTICS:
        ( A ) LENGTH: 301 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:72:

|     |     |     |     |     |     |     |     |     |     |     |     |     |     |     |
|-----|-----|-----|-----|-----|-----|-----|-----|-----|-----|-----|-----|-----|-----|-----|
| Ile 1 | Phe | Thr | Ile | Ala 5 | Leu | Ala | Tyr | Gly | Ala 10 | Val | Ile | Ile | Leu | Gly 15 | Val |
| Ser | Gly | Asn | Leu | Ala | Leu | Ile | Ile | Ile | Ile | Leu | Lys | Gln | Lys | Glu | Leu |

|  |  |  |  |  | 20 |  |  |  | 25 |  |  |  | 30 |  |
|---|---|---|---|---|---|---|---|---|---|---|---|---|---|---|
| Ile | Leu | Ile 35 | Val | Asn | Leu | Ser | Phe 40 | Ser | Asp | Leu | Leu 45 | Val | Ala | Val | Trp |
| Leu | Pro 50 | Phe | Thr | Phe | Val | Tyr 55 | Thr | Leu | Ile | Cys | His 60 | Trp | Val | Phe | Gly |
| Glu 65 | Cys | Cys | Lys | Leu | Asn 70 | Pro | Phe | Val | Gln | Cys 75 | Val | Ser | Ile | Thr | Val 80 |
| Ser | Ile | Phe | Ser | Leu 85 | Val | Leu | Ile | Ala | Glu 90 | Arg | His | Gln | Leu 95 | Ile |
| Ile | Asn | Pro | Arg 100 | Gly | Trp | Arg | Pro | Asn 105 | Asn | Arg | His | Ala | Tyr 110 | Ile | Gly |
| Ile | Thr | Val 115 | Ile | Trp | Val | Ile | Ala 120 | Val | Ala | Ser | Ser | Leu 125 | Pro | Phe | Val |
| Ile | Tyr 130 | Gln | Ile | Leu | Thr | Asp 135 | Glu | Pro | Phe | Gln | Asn 140 | Val | Ser | Leu | Ala |
| Ala 145 | Phe | Lys | Asp | Lys | Tyr 150 | Val | Cys | Phe | Asp | Lys 155 | Phe | Pro | Ser | Asp | Ser 160 |
| His | Arg | Leu | Ser | Tyr 165 | Thr | Thr | Leu | Leu | Leu 170 | Val | Leu | Gln | Tyr | Phe 175 | Gly |
| Pro | Leu | Cys | Phe 180 | Ile | Phe | Ile | Cys | Tyr 185 | Phe | Lys | Ile | Tyr | Ile 190 | Arg | Leu |
| Lys | Arg | Arg 195 | Asn | Asn | Met | Met | Lys 200 | Ile | Arg | Asp | Ser | Lys 205 | Tyr | Arg | Ser |
| Ser | Glu 210 | Thr | Lys | Arg | Ile | Asn 215 | Val | Met | Leu | Leu | Ser 220 | Ile | Val | Val | Ala |
| Phe 225 | Ala | Val | Cys | Trp | Leu 230 | Pro | Leu | Thr | Ile | Phe 235 | Asn | Ile | Val | Phe | Asp 240 |
| Trp | Asn | His | Gln | Ile 245 | Ile | Ala | Thr | Cys | Asn 250 | His | Asn | Leu | Leu | Phe 255 | Leu |
| Leu | Cys | His | Leu 260 | Thr | Leu | Ser | Thr | Cys 265 | Val | Asn | Pro | Ile | Phe 270 | Tyr | Gly |
| Phe | Leu | Asn 275 | Lys | Asn | Phe | Gln | Arg 280 | Asp | Leu | Gln | Phe | Phe 285 | Phe | Asn | Phe |
| Cys | Asp 290 | Phe | Arg | Ser | Arg | Asp 295 | Gly | Arg | Thr | Thr | Arg 300 | Leu |

(2) INFORMATION FOR SEQ ID NO:73:

(i) SEQUENCE CHARACTERISTICS:
  (A) LENGTH: 334 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:73:

| Leu 1 | Thr | Ser | Val | Val 5 | Phe | Ile | Leu | Ile | Cys 10 | Cys | Phe | Ile | Ile | Leu 15 | Glu |
|---|---|---|---|---|---|---|---|---|---|---|---|---|---|---|---|
| Asn | Ile | Phe | Val 20 | Leu | Leu | Thr | Ile | Trp 25 | Lys | Thr | Lys | Lys | Phe 30 | His | Arg |
| Pro | Met | Tyr 35 | Tyr | Phe | Ile | Gly | Asn 40 | Ile | Ala | Leu | Ser | Asp 45 | Leu | Ile | Ala |
| Gly | Val | Ala 50 | Tyr | Thr | Ala | Asn | Leu 55 | Leu | Leu | Ser | Gly | Ala 60 | Thr | Thr | Tyr |
| Lys 65 | Leu | Thr | Pro | Ala | Gln 70 | Trp | Phe | Leu | Arg | Glu 75 | Gly | Ser | Met | Phe | Val 80 |

| | | | | | | | | | | | | | | |
|---|---|---|---|---|---|---|---|---|---|---|---|---|---|---|
|Ala|Leu|Ser|Leu|Ser 85|Val|Phe|Ser|Leu|Leu 90|Ala|Ile|Ala|Ile|Glu 95|Arg|
|Tyr|Ile|Thr|Met 100|Leu|Lys|Met|Leu|His 105|Asn|Gly|Ser|Asn|Asn 110|Phe|Arg|
|Leu|Phe|Leu 115|Leu|Ile|Ser|Ala|Cys 120|Trp|Val|Ile|Ser|Leu 125|Ile|Leu|Gly|
|Gly|Leu 130|Pro|Ile|Met|Gly|Trp 135|Asn|Cys|Ile|Ser|Ala 140|Leu|Ser|Ser|Cys|
|Ser 145|Thr|Val|Leu|Pro|Leu 150|Tyr|His|Lys|His|Tyr 155|Ile|Leu|Phe|Cys|Thr 160|
|Leu|Ile|Val|Phe|Thr 165|Leu|Leu|Leu|Leu|Ser 170|Ile|Val|Ile|Leu|Tyr 175|Cys|
|Arg|Ile|Tyr|Ser 180|Leu|Val|Arg|Thr|Arg 185|Ser|Arg|Arg|Leu|Thr 190|Phe|Arg|
|Lys|Asn|Ile 195|Ser|Lys|Ala|Ser|Arg 200|Ser|Ser|Glu|Asn|Val 205|Ala|Leu|Leu|
|Lys|Thr 210|Val|Ile|Ile|Val|Leu 215|Ser|Val|Phe|Ile|Ala 220|Cys|Trp|Ala|Pro|
|Leu 225|Phe|Ile|Leu|Leu|Leu 230|Leu|Asp|Val|Gly|Cys 235|Lys|Val|Lys|Thr|Cys 240|
|Asp|Ile|Leu|Phe|Arg 245|Ala|Glu|Tyr|Phe|Leu 250|Val|Ile|Ala|Val|Ile 255|Asn|
|Ser|Gly|Thr|Asn 260|Pro|Ile|Ile|Tyr|Thr 265|Leu|Thr|Asn|Lys|Glu 270|Met|Arg|
|Arg|Ala|Phe 275|Ile|Arg|Ile|Met|Cys 280|Cys|Lys|Cys|Pro|Ser 285|Gly|Asp|Ser|
|Ala|Gly 290|Lys|Phe|Lys|Arg|Pro 295|Ile|Ile|Ala|Gly|Met 300|Glu|Phe|Ser|Arg|
|Ser 305|Lys|Ser|Asp|Asn|Ser 310|Ser|His|Pro|Gln|Lys 315|Asp|Glu|Gly|Asp|Asn 320|
|Pro|Glu|Thr|Ile|Met 325|Ser|Ser|Gly|Asn|Val 330|Asn|Ser|Ser|Ser| | |

( 2 ) INFORMATION FOR SEQ ID NO:74:

( i ) SEQUENCE CHARACTERISTICS:
        ( A ) LENGTH: 236 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:74:

| | | | | | | | | | | | | | | |
|---|---|---|---|---|---|---|---|---|---|---|---|---|---|---|
|Ile 1|Thr|Tyr|Tyr|Ile 5|Leu|Ile|Gly|Leu|Cys 10|Ala|Val|Val|Gly|Asn 15|Ile|
|Leu|Leu|Val|Ile 20|Trp|Val|Val|Lys|Leu 25|Asn|Arg|Thr|Leu|Arg 30|Thr|Thr|
|Thr|Phe|Tyr 35|Phe|Ile|Val|Ser|Ile 40|Ala|Leu|Ala|Asp|Ile 45|Ala|Val|Leu|
|Val|Ile 50|Pro|Leu|Ala|Ile|Ala 55|Ser|Ala|Trp|Arg|Ser 60|Arg|Cys|Thr|Ser|
|Asn 65|Cys|Leu|Phe|Met|Ser 70|Cys|Val|Leu|Leu|Val 75|Phe|Thr|His|Ala|Ser 80|
|Ile|Met|Ser|Leu|Leu 85|Ala|Ile|Ala|Val|Asp 90|Arg|Tyr|Leu|Arg|Val 95|Lys|

```
Leu Thr Val Arg Tyr Arg Thr Val Thr Thr Gln Arg Arg Ile Trp Leu
            100             105             110

Phe Leu Gly Leu Cys Trp Leu Val Ser Phe Leu Val Gly Leu Thr Pro
            115             120             125

Trp Gly Trp Asn Arg Lys Val Thr Leu Glu Leu Ser Gln Asn Ser Ser
    130             135             140

Thr Leu Arg Glu Phe Lys Thr Pro Lys Ser Leu Phe Leu Val Leu Phe
145             150             155                         160

Leu Phe Ala Leu Cys Trp Leu Pro Leu Ser Ile Ile Asn Phe Val Ser
            165             170                     175

Tyr Phe Asn Val Lys Ile Pro Glu Thr Leu Leu Gly Ile Leu Leu Ser
            180             185             190

His Ala Asn Ser Leu Pro Ile Val Tyr Ala Cys Lys Lys Lys Phe Lys
            195             200             205

Glu Thr Tyr Phe Val Ile Leu Arg Ala Cys Arg Leu Cys Gln Thr Ser
    210             215             220

Asp Ser Leu Asp Ser Asn Leu Glu Gln Thr Thr Glu
225             230             235
```

(2) INFORMATION FOR SEQ ID NO:75:

(i) SEQUENCE CHARACTERISTICS:
        (A) LENGTH: 322 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

```
Ala Ile Leu Ile Ser Phe Ile Tyr Ser Trp Cys Leu Val Gly Leu Cys
1               5               10              15

Gly Asn Ser Met Val Ile Tyr Val Ile Leu Arg Tyr Ala Lys Met Lys
            20              25              30

Thr Ala Thr Asn Ile Tyr Ile Leu Asn Ile Ala Ile Ala Asp Glu Leu
            35              40              45

Leu Val Pro Phe Leu Val Thr Ser Thr Leu Leu Arg His Trp Pro Phe
    50              55              60

Gly Ala Leu Leu Cys Arg Leu Val Leu Ser Val Asp Ala Val Asn Met
65              70              75                          80

Phe Thr Ser Ile Tyr Cys Leu Thr Val Leu Ser Val Asp Arg Tyr Val
            85              90              95

Ala Val Val His Pro Ile Lys Ala Ala Arg Tyr Arg Arg Pro Thr Val
            100             105             110

Ala Lys Val Val Asn Leu Gly Val Trp Val Leu Ser Leu Leu Val Ile
            115             120             125

Leu Pro Ile Trp Phe Ser Arg Thr Ala Ala Asn Ser Asp Gly Thr Val
    130             135             140

Ala Cys Asn Met Ile Trp Glu Pro Ala Gln Phe Trp Leu Val Gly Phe
145             150             155                         160

Val Leu Tyr Thr Phe Leu Met Phe Leu Leu Pro Val Gly Ala Ile Cys
            165             170             175

Leu Cys Tyr Val Leu Ile Ile Ala Lys Met Arg Met Val Ala Leu Lys
            180             185             190

Ala Gly Trp Gln Gln Arg Lys Arg Ser Glu Arg Lys Ile Thr Leu Val
            195             200             205

Met Met Val Val Met Val Phe Val Ile Cys Trp Phe Tyr Val Val Gln
```

|     |     |     |     | 210 |     |     |     |     | 215 |     |     |     |     | 220 |     |
| --- | --- | --- | --- | --- | --- | --- | --- | --- | --- | --- | --- | --- | --- | --- | --- |
| Leu | Val | Asn | Val | Phe | Ala | Glu | Gln | Asp | Asp | Ala | Thr | Val | Ser | Gln | Leu |
| 225 |     |     |     | 230 |     |     |     |     | 235 |     |     |     |     |     | 240 |
| Ser | Val | Ile | Leu | Gly | Tyr | Ala | Asn | Ser | Cys | Ala | Asn | Pro | Ile | Leu | Tyr |
|     |     |     |     | 245 |     |     |     |     | 250 |     |     |     |     | 255 |     |
| Gly | Phe | Leu | Ser | Asp | Asn | Phe | Lys | Arg | Ser | Phe | Gln | Arg | Ile | Leu | Cys |
|     |     |     |     | 260 |     |     |     |     | 265 |     |     |     |     | 270 |     |
| Leu | Ser | Leu | Asn | Ala | Ala | Glu | Glu | Pro | Val | Asp | Tyr | Tyr | Ala | Thr | Ala |
|     |     |     | 275 |     |     |     | 280 |     |     |     |     | 285 |     |     |     |
| Leu | Lys | Ser | Arg | Ala | Tyr | Ser | Val | Glu | Asp | Phe | Gln | Pro | Glu | Asn | Leu |
|     |     | 290 |     |     |     | 295 |     |     |     |     | 300 |     |     |     |     |
| Glu | Ser | Gly | Gly | Val | Phe | Arg | Asn | Cys | Thr | Cys | Ala | Ser | Arg | Ile | Ser |
| 305 |     |     |     |     | 310 |     |     |     |     | 315 |     |     |     |     | 320 |
| Thr | Leu |     |     |     |     |     |     |     |     |     |     |     |     |     |     |

( 2 ) INFORMATION FOR SEQ ID NO:76:

( i ) SEQUENCE CHARACTERISTICS:
( A ) LENGTH: 298 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:76:

| Val | Thr | Asn | Tyr | Ile | Phe | Leu | Leu | Leu | Cys | Leu | Cys | Gly | Leu | Val | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Asn | Gly | Leu | Val | Leu | Trp | Phe | Phe | Gly | Phe | Ser | Ile | Lys | Arg | Thr | Pro |
|     |     |     | 20  |     |     |     |     | 25  |     |     |     |     | 30  |     |     |
| Phe | Ser | Ile | Tyr | Ile | Tyr | Phe | Leu | His | Ile | Ala | Ser | Ala | Asp | Gly | Ile |
|     |     | 35  |     |     |     |     | 40  |     |     |     |     | 45  |     |     |     |
| Tyr | Leu | Phe | Ser | Lys | Ala | Val | Ile | Ala | Leu | Leu | Asn | Met | Gly | Thr | Phe |
|     | 50  |     |     |     |     | 55  |     |     |     |     | 60  |     |     |     |     |
| Leu | Gly | Ser | Phe | Pro | Asp | Tyr | Val | Arg | Arg | Val | Ser | Arg | Ile | Val | Gly |
| 65  |     |     |     |     | 70  |     |     |     |     | 75  |     |     |     |     | 80  |
| Leu | Thr | Phe | Phe | Ala | Gly | Val | Ser | Leu | Leu | Pro | Ala | Ile | Ser | Ile | Glu |
|     |     |     |     | 85  |     |     |     |     | 90  |     |     |     |     | 95  |     |
| Arg | Cys | Val | Ser | Val | Ile | Phe | Pro | Met | Trp | Tyr | Trp | Arg | Arg | Arg | Pro |
|     |     |     | 100 |     |     |     |     | 105 |     |     |     |     | 110 |     |     |
| Lys | Arg | Leu | Ser | Ala | Gly | Val | Cys | Ala | Leu | Leu | Trp | Leu | Leu | Ser | Phe |
|     |     |     | 115 |     |     |     |     | 120 |     |     |     |     | 125 |     |     |
| Leu | Val | Thr | Ser | Ile | His | Asn | Tyr | Phe | Cys | Leu | Leu | Gly | His | Glu | Ala |
|     | 130 |     |     |     |     | 135 |     |     |     |     | 140 |     |     |     |     |
| Ser | Gly | Thr | Ala | Cys | Leu | Asn | Met | Asp | Ile | Ser | Leu | Leu | Gly | Ile | Leu |
| 145 |     |     |     |     | 150 |     |     |     |     | 155 |     |     |     |     | 160 |
| Leu | Phe | Phe | Leu | Phe | Cys | Pro | Ile | Met | Val | Leu | Pro | Cys | Ile | Ala | Leu |
|     |     |     |     | 165 |     |     |     |     | 170 |     |     |     |     | 175 |     |
| Leu | His | Val | Glu | Cys | Arg | Ala | Arg | Arg | Arg | Gln | Arg | Ser | Ala | Lys | Leu |
|     |     |     | 180 |     |     |     |     | 185 |     |     |     |     | 190 |     |     |
| Asn | His | Val | Val | Leu | Ala | Ile | Val | Ser | Val | Phe | Leu | Val | Ser | Ser | Ile |
|     |     | 195 |     |     |     |     | 200 |     |     |     |     | 205 |     |     |     |
| Tyr | Leu | Gly | Ile | Asp | Trp | Phe | Leu | Phe | Trp | Val | Phe | Gln | Ile | Pro | Ala |
|     | 210 |     |     |     |     | 215 |     |     |     |     | 220 |     |     |     |     |
| Pro | Phe | Pro | Glu | Tyr | Val | Arg | Asp | Leu | Cys | Ile | Cys | Ile | Asn | Ser | Ser |
| 225 |     |     |     |     | 230 |     |     |     |     | 235 |     |     |     |     | 240 |

```
Ala Lys Pro Ile Val Tyr Phe Ile Ala Gly Arg Asp Lys Ser Gln Arg
                245                 250                 255

Leu Trp Glu Pro Leu Arg Val Val Phe Gln Arg Ala Leu Arg Asp Gly
            260                 265                 270

Ala Glu Pro Gly Asp Ala Ala Ser Ser Thr Pro Asn Thr Val Thr Met
            275                 280                 285

Glu Met Gln Cys Pro Ser Gly Asn Ala Ser
            290                 295
```

(2) INFORMATION FOR SEQ ID NO:77:

(i) SEQUENCE CHARACTERISTICS:
    (A) LENGTH: 299 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:77:

```
Thr Thr Glu Ala Val Leu Asn Thr Phe Ile Ile Phe Val Gly Gly Pro
1               5                   10                  15

Ala Ile Val Leu Ile Thr Gln Leu Leu Thr Asn Arg Val Leu Gly Tyr
            20                  25                  30

Ser Thr Pro Thr Ile Tyr Met Arg Asn Leu Tyr Ser Thr Asn Phe Leu
            35                  40                  45

Thr Leu Thr Val Leu Pro Phe Ile Val Leu Ser Asn Gln Trp Leu Leu
50                  55                  60

Pro Ala Cys Tyr Val Ala Ser Cys Lys Phe Leu Ser Val Ile Tyr Tyr
65                  70                  75                  80

Ser Ser Cys Thr Val Gly Phe Ala Thr Val Ala Leu Ile Ala Ala Asp
                85                  90                  95

Arg Tyr Arg Val Leu His Lys Arg Thr Tyr Ala Arg Gln Ser Tyr Arg
            100                 105                 110

Ser Leu Leu Leu Thr Trp Leu Ala Gly Leu Ile Phe Ser Val Pro Ala
            115                 120                 125

Ala Val Tyr Thr Thr Val Val Met His His Asp Ala Asn Asp Thr Asn
130                 135                 140

Asn Thr Asn Gly His Ala Thr Cys Val Leu Tyr Phe Val Ala Glu Glu
145                 150                 155                 160

Val His Thr Val Leu Leu Ser Trp Lys Val Leu Leu Thr Met Val Trp
            165                 170                 175

Gly Ala Ala Pro Val Ile Leu Phe Tyr Ala Phe Phe Tyr Ser Thr Val
            180                 185                 190

Gln Arg Thr Ser Gln Lys Gln Arg Ser Arg Thr Leu Thr Phe Val Ser
            195                 200                 205

Val Leu Leu Ile Ser Phe Val Ala Leu Gln Thr Pro Tyr Val Ser Leu
            210                 215                 220

Met Ile Phe Asn Ser Tyr Ala Thr Thr Ala Trp Pro Met Cys Glu His
225                 230                 235                 240

Leu Thr Leu Arg Arg Thr Ile Gly Thr Leu Ala Arg Val Val Pro His
            245                 250                 255

Leu His Cys Leu Ile Asn Pro Ile Leu Tyr Ala Leu Leu Cys His Asp
            260                 265                 270

Phe Leu Gln Arg Met Arg Gln Cys Phe Arg Gly Gln Leu Ile Asp Arg
            275                 280                 285

Ala Phe Leu Arg Ser Gln Gln Asn Gln Arg Ala
```

(2) INFORMATION FOR SEQ ID NO:78:

(i) SEQUENCE CHARACTERISTICS:
        (A) LENGTH: 283 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:78:

```
Leu Gly Val Trp Leu Met Ile Val Gly Thr Phe Leu Leu Val Ile Thr
 1               5                  10                  15
Thr Ile Leu Tyr Tyr Arg Arg Lys Lys Lys Ser Pro Ser Asp Thr Tyr
             20                  25                  30
Ile Cys Asn Leu Ala Val Ala Asp Leu Leu Ile Val Val Gly Leu Pro
         35                  40                  45
Phe Phe Leu Glu Tyr Ala Lys His His Pro Lys Leu Ser Arg Glu Val
     50                  55                  60
Val Cys Ser Gly Leu Asn Ala Cys Phe Tyr Ile Cys Leu Phe Ala Gly
 65                  70                  75                  80
Val Cys Phe Leu Ile Asn Leu Ser Met Asp Arg Tyr Cys Val Ile Val
                 85                  90                  95
Trp Gly Val Glu Leu Asn Arg Val Arg Asn Asn Lys Arg Ala Thr Cys
                100                 105                 110
Trp Val Val Ile Phe Trp Ile Ile Ala Val Leu Met Gly Met Pro His
             115                 120                 125
Tyr Ile Met Tyr Ser His Thr Asn Asn Glu Cys Val Gly Trp Phe Ala
130                 135                 140
Asn Glu Thr Ser Cys Trp Phe Pro Val Phe Leu Asn Thr Lys Val Asn
145                 150                 155                 160
Ile Cys Gly Tyr Leu Ala Pro Ile Ala Leu Met Ala Tyr Tyr Asn Arg
             165                 170                 175
Met Val Arg Phe Ile Ile Asn Tyr Val Gly Lys Trp Phe Met Gln Thr
         180                 185                 190
Leu His Val Leu Leu Val Val Val Ser Phe Ala Ser Phe Trp Phe
     195                 200                 205
Pro Phe Asn Leu Ala Leu Phe Leu Glu Ser Ile Arg Leu Ile Ala Gly
210                 215                 220
Val Tyr Asn Asp Thr Leu Gln Asn Val Ile Ile Phe Cys Leu Tyr Val
225                 230                 235                 240
Gly Gln Phe Ile Ala Tyr Val Arg Ala Cys Leu Asn Pro Gly Ile Tyr
             245                 250                 255
Ile Leu Val Cys Thr Trp Phe Leu Arg Val Phe Ala Cys Cys Cys Val
         260                 265                 270
Lys Gln Glu Ile Pro Tyr Gln Asp Ile Asp Ile
         275                 280
```

(2) INFORMATION FOR SEQ ID NO:79:

(i) SEQUENCE CHARACTERISTICS:
        (A) LENGTH: 295 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:79:

```
Pro Val Thr Leu Phe Leu Tyr Gly Val Val Phe Leu Phe Gly Ser Ile
1               5                   10                  15

Gly Asn Phe Leu Val Ile Phe Thr Ile Thr Trp Arg Arg Arg Ile Gln
            20                  25                  30

Cys Ser Gly Asp Val Tyr Phe Ile Asn Leu Ala Ala Ala Asp Leu Leu
            35                  40                  45

Phe Val Cys Thr Leu Pro Leu Trp Met Gln Tyr Leu Leu Asp His Asn
        50                  55                  60

Ser Leu Ala Ser Leu Ile Pro Cys Thr Leu Leu Thr Ala Cys Phe Tyr
65                  70                  75                  80

Val Ala Ile Thr Ala Ser Leu Cys Phe Ile Thr Glu Ile Ala Leu Ile
                85                  90                  95

Asp Arg Tyr Tyr Ala Ile Val Tyr Met Arg Tyr Arg Pro Val Lys Ile
            100                 105                 110

Gln Ala Cys Leu Phe Ser Ile Phe Trp Trp Ile Phe Ala Val Ile Ile
        115                 120                 125

Ala Ile Pro His Phe Met Val Val Ile Thr Lys Lys Asp Asn Gln Cys
        130                 135                 140

Met Thr Asp Tyr Asp Tyr Leu Glu Val Ser Tyr Pro Ile Ile Leu Asn
145                 150                 155                 160

Val Glu Leu Met Leu Gly Ala Phe Val Ile Pro Leu Ser Val Ile Ser
                165                 170                 175

Tyr Cys Tyr Tyr Arg Ile Ser Arg Ile Val Ala Val Ser Gln Ser Arg
            180                 185                 190

His Lys Gly Arg Ile Val Arg Val Leu Ile Ala Trp Leu Val Phe Ile
        195                 200                 205

Ile Phe Trp Leu Pro Tyr His Leu Thr Leu Phe Val Asp Thr Ile Ile
    210                 215                 220

Lys Leu Leu Lys Trp Ile Ser Ser Cys Glu Phe Glu Arg Ser Leu
225                 230                 235                 240

Lys Arg Ala Leu Ile Leu Thr Glu Ser Leu Ala Phe Cys His Cys Cys
                245                 250                 255

Leu Asn Pro Leu Leu Tyr Val Phe Val Ile Gly Thr Lys Phe Arg Lys
            260                 265                 270

Asn Tyr Thr Val Cys Trp Pro Ser Phe Ala Ser Asp Ser Phe Pro Ala
        275                 280                 285

Met Tyr Pro Gly Thr Arg Ala
290                 295
```

( 2 ) INFORMATION FOR SEQ ID NO:80:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:80:

```
Asp Asp Asp Asp Asn Ile Trp Ser Ile Phe Asp Trp Ile Gly Tyr Leu
1               5                   10                  15

Asn Ser Ile Ser Met Val Ile Tyr Thr Leu Phe Lys Lys Lys Lys
            20                  25                  30
```

( 2 ) INFORMATION FOR SEQ ID NO:81:

( i ) SEQUENCE CHARACTERISTICS:
    ( A ) LENGTH: 34 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:81:

| Asp | Asp | Asp | Asp | Asn | Ile | Trp | Asn | Ile | Phe | Ser | Thr | Ile | Gly | Tyr | Leu |
|---|---|---|---|---|---|---|---|---|---|---|---|---|---|---|---|
| 1 | | | | 5 | | | | | 10 | | | | | 15 | |
| Asn | Ser | Ile | Ser | Pro | Val | Ser | Val | Ile | Met | His | Ile | Tyr | Gly | Lys | Lys |
| | | | 20 | | | | | 25 | | | | | 30 | | |
| Lys | Lys | | | | | | | | | | | | | | |

( 2 ) INFORMATION FOR SEQ ID NO:82:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:82:

| Asp | Asp | Asp | Asp | Gly | Tyr | Ser | Ile | Tyr | Asp | Thr | Leu | Val | Thr | Phe | Ala |
|---|---|---|---|---|---|---|---|---|---|---|---|---|---|---|---|
| 1 | | | | 5 | | | | | 10 | | | | | 15 | |
| Ile | Asn | Pro | Val | Tyr | Ile | Thr | Val | Phe | Lys | Lys | Lys | Lys | | | |
| | | | 20 | | | | | 25 | | | | | | | |

( 2 ) INFORMATION FOR SEQ ID NO:83:

( i ) SEQUENCE CHARACTERISTICS:
    ( A ) LENGTH: 31 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:83:

| Asp | Asp | Asp | Asp | Asn | Ala | Trp | Ser | Ala | Phe | Asp | Trp | Ala | Leu | Tyr | Leu |
|---|---|---|---|---|---|---|---|---|---|---|---|---|---|---|---|
| 1 | | | | 5 | | | | | 10 | | | | | 15 | |
| Asn | Ser | Ile | Ser | Met | Ala | Ile | Tyr | Thr | Tyr | Ala | Lys | Lys | Lys | Lys | |
| | | | 20 | | | | | 25 | | | | | 30 | | |

( 2 ) INFORMATION FOR SEQ ID NO:84:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:84:

| Leu | Phe | Ser | Phe | Ile | Thr | Trp | Leu | Gly | Tyr | Ala | Asn | Ser | Ser | Leu | Asn |
|---|---|---|---|---|---|---|---|---|---|---|---|---|---|---|---|
| 1 | | | | 5 | | | | | 10 | | | | | 15 | |
| Pro | Ile | Ile | Tyr | Thr | Thr | Phe | | | | | | | | | |
| | | | 20 | | | | | | | | | | | | |

( 2 ) INFORMATION FOR SEQ ID NO:85:

( i ) SEQUENCE CHARACTERISTICS:

( A ) LENGTH: 23 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:85:

Tyr Thr Ile Tyr Ser Ser Ser Val Val Phe Phe Ala Pro Ser Leu Ala
1               5                   10                  15

Ile Met Val Ile Thr Tyr Thr
            20

( 2 ) INFORMATION FOR SEQ ID NO:86:

( i ) SEQUENCE CHARACTERISTICS:
( A ) LENGTH: 22 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:86:

Ile Trp Leu Thr Ser Asp Ile Met Ser Thr Ser Ser Ile Leu His Asn
1               5                   10                  15

Leu Cys Val Ile Ser Phe
            20

( 2 ) INFORMATION FOR SEQ ID NO:87:

( i ) SEQUENCE CHARACTERISTICS:
( A ) LENGTH: 30 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:87:

Ile Trp Ser Ile Phe Ser Ser Asp Ile Val Val Gly Tyr Ala Asn His
1               5                   10                  15

Ser Ser Leu Ala Ile Met Cys Pro Ile Val Ile Tyr Thr Val
            20                  25                  30

( 2 ) INFORMATION FOR SEQ ID NO:88:

( i ) SEQUENCE CHARACTERISTICS:
( A ) LENGTH: 29 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:88:

Ile Phe Thr Ile Phe Ser Ser Asp Ile Ala Val Gly Tyr Ala Asn His
1               5                   10                  15

Ser Ser Ala Ala Ile Met Pro Ile Val Ile Tyr Ser Val
            20                  25

( 2 ) INFORMATION FOR SEQ ID NO:89:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:89:

```
Lys Asn Ala Ser Ala Leu Leu Ser Val Ile Ile Ile Asn Ser Ile Gly
1               5                   10                  15
Gly Asn Val Val Thr Ala Val Ser
            20
```

( 2 ) INFORMATION FOR SEQ ID NO:90:

( i ) SEQUENCE CHARACTERISTICS:
           ( A ) LENGTH: 22 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:90:

```
Tyr Phe Leu Met Ser Leu Ala Val Thr Asp Leu Val Val Ser Phe Val
1               5                   10                  15
Met Pro Val Ser Ala Leu
            20
```

( 2 ) INFORMATION FOR SEQ ID NO:91:

( i ) SEQUENCE CHARACTERISTICS:
           ( A ) LENGTH: 23 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:91:

```
Ala Ile Thr Lys Ile Ala Ile Thr Trp Ala Ile Ser Gly Val Ser Val
1               5                   10                  15
Pro Phe Ile Pro Val Trp Gly
            20
```

( 2 ) INFORMATION FOR SEQ ID NO:92:

( i ) SEQUENCE CHARACTERISTICS:
           ( A ) LENGTH: 24 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:92:

```
Leu Gly Ile Ile Phe Gly Thr Phe Ile Ile Ile Trp Leu Pro Phe Phe
1               5                   10                  15
Ile Thr Asn Leu Val Ser Pro Ile
            20
```

( 2 ) INFORMATION FOR SEQ ID NO:93:

( i ) SEQUENCE CHARACTERISTICS:
           ( A ) LENGTH: 23 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:93:

```
    Ile  Trp  Ile  Ser  Leu  Asp  Val  Leu  Phe  Ser  Thr  Ala  Ser  Ser  Ile  Met
    1              5                        10                       15

His  Leu  Cys  Ala  Ile  Ser  Leu
                   20
```

( 2 ) INFORMATION FOR SEQ ID NO:94:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:94:

```
    Gly  Tyr  Thr  Ile  Tyr  Ser  Thr  Leu  Val  Thr  Phe  Tyr  Ile  Pro  Ser  Val
    1              5                        10                       15

Ile  Met  Val  Ile  Thr  Tyr  Gly
                   20
```

( 2 ) INFORMATION FOR SEQ ID NO:95:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:95:

```
    Leu  Leu  Asn  Phe  Phe  Asn  Trp  Ile  Gly  Tyr  Leu  Asn  Ser  Leu  Ile  Asn
    1              5                        10                       15

Pro  Val  Ile  Tyr  Thr  Leu  Phe
                   20
```

( 2 ) INFORMATION FOR SEQ ID NO:96:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:96:

```
    Tyr  Ala  Ile  Phe  Val  Leu  Tyr  Ala  Ser  Ala  Trp  Leu  Ser  Phe  Leu  Asn
    1              5                        10                       15

Cys  Pro  Phe  Ile  Val  Thr  Leu  Asn  Ile
                   20                      25
```

( 2 ) INFORMATION FOR SEQ ID NO:97:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:97:

```
    Tyr  Ala  Ile  Phe  Val  Leu  Tyr  Ala  Thr  Ala  Trp  Leu  Ser  Phe  Leu  Asn
    1              5                        10                       15
```

```
    Cys  Pro  Phe  Ile  Val  Thr  Leu  Asn  Ile
                   20                   25
```

( 2 ) INFORMATION FOR SEQ ID NO:98:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:98:

```
    Tyr  Ala  Ile  Phe  Val  Leu  Tyr  Ala  Thr  Ala  Trp  Leu  Thr  Phe  Leu  Asn
    1                   5                        10                       15

Cys  Pro  Phe  Ile  Val  Thr  Leu  Asn  Ile
                   20                   25
```

( 2 ) INFORMATION FOR SEQ ID NO:99:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:99:

```
    Tyr  Ala  Ile  Phe  Val  Leu  Tyr  Ala  Ser  Ala  Trp  Leu  Thr  Phe  Leu  Asn
    1                   5                        10                       15

Cys  Pro  Phe  Ile  Val  Thr  Leu  Asn  Ile
                   20                   25
```

( 2 ) INFORMATION FOR SEQ ID NO:100:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:100:

```
    Trp  Ala  Ile  Phe  Val  Leu  Tyr  Ala  Ser  Ala  Trp  Leu  Ser  Phe  Leu  Asn
    1                   5                        10                       15

Cys  Pro  Phe  Ile  Val  Thr  Leu  Asn  Ile
                   20                   25
```

( 2 ) INFORMATION FOR SEQ ID NO:101:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:101:

```
    Trp  Ala  Ile  Phe  Val  Leu  Tyr  Ala  Thr  Ala  Trp  Leu  Ser  Phe  Leu  Asn
    1                   5                        10                       15

Cys  Pro  Phe  Ile  Val  Thr  Leu  Asn  Ile
                   20                   25
```

(2) INFORMATION FOR SEQ ID NO:102:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:102:

```
Trp Ala Ile Phe Val Leu Tyr Ala Thr Ala Trp Leu Thr Phe Leu Asn
 1               5                  10                  15
Cys Pro Phe Ile Val Thr Leu Asn Ile
            20                  25
```

(2) INFORMATION FOR SEQ ID NO:103:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:103:

```
Trp Ala Ile Phe Val Leu Tyr Ala Ser Ala Trp Leu Thr Phe Leu Asn
 1               5                  10                  15
Cys Pro Phe Ile Val Thr Leu Asn Ile
            20                  25
```

(2) INFORMATION FOR SEQ ID NO:104:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:104:

```
Tyr Ala Val Phe Val Leu Tyr Ala Ser Ala Trp Leu Ser Phe Leu Asn
 1               5                  10                  15
Met Pro Phe Ile Val Thr Leu Asn Ile
            20                  25
```

(2) INFORMATION FOR SEQ ID NO:105:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:105:

```
Tyr Ala Val Phe Val Leu Tyr Ala Thr Ala Trp Leu Ser Phe Leu Asn
 1               5                  10                  15
Met Pro Phe Ile Val Thr Leu Asn Ile
            20                  25
```

(2) INFORMATION FOR SEQ ID NO:106:

(i) SEQUENCE CHARACTERISTICS:
        (A) LENGTH: 25 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:106:

| Tyr | Ala | Val | Phe | Val | Leu | Tyr | Ala | Thr | Ala | Trp | Leu | Thr | Phe | Leu | Asn |
|---|---|---|---|---|---|---|---|---|---|---|---|---|---|---|---|
| 1 | | | | 5 | | | | | 10 | | | | | 15 | |

| Met | Pro | Phe | Ile | Val | Thr | Leu | Asn | Ile |
|---|---|---|---|---|---|---|---|---|
| | | | 20 | | | | | 25 |

(2) INFORMATION FOR SEQ ID NO:107:

(i) SEQUENCE CHARACTERISTICS:
   (A) LENGTH: 25 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:107:

| Tyr | Ala | Val | Phe | Val | Leu | Tyr | Ala | Ser | Ala | Trp | Leu | Thr | Phe | Leu | Asn |
|---|---|---|---|---|---|---|---|---|---|---|---|---|---|---|---|
| 1 | | | | 5 | | | | | 10 | | | | | 15 | |

| Met | Pro | Phe | Ile | Val | Thr | Leu | Asn | Ile |
|---|---|---|---|---|---|---|---|---|
| | | | 20 | | | | | 25 |

(2) INFORMATION FOR SEQ ID NO:108:

(i) SEQUENCE CHARACTERISTICS:
   (A) LENGTH: 30 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:108:

| Tyr | Ala | Ile | Phe | Val | Leu | Tyr | Ala | Ser | Ala | Trp | Leu | Ser | Phe | Leu | Asn |
|---|---|---|---|---|---|---|---|---|---|---|---|---|---|---|---|
| 1 | | | | 5 | | | | | 10 | | | | | 15 | |

| Cys | Val | Thr | Ala | Ser | Ile | Pro | Phe | Ile | Val | Thr | Leu | Asn | Ile |
|---|---|---|---|---|---|---|---|---|---|---|---|---|---|
| | | | 20 | | | | | 25 | | | | | 30 |

(2) INFORMATION FOR SEQ ID NO:109:

(i) SEQUENCE CHARACTERISTICS:
   (A) LENGTH: 32 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:109:

| Tyr | Ala | Ile | Phe | Val | Leu | Tyr | Ala | Ser | Ala | Trp | Leu | Ser | Phe | Leu | Asn |
|---|---|---|---|---|---|---|---|---|---|---|---|---|---|---|---|
| 1 | | | | 5 | | | | | 10 | | | | | 15 | |

| Cys | Thr | Ser | Ser | Ile | Val | Val | Thr | Ala | Ser | Ile | Val | Thr | Leu | Asn | Ile |
|---|---|---|---|---|---|---|---|---|---|---|---|---|---|---|---|
| | | | 20 | | | | | 25 | | | | | 30 | | |

(2) INFORMATION FOR SEQ ID NO:110:

(i) SEQUENCE CHARACTERISTICS:
   (A) LENGTH: 27 amino acids
   (B) TYPE: amino acid
   (C) STRANDEDNESS: single
   (D) TOPOLOGY: linear ( i i ) MOLECULE TYPE: peptide ( x i ) SEQUENCE DESCRIPTION: SEQ ID NO:110:

Tyr Ala Ile Phe Val Leu Tyr Ala Ser Ala Trp Leu Ser Phe Leu Asn
1               5                   10                  15

Val Thr Leu Asn Ile Cys Thr Ser Ser Ile Val
            20              25

( 2 ) INFORMATION FOR SEQ ID NO:111:

( i ) SEQUENCE CHARACTERISTICS:
( A ) LENGTH: 31 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:111:

Tyr Ala Ile Phe Val Leu Tyr Ala Ser Ala Trp Leu Ser Phe Leu Asn
1               5                   10                  15

Thr Ala Ser Ile Leu Asn Leu Met Phe Ile Val Thr Leu Asn Ile
            20                  25                  30

( 2 ) INFORMATION FOR SEQ ID NO:112:

( i ) SEQUENCE CHARACTERISTICS:
( A ) LENGTH: 31 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:112:

Tyr Ala Ile Phe Val Leu Tyr Ala Ser Ala Trp Leu Ser Phe Leu Asn
1               5                   10                  15

Met Ala Ser Ile Leu Asn Leu Pro Phe Ile Val Thr Leu Asn Ile
            20                  25                  30

( 2 ) INFORMATION FOR SEQ ID NO:113:

( i ) SEQUENCE CHARACTERISTICS:
( A ) LENGTH: 31 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:113:

Tyr Ala Ile Phe Val Leu Tyr Ala Ser Ala Trp Leu Ser Phe Leu Asn
1               5                   10                  15

Ser Gly Ile Leu Leu Leu Ala Pro Phe Ile Val Thr Leu Asn Ile
            20                  25                  30

( 2 ) INFORMATION FOR SEQ ID NO:114:

( i ) SEQUENCE CHARACTERISTICS:
( A ) LENGTH: 32 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:114:

```
Tyr  Ala  Ile  Phe  Val  Leu  Tyr  Ala  Ser  Ala  Trp  Leu  Ser  Phe  Leu  Asn
1              5                        10                       15

Met  Ser  Gly  Ile  Leu  Leu  Leu  Ala  Pro  Phe  Ile  Val  Thr  Leu  Asn  Ile
               20                  25                       30
```

( 2 ) INFORMATION FOR SEQ ID NO:115:

( i ) SEQUENCE CHARACTERISTICS:
    ( A ) LENGTH: 35 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:115:

```
Tyr  Ala  Ile  Phe  Val  Leu  Tyr  Ala  Ser  Ala  Trp  Leu  Ser  Phe  Leu  Asn
1              5                        10                       15

Ser  Glu  Leu  Ser  Val  Tyr  Thr  Leu  Thr  Val  Cys  Pro  Phe  Ile  Val  Thr
               20                  25                       30

Leu  Asn  Ile
          35
```

( 2 ) INFORMATION FOR SEQ ID NO:116:

( i ) SEQUENCE CHARACTERISTICS:
    ( A ) LENGTH: 35 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:116:

```
Tyr  Ala  Ile  Phe  Val  Leu  Tyr  Ala  Ser  Ala  Trp  Leu  Ser  Phe  Leu  Asn
1              5                        10                       15

Met  Ser  Glu  Leu  Ser  Val  Tyr  Thr  Leu  Thr  Val  Pro  Phe  Ile  Val  Thr
               20                  25                       30

Leu  Asn  Ile
          35
```

( 2 ) INFORMATION FOR SEQ ID NO:117:

( i ) SEQUENCE CHARACTERISTICS:
    ( A ) LENGTH: 36 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:117:

```
Tyr  Ala  Ile  Phe  Val  Leu  Tyr  Ala  Ser  Ala  Trp  Leu  Ala  Ser  Glu  Leu
1              5                        10                       15

Ser  Val  Tyr  Thr  Leu  Thr  Val  Ser  Phe  Leu  Asn  Cys  Pro  Phe  Ile  Val
               20                  25                       30

Thr  Leu  Asn  Ile
               35
```

( 2 ) INFORMATION FOR SEQ ID NO:118:

( i ) SEQUENCE CHARACTERISTICS:
    ( A ) LENGTH: 31 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:118:

Tyr Ala Ile Phe Val Leu Tyr Ala Ser Ala Trp Leu Ala Ser Glu Leu
1               5                   10                  15

Ser Val Tyr Thr Leu Thr Val Pro Phe Ile Val Thr Leu Asn Ile
            20                  25                  30

( 2 ) INFORMATION FOR SEQ ID NO:119:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:119:

Tyr Ala Ile Phe Val Leu Tyr Ala Ser Ala Trp Leu Ser Phe Leu Ala
1               5                   10                  15

Ser Glu Leu Ser Val Tyr Ala Ser Glu Leu Ser Ser Thr Leu Thr Thr
            20                  25                  30

Val Asn Met Pro Phe Ile Val Thr Leu Asn Ile
            35                  40

( 2 ) INFORMATION FOR SEQ ID NO:120:

( i ) SEQUENCE CHARACTERISTICS:
( A ) LENGTH: 34 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:120:

Tyr Ala Ile Phe Val Leu Tyr Ala Ser Ala Trp Leu Ser Phe Leu Asn
1               5                   10                  15

Gly Gly Glu Ile Ala Leu Trp Ser Leu Cys Pro Phe Ile Val Thr Leu
            20                  25                  30

Asn Ile ( 2 ) INFORMATION FOR SEQ ID NO:121:

( i ) SEQUENCE CHARACTERISTICS:
( A ) LENGTH: 31 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:121:

Tyr Ala Ile Phe Val Leu Tyr Ala Ser Ala Trp Leu Ser Phe Leu Asn
1               5                   10                  15

Gly Gly Glu Ile Ala Leu Trp Ser Leu Ile Val Thr Leu Asn Ile
            20                  25                  30

( 2 ) INFORMATION FOR SEQ ID NO:122:

( i ) SEQUENCE CHARACTERISTICS:
( A ) LENGTH: 31 amino acids
( B ) TYPE: amino acid
( C ) STRANDEDNESS: single (D) TOPOLOGY: linear (ii) MOLECULE TYPE: peptide (xi) SEQUENCE DESCRIPTION: SEQ ID NO:122:

```
Tyr Ala Ile Phe Val Leu Tyr Ala Ser Ala Trp Leu Gly Gly Glu Ile
1               5                   10                  15
Ala Leu Trp Ser Leu Asn Cys Pro Phe Ile Val Thr Leu Asn Ile
                20              25                  30
```

(2) INFORMATION FOR SEQ ID NO:123:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:123:

```
Tyr Ala Ile Phe Val Leu Tyr Ala Gly Gly Glu Ile Ala Leu Trp Ser
1               5                   10                  15
Leu Ser Phe Leu Asn Cys Pro Phe Ile Val Thr Leu Asn Ile
                20              25                  30
```

(2) INFORMATION FOR SEQ ID NO:124:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:124:

```
Tyr Ala Ile Phe Val Leu Tyr Ala Ser Ala Trp Leu Ser Phe Phe Phe
1               5                   10                  15
Leu Leu Phe Gly Tyr Leu Gly Asn Phe Leu Leu Asn Cys Pro Phe Ile
                20              25                  30
Val Thr Leu Asn Ile
            35
```

(2) INFORMATION FOR SEQ ID NO:125:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:125:

```
Tyr Ala Ile Phe Val Leu Tyr Ala Ser Ala Trp Leu Phe Phe Phe Leu
1               5                   10                  15
Leu Phe Gly Tyr Leu Gly Asn Phe Leu Leu Pro Phe Ile Val Thr Leu
                20              25                  30
Asn Ile
```

(2) INFORMATION FOR SEQ ID NO:126:

(i) SEQUENCE CHARACTERISTICS:
        (A) LENGTH: 45 amino acids
        (B) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:126:

| Tyr | Ala | Ile | Phe | Val | Leu | Tyr | Ala | Ser | Ala | Trp | Leu | Ser | Phe | Leu | Asn |
|---|---|---|---|---|---|---|---|---|---|---|---|---|---|---|---|
| 1 | | | | 5 | | | | | 10 | | | | | 15 | |

| Thr | Ala | Cys | Phe | Tyr | Val | Ala | Ile | Thr | Ala | Ser | Leu | Cys | Phe | Ile | Thr |
|---|---|---|---|---|---|---|---|---|---|---|---|---|---|---|---|
| | | | 20 | | | | | 25 | | | | | 30 | | |

| Glu | Ile | Ala | Leu | Ile | Pro | Phe | Ile | Val | Thr | Leu | Asn | Ile |
|---|---|---|---|---|---|---|---|---|---|---|---|---|
| | | | 35 | | | | 40 | | | | | 45 |

( 2 ) INFORMATION FOR SEQ ID NO:127:

( i ) SEQUENCE CHARACTERISTICS:
( A ) LENGTH: 42 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:127:

| Tyr | Ala | Ile | Phe | Val | Leu | Tyr | Ala | Ser | Ala | Trp | Leu | Thr | Ala | Cys | Phe |
|---|---|---|---|---|---|---|---|---|---|---|---|---|---|---|---|
| 1 | | | | 5 | | | | | 10 | | | | | 15 | |

| Tyr | Val | Ala | Ile | Thr | Ala | Ser | Leu | Cys | Phe | Ile | Thr | Glu | Ile | Ala | Leu |
|---|---|---|---|---|---|---|---|---|---|---|---|---|---|---|---|
| | | | 20 | | | | | 25 | | | | | 30 | | |

| Ile | Cys | Pro | Phe | Ile | Val | Thr | Leu | Asn | Ile |
|---|---|---|---|---|---|---|---|---|---|
| | | | 35 | | | | 40 | | |

( 2 ) INFORMATION FOR SEQ ID NO:128:

( i ) SEQUENCE CHARACTERISTICS:
( A ) LENGTH: 42 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:128:

| Tyr | Ala | Ile | Phe | Val | Leu | Tyr | Ala | Thr | Ala | Cys | Phe | Tyr | Val | Ala | Ile |
|---|---|---|---|---|---|---|---|---|---|---|---|---|---|---|---|
| 1 | | | | 5 | | | | | 10 | | | | | 15 | |

| Thr | Ala | Ser | Leu | Cys | Phe | Ile | Thr | Glu | Ile | Ala | Leu | Ile | Ser | Phe | Leu |
|---|---|---|---|---|---|---|---|---|---|---|---|---|---|---|---|
| | | | 20 | | | | | 25 | | | | | 30 | | |

| Asn | Cys | Pro | Phe | Ile | Val | Thr | Leu | Asn | Ile |
|---|---|---|---|---|---|---|---|---|---|
| | | | 35 | | | | 40 | | |

( 2 ) INFORMATION FOR SEQ ID NO:129:

( i ) SEQUENCE CHARACTERISTICS:
( A ) LENGTH: 42 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:129:

| Tyr | Ala | Ile | Thr | Ala | Cys | Phe | Tyr | Val | Ala | Ile | Thr | Ala | Ser | Leu | Cys |
|---|---|---|---|---|---|---|---|---|---|---|---|---|---|---|---|
| 1 | | | | 5 | | | | | 10 | | | | | 15 | |

| Phe | Ile | Thr | Glu | Ile | Ala | Leu | Ile | Ala | Ser | Ala | Trp | Leu | Ser | Phe | Leu |
|---|---|---|---|---|---|---|---|---|---|---|---|---|---|---|---|
| | | | 20 | | | | | 25 | | | | | 30 | | |

| Asn | Cys | Pro | Phe | Ile | Val | Thr | Leu | Asn | Ile |
|---|---|---|---|---|---|---|---|---|---|

(2) INFORMATION FOR SEQ ID NO:130:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:130:

```
Tyr Ala Ile Phe Val Leu Tyr Ala Thr Ala Cys Phe Tyr Val Ala Ile
  1               5                  10                  15
Ile Thr Glu Ile Ala Leu Ile Ser Ala Trp Leu Ser Phe Leu Asn Cys
              20                  25                  30
Pro Phe Ile Val Thr Leu Asn Ile
              35              40
```

(2) INFORMATION FOR SEQ ID NO:131:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:131:

```
Tyr Ala Ile Phe Val Leu Tyr Ala Ser Ala Trp Leu Ser Phe Leu Asn
  1               5                  10                  15
Ala Cys Phe Tyr Ile Cys Leu Phe Ala Gly Val Cys Phe Leu Ile Pro
              20                  25                  30
Phe Ile Val Thr Leu Asn Ile
              35
```

(2) INFORMATION FOR SEQ ID NO:132:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:132:

```
Tyr Ala Ile Phe Val Leu Tyr Ala Ser Ala Trp Asn Ala Cys Phe Tyr
  1               5                  10                  15
Ile Cys Leu Phe Ala Gly Val Met Phe Leu Ile Leu Ser Phe Leu Asn
              20                  25                  30
Cys Pro Phe Ile Val Thr Leu Asn Ile
              35                  40
```

(2) INFORMATION FOR SEQ ID NO:133:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:133:

```
Tyr Ala Ile Phe Val Leu Tyr Phe Tyr Ile Cys Leu Phe Ala Gly Val
1               5                   10                  15

Cys Phe Leu Ile Ala Ser Ala Trp Leu Ser Phe Leu Asn Cys Pro Phe
                20                  25                  30

Ile Val Thr Leu Asn Ile
            35
```

( 2 ) INFORMATION FOR SEQ ID NO:134:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:134:

```
Tyr Ala Ile Phe Val Leu Tyr Ala Ser Val Asp Ala Val Asn Met Phe
1               5                   10                  15

Thr Ser Ala Trp Leu Ser Phe Leu Asn Cys Pro Phe Ile Val Thr Leu
                20                  25                  30

Asn Ile
```

( 2 ) INFORMATION FOR SEQ ID NO:135:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:135:

```
Tyr Ala Ile Phe Ser Val Asp Ala Val Asn Met Phe Thr Val Leu Tyr
1               5                   10                  15

Ala Ser Ala Trp Leu Ser Phe Leu Asn Cys Pro Phe Ile Val Thr Leu
                20                  25                  30

Asn Ile
```

( 2 ) INFORMATION FOR SEQ ID NO:136:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:136:

```
Tyr Ala Ile Phe Val Leu Tyr Ala Ser Ala Trp Leu Ser Val Asp Ala
1               5                   10                  15

Val Asn Met Phe Thr Ser Phe Leu Asn Cys Pro Phe Ile Val Thr Leu
                20                  25                  30

Asn Ile
```

( 2 ) INFORMATION FOR SEQ ID NO:137:

( i ) SEQUENCE CHARACTERISTICS:
        ( A ) LENGTH: 33 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:137:

Tyr Ala Ile Phe Val Leu Tyr Ala Ser Ala Trp Leu Ser Phe Leu Asn
1               5                   10                  15

Ser Val Asp Ala Val Asn Met Phe Thr Pro Phe Ile Val Thr Leu Asn
            20                  25                  30

Ile (2) INFORMATION FOR SEQ ID NO:138:

(i) SEQUENCE CHARACTERISTICS:
    (A) LENGTH: 34 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:138:

Tyr Ala Ile Phe Val Leu Tyr Ala Ser Ala Trp Leu Ser Phe Leu Asn
1               5                   10                  15

Cys Pro Phe Ile Val Ser Val Asp Ala Val Asn Met Phe Thr Thr Leu
            20                  25                  30

Asn Ile (2) INFORMATION FOR SEQ ID NO:139:

(i) SEQUENCE CHARACTERISTICS:
    (A) LENGTH: 31 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:139:

Tyr Ala Ile Phe Val Leu Tyr Ala Ser Ala Trp Leu Ser Val Asp Met
1               5                   10                  15

Phe Thr Ser Phe Leu Asn Cys Pro Phe Ile Val Thr Leu Asn Ile
            20                  25                  30

(2) INFORMATION FOR SEQ ID NO:140:

(i) SEQUENCE CHARACTERISTICS:
    (A) LENGTH: 34 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:140:

Tyr Ala Ile Ser Val Asp Ala Val Asn Met Phe Thr Phe Val Leu Tyr
1               5                   10                  15

Ala Ser Ala Trp Leu Ser Phe Leu Asn Cys Pro Phe Ile Val Thr Leu
            20                  25                  30

Asn Ile (2) INFORMATION FOR SEQ ID NO:141:

(i) SEQUENCE CHARACTERISTICS:
    (A) LENGTH: 35 amino acids ( B ) TYPE: amino acid
                    ( C ) STRANDEDNESS: single
                    ( D ) TOPOLOGY: linear ( i i ) MOLECULE TYPE: peptide ( x i ) SEQUENCE DESCRIPTION: SEQ ID NO:141:

```
Tyr  Ala  Ile  Phe  Ser  Leu  Ser  Val  Phe  Ser  Leu  Leu  Ala  Ile  Val  Leu
1                   5                        10                       15
Tyr  Ala  Ser  Ala  Trp  Leu  Ser  Phe  Leu  Asn  Cys  Pro  Phe  Ile  Val  Thr
               20                       25                       30
Leu  Asn  Ile
          35
```

( 2 ) INFORMATION FOR SEQ ID NO:142:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:142:

```
Tyr  Ala  Ile  Phe  Val  Leu  Tyr  Ala  Ser  Leu  Ser  Val  Phe  Ser  Leu  Leu
1                   5                        10                       15
Ala  Ile  Ser  Ala  Trp  Leu  Ser  Phe  Leu  Asn  Cys  Pro  Phe  Ile  Val  Thr
               20                       25                       30
Leu  Asn  Ile
          35
```

( 2 ) INFORMATION FOR SEQ ID NO:143:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:143:

```
Tyr  Ala  Ile  Phe  Val  Leu  Tyr  Ala  Ser  Ala  Trp  Leu  Ser  Leu  Ser  Val
1                   5                        10                       15
Phe  Ser  Leu  Leu  Ala  Ile  Ser  Phe  Leu  Asn  Cys  Pro  Phe  Ile  Val  Thr
               20                       25                       30
Leu  Asn  Ile
          35
```

( 2 ) INFORMATION FOR SEQ ID NO:144:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:144:

```
Tyr  Ala  Ile  Phe  Val  Leu  Tyr  Ala  Ser  Ala  Trp  Leu  Ser  Phe  Leu  Ser
1                   5                        10                       15
Leu  Ser  Val  Phe  Ser  Leu  Leu  Ala  Ile  Asn  Cys  Pro  Phe  Ile  Val  Thr
               20                       25                       30
```

Leu Asn Ile
           35

( 2 ) INFORMATION FOR SEQ ID NO:145:

( i ) SEQUENCE CHARACTERISTICS:
            ( A ) LENGTH: 34 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:145:

Tyr Ala Ile Phe Val Leu Tyr Ala Ser Ala Trp Leu Ser Phe Leu Asn
1               5                   10                  15

Pro Phe Ser Leu Ser Val Phe Ser Leu Leu Ala Ile Ile Val Thr Leu
                20              25                      30

Asn Ile ( 2 ) INFORMATION FOR SEQ ID NO:146:

( i ) SEQUENCE CHARACTERISTICS:
            ( A ) LENGTH: 30 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:146:

Tyr Ala Ile Phe Val Leu Tyr Ala Thr Ala Trp Leu Thr Phe Leu Asn
1               5                   10                  15

Cys Val Thr Ala Thr Ile Pro Phe Ile Val Thr Leu Asn Ile
                20              25                  30

( 2 ) INFORMATION FOR SEQ ID NO:147:

( i ) SEQUENCE CHARACTERISTICS:
            ( A ) LENGTH: 32 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:147:

Tyr Ala Ile Phe Val Leu Tyr Ala Thr Ala Trp Leu Ser Phe Leu Asn
1               5                   10                  15

Cys Thr Ser Ser Ile Val Val Thr Ala Thr Ile Val Thr Leu Asn Ile
                20              25                      30

( 2 ) INFORMATION FOR SEQ ID NO:148:

( i ) SEQUENCE CHARACTERISTICS:
            ( A ) LENGTH: 27 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:148:

Tyr Ala Ile Phe Val Leu Tyr Ala Thr Ala Trp Leu Ser Phe Leu Asn
1               5                   10                  15

Val Thr Leu Asn Ile Cys Thr Thr Thr Ile Val
                20              25

(2) INFORMATION FOR SEQ ID NO:149:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:149:

```
Tyr Ala Ile Phe Val Leu Tyr Ala Thr Ala Trp Leu Thr Phe Leu Asn
 1               5                  10                  15
Thr Ala Thr Ile Leu Asn Leu Met Phe Ile Val Thr Leu Asn Ile
            20                  25                  30
```

(2) INFORMATION FOR SEQ ID NO:150:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:150:

```
Tyr Ala Ile Phe Val Leu Tyr Ala Thr Ala Trp Leu Ser Phe Leu Asn
 1               5                  10                  15
Met Ala Thr Ile Leu Asn Leu Pro Phe Ile Val Thr Leu Asn Ile
            20                  25                  30
```

(2) INFORMATION FOR SEQ ID NO:151:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:151:

```
Tyr Ala Ile Phe Val Leu Tyr Ala Thr Ala Trp Leu Thr Phe Leu Asn
 1               5                  10                  15
Ser Gly Ile Leu Leu Leu Ala Pro Phe Ile Val Thr Leu Asn Ile
            20                  25                  30
```

(2) INFORMATION FOR SEQ ID NO:152:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:152:

```
Tyr Ala Ile Phe Val Leu Tyr Ala Ser Ala Trp Leu Thr Phe Leu Asn
 1               5                  10                  15
Met Thr Gly Ile Leu Leu Leu Ala Pro Phe Ile Val Thr Leu Asn Ile
            20                  25                  30
```

(2) INFORMATION FOR SEQ ID NO:153:

( i ) SEQUENCE CHARACTERISTICS:
  ( A ) LENGTH: 35 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:153:

```
Tyr Ala Ile Phe Val Leu Tyr Ala Ser Ala Trp Leu Thr Phe Leu Asn
1               5                   10                  15
Thr Glu Leu Thr Val Tyr Thr Leu Thr Val Cys Pro Phe Ile Val Thr
                20                  25                  30
Leu Asn Ile
        35
```

( 2 ) INFORMATION FOR SEQ ID NO:154:

( i ) SEQUENCE CHARACTERISTICS:
    ( A ) LENGTH: 35 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:154:

```
Tyr Ala Ile Phe Val Leu Tyr Ala Ser Ala Trp Leu Thr Phe Leu Asn
1               5                   10                  15
Met Thr Glu Leu Thr Val Tyr Thr Leu Thr Val Pro Phe Ile Val Thr
                20                  25                  30
Leu Asn Ile
        35
```

( 2 ) INFORMATION FOR SEQ ID NO:155:

( i ) SEQUENCE CHARACTERISTICS:
    ( A ) LENGTH: 36 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:155:

```
Tyr Ala Ile Phe Val Leu Tyr Ala Thr Ala Trp Leu Ala Thr Glu Leu
1               5                   10                  15
Thr Val Tyr Thr Leu Thr Val Thr Phe Leu Asn Cys Pro Phe Ile Val
                20                  25                  30
Thr Leu Asn Ile
            35
```

( 2 ) INFORMATION FOR SEQ ID NO:156:

( i ) SEQUENCE CHARACTERISTICS:
    ( A ) LENGTH: 31 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:156:

```
Tyr Ala Ile Phe Val Leu Tyr Ala Ser Ala Trp Leu Ala Thr Glu Leu
1               5                   10                  15
Ser Val Tyr Thr Leu Thr Val Pro Phe Ile Val Thr Leu Asn Ile
```

(2) INFORMATION FOR SEQ ID NO:157:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:157:

```
Tyr Ala Ile Phe Val Leu Tyr Ala Thr Ala Trp Leu Ser Phe Leu Ala
  1               5                  10                  15
Thr Glu Leu Ser Val Tyr Ala Ser Glu Leu Ser Thr Thr Leu Thr Thr
                 20                  25                  30
Val Asn Met Pro Phe Ile Val Thr Leu Asn Ile
             35                  40
```

(2) INFORMATION FOR SEQ ID NO:158:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:158:

```
Tyr Ala Ile Phe Val Leu Tyr Ala Thr Ala Trp Leu Ser Phe Leu Asn
  1               5                  10                  15
Gly Gly Glu Ile Ala Leu Trp Thr Leu Cys Pro Phe Ile Val Thr Leu
                 20                  25                  30
Asn Ile
```

(2) INFORMATION FOR SEQ ID NO:159:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:159:

```
Tyr Ala Ile Phe Val Leu Tyr Ala Ser Ala Trp Leu Thr Phe Leu Asn
  1               5                  10                  15
Gly Gly Glu Ile Ala Leu Trp Thr Leu Ile Val Thr Leu Asn Ile
                 20                  25                  30
```

(2) INFORMATION FOR SEQ ID NO:160:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:160:

```
Tyr Ala Ile Phe Val Leu Tyr Ala Ser Ala Trp Leu Gly Gly Glu Ile
  1               5                  10                  15
```

```
         Ala  Leu  Trp  Thr  Leu  Asn  Cys  Pro  Phe  Ile  Val  Thr  Leu  Asn  Ile
                   20                       25                       30
```

( 2 ) INFORMATION FOR SEQ ID NO:161:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:161:

```
    Tyr  Ala  Ile  Phe  Val  Leu  Tyr  Ala  Gly  Gly  Glu  Ile  Ala  Leu  Trp  Thr
    1                   5                        10                       15

Leu  Ser  Phe  Leu  Asn  Cys  Pro  Phe  Ile  Val  Thr  Leu  Asn  Ile
                   20                       25                       30
```

( 2 ) INFORMATION FOR SEQ ID NO:162:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:162:

```
    Tyr  Ala  Ile  Phe  Val  Leu  Tyr  Ala  Thr  Ala  Trp  Leu  Ser  Phe  Phe  Phe
    1                   5                        10                       15

Leu  Leu  Phe  Gly  Tyr  Leu  Gly  Asn  Phe  Leu  Leu  Asn  Cys  Pro  Phe  Ile
                   20                       25                       30

Val  Thr  Leu  Asn  Ile
                   35
```

( 2 ) INFORMATION FOR SEQ ID NO:163:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:163:

```
    Tyr  Ala  Ile  Phe  Val  Leu  Tyr  Ala  Thr  Ala  Trp  Leu  Phe  Phe  Phe  Leu
    1                   5                        10                       15

Leu  Phe  Gly  Tyr  Leu  Gly  Asn  Phe  Leu  Leu  Pro  Phe  Ile  Val  Thr  Leu
                   20                       25                       30

Asn  Ile
```

( 2 ) INFORMATION FOR SEQ ID NO:164:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:164:

```
    Tyr  Ala  Ile  Phe  Val  Leu  Tyr  Ala  Thr  Ala  Trp  Leu  Thr  Phe  Leu  Asn
    1                   5                        10                       15
```

```
    Thr Ala Cys Phe Tyr Val Ala Ile Thr Ala Ser Leu Cys Phe Ile Thr
                 20                  25                  30

Glu Ile Ala Leu Ile Pro Phe Ile Val Thr Leu Asn Ile
                 35                  40                  45
```

( 2 ) INFORMATION FOR SEQ ID NO:165:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:165:

```
    Tyr Ala Ile Phe Val Leu Tyr Ala Thr Ala Trp Leu Thr Ala Cys Phe
    1                5                  10                  15

Tyr Val Ala Ile Thr Ala Thr Leu Cys Phe Ile Thr Glu Ile Ala Leu
                 20                  25                  30

Ile Cys Pro Phe Ile Val Thr Leu Asn Ile
                 35                  40
```

( 2 ) INFORMATION FOR SEQ ID NO:166:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:166:

```
    Tyr Ala Ile Phe Val Leu Tyr Ala Thr Ala Cys Phe Tyr Val Ala Ile
    1                5                  10                  15

Thr Ala Thr Leu Cys Phe Ile Thr Glu Ile Ala Leu Ile Ser Phe Leu
                 20                  25                  30

Asn Cys Pro Phe Ile Val Thr Leu Asn Ile
                 35                  40
```

( 2 ) INFORMATION FOR SEQ ID NO:167:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:167:

```
    Tyr Ala Ile Thr Ala Cys Phe Tyr Val Ala Ile Thr Ala Ser Leu Cys
    1                5                  10                  15

Phe Ile Thr Glu Ile Ala Leu Ile Ala Thr Ala Trp Leu Thr Phe Leu
                 20                  25                  30

Asn Cys Pro Phe Ile Val Thr Leu Asn Ile
                 35                  40
```

( 2 ) INFORMATION FOR SEQ ID NO:168:

( i ) SEQUENCE CHARACTERISTICS:
        ( A ) LENGTH: 40 amino acids
        ( B ) TYPE: amino acid
        ( C ) STRANDEDNESS: single ( D ) TOPOLOGY: linear ( i i ) MOLECULE TYPE: peptide ( x i ) SEQUENCE DESCRIPTION: SEQ ID NO:168:

```
Tyr Ala Ile Phe Val Leu Tyr Ala Thr Ala Cys Phe Tyr Val Ala Ile
 1               5                  10                      15

Ile Thr Glu Ile Ala Leu Ile Thr Ala Trp Leu Thr Phe Leu Asn Cys
            20                  25                  30

Pro Phe Ile Val Thr Leu Asn Ile
         35              40
```

( 2 ) INFORMATION FOR SEQ ID NO:169:

( i ) SEQUENCE CHARACTERISTICS:
        ( A ) LENGTH: 39 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:169:

```
Tyr Ala Ile Phe Val Leu Tyr Ala Ser Ala Trp Leu Thr Phe Leu Asn
 1               5                  10                      15

Ala Cys Phe Tyr Ile Cys Leu Phe Ala Gly Val Cys Phe Leu Ile Pro
            20                  25                  30

Phe Ile Val Thr Leu Asn Ile
         35
```

( 2 ) INFORMATION FOR SEQ ID NO:170:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:170:

```
Tyr Ala Ile Phe Val Leu Tyr Ala Ser Ala Trp Asn Ala Cys Phe Tyr
 1               5                  10                      15

Ile Cys Leu Phe Ala Gly Val Met Phe Leu Ile Leu Thr Phe Leu Asn
            20                  25                  30

Cys Pro Phe Ile Val Thr Leu Asn Ile
         35              40
```

( 2 ) INFORMATION FOR SEQ ID NO:171:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:171:

```
Tyr Ala Ile Phe Val Leu Tyr Phe Tyr Ile Cys Leu Phe Ala Gly Val
 1               5                  10                      15

Cys Phe Leu Ile Ala Thr Ala Trp Leu Thr Phe Leu Asn Cys Pro Phe
            20                  25                  30

Ile Val Thr Leu Asn Ile
         35
```

( 2 ) INFORMATION FOR SEQ ID NO:172:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:172:

```
Tyr Ala Ile Phe Val Leu Tyr Ala Thr Val Asp Ala Val Asn Met Phe
1               5                   10                  15
Thr Thr Ala Trp Leu Thr Phe Leu Asn Cys Pro Phe Ile Val Thr Leu
            20                  25                  30
Asn Ile
```

( 2 ) INFORMATION FOR SEQ ID NO:173:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:173:

```
Tyr Ala Ile Phe Thr Val Asp Ala Val Asn Met Phe Thr Val Leu Tyr
1               5                   10                  15
Ala Thr Ala Trp Leu Thr Phe Leu Asn Cys Pro Phe Ile Val Thr Leu
            20                  25                  30
Asn Ile
```

( 2 ) INFORMATION FOR SEQ ID NO:174:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:174:

```
Tyr Ala Ile Phe Val Leu Tyr Ala Thr Ala Trp Leu Thr Val Asp Ala
1               5                   10                  15
Val Asn Met Phe Thr Ser Phe Leu Asn Cys Pro Phe Ile Val Thr Leu
            20                  25                  30
Asn Ile
```

( 2 ) INFORMATION FOR SEQ ID NO:175:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:175:

```
Tyr Ala Ile Phe Val Leu Tyr Ala Thr Ala Trp Leu Ser Phe Leu Asn
1               5                   10                  15
```

```
Thr  Val  Asp  Ala  Val  Asn  Met  Phe  Thr  Pro  Phe  Ile  Val  Thr  Leu  Asn
          20                      25                          30

Ile
```

(2) INFORMATION FOR SEQ ID NO:176:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:176:

```
Tyr  Ala  Ile  Phe  Val  Leu  Tyr  Ala  Ser  Ala  Trp  Leu  Thr  Phe  Leu  Asn
1                     5                          10                          15

Cys  Pro  Phe  Ile  Val  Ser  Val  Asp  Ala  Val  Asn  Met  Phe  Thr  Thr  Leu
               20                         25                          30

Asn  Ile
```

(2) INFORMATION FOR SEQ ID NO:177:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:177:

```
Tyr  Ala  Ile  Phe  Val  Leu  Tyr  Ala  Thr  Ala  Trp  Leu  Ser  Val  Asp  Met
1                     5                          10                          15

Phe  Thr  Thr  Phe  Leu  Asn  Cys  Pro  Phe  Ile  Val  Thr  Leu  Asn  Ile
               20                         25                          30
```

(2) INFORMATION FOR SEQ ID NO:178:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:178:

```
Tyr  Ala  Ile  Ser  Val  Asp  Ala  Val  Asn  Met  Phe  Thr  Phe  Val  Leu  Tyr
1                     5                          10                          15

Ala  Thr  Ala  Trp  Leu  Ser  Phe  Leu  Asn  Cys  Pro  Phe  Ile  Val  Thr  Leu
               20                         25                          30

Asn  Ile
```

(2) INFORMATION FOR SEQ ID NO:179:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:179:

```
Tyr  Ala  Ile  Phe  Val  Leu  Tyr  Ala  Ser  Leu  Thr  Val  Phe  Ser  Leu  Leu
```

```
              1               5                    10                       15
      Ala Ile Ser Ala Trp Leu Thr Phe Leu Asn Cys Pro Phe Ile Val Thr
                      20                    25                  30

Leu Asn Ile
              35
```

( 2 ) INFORMATION FOR SEQ ID NO:180:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:180:

```
      Tyr Ala Ile Phe Val Leu Tyr Ala Ser Ala Trp Leu Thr Leu Ser Val
      1               5                   10                      15

Phe Thr Leu Leu Ala Ile Ser Phe Leu Asn Cys Pro Phe Ile Val Thr
                      20                  25                  30

Leu Asn Ile
              35
```

( 2 ) INFORMATION FOR SEQ ID NO:181:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:181:

```
      Tyr Ala Ile Phe Val Leu Tyr Ala Ser Ala Trp Leu Thr Phe Leu Ser
      1               5                   10                      15

Leu Ser Val Phe Thr Leu Leu Ala Ile Asn Cys Pro Phe Ile Val Thr
                      20                  25                  30

Leu Asn Ile
              35
```

( 2 ) INFORMATION FOR SEQ ID NO:182:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:182:

```
      Tyr Ala Ile Phe Val Leu Tyr Ala Ser Ala Trp Leu Thr Phe Leu Asn
      1               5                   10                      15

Pro Phe Ser Leu Ser Val Phe Ser Leu Leu Ala Ile Ile Val Thr Leu
                      20                  25                  30

Asn Ile
```

( 2 ) INFORMATION FOR SEQ ID NO:183:

( i ) SEQUENCE CHARACTERISTICS:
        ( A ) LENGTH: 37 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:183:

```
Tyr Ala Ile Phe Val Leu Tyr Ala Ser Ala Trp Leu Ser Phe Leu Asn
1               5                   10                  15
Leu Gly Gly Val Thr Ala Ser Phe Thr Ala Ser Val Gly Pro Phe Ile
                20                  25                  30
Val Thr Leu Asn Ile
                35
```

(2) INFORMATION FOR SEQ ID NO:184:

(i) SEQUENCE CHARACTERISTICS:
    (A) LENGTH: 34 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:184:

```
Tyr Ala Ile Phe Val Leu Tyr Ala Ser Ala Trp Leu Ser Phe Leu Asn
1               5                   10                  15
Leu Gly Gly Val Thr Ala Ser Phe Thr Ala Ser Val Gly Val Thr Leu
                20                  25                  30
Asn Ile
```

(2) INFORMATION FOR SEQ ID NO:185:

(i) SEQUENCE CHARACTERISTICS:
    (A) LENGTH: 38 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:185:

```
Tyr Ala Ile Phe Val Leu Leu Gly Gly Val Thr Ala Ser Phe Thr Ala
1               5                   10                  15
Ser Val Asn Tyr Ala Ser Ala Trp Leu Ser Phe Leu Asn Cys Pro Phe
                20                  25                  30
Ile Val Thr Leu Asn Ile
                35
```

(2) INFORMATION FOR SEQ ID NO:186:

(i) SEQUENCE CHARACTERISTICS:
    (A) LENGTH: 32 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:186:

```
Tyr Ala Ile Phe Val Leu Tyr Ala Ile Phe Phe Phe Leu Leu Phe Ser
1               5                   10                  15
Ala Trp Leu Ser Phe Leu Asn Cys Pro Phe Ile Val Thr Leu Asn Ile
                20                  25                  30
```

(2) INFORMATION FOR SEQ ID NO:187:

( i ) SEQUENCE CHARACTERISTICS:
 ( A ) LENGTH: 38 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:187:

Tyr Ala Ile Phe Val Leu Tyr Ala Ser Ala Trp Leu Ser Phe Leu Asn
1               5                   10                  15

Cys Pro Phe Ile Val Thr Leu Asn Ile Ile Phe Phe Phe Leu Leu Phe
            20                  25                  30

Ile Val Thr Leu Asn Ile
            35

( 2 ) INFORMATION FOR SEQ ID NO:188:

( i ) SEQUENCE CHARACTERISTICS:
  ( A ) LENGTH: 32 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:188:

Tyr Ala Ile Phe Val Leu Tyr Ala Ser Ala Trp Ile Phe Phe Phe Leu
1               5                   10                  15

Leu Phe Leu Ser Phe Leu Asn Cys Pro Phe Ile Val Thr Leu Asn Ile
            20                  25                  30

( 2 ) INFORMATION FOR SEQ ID NO:189:

( i ) SEQUENCE CHARACTERISTICS:
  ( A ) LENGTH: 41 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:189:

Tyr Ala Ile Phe Val Leu Tyr Ala Ser Ala Trp Leu Phe Phe Thr Val
1               5                   10                  15

Leu Ala Ser Glu Leu Ser Val Tyr Thr Leu Thr Val Ser Phe Leu Asn
            20                  25                  30

Cys Pro Phe Ile Val Thr Leu Asn Ile
            35                  40

( 2 ) INFORMATION FOR SEQ ID NO:190:

( i ) SEQUENCE CHARACTERISTICS:
  ( A ) LENGTH: 34 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:190:

Tyr Ala Ile Phe Val Leu Tyr Ala Ser Ala Trp Leu Ser Phe Leu Phe
1               5                   10                  15

Ala Thr Leu Gly Gly Glu Ile Ala Leu Cys Pro Phe Ile Val Thr Leu
            20                  25                  30

Asn Ile ( 2 ) INFORMATION FOR SEQ ID NO:191:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:191:

```
Tyr Ala Ile Phe Val Leu Tyr Ala Phe Ala Thr Leu Gly Gly Glu Ile
1               5                   10                  15
Ala Leu Ser Ala Trp Leu Ser Phe Leu Asn Cys Pro Phe Ile Val Thr
            20                  25                  30
Leu Asn Ile
        35
```

( 2 ) INFORMATION FOR SEQ ID NO:192:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:192:

```
Tyr Ala Ile Phe Phe Thr Val Leu Ala Ser Glu Leu Ser Val Tyr Thr
1               5                   10                  15
Leu Thr Val Tyr Ala Ser Ala Trp Leu Ser Phe Leu Asn Cys Pro Phe
            20                  25                  30
Ile Val Thr Leu Asn Ile
        35
```

( 2 ) INFORMATION FOR SEQ ID NO:193:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:193:

```
Tyr Ala Ile Phe Phe Pro Ile Ala Ala Leu Phe Ala Ser Ile Ala Ser
1               5                   10                  15
Ala Trp Leu Ser Phe Leu Asn Cys Pro Phe Ile Val Thr Leu Asn Ile
            20                  25                  30
```

( 2 ) INFORMATION FOR SEQ ID NO:194:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:194:

```
Tyr Ala Ile Phe Val Leu Tyr Ala Ser Ala Trp Leu Ser Phe Phe Pro
1               5                   10                  15
```

```
          Ile  Ala  Ala  Leu  Phe  Ala  Ser  Ile  Pro  Phe  Ile  Val  Thr  Leu  Asn  Ile
                         20                           25                       30
```

(2) INFORMATION FOR SEQ ID NO:195:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:195:

```
   Tyr  Ala  Ile  Phe  Val  Leu  Tyr  Ala  Ser  Ala  Trp  Leu  Ser  Phe  Leu  Asn
   1                   5                        10                       15

Cys  Pro  Phe  Phe  Pro  Ile  Ala  Ala  Leu  Phe  Ala  Ser  Ile  Leu  Asn  Ile
                       20                      25                       30
```

(2) INFORMATION FOR SEQ ID NO:196:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:196:

```
   Tyr  Ala  Ile  Phe  Val  Leu  Tyr  Ala  Ser  Ala  Trp  Leu  Ser  Leu  Asp  Val
   1                   5                        10                       15

Leu  Phe  Ser  Thr  Ala  Ser  Ile  Met  His  Leu  Ser  Phe  Leu  Asn  Gly  Gly
                       20                      25                       30

Glu  Ile  Ala  Leu  Trp  Ser  Leu  Ile  Val  Thr  Leu  Asn  Ile
                       35                      40                       45
```

(2) INFORMATION FOR SEQ ID NO:197:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:197:

```
   Tyr  Ala  Ile  Phe  Val  Leu  Tyr  Ala  Ser  Leu  Asp  Val  Leu  Phe  Ser  Thr
   1                   5                        10                       15

Ala  Ser  Ile  Met  His  Leu  Ile  Ala  Leu  Trp  Ser  Leu  Asn  Cys  Pro  Phe
                       20                      25                       30

Ile  Val  Thr  Leu  Asn  Ile
                       35
```

(2) INFORMATION FOR SEQ ID NO:198:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:198:

```
   Tyr  Ala  Ile  Phe  Val  Leu  Tyr  Ala  Gly  Gly  Glu  Ile  Ala  Leu  Trp  Ser
```

|   | 1 |   |   | 5 |   |   |   |   | 10 |   |   |   |   | 15 |
|---|---|---|---|---|---|---|---|---|----|---|---|---|---|----|
| Leu | Ser | Phe | Leu | Asn | Ser | Leu | Asp | Val | Leu | Phe | Ser | Thr | Ala | Ser | Ile |
|     |     |     | 20  |     |     |     |     | 25  |     |     |     | 30  |     |     |     |

Met His Leu Pro Phe Ile Val Thr Leu Asn Ile
          35                 40

( 2 ) INFORMATION FOR SEQ ID NO:199:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:199:

Tyr Ala Ile Phe Val Leu Tyr Ala Ser Ala Trp Leu Ser Phe Phe Asp
1                 5                   10                  15

Val Leu Phe Ser Thr Ala Ser Ile Met His Leu Phe Gly Tyr Leu Gly
                20                  25                  30

Asn Phe Leu Leu Asn Cys Pro Phe Ile Val Thr Leu Asn Ile
                35                  40                  45

( 2 ) INFORMATION FOR SEQ ID NO:200:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:200:

Tyr Ala Ile Phe Val Leu Tyr Ala Ser Ala Trp Leu Phe Phe Phe Leu
1                 5                   10                  15

Leu Phe Gly Tyr Leu Ser Leu Asp Val Leu Phe Ser Thr Ala Ser Ile
                20                  25                  30

Met His Leu Gly Asn Phe Leu Leu Pro Phe Ile Val Thr Leu Asn Ile
                35                  40                  45

( 2 ) INFORMATION FOR SEQ ID NO:201:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:201:

Tyr Ala Ile Phe Val Leu Tyr Ala Ser Ala Trp Leu Ser Phe Leu Asn
1                 5                   10                  15

Thr Ala Cys Phe Tyr Val Ala Ile Thr Ala Ser Leu Ser Leu Met His
                20                  25                  30

Leu Phe Ile Thr Glu Ile Ala Leu Ile Pro Phe Ile Val Thr Leu Asn
                35                  40                  45

Ile ( 2 ) INFORMATION FOR SEQ ID NO:202:

( i ) SEQUENCE CHARACTERISTICS:

(A) LENGTH: 49 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:202:

```
Tyr Ala Ser Leu Asp Val Leu Phe Ser Thr Ala Ile Met His Leu Ser
 1               5                  10                  15

Ala Trp Leu Thr Ala Cys Phe Tyr Val Ala Ile Thr Ala Ser Leu Cys
                20                  25                  30

Phe Ile Thr Glu Ile Ala Leu Ile Cys Pro Phe Ile Val Thr Leu Asn
            35                  40                  45

Ile
```

(2) INFORMATION FOR SEQ ID NO:203:

(i) SEQUENCE CHARACTERISTICS:
    (A) LENGTH: 47 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:203:

```
Tyr Ala Ile Phe Val Leu Tyr Ala Thr Ala Cys Phe Tyr Val Ala Ile
 1               5                  10                  15

Thr Ala Ser Leu Ser Phe Leu Asn Cys Pro Phe Ile Val Thr Leu Asn
                20                  25                  30

Ile Ser Leu Asp Val Leu Phe Ser Thr Ala Ser Ile Met His Leu
            35                  40                  45
```

(2) INFORMATION FOR SEQ ID NO:204:

(i) SEQUENCE CHARACTERISTICS:
    (A) LENGTH: 42 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:204:

```
Tyr Ala Ile Thr Ala Cys Phe Tyr Val Ala Ile Thr Ala Ser Leu Cys
 1               5                  10                  15

Phe Ile Thr Glu Ile Ala Leu Ile Ala Ser Ala Trp Leu Ser Phe Leu
                20                  25                  30

Asn Cys Pro Phe Ile Val Thr Leu Asn Ile
            35                  40
```

(2) INFORMATION FOR SEQ ID NO:205:

(i) SEQUENCE CHARACTERISTICS:
    (A) LENGTH: 48 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:205:

```
Tyr Ala Ile Phe Val Leu Tyr Ala Thr Ala Cys Phe Tyr Ser Thr Ala
 1               5                  10                  15
```

```
Ser  Ile  Leu  Asn  Leu  Ile  Met  His  Leu  Cys  Ala  Ile  Ser  Leu  Val  Ala
               20                  25                       30

Ile  Ile  Thr  Glu  Ile  Ala  Leu  Ile  Ser  Ala  Trp  Leu  Ser  Phe  Leu  Asn
               35                  40                       45
```

( 2 ) INFORMATION FOR SEQ ID NO:206:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:206:

```
Tyr  Ala  Ile  Phe  Val  Leu  Tyr  Ala  Ser  Ala  Trp  Leu  Ser  Phe  Leu  Asn
1                   5                        10                      15

Ala  Cys  Phe  Tyr  Ile  Cys  Leu  Phe  Ala  Ser  Ile  Leu  Asn  Leu  Ile  Met
               20                  25                       30

His  Leu  Gly  Val  Cys  Phe  Leu  Ile  Pro  Phe  Ile  Val  Thr  Leu  Asn  Ile
               35                  40                       45
```

( 2 ) INFORMATION FOR SEQ ID NO:207:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:207:

```
Tyr  Ala  Ile  Phe  Val  Leu  Tyr  Ala  Ser  Ala  Trp  Asn  Ala  Ser  Ile  Leu
1                   5                        10                      15

Asn  Leu  Ile  Met  His  Leu  Cys  Phe  Tyr  Ile  Cys  Leu  Phe  Ala  Gly  Val
               20                  25                       30

Met  Leu  Ile  Leu  Ser  Phe  Leu  Asn  Cys  Pro  Phe  Ile  Val  Thr  Leu  Asn
               35                  40                       45

Ile
```

( 2 ) INFORMATION FOR SEQ ID NO:208:

( i ) SEQUENCE CHARACTERISTICS:
        ( A ) LENGTH: 50 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:208:

```
Tyr  Ala  Ile  Phe  Pro  Phe  Val  Gln  Cys  Val  Val  Ser  Ile  Phe  Ser  Leu
1                   5                        10                      15

Val  Leu  Ile  Ala  Val  Val  Leu  Tyr  Phe  Tyr  Ile  Ala  Gly  Val  Cys  Phe
               20                  25                       30

Leu  Ile  Ala  Ser  Ala  Trp  Leu  Ser  Phe  Leu  Asn  Cys  Pro  Phe  Ile  Val
               35                  40                       45

Thr  Ile
     50
```

( 2 ) INFORMATION FOR SEQ ID NO:209:

( i ) SEQUENCE CHARACTERISTICS:
(A) LENGTH: 49 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:209:

```
Pro Phe Val Gln Cys Val Ser Ile Thr Val Ser Ile Phe Ser Leu Val
 1               5                  10                  15
Leu Ile Ala Val Tyr Ala Ile Phe Val Leu Tyr Ala Ser Val Asp Ala
            20                  25                  30
Val Asn Met Phe Thr Ser Ala Trp Cys Pro Phe Ile Val Thr Leu Asn
        35                  40                  45
Ile
```

( 2 ) INFORMATION FOR SEQ ID NO:210:

( i ) SEQUENCE CHARACTERISTICS:
(A) LENGTH: 38 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:210:

```
Tyr Ala Ile Phe Gly Asp Trp Ser Ser Val Asp Ala Val Asn Met Phe
 1               5                  10                  15
Thr Val Leu Tyr Ala Ser Ala Trp Leu Ser Phe Leu Asn Cys Pro Phe
            20                  25                  30
Ile Val Thr Leu Asn Ile
        35
```

( 2 ) INFORMATION FOR SEQ ID NO:211:

( i ) SEQUENCE CHARACTERISTICS:
(A) LENGTH: 38 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:211:

```
Tyr Ala Ile Phe Val Leu Tyr Ala Gly Asp Trp Ser Ser Ala Trp Leu
 1               5                  10                  15
Ser Val Asp Ala Val Asn Met Phe Thr Ser Phe Leu Asn Cys Pro Phe
            20                  25                  30
Ile Val Thr Leu Asn Ile
        35
```

( 2 ) INFORMATION FOR SEQ ID NO:212:

( i ) SEQUENCE CHARACTERISTICS:
(A) LENGTH: 37 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:212:

```
Tyr Ala Ile Phe Val Leu Tyr Ala Ser Ala Trp Leu Gly Asp Trp Ser
 1               5                  10                  15
```

```
              Ser  Phe  Leu  Asn  Ser  Val  Asp  Ala  Val  Asn  Met  Phe  Thr  Pro  Phe  Ile
                             20                       25                      30

Val  Thr  Leu  Asn  Ile
                             35
```

( 2 ) INFORMATION FOR SEQ ID NO:213:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:213:

```
              Tyr  Ala  Ile  Phe  Val  Leu  Tyr  Ala  Ser  Ala  Trp  Leu  Ser  Phe  Leu  Asn
              1                    5                       10                      15

Cys  Pro  Phe  Ile  Val  Gly  Asp  Trp  Ser  Ser  Val  Asp  Ala  Val  Asn  Met
                             20                       25                      30

Phe  Thr  Thr  Leu  Asn  Ile
                             35
```

( 2 ) INFORMATION FOR SEQ ID NO:214:

( i ) SEQUENCE CHARACTERISTICS:
        ( A ) LENGTH: 39 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:214:

```
              Tyr  Ala  Ile  Phe  Val  Leu  Tyr  Ala  Ser  Ala  Trp  Leu  Gly  Tyr  Leu  Gly
              1                    5                       10                      15

Ser  Val  Asp  Met  Phe  Thr  Ser  Phe  Leu  Asn  Cys  Pro  Phe  Ile  Val  Thr
                             20                       25                      30

Gly  Asp  Trp  Ser  Leu  Asn  Ile
                             35
```

( 2 ) INFORMATION FOR SEQ ID NO:215:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:215:

```
              Tyr  Ala  Ile  Ser  Val  Asp  Ala  Val  Asn  Met  Phe  Thr  Phe  Val  Leu  Tyr
              1                    5                       10                      15

Ala  Gly  Tyr  Leu  Gly  Ser  Ala  Trp  Leu  Ser  Phe  Leu  Asn  Cys  Pro  Phe
                             20                       25                      30

Ile  Val  Thr  Leu  Asn  Ile
                             35
```

( 2 ) INFORMATION FOR SEQ ID NO:216:

( i ) SEQUENCE CHARACTERISTICS:
        ( A ) LENGTH: 39 amino acids
        ( B ) TYPE: amino acid
        ( C ) STRANDEDNESS: single ( D ) TOPOLOGY: linear ( i i ) MOLECULE TYPE: peptide ( x i ) SEQUENCE DESCRIPTION: SEQ ID NO:216:

| Tyr | Ala | Ile | Phe | Ser | Leu | Ser | Val | Phe | Ser | Leu | Leu | Ala | Ile | Val | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Tyr | Ala | Ser | Ala | Trp | Leu | Gly | Tyr | Leu | Gly | Ser | Phe | Leu | Asn | Cys | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Phe | Ile | Val | Thr | Leu | Asn | Ile |
|-----|-----|-----|-----|-----|-----|-----|
|     |     |     | 35  |     |     |     |

( 2 ) INFORMATION FOR SEQ ID NO:217:

( i ) SEQUENCE CHARACTERISTICS:
( A ) LENGTH: 44 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:217:

| Tyr | Ala | Ile | Phe | Val | Leu | Tyr | Ala | Gly | Tyr | Leu | Gly | Ala | Gly | Asn | Met |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Ser | Leu | Ser | Val | Phe | Ser | Leu | Leu | Ala | Ile | Ser | Ala | Trp | Leu | Ser |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Phe | Leu | Asn | Cys | Pro | Phe | Ile | Val | Thr | Leu | Asn | Ile |
|-----|-----|-----|-----|-----|-----|-----|-----|-----|-----|-----|-----|
|     |     |     | 35  |     |     |     |     | 40  |     |     |     |

( 2 ) INFORMATION FOR SEQ ID NO:218:

( i ) SEQUENCE CHARACTERISTICS:
( A ) LENGTH: 38 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:218:

| Tyr | Ala | Ile | Phe | Val | Leu | Tyr | Ala | Ser | Ala | Trp | Leu | Ser | Leu | Ser | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | Gly | Asn | Met | Ser | Leu | Leu | Ala | Ile | Ser | Phe | Leu | Asn | Cys | Pro | Phe |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ile | Val | Thr | Leu | Asn | Ile |
|-----|-----|-----|-----|-----|-----|
|     |     |     | 35  |     |     |

( 2 ) INFORMATION FOR SEQ ID NO:219:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:219:

| Tyr | Ala | Ile | Phe | Val | Leu | Tyr | Ala | Ser | Ala | Trp | Leu | Ser | Phe | Leu | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Ser | Val | Phe | Gly | Gly | Ser | Leu | Leu | Ala | Ile | Asn | Cys | Pro | Phe | Ile |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Val | Thr | Leu | Asn | Ile |
|-----|-----|-----|-----|-----|
|     |     |     | 35  |     |

( 2 ) INFORMATION FOR SEQ ID NO:220:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:220:

```
Tyr Ala Ile Phe Val Leu Tyr Ala Ser Ala Trp Leu Ser Phe Leu Asn
1               5                   10                  15

Pro Phe Ser Leu Ser Val Phe Gly Ser Leu Leu Ala Ile Ile Val Thr
            20              25                  30

Leu Asn Ile
        35
```

( 2 ) INFORMATION FOR SEQ ID NO:221:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:221:

```
Tyr Ala Ile Phe Val Leu Tyr Ala Thr Ala Trp Leu Thr Phe Leu Ser
1               5                   10                  15

Leu Ala Asn Cys Val Thr Ala Thr Ile Pro Phe Ile Val Thr Leu Asn
            20              25                  30

Ile
```

( 2 ) INFORMATION FOR SEQ ID NO:222:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:222:

```
Tyr Ala Ile Phe Val Leu Tyr Ala Thr Ala Trp Leu Ser Phe Leu Asn
1               5                   10                  15

Cys Thr Ser Leu Ala Ser Ser Ile Val Val Thr Ala Thr Ile Val Thr
            20              25                  30

Leu Asn Ile
        35
```

( 2 ) INFORMATION FOR SEQ ID NO:223:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:223:

```
Tyr Ala Ile Phe Val Leu Tyr Ala Thr Ala Trp Leu Ser Phe Leu Asn
```

```
                        1               5                              10                           15

Val  Thr  Leu  Asn  Ile  Ser  Leu  Ala  Cys  Thr  Thr  Thr  Ile  Val
                                 20                         25                        30
```

( 2 ) INFORMATION FOR SEQ ID NO:224:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:224:

```
    Tyr  Ala  Ile  Phe  Val  Leu  Tyr  Ala  Thr  Ala  Trp  Leu  Thr  Phe  Leu  Asn
    1                    5                              10                           15

Thr  Ala  Thr  Ile  Leu  Ser  Leu  Ala  Asn  Leu  Met  Phe  Ile  Val  Thr  Leu
                         20                         25                        30

Asn  Ile
```

( 2 ) INFORMATION FOR SEQ ID NO:225:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:225:

```
    Tyr  Ala  Ile  Phe  Val  Leu  Tyr  Ala  Thr  Ala  Trp  Leu  Ser  Phe  Leu  Asn
    1                    5                              10                           15

Met  Ala  Thr  Ile  Leu  Asn  Leu  Pro  Phe  Ser  Val  Asp  Ala  Val  Ile  Val
                         20                         25                        30

Thr  Leu  Asn  Ile
                    35
```

( 2 ) INFORMATION FOR SEQ ID NO:226:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:226:

```
    Ile  Ser  Thr  Met  Tyr  Thr  Val  Thr  Gly  Arg  Trp  Thr  Leu  Gly  Gln  Val
    1                    5                              10                           15

Val  Cys  Asp  Phe  Trp  Leu  Ser  Ser  Asp  Ile  Thr  Cys  Cys  Thr  Ala  Ser
                         20                         25                        30

Ile  Leu  His  Leu  Cys  Val  Ile  Ala  Leu
                    35                       40
```

( 2 ) INFORMATION FOR SEQ ID NO:227:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:227:

Ile Leu Tyr Gly Tyr Arg Trp Pro Leu Pro Ser Lys Leu Cys Ala Val
1               5                   10                  15

Trp Ile Tyr Leu Asp Val Leu Phe Ser Thr Ala Ser Ile Met His Leu
            20                  25                  30

Cys Ala Ile Ser Leu
            35

( 2 ) INFORMATION FOR SEQ ID NO:228:

( i ) SEQUENCE CHARACTERISTICS:
        ( A ) LENGTH: 39 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:228:

Ile Ile Tyr Ile Val Met Asp Arg Trp Lys Leu Gly Tyr Phe Leu Cys
1               5                   10                  15

Glu Val Trp Leu Ser Val Asp Met Thr Cys Cys Thr Cys Ser Ile Leu
            20                  25                  30

His Leu Cys Val Ile Ala Leu
            35

( 2 ) INFORMATION FOR SEQ ID NO:229:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:229:

Ile Ala Asp Lys Thr Val Arg Val Ala Met Gly Ala Glu Asn Asp Leu
1               5                   10                  15

Gly Tyr Asn Phe Arg Ser Asp Asp Val Cys Gly His Cys Trp Gln Trp
            20                  25                  30

Tyr Cys Ser Leu
            35

( 2 ) INFORMATION FOR SEQ ID NO:230:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:230:

Ile Leu Asn Tyr Trp Pro Phe Gly Leu Ala Leu Cys His Phe Val Asn
1               5                   10                  15

Tyr Ser Gln Ala Val Ser Val Leu Val Ser Ala Tyr Thr Leu Val Ala
            20                  25                  30

Ile Ser Ile
            35

( 2 ) INFORMATION FOR SEQ ID NO:231:

( i ) SEQUENCE CHARACTERISTICS:
 ( A ) LENGTH: 36 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:231:

Ile Leu Gly Arg Trp Glu Phe Gly Ile His Leu Cys Lys Leu Trp Leu
1               5                   10                  15

Thr Cys Asp Val Leu Cys Cys Thr Ser Ser Ile Leu Asn Leu Cys Ala
            20                  25                  30

Ile Ala Leu Asp
        35

( 2 ) INFORMATION FOR SEQ ID NO:232:

( i ) SEQUENCE CHARACTERISTICS:
  ( A ) LENGTH: 35 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:232:

Ile Met Ala Ser Val Met His Arg His Cys Leu Pro Leu Ile Gly Ile
1               5                   10                  15

Cys Leu Ser Ser Glu Arg His Cys Leu Val Ser Ile Phe Val Glu Leu
            20                  25                  30

Gly Ala Leu
        35

( 2 ) INFORMATION FOR SEQ ID NO:233:

( i ) SEQUENCE CHARACTERISTICS:
  ( A ) LENGTH: 35 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:233:

Tyr Ala Ile Phe Val Leu Tyr Ala Ser Ala Trp Leu Ser Phe Leu Asn
1               5                   10                  15

Cys Pro Phe Ile Ser Ile Leu His Leu Cys Val Ile Ala Leu Val Thr
            20                  25                  30

Leu Asn Ile
        35

( 2 ) INFORMATION FOR SEQ ID NO:234:

( i ) SEQUENCE CHARACTERISTICS:
  ( A ) LENGTH: 36 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:234:

Tyr Ala Ile Phe Val Leu Tyr Ala Thr Ala Trp Leu Ser Phe Leu Asn
1               5                   10                  15

```
       Cys  Pro  Phe  Ile  Ser  Ile  Leu  Asn  Leu  Cys  Ala  Ile  Ala  Leu  Asp  Val
                      20                      25                      30

Thr  Leu  Asn  Ile
                      35
```

( 2 ) INFORMATION FOR SEQ ID NO:235:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:235:

```
       Tyr  Ala  Ile  Phe  Val  Leu  Tyr  Ala  Thr  Ala  Trp  Leu  Thr  Phe  Leu  Asn
       1                      5                       10                      15

Cys  Pro  Phe  Ile  Ser  Ile  Phe  Val  Glu  Leu  Gly  Ala  Leu  Val  Thr  Leu
                           20                      25                      30

Asn  Ile
```

( 2 ) INFORMATION FOR SEQ ID NO:236:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:236:

```
       Tyr  Ala  Ile  Phe  Val  Leu  Tyr  Ala  Ser  Ala  Trp  Leu  Thr  Phe  Leu  Asn
       1                      5                       10                      15

Cys  Pro  Phe  Ile  Ser  Ile  Phe  Val  Glu  Leu  Ser  Ile  Met  His  Leu  Cys
                           20                      25                      30

Ala  Ile  Ser  Leu  Gly  Ala  Leu  Val  Thr  Leu  Asn  Ile
                      35                      40
```

( 2 ) INFORMATION FOR SEQ ID NO:237:

( i ) SEQUENCE CHARACTERISTICS:
        ( A ) LENGTH: 52 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:237:

```
       Trp  Ala  Ile  Phe  Val  Leu  Tyr  Ala  Ile  Leu  Gly  Arg  Trp  Glu  Phe  Gly
       1                      5                       10                      15

Ile  His  Leu  Cys  Lys  Leu  Trp  Leu  Thr  Ser  Ala  Trp  Leu  Ser  Ile  Met
                           20                      25                      30

His  Leu  Cys  Ala  Ile  Ser  Leu  Ser  Phe  Leu  Asn  Cys  Pro  Phe  Ile  Val
                      35                      40                      45

Thr  Leu  Asn  Ile
                 50
```

( 2 ) INFORMATION FOR SEQ ID NO:238:

( i ) SEQUENCE CHARACTERISTICS:
        ( A ) LENGTH: 52 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:238:

```
Trp Ala Ile Phe Val Leu Tyr Ala Ile Leu Gly Arg Trp Glu Phe Gly
1               5                   10                  15
Ile His Leu Cys Lys Leu Trp Leu Thr Thr Ala Trp Leu Ser Ile Met
                20                  25                  30
His Leu Cys Ala Ile Ser Leu Ser Phe Leu Asn Cys Pro Phe Ile Val
            35                  40                  45
Thr Leu Asn Ile
        50
```

(2) INFORMATION FOR SEQ ID NO:239:

(i) SEQUENCE CHARACTERISTICS:
(A) LENGTH: 35 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:239:

```
Trp Ala Ile Phe Val Leu Tyr Ala Thr Ala Trp Leu Thr Phe Leu Asn
1               5                   10                  15
Cys Pro Phe Ser Ile Met His Leu Cys Ala Ile Ser Leu Ile Val Thr
                20                  25                  30
Leu Asn Ile
        35
```

(2) INFORMATION FOR SEQ ID NO:240:

(i) SEQUENCE CHARACTERISTICS:
(A) LENGTH: 35 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:240:

```
Trp Ala Ile Phe Val Leu Tyr Ala Ser Ala Trp Leu Thr Phe Leu Asn
1               5                   10                  15
Cys Pro Phe Ile Ser Ile Met His Leu Cys Ala Ile Ser Leu Val Thr
                20                  25                  30
Leu Asn Ile
        35
```

(2) INFORMATION FOR SEQ ID NO:241:

(i) SEQUENCE CHARACTERISTICS:
(A) LENGTH: 35 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:241:

```
Tyr Ala Val Phe Val Leu Tyr Ala Ser Ala Trp Leu Ser Phe Leu Asn
1               5                   10                  15
Met Ser Ile Met His Leu Cys Ala Ile Ser Leu Pro Phe Ile Val Thr
```

Leu Asn Ile
    35

( 2 ) INFORMATION FOR SEQ ID NO:242:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:242:

Tyr Ala Val Phe Val Leu Tyr Ala Thr Ala Trp Leu Ser Phe Leu Asn
1               5                   10                  15

Met Pro Phe Ser Ile Leu Asn Leu Cys Ala Ile Ala Leu Asp Ile Val
                20                  25                  30

Thr Leu Asn Ile
    35

( 2 ) INFORMATION FOR SEQ ID NO:243:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:243:

Tyr Ala Val Phe Val Leu Tyr Ala Thr Ala Trp Leu Ser Ile Leu Asn
1               5                   10                  15

Leu Cys Ala Ile Ala Leu Asp Thr Phe Leu Asn Met Pro Phe Ile Val
                20                  25                  30

Thr Leu Asn Ile
    35

( 2 ) INFORMATION FOR SEQ ID NO:244:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:244:

Tyr Ala Val Phe Val Leu Tyr Ala Ser Ile Leu Asn Leu Cys Ala Ile
1               5                   10                  15

Ala Leu Asp Ser Ala Trp Leu Thr Phe Leu Asn Met Pro Phe Ile Val
                20                  25                  30

Thr Leu Asn Ile
    35

( 2 ) INFORMATION FOR SEQ ID NO:245:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:245:

| Tyr | Ala | Ile | Phe | Val | Leu | Tyr | Ala | Ser | Ala | Trp | Leu | Ser | Phe | Leu | Asn |
|---|---|---|---|---|---|---|---|---|---|---|---|---|---|---|---|
| 1 | | | | 5 | | | | | 10 | | | | | 15 | |

| Cys | Val | Thr | Ala | Ser | Ile | Pro | Phe | Cys | Leu | Val | Ser | Ile | Phe | Val | Glu |
|---|---|---|---|---|---|---|---|---|---|---|---|---|---|---|---|
| | | | 20 | | | | | 25 | | | | | 30 | | |

| Leu | Gly | Ala | Leu | Ile | Val | Thr | Leu | Asn | Ile |
|---|---|---|---|---|---|---|---|---|---|
| | | 35 | | | | | 40 | | |

(2) INFORMATION FOR SEQ ID NO:246:

(i) SEQUENCE CHARACTERISTICS:
        (A) LENGTH: 40 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:246:

| Tyr | Ala | Ile | Phe | Val | Leu | Tyr | Ala | Ser | Ala | Trp | Leu | Ser | Phe | Leu | Asn |
|---|---|---|---|---|---|---|---|---|---|---|---|---|---|---|---|
| 1 | | | | 5 | | | | | 10 | | | | | 15 | |

| Cys | Leu | Val | Ser | Ile | Phe | Val | Glu | Leu | Gly | Ala | Leu | Ile | Val | Val | Thr |
|---|---|---|---|---|---|---|---|---|---|---|---|---|---|---|---|
| | | | 20 | | | | | 25 | | | | | 30 | | |

| Ala | Ser | Ile | Val | Thr | Leu | Asn | Ile |
|---|---|---|---|---|---|---|---|
| | | 35 | | | | | 40 |

(2) INFORMATION FOR SEQ ID NO:247:

(i) SEQUENCE CHARACTERISTICS:
        (A) LENGTH: 34 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:247:

| Tyr | Ala | Ile | Phe | Val | Leu | Tyr | Ala | Ser | Ala | Trp | Leu | Ser | Phe | Leu | Asn |
|---|---|---|---|---|---|---|---|---|---|---|---|---|---|---|---|
| 1 | | | | 5 | | | | | 10 | | | | | 15 | |

| Val | Thr | Leu | Asn | Cys | Leu | Val | Ser | Ile | Phe | Val | Glu | Leu | Gly | Ala | Leu |
|---|---|---|---|---|---|---|---|---|---|---|---|---|---|---|---|
| | | | 20 | | | | | 25 | | | | | 30 | | |

| Ile | Ile |
|---|---|
| | |

(2) INFORMATION FOR SEQ ID NO:248:

(i) SEQUENCE CHARACTERISTICS:
        (A) LENGTH: 43 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:248:

| Tyr | Ala | Ile | Phe | Val | Leu | Tyr | Ala | Ser | Ala | Trp | Leu | Ser | Phe | Leu | Asn |
|---|---|---|---|---|---|---|---|---|---|---|---|---|---|---|---|
| 1 | | | | 5 | | | | | 10 | | | | | 15 | |

| Thr | Ala | Ser | Ile | Leu | Asn | Leu | Met | Phe | Ile | Cys | Leu | Val | Ser | Ile | Phe |
|---|---|---|---|---|---|---|---|---|---|---|---|---|---|---|---|
| | | | 20 | | | | | 25 | | | | | 30 | | |

| Val | Glu | Leu | Gly | Ala | Leu | Val | Thr | Leu | Asn | Ile |
|---|---|---|---|---|---|---|---|---|---|---|
| | | | 35 | | | | | 40 | | |

(2) INFORMATION FOR SEQ ID NO:249:

( i ) SEQUENCE CHARACTERISTICS:
    ( A ) LENGTH: 42 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:249:

Tyr Ala Ile Phe Val Leu Tyr Ala Ser Ala Trp Leu Ser Phe Leu Asn
1               5                   10                  15

Met Ala Ser Ile Leu Asn Leu Pro Phe Cys Leu Val Ser Ile Phe Val
            20                  25                  30

Glu Leu Gly Ala Leu Val Thr Leu Asn Ile
        35                  40

( 2 ) INFORMATION FOR SEQ ID NO:250:

( i ) SEQUENCE CHARACTERISTICS:
    ( A ) LENGTH: 56 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:250:

Tyr Ala Ile Phe Val Leu Tyr Ala Ser Ala Trp Leu Ser Phe Leu Asn
1               5                   10                  15

Ile Leu Gly Arg Trp Glu Phe Gly Ile His Leu Cys Lys Leu Trp Leu
            20                  25                  30

Thr Cys Asp Val Leu Cys Cys Thr Ser Ser Gly Ile Leu Leu Leu Ala
        35                  40                      45

Pro Phe Ile Val Thr Leu Asn Ile
    50                  55

( 2 ) INFORMATION FOR SEQ ID NO:251:

( i ) SEQUENCE CHARACTERISTICS:
    ( A ) LENGTH: 57 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:251:

Tyr Ala Ile Phe Val Leu Tyr Ala Ser Ala Trp Leu Ser Phe Leu Asn
1               5                   10                  15

Met Ile Leu Gly Arg Trp Glu Phe Gly Ile His Leu Cys Lys Leu Trp
            20                  25                  30

Leu Thr Cys Asp Val Leu Cys Cys Thr Ser Ser Gly Ile Leu Leu Leu
        35                  40                      45

Ala Pro Phe Ile Val Thr Leu Asn Ile
    50                  55

( 2 ) INFORMATION FOR SEQ ID NO:252:

( i ) SEQUENCE CHARACTERISTICS:
    ( A ) LENGTH: 60 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:252:

| Tyr | Ala | Ile | Phe | Val | Leu | Tyr | Ala | Ser | Ala | Trp | Leu | Ile | Leu | Gly | Arg |
| 1 | | | | 5 | | | | | 10 | | | | | 15 | |
| Trp | Glu | Phe | Gly | Ile | His | Leu | Cys | Lys | Leu | Trp | Leu | Thr | Cys | Asp | Val |
| | | | 20 | | | | | 25 | | | | | 30 | | |
| Leu | Cys | Cys | Thr | Ser | Ser | Phe | Leu | Asn | Ser | Glu | Leu | Ser | Val | Tyr | Thr |
| | | | 35 | | | | | 40 | | | | | 45 | | |
| Leu | Thr | Val | Cys | Pro | Phe | Ile | Val | Thr | Leu | Asn | Ile | | | | |
| | | 50 | | | | | 55 | | | | 60 | | | | |

( 2 ) INFORMATION FOR SEQ ID NO:253:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:253:

| Tyr | Ala | Ile | Phe | Val | Leu | Tyr | Ala | Ile | Leu | Gly | Arg | Trp | Glu | Phe | Gly |
| 1 | | | | 5 | | | | | 10 | | | | | 15 | |
| Ile | His | Leu | Cys | Lys | Leu | Trp | Leu | Thr | Cys | Asp | Val | Leu | Cys | Cys | Thr |
| | | | 20 | | | | | 25 | | | | | 30 | | |
| Ser | Ser | Ala | Trp | Leu | Ser | Phe | Leu | Asn | Met | Ser | Glu | Leu | Ser | Val | Tyr |
| | | | 35 | | | | | 40 | | | | | 45 | | |
| Thr | Leu | Thr | Val | Pro | Phe | Ile | Val | Thr | Leu | Asn | Ile | | | | |
| | | 50 | | | | | 55 | | | | 60 | | | | |

( 2 ) INFORMATION FOR SEQ ID NO:254:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:254:

| Tyr | Ala | Ile | Phe | Val | Leu | Tyr | Ala | Ser | Ala | Trp | Leu | Ala | Ser | Arg | Trp |
| 1 | | | | 5 | | | | | 10 | | | | | 15 | |
| Pro | Leu | Pro | Leu | Ser | Val | Tyr | Thr | Leu | Thr | Val | Ser | Phe | Leu | Asn | Cys |
| | | | 20 | | | | | 25 | | | | | 30 | | |
| Pro | Phe | Ile | Val | Thr | Leu | Asn | Ile | | | | | | | | |
| | | | 35 | | | | 40 | | | | | | | | |

( 2 ) INFORMATION FOR SEQ ID NO:255:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:255:

| Tyr | Ala | Ile | Phe | Val | Leu | Tyr | Ala | Ser | Ala | Trp | Leu | Ala | Ser | Glu | Leu |
| 1 | | | | 5 | | | | | 10 | | | | | 15 | |
| Ile | Leu | Tyr | Tyr | Trp | Arg | Trp | Pro | Leu | Pro | Cys | Leu | His | Asp | Leu | Val |
| | | | 20 | | | | | 25 | | | | | 30 | | |

Trp Leu Cys Thr Cys Ser Ile Leu His Leu Cys Val Ile Ala Leu Ser
　　　　 35　　　　　　　　　　　 40　　　　　　　　　　　 45

Val Tyr Thr Leu Thr Val Pro Phe Ile Val Thr Leu Asn Ile
　　 50　　　　　　　　　　 55　　　　　　　　　　 60

( 2 ) INFORMATION FOR SEQ ID NO:256:

( i ) SEQUENCE CHARACTERISTICS:
　　　　( A ) LENGTH: 59 amino acids
　　　　( B ) TYPE: amino acid
　　　　( C ) STRANDEDNESS: single
　　　　( D ) TOPOLOGY: linear ( i i ) MOLECULE TYPE: peptide ( x i ) SEQUENCE DESCRIPTION: SEQ ID NO:256:

Tyr Ala Ile Phe Val Leu Tyr Ala Ser Ala Trp Leu Ser Phe Leu Ala
1　　　　　　　　　 5　　　　　　　　　　 10　　　　　　　　　　 15

Ser Glu Leu Ser Val Tyr Ala Ser Glu Leu Ser Ser Thr Leu His Asp
　　　　　　 20　　　　　　　　　　 25　　　　　　　　　　 30

Leu Val Trp Leu Trp Leu Asp Val Phe Cys Val Ile Ala Leu Thr Thr
　　　　 35　　　　　　　　　　　 40　　　　　　　　　　　 45

Val Asn Met Pro Phe Ile Val Thr Leu Asn Ile
　　 50　　　　　　　　　　 55

( 2 ) INFORMATION FOR SEQ ID NO:257:

( i ) SEQUENCE CHARACTERISTICS:
　　　　( A ) LENGTH: 60 amino acids
　　　　( B ) TYPE: amino acid
　　　　( C ) STRANDEDNESS: single
　　　　( D ) TOPOLOGY: linear ( i i ) MOLECULE TYPE: peptide ( x i ) SEQUENCE DESCRIPTION: SEQ ID NO:257:

Tyr Ala Ile Phe Val Leu Tyr Ala Ser Ala Trp Leu Ser Phe Leu Asn
1　　　　　　　　　 5　　　　　　　　　　 10　　　　　　　　　　 15

Gly Gly Glu Ile Ala Leu Trp Ser Leu Cys Pro Phe Ile Ile Leu Tyr
　　　　　　 20　　　　　　　　　　 25　　　　　　　　　　 30

Tyr Trp Arg Trp Pro Leu Pro Cys Leu His Asp Leu Val Ser Ile Leu
　　　　 35　　　　　　　　　　　 40　　　　　　　　　　　 45

His Leu Cys Val Ile Ala Leu Val Thr Leu Asn Ile
　　 50　　　　　　　　　　 55　　　　　　　　　　 60

( 2 ) INFORMATION FOR SEQ ID NO:258:

( i ) SEQUENCE CHARACTERISTICS:
　　　　( A ) LENGTH: 51 amino acids
　　　　( B ) TYPE: amino acid
　　　　( C ) STRANDEDNESS: single
　　　　( D ) TOPOLOGY: linear ( i i ) MOLECULE TYPE: peptide ( x i ) SEQUENCE DESCRIPTION: SEQ ID NO:258:

Tyr Val Trp Leu Trp Leu Asp Val Phe Cys Cys Thr Cys Ser Ile Leu
1　　　　　　　　　 5　　　　　　　　　　 10　　　　　　　　　　 15

His Leu Cys Val Ile Ala Leu Phe Val Leu Tyr Ala Ser Ala Trp Leu
　　　　　　 20　　　　　　　　　　 25　　　　　　　　　　 30

Ser Phe Leu Asn Gly Gly Glu Ile Ala Leu Trp Ser Leu Ile Val Thr
　　　　 35　　　　　　　　　　　 40　　　　　　　　　　　 45

Leu Asn Ile

50

( 2 ) INFORMATION FOR SEQ ID NO:259:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:259:

```
Tyr Ala Ile Phe Val Leu Tyr Ala Ser Ala Trp Leu Ala Ile Ile Leu
1               5                   10                  15
Tyr Tyr Trp Arg Trp Pro Leu Pro Cys Leu His Asp Leu Gly Gly Glu
            20                  25                  30
Ile Ala Leu Trp Ser Leu Asn Cys Pro Phe Ile Val Thr Leu Asn Ile
            35                  40                  45
```

( 2 ) INFORMATION FOR SEQ ID NO:260:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:260:

```
Cys Asp Val Phe Val Phe Val Asp Ile Met Leu Cys Thr Ala Ser Ile
1               5                   10                  15
Phe Asn Leu Cys Ala Ile Ser Val Gly
            20                  25
```

( 2 ) INFORMATION FOR SEQ ID NO:261:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:261:

```
Tyr Ala Ile Phe Val Leu Tyr Asp Ile Met Leu Cys Thr Ala Ser Ile
1               5                   10                  15
Phe Asn Leu Cys Ala Ile Ser Val Gly
            20                  25
```

( 2 ) INFORMATION FOR SEQ ID NO:262:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:262:

```
Asp Tyr Ala Ile Phe Val Phe Val Asp Ile Met Leu Met Thr Ala Ser
1               5                   10                  15
Ile Phe Asn Leu Met Ala Ile Ser Val Gly
            20                  25
```

(2) INFORMATION FOR SEQ ID NO:263:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:263:

```
Asp Tyr Ala Ile Phe Val Phe Val Asp Ile Met Leu His Thr Thr Ala
 1               5                  10                      15

Ser Thr Ile Phe Asn Leu Met Ala Thr Ile Thr Val Gly
            20                  25
```

(2) INFORMATION FOR SEQ ID NO:264:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:264:

```
Cys Asp Val Ala Val Val Tyr Ser Ser Asp Ile Met Leu Phe Tyr Val
 1               5                  10                      15

Cys Thr Ala Ser Ile Phe Ser Ser Asn Leu Cys Ala Ile Ser Ser Val
            20                  25                  30

Gly
```

(2) INFORMATION FOR SEQ ID NO:265:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:265:

```
Phe Leu Phe Cys Ser Leu Gly Ser Phe Tyr Ile Pro Ile Ala Val Ile
 1               5                  10                      15

Leu Val Asp Ile Met Leu Cys Thr Ala Ser Ile Phe Asn Leu Cys Ala
            20                  25                  30

Ile Ser Val Gly
            35
```

(2) INFORMATION FOR SEQ ID NO:266:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:266:

```
Tyr Ala Ile Phe Val Leu Tyr Asp Phe Leu Phe Cys Ser Leu Gly Ser
 1               5                  10                      15

Phe Tyr Ile Pro Ile Ala Val Ile Leu Ile Met Leu Cys Thr Ala Ser
```

Ile Phe Asn Leu Cys Ala Ile Ser Val Gly
            35                      40

( 2 ) INFORMATION FOR SEQ ID NO:267:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:267:

Asp Tyr Ala Ile Phe Val Phe Val Asp Ile Met Leu Met Thr Ala Ser
1               5                   10                  15
Ile Phe Leu Phe Cys Ser Leu Gly Ser Phe Tyr Ile Pro Ile Ala Val
            20                  25                  30
Ile Leu Ile Ser Val Gly
            35

( 2 ) INFORMATION FOR SEQ ID NO:268:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:268:

Asp Tyr Ala Ile Phe Val Phe Val Asp Ile Met Leu His Thr Thr Ala
1               5                   10                  15
Ser Thr Ile Phe Asn Leu Met Ala Phe Leu Phe Cys Ser Leu Gly Ser
            20                  25                  30
Phe Tyr Ile Pro Ile Ala Val Ile Leu Thr Ile Thr Val Gly
            35                  40                  45

( 2 ) INFORMATION FOR SEQ ID NO:269:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:269:

Cys Asp Val Ala Val Val Tyr Ser Ser Asp Ile Met Leu Phe Tyr Val
1               5                   10                  15
Cys Thr Ala Ser Ile Phe Ser Ser Asn Leu Phe Leu Phe Cys Ser Leu
            20                  25                  30
Gly Ser Phe Tyr Cys Ala Ile Ser Ser Val Gly
            35                  40

( 2 ) INFORMATION FOR SEQ ID NO:270:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:270:

| Cys | Asp | Val | Phe | Val | Phe | Val | Asp | Ile | Met | Leu | Cys | Thr | Ala | Ser | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | Asn | Trp | Tyr | Ile | Leu | Ser | Ser | Ile | Gly | Ser | Phe | Phe | Ala | Pro | Cys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Leu | Ile | Leu | Leu | Val | Tyr | Leu | Leu | Cys | Ala | Ile | Ser | Val | Gly |
|-----|-----|-----|-----|-----|-----|-----|-----|-----|-----|-----|-----|-----|-----|
|     |     | 35  |     |     |     | 40  |     |     |     |     | 45  |     |     |

(2) INFORMATION FOR SEQ ID NO:271:

(i) SEQUENCE CHARACTERISTICS:
  (A) LENGTH: 46 amino acids
  (B) TYPE: amino acid
  (C) STRANDEDNESS: single
  (D) TOPOLOGY: linear (i i) MOLECULE TYPE: peptide (x i) SEQUENCE DESCRIPTION: SEQ ID NO:271:

| Tyr | Ala | Ile | Phe | Val | Leu | Tyr | Asp | Ile | Met | Leu | Cys | Thr | Ala | Ser | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | Asn | Leu | Cys | Ala | Ile | Trp | Tyr | Ile | Leu | Ser | Ser | Ile | Gly | Ser | Phe |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Phe | Ala | Pro | Cys | Leu | Ile | Leu | Leu | Val | Tyr | Leu | Ser | Val | Gly |
|-----|-----|-----|-----|-----|-----|-----|-----|-----|-----|-----|-----|-----|-----|
|     |     | 35  |     |     |     | 40  |     |     |     |     | 45  |     |     |

(2) INFORMATION FOR SEQ ID NO:272:

(i) SEQUENCE CHARACTERISTICS:
  (A) LENGTH: 43 amino acids
  (B) TYPE: amino acid
  (C) STRANDEDNESS: single
  (D) TOPOLOGY: linear (i i) MOLECULE TYPE: peptide (x i) SEQUENCE DESCRIPTION: SEQ ID NO:272:

| Asp | Tyr | Ala | Ile | Phe | Val | Phe | Val | Asp | Ile | Trp | Tyr | Ile | Leu | Ser | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ile | Gly | Ser | Phe | Phe | Ala | Pro | Cys | Leu | Ile | Leu | Leu | Val | Tyr | Leu | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Ile | Phe | Asn | Leu | Met | Ala | Ile | Ser | Val | Gly |
|-----|-----|-----|-----|-----|-----|-----|-----|-----|-----|-----|
|     |     | 35  |     |     |     | 40  |     |     |     |     |

(2) INFORMATION FOR SEQ ID NO:273:

(i) SEQUENCE CHARACTERISTICS:
  (A) LENGTH: 45 amino acids
  (B) TYPE: amino acid
  (C) STRANDEDNESS: single
  (D) TOPOLOGY: linear (i i) MOLECULE TYPE: peptide (x i) SEQUENCE DESCRIPTION: SEQ ID NO:273:

| Asp | Tyr | Ala | Ile | Trp | Tyr | Ile | Leu | Ser | Ser | Ile | Gly | Ser | Phe | Phe | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Pro | Cys | Leu | Ile | Leu | Leu | Val | Tyr | Leu | Ile | Met | Leu | His | Thr | Thr | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Thr | Ile | Phe | Asn | Leu | Met | Ala | Thr | Ile | Thr | Val | Gly |
|-----|-----|-----|-----|-----|-----|-----|-----|-----|-----|-----|-----|-----|
|     |     | 35  |     |     |     | 40  |     |     |     |     | 45  |     |

( 2 ) INFORMATION FOR SEQ ID NO:274:

( i ) SEQUENCE CHARACTERISTICS:
    ( A ) LENGTH: 49 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:274:

```
Cys Asp Val Ala Val Val Tyr Ser Ser Asp Ile Met Leu Phe Tyr Val
1               5                   10                  15

Cys Trp Tyr Ile Leu Ser Ser Ile Gly Ser Phe Phe Ala Pro Cys Leu
            20                  25                  30

Ile Leu Leu Val Tyr Leu Ser Ser Asn Leu Cys Ala Ile Ser Ser Val
        35                  40                  45

Gly
```

( 2 ) INFORMATION FOR SEQ ID NO:275:

( i ) SEQUENCE CHARACTERISTICS:
    ( A ) LENGTH: 47 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:275:

```
Cys Asp Val Phe Val Phe Val Asp Ile Met Leu Cys Thr Ala Ser Ile
1               5                   10                  15

Phe Trp Tyr Val Ile Ser Ser Ser Ile Gly Ser Phe Phe Ala Pro Cys
            20                  25                  30

Leu Ile Asn His Leu Val Tyr Asn Leu Cys Ala Ile Ser Val Gly
        35                  40                  45
```

( 2 ) INFORMATION FOR SEQ ID NO:276:

( i ) SEQUENCE CHARACTERISTICS:
    ( A ) LENGTH: 47 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:276:

```
Tyr Ala Ile Phe Val Leu Tyr Asp Ile Met Leu Cys Thr Ala Ser Ile
1               5                   10                  15

Phe Asn Leu Cys Ala Ile Trp Tyr Val Ile Ser Ser Ser Ile Gly Ser
            20                  25                  30

Phe Phe Ala Pro Cys Leu Ile Asn His Leu Val Tyr Ser Val Gly
        35                  40                  45
```

( 2 ) INFORMATION FOR SEQ ID NO:277:

( i ) SEQUENCE CHARACTERISTICS:
    ( A ) LENGTH: 48 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:277:

```
        Asp  Tyr  Ala  Ile  Phe  Val  Phe  Val  Trp  Tyr  Val  Ile  Ser  Ser  Ser  Ile
        1              5                        10                       15

Gly  Ser  Phe  Phe  Ala  Pro  Cys  Leu  Ile  Asn  His  Leu  Val  Tyr  Asp  Ile
                       20                       25                       30

Met  Leu  Met  Thr  Ala  Ser  Ile  Phe  Asn  Leu  Met  Ala  Ile  Ser  Val  Gly
                  35                       40                       45
```

( 2 ) INFORMATION FOR SEQ ID NO:278:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:278:

```
        Asp  Tyr  Ala  Ile  Phe  Val  Phe  Val  Asp  Ile  Met  Leu  His  Thr  Thr  Ala
        1              5                        10                       15

Ser  Thr  Ile  Phe  Trp  Tyr  Val  Ile  Ser  Ser  Ser  Ile  Gly  Ser  Phe  Phe
                       20                       25                       30

Ala  Pro  Cys  Leu  Ile  Asn  His  Leu  Val  Tyr  Thr  Val  Gly
                  35                       40                       45
```

( 2 ) INFORMATION FOR SEQ ID NO:279:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:279:

```
        Cys  Asp  Val  Ala  Val  Val  Tyr  Ser  Ser  Asp  Ile  Met  Leu  Phe  Tyr  Val
        1              5                        10                       15

Cys  Thr  Ala  Ser  Ile  Phe  Ser  Trp  Tyr  Val  Ile  Ser  Ile  Gly  Ser  Phe
                       20                       25                       30

Phe  Ala  Ile  Asn  His  Leu  Val  Tyr  Asn  Leu  Cys  Ala  Ile  Ser  Ser  Val
                  35                       40                       45

Gly
```

( 2 ) INFORMATION FOR SEQ ID NO:280:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:280:

```
        Cys  Asp  Val  Phe  Val  Phe  Val  Asp  Ile  Met  Leu  Cys  Thr  Ala  Ser  Ile
        1              5                        10                       15

Phe  Asn  Leu  Cys  Ala  Ile  Thr  Tyr  Ala  Ile  Ser  Ser  Ser  Val  Ile  Ser
                       20                       25                       30

Phe  Tyr  Ile  Pro  Val  Ala  Ile  Leu  Val  Thr  Tyr  Thr
                  35                       40
```

( 2 ) INFORMATION FOR SEQ ID NO:281:

( i ) SEQUENCE CHARACTERISTICS:
   ( A ) LENGTH: 47 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:281:

```
Tyr Ala Ile Phe Val Leu Tyr Asp Ile Met Leu Cys Thr Ala Thr Tyr
1               5                   10                  15
Ala Ile Ser Ser Ser Val Ile Ser Phe Tyr Ile Pro Val Ala Ile Leu
            20                  25                  30
Val Thr Tyr Thr Ser Ile Phe Asn Leu Cys Ala Ile Ser Val Gly
            35                  40                  45
```

( 2 ) INFORMATION FOR SEQ ID NO:282:

( i ) SEQUENCE CHARACTERISTICS:
   ( A ) LENGTH: 41 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:282:

```
Asp Tyr Ala Ile Phe Val Phe Val Asp Ile Met Leu Met Thr Ala Thr
1               5                   10                  15
Tyr Ala Ile Ser Ser Ser Val Ile Ser Phe Tyr Ile Pro Val Ala Ile
            20                  25                  30
Leu Val Thr Tyr Thr Ile Ser Val Gly
            35                  40
```

( 2 ) INFORMATION FOR SEQ ID NO:283:

( i ) SEQUENCE CHARACTERISTICS:
   ( A ) LENGTH: 46 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:283:

```
Thr Tyr Ala Ile Ser Ser Ser Val Ile Ser Phe Tyr Ile Pro Val Ala
1               5                   10                  15
Thr Asp Tyr Ala Ile Phe Val Phe Val Asp Ile Met Leu His Thr Thr
            20                  25                  30
Ala Ser Thr Ile Phe Asn Leu Met Ala Thr Ile Thr Val Gly
            35                  40                  45
```

( 2 ) INFORMATION FOR SEQ ID NO:284:

( i ) SEQUENCE CHARACTERISTICS:
   ( A ) LENGTH: 45 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:284:

```
Cys Asp Val Ala Val Val Tyr Ser Ser Asp Ile Met Leu Phe Tyr Val
1               5                   10                  15
Cys Thr Ala Thr Tyr Ala Ile Ser Ser Ser Val Ile Ser Phe Tyr Ile
```

```
                              20                      25                         30
        Pro  Val  Ala  Ile  Leu  Val  Thr  Tyr  Thr  Ser  Ser  Val  Gly
                         35                      40                     45
```

( 2 ) INFORMATION FOR SEQ ID NO:285:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:285:

```
        Cys  Asp  Val  Phe  Val  Phe  Val  Asp  Phe  Val  Ile  Tyr  Ser  Ser  Val  Val
        1                   5                        10                       15

Ser  Phe  Tyr  Leu  Pro  Phe  Gly  Val  Thr  Val  Leu  Val  Tyr  Ala  Cys  Thr
                         20                      25                       30

Ala  Ser  Ile  Phe  Asn  Leu  Cys  Ala  Ile  Ser  Val  Gly
                         35                      40
```

( 2 ) INFORMATION FOR SEQ ID NO:286:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:286:

```
        Tyr  Ala  Ile  Phe  Val  Leu  Tyr  Asp  Phe  Val  Ile  Tyr  Ser  Ser  Val  Val
        1                   5                        10                       15

Ser  Phe  Tyr  Leu  Pro  Phe  Gly  Val  Thr  Val  Leu  Val  Tyr  Ala  Ser  Ile
                         20                      25                       30

Phe  Asn  Leu  Cys  Ala  Ile  Ser  Val  Gly
                    35                   40
```

( 2 ) INFORMATION FOR SEQ ID NO:287:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:287:

```
        Asp  Tyr  Ala  Ile  Phe  Val  Phe  Val  Asp  Phe  Val  Ile  Tyr  Ser  Ser  Val
        1                   5                        10                       15

Val  Ser  Phe  Tyr  Leu  Pro  Phe  Gly  Val  Thr  Val  Leu  Val  Tyr  Ala  Thr
                         20                      25                       30

Ala  Ser  Ile  Phe  Asn  Leu  Met  Ala  Ile  Ser  Val  Gly
                         35                      40
```

( 2 ) INFORMATION FOR SEQ ID NO:288:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:288:

```
Asp Tyr Ala Ile Phe Val Phe Val Asp Phe Val Ile Tyr Ser Ser Val
1               5                   10                  15

Val Ser Phe Tyr Leu Pro Phe Gly Val Thr Val Leu Val Tyr Ala His
                20                  25                  30

Thr Thr Ala Ser Thr Ile Phe Asn Leu Met Ala Thr Ile Thr Val Gly
            35              40                  45
```

( 2 ) INFORMATION FOR SEQ ID NO:289:

( i ) SEQUENCE CHARACTERISTICS:
        ( A ) LENGTH: 47 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:289:

```
Cys Asp Val Ala Val Val Tyr Ser Ser Asp Phe Val Ile Tyr Ser Ser
1               5                   10                  15

Val Val Ser Phe Tyr Leu Pro Phe Gly Val Thr Val Tyr Val Cys Thr
                20                  25                  30

Ala Ser Ile Phe Ser Ser Asn Leu Cys Ala Ile Ser Ser Val Gly
            35              40                  45
```

( 2 ) INFORMATION FOR SEQ ID NO:290:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:290:

```
Cys Asp Val Phe Val Phe Val Asp Ile Met Leu Cys Thr Ala Ser Tyr
1               5                   10                  15

Thr Ile Tyr Ser Thr Cys Gly Ala Phe Tyr Ile Pro Ser Val Leu Leu
                20                  25                  30

Ile Ile Leu Tyr Gly Asn Leu Cys Ala Ile Ser Val Gly
            35              40                  45
```

( 2 ) INFORMATION FOR SEQ ID NO:291:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:291:

```
Tyr Ala Ile Phe Val Leu Tyr Asp Ile Met Leu Cys Thr Ala Ser Tyr
1               5                   10                  15

Thr Ile Tyr Ser Thr Cys Gly Ala Phe Tyr Ile Pro Ser Val Leu Leu
                20                  25                  30

Ile Ile Leu Tyr Gly Asn Leu Cys Ala Ile Ser Val Gly
            35              40                  45
```

( 2 ) INFORMATION FOR SEQ ID NO:292:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:292:

```
Asp Tyr Ala Ile Phe Val Phe Val Asp Ile Met Leu Met Thr Ala Ser
1               5                   10                  15
Tyr Thr Ile Tyr Ser Thr Cys Gly Ala Phe Tyr Ile Pro Ser Val Leu
            20                  25                  30
Leu Ile Ile Leu Tyr Gly Asn Leu Met Ala Ile Ser Val Gly
        35                  40                  45
```

( 2 ) INFORMATION FOR SEQ ID NO:293:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:293:

```
Asp Tyr Ala Ile Phe Val Phe Val Asp Ile Met Leu His Thr Thr Ala
1               5                   10                  15
Ser Tyr Thr Ile Tyr Ser Thr Cys Gly Ala Phe Tyr Ile Pro Ser Val
            20                  25                  30
Leu Leu Ile Ile Leu Tyr Gly Met Ala Thr Ile Thr Val Gly
        35                  40                  45
```

( 2 ) INFORMATION FOR SEQ ID NO:294:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:294:

```
Cys Asp Val Ala Val Val Tyr Ser Ser Asp Ile Met Ser Tyr Thr Ile
1               5                   10                  15
Tyr Ser Thr Cys Gly Ala Phe Tyr Ile Pro Ser Val Leu Leu Ile Ile
            20                  25                  30
Leu Tyr Gly Ile Phe Ser Ser Asn Leu Cys Ala Ile Ser Ser Val Gly
        35                  40                  45
```

( 2 ) INFORMATION FOR SEQ ID NO:295:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:295:

```
Cys Asp Val Phe Val Phe Phe Val Leu Ile Gly Ser Phe Val Ala Val
1               5                   10                  15
```

```
        Asp  Ile  Met  Leu  Cys  Thr  Ala  Ser  Ile  Phe  Asn  Leu  Cys  Ala  Ile  Ser
                       20                       25                            30

Val  Gly
```

(2) INFORMATION FOR SEQ ID NO:296:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:296:

```
        Tyr  Ala  Ile  Phe  Val  Leu  Tyr  Phe  Val  Leu  Ile  Gly  Ser  Phe  Val  Ala
        1                        5                        10                      15

Asp  Ile  Met  Leu  Cys  Thr  Ala  Ser  Ile  Phe  Asn  Leu  Cys  Ala  Ile  Ser
                       20                       25                            30

Val  Gly
```

(2) INFORMATION FOR SEQ ID NO:297:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:297:

```
        Asp  Tyr  Ala  Ile  Phe  Val  Phe  Val  Phe  Val  Leu  Ile  Gly  Ser  Phe  Val
        1                        5                        10                      15

Ala  Asp  Ile  Met  Leu  Met  Thr  Ala  Ser  Ile  Phe  Asn  Leu  Met  Ala  Ile
                       20                       25                            30

Ser  Val  Gly
                  35
```

(2) INFORMATION FOR SEQ ID NO:298:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:298:

```
        Asp  Tyr  Ala  Ile  Phe  Val  Phe  Val  Phe  Val  Leu  Ile  Gly  Ser  Phe  Val
        1                        5                        10                      15

Ala  Asp  Ile  Met  Leu  His  Thr  Thr  Ala  Ser  Thr  Ile  Phe  Asn  Leu  Met
                       20                       25                            30

Ala  Thr  Ile  Thr  Val  Gly
                       35
```

(2) INFORMATION FOR SEQ ID NO:299:

(i) SEQUENCE CHARACTERISTICS:
        (A) LENGTH: 42 amino acids
        (B) TYPE: amino acid
        (C) STRANDEDNESS: single
        (D) TOPOLOGY: linear ( i i ) MOLECULE TYPE: peptide ( x i ) SEQUENCE DESCRIPTION: SEQ ID NO:299:

Cys Asp Val Ala Val Val Tyr Ser Ser Phe Val Leu Ile Gly Ser Phe
1               5                   10                  15

Val Ala Asp Ile Met Leu Phe Tyr Val Cys Thr Ala Ser Ile Phe Ser
            20                  25                  30

Ser Asn Leu Cys Ala Ile Ser Ser Val Gly
        35                  40

( 2 ) INFORMATION FOR SEQ ID NO:300:

( i ) SEQUENCE CHARACTERISTICS:
    ( A ) LENGTH: 33 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:300:

Cys Asp Val Phe Val Phe Val Asp Ile Met Leu Cys Phe Phe Ile Pro
1               5                   10                  15

Thr Leu Ile Met Val Ile Thr Tyr Phe Asn Leu Cys Ala Ile Ser Val
            20                  25                  30

Gly ( 2 ) INFORMATION FOR SEQ ID NO:301:

( i ) SEQUENCE CHARACTERISTICS:
    ( A ) LENGTH: 34 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:301:

Tyr Ala Ile Phe Val Leu Tyr Asp Ile Met Leu Cys Phe Phe Ile Pro
1               5                   10                  15

Thr Leu Ile Met Val Ile Thr Tyr Phe Phe Asn Leu Cys Ala Ile Ser
            20                  25                  30

Val Gly ( 2 ) INFORMATION FOR SEQ ID NO:302:

( i ) SEQUENCE CHARACTERISTICS:
    ( A ) LENGTH: 34 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:302:

Asp Tyr Ala Ile Phe Val Phe Val Asp Ile Met Leu Met Phe Phe Ile
1               5                   10                  15

Pro Thr Leu Ile Met Val Ile Thr Tyr Phe Asn Leu Met Ala Ile Ser
            20                  25                  30

Val Gly ( 2 ) INFORMATION FOR SEQ ID NO:303:

( i ) SEQUENCE CHARACTERISTICS:

( A ) LENGTH: 36 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:303:

| Asp | Tyr | Ala | Ile | Phe | Val | Phe | Val | Asp | Ile | Met | Leu | His | Thr | Phe | Phe |
|---|---|---|---|---|---|---|---|---|---|---|---|---|---|---|---|
| 1 | | | | 5 | | | | | 10 | | | | | 15 | |
| Ile | Pro | Thr | Leu | Ile | Met | Val | Ile | Thr | Tyr | Phe | Asn | Leu | Met | Ala | Thr |
| | | | 20 | | | | | 25 | | | | | 30 | | |
| Ile | Thr | Val | Gly | | | | | | | | | | | | |
| | | | 35 | | | | | | | | | | | | |

( 2 ) INFORMATION FOR SEQ ID NO:304:

( i ) SEQUENCE CHARACTERISTICS:
( A ) LENGTH: 41 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:304:

| Cys | Asp | Val | Ala | Val | Val | Tyr | Ser | Ser | Asp | Ile | Met | Leu | Phe | Tyr | Val |
|---|---|---|---|---|---|---|---|---|---|---|---|---|---|---|---|
| 1 | | | | 5 | | | | | 10 | | | | | 15 | |
| Cys | Phe | Phe | Ile | Pro | Thr | Leu | Ile | Met | Val | Ile | Thr | Tyr | Phe | Ser | Ser |
| | | | 20 | | | | | 25 | | | | | 30 | | |
| Asn | Leu | Cys | Ala | Ile | Ser | Ser | Val | Gly | | | | | | | |
| | | 35 | | | | | 40 | | | | | | | | |

( 2 ) INFORMATION FOR SEQ ID NO:305:

( i ) SEQUENCE CHARACTERISTICS:
( A ) LENGTH: 44 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:305:

| Cys | Asp | Val | Val | Tyr | Gly | Leu | Val | Asp | Gly | Leu | Val | Thr | Phe | Tyr | Leu |
|---|---|---|---|---|---|---|---|---|---|---|---|---|---|---|---|
| 1 | | | | 5 | | | | | 10 | | | | | 15 | |
| Pro | Leu | Leu | Ile | Met | Cys | Ile | Thr | Tyr | Tyr | Asp | Ile | Met | Leu | Cys | Thr |
| | | | 20 | | | | | 25 | | | | | 30 | | |
| Ala | Ser | Ile | Phe | Asn | Leu | Cys | Ala | Ile | Ser | Val | Gly | | | | |
| | | 35 | | | | | 40 | | | | | | | | |

( 2 ) INFORMATION FOR SEQ ID NO:306:

( i ) SEQUENCE CHARACTERISTICS:
( A ) LENGTH: 44 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:306:

| Tyr | Ala | Ile | Val | Tyr | Gly | Leu | Val | Asp | Gly | Leu | Val | Thr | Phe | Tyr | Leu |
|---|---|---|---|---|---|---|---|---|---|---|---|---|---|---|---|
| 1 | | | | 5 | | | | | 10 | | | | | 15 | |
| Pro | Leu | Leu | Ile | Met | Cys | Ile | Thr | Tyr | Tyr | Asp | Ile | Met | Leu | Cys | Thr |
| | | | 20 | | | | | 25 | | | | | 30 | | |

```
        Ala  Ser  Ile  Phe  Asn  Leu  Cys  Ala  Ile  Ser  Val  Gly
                  35                       40
```

( 2 ) INFORMATION FOR SEQ ID NO:307:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:307:

```
Asp  Tyr  Ala  Ile  Val  Tyr  Gly  Leu  Val  Asp  Gly  Leu  Val  Thr  Phe  Tyr
1                   5                        10                       15

Leu  Pro  Leu  Leu  Ile  Met  Cys  Ile  Thr  Tyr  Tyr  Asp  Ile  Met  Leu  Met
               20                       25                       30

Thr  Ala  Ser  Ile  Phe  Asn  Leu  Met  Ala  Ile  Ser  Val  Gly
               35                  40                       45
```

( 2 ) INFORMATION FOR SEQ ID NO:308:

( i ) SEQUENCE CHARACTERISTICS:
        ( A ) LENGTH: 47 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:308:

```
Asp  Tyr  Ala  Ile  Val  Tyr  Gly  Leu  Val  Asp  Gly  Leu  Val  Thr  Phe  Tyr
1                   5                        10                       15

Leu  Pro  Leu  Leu  Ile  Met  Cys  Ile  Ser  Ser  Asp  Ile  Met  Leu  His  Thr
               20                       25                       30

Thr  Ala  Ser  Thr  Ile  Phe  Asn  Leu  Met  Ala  Thr  Ile  Thr  Val  Gly
               35                       40                  45
```

( 2 ) INFORMATION FOR SEQ ID NO:309:

( i ) SEQUENCE CHARACTERISTICS:
        ( A ) LENGTH: 47 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:309:

```
Cys  Asp  Val  Val  Tyr  Asp  Gly  Leu  Val  Thr  Phe  Tyr  Leu  Pro  Leu  Leu
1                   5                        10                       15

Ile  Met  Cys  Ile  Thr  Tyr  Tyr  Asp  Ile  Met  Leu  Phe  Tyr  Val  Cys  Thr
               20                       25                       30

Ala  Ser  Ile  Phe  Ser  Ser  Asn  Leu  Cys  Ala  Ile  Ser  Ser  Val  Gly
               35                       40                  45
```

( 2 ) INFORMATION FOR SEQ ID NO:310:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:310:

```
Cys Asp Val Phe Val Phe Val Asp Ile Met Leu Leu Val Ile Phe Leu
1               5                   10                  15
Gly Leu Val Ile Val Ile Pro Phe Val Leu Ile Ile Val Ser Tyr Ala
            20                  25                  30
Ser Ile Phe Asn Leu Cys Ala Ile Ser Val Gly
            35              40
```

( 2 ) INFORMATION FOR SEQ ID NO:311:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:311:

```
Tyr Ala Ile Phe Val Leu Tyr Asp Ile Met Leu Leu Val Ile Phe Leu
1               5                   10                  15
Gly Leu Val Ile Val Ile Pro Phe Val Leu Ile Ile Val Ser Tyr Ala
            20                  25                  30
Ile Phe Asn Leu Cys Ala Ile Ser Val Gly
            35              40
```

( 2 ) INFORMATION FOR SEQ ID NO:312:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:312:

```
Asp Tyr Ala Ile Phe Val Phe Val Asp Ile Met Leu Met Leu Val Ile
1               5                   10                  15
Phe Leu Gly Leu Val Ile Val Ile Pro Phe Val Leu Ile Ile Val Ser
            20                  25                  30
Tyr Ala Ile Phe Asn Leu Met Ala Ile Ser Val Gly
            35              40
```

( 2 ) INFORMATION FOR SEQ ID NO:313:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:313:

```
Asp Tyr Ala Ile Phe Val Phe Val Asp Ile Met Leu His Thr Leu Val
1               5                   10                  15
Ile Phe Leu Gly Leu Val Ile Val Ile Pro Phe Val Leu Ile Ile Val
            20                  25                  30
Ser Tyr Ala Ile Phe Asn Leu Met Ala Thr Ile Thr Val Gly
            35              40              45
```

( 2 ) INFORMATION FOR SEQ ID NO:314:

( i ) SEQUENCE CHARACTERISTICS:
    ( A ) LENGTH: 48 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:314:

```
Cys Asp Val Ala Val Val Tyr Ser Ser Asp Ile Met Leu Phe Leu Val
 1               5                  10                  15
Ile Phe Leu Gly Leu Val Ile Val Ile Pro Phe Val Leu Ile Ile Val
                20                  25                  30
Ser Tyr Ala Ile Phe Ser Ser Asn Leu Cys Ala Ile Ser Ser Val Gly
            35                  40                  45
```

( 2 ) INFORMATION FOR SEQ ID NO:315:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:315:

```
Cys Asp Val Phe Val Phe Val Asp Ile Met Leu Cys Thr Ala Leu Met
 1               5                  10                  15
Ile Tyr Ile Leu Gly Gly Leu Ile Ile Ile Ile Pro Phe Leu Leu Ile
                20                  25                  30
Val Met Ser Tyr Val Ser Ile Phe Asn Leu Cys Ala Ile Ser Val Gly
            35                  40                  45
```

( 2 ) INFORMATION FOR SEQ ID NO:316:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:316:

```
Tyr Ala Ile Phe Val Leu Tyr Asp Ile Met Leu Cys Thr Ala Leu Met
 1               5                  10                  15
Ile Tyr Ile Leu Gly Gly Leu Ile Ile Ile Ile Pro Phe Leu Leu Ile
                20                  25                  30
Val Met Ser Tyr Val Ser Ile Phe Asn Leu Cys Ala Ile Ser Val Gly
            35                  40                  45
```

( 2 ) INFORMATION FOR SEQ ID NO:317:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:317:

```
Asp Tyr Ala Ile Phe Val Phe Val Asp Ile Met Leu Met Thr Ala Ser
 1               5                  10                  15
```

```
          Ile  Phe  Asn  Leu  Met  Ile  Tyr  Ile  Leu  Gly  Gly  Leu  Ile  Ile  Ile  Ile
                         20                       25                       30

Pro  Phe  Leu  Leu  Ile  Val  Met  Ser  Tyr  Val  Leu  Met  Ala  Ile  Ser  Val
                         35                       40                       45

Gly
```

( 2 ) INFORMATION FOR SEQ ID NO:318:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:318:

```
          Asp  Tyr  Ala  Ile  Phe  Val  Phe  Val  Asp  Ile  Met  Leu  His  Thr  Thr  Ala
          1                   5                        10                       15

Ser  Thr  Ile  Leu  Met  Ile  Tyr  Ile  Leu  Gly  Gly  Leu  Ile  Ile  Ile  Ile
                         20                       25                       30

Pro  Phe  Leu  Leu  Ile  Val  Met  Ser  Tyr  Val  Ile  Thr  Val  Gly
                         35                       40                       45
```

( 2 ) INFORMATION FOR SEQ ID NO:319:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:319:

```
          Cys  Asp  Val  Ala  Val  Val  Tyr  Ser  Ser  Asp  Ile  Met  Leu  Phe  Tyr  Val
          1                   5                        10                       15

Cys  Thr  Ala  Tyr  Ile  Leu  Gly  Gly  Leu  Ile  Pro  Phe  Leu  Leu  Ile  Val
                         20                       25                       30

Met  Thr  Tyr  Val  Ser  Ile  Phe  Thr  Asn  Leu  Cys  Ala  Ile  Ser  Ser  Val
                         35                       40                       45

Gly
```

( 2 ) INFORMATION FOR SEQ ID NO:320:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:320:

```
          Cys  Asp  Val  Phe  Val  Phe  Val  Asp  Ile  Met  Leu  Cys  Thr  Ala  Ser  Ile
          1                   5                        10                       15

Phe  Asn  Leu  Leu  Met  Ile  His  Ile  Met  Glu  Val  Ile  Ile  Ile  Val  Ile
                         20                       25                       30

Pro  Phe  Val  Leu  Ile  Val  Ile  Ser  Tyr  Ala  Cys  Ala  Ile  Ser  Val  Gly
                         35                       40                       45
```

( 2 ) INFORMATION FOR SEQ ID NO:321:

( i ) SEQUENCE CHARACTERISTICS:

(A) LENGTH: 48 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:321:

| Tyr | Ala | Ile | Phe | Val | Leu | Tyr | Asp | Ile | Met | Leu | Cys | Thr | Ala | Ser | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Phe | Asn | Leu | Leu | Met | Ile | His | Ile | Met | Glu | Val | Ile | Ile | Ile | Val | Ile |
|     |     |     | 20  |     |     |     |     | 25  |     |     |     |     | 30  |     |     |
| Pro | Phe | Val | Leu | Ile | Val | Ile | Ser | Tyr | Ala | Cys | Ala | Ile | Ser | Val | Gly |
|     |     |     | 35  |     |     |     | 40  |     |     |     |     | 45  |     |     |     |

(2) INFORMATION FOR SEQ ID NO:322:

(i) SEQUENCE CHARACTERISTICS:
(A) LENGTH: 45 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:322:

| Asp | Tyr | Ala | Ile | Phe | Val | Phe | Val | Asp | Ile | Met | Leu | Met | Thr | Ala | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ile | Phe | Leu | Met | Ile | His | Ile | Met | Glu | Val | Ile | Ile | Ile | Val | Ile | Pro |
|     |     |     | 20  |     |     |     |     | 25  |     |     |     |     | 30  |     |     |
| Phe | Val | Leu | Ile | Val | Ile | Ser | Tyr | Ala | Ile | Ser | Val | Gly |
|     |     |     | 35  |     |     |     | 40  |     |     |     |     | 45  |

(2) INFORMATION FOR SEQ ID NO:323:

(i) SEQUENCE CHARACTERISTICS:
(A) LENGTH: 46 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:323:

| Asp | Tyr | Ala | Ile | Phe | Val | Phe | Val | Asp | Ile | Met | Leu | His | Thr | Thr | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Thr | Ile | Leu | Met | Ile | His | Ile | Met | Glu | Val | Ile | Ile | Ile | Val | Ile |
|     |     |     | 20  |     |     |     |     | 25  |     |     |     |     | 30  |     |     |
| Pro | Phe | Val | Leu | Ile | Val | Ile | Ser | Tyr | Ala | Ile | Thr | Val | Gly |
|     |     |     | 35  |     |     |     | 40  |     |     |     |     | 45  |     |

(2) INFORMATION FOR SEQ ID NO:324:

(i) SEQUENCE CHARACTERISTICS:
(A) LENGTH: 51 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:324:

| Cys | Asp | Val | Ala | Val | Val | Tyr | Ser | Ser | Asp | Ile | Met | Leu | Phe | Tyr | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Cys | Thr | Ala | Ser | Ile | Phe | Leu | Met | Ile | His | Ile | Met | Glu | Val | Ile | Ile |
|     |     |     | 20  |     |     |     |     | 25  |     |     |     |     | 30  |     |     |

Ile Val Ile Pro Phe Val Leu Ile Val Ile Ser Tyr Ala Ala Ile Ser
        35                  40                  45

Ser Val Gly
    50

(2) INFORMATION FOR SEQ ID NO:325:

(i) SEQUENCE CHARACTERISTICS:
       (A) LENGTH: 97 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:325:

Asn Trp Pro Ala Leu Ser Ile Val Val Ile Ile Ile Asn Thr Ile Gly
1               5                   10                  15

Gly Asn Ile Leu Val Ile Met Ala Val Ser Ile Tyr Thr Ser Leu Asp
            20                  25                  30

Val Met Leu Cys Thr Ala Ser Ile Leu Asn Leu Leu Ile Ser Leu Phe
            35                  40                  45

Val Leu Ile Gly Ser Phe Val Ala Phe Phe Ile Pro Leu Thr Ile Met
            50              55                  60

Val Ile Thr Tyr Phe Leu Phe Asn Val Phe Phe Val Trp Ile Gly Tyr
65                      70                  75                  80

Val Cys Ser Ser Ser Leu Gly Ile Asn Pro Val Ile Ile Tyr Thr Leu
                85                  90                  95

Phe (2) INFORMATION FOR SEQ ID NO:326:

(i) SEQUENCE CHARACTERISTICS:
       (A) LENGTH: 97 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:326:

Asn Trp Pro Ala Leu Ser Ile Val Val Ile Ile Ile Asn Thr Ile Gly
1               5                   10                  15

Gly Asn Ile Leu Val Ile Met Ala Val Thr Ile Tyr Thr Thr Leu Asp
            20                  25                  30

Val Met Leu Cys Thr Ala Thr Ile Leu Asn Leu Leu Ile Ser Leu Phe
            35                  40                  45

Val Leu Ile Gly Thr Phe Val Ala Phe Phe Ile Pro Leu Thr Ile Met
            50              55                  60

Val Ile Thr Tyr Phe Leu Phe Asn Val Phe Phe Val Trp Ile Gly Tyr
65                      70                  75                  80

Val Cys Thr Thr Thr Leu Gly Ile Asn Pro Val Ile Ile Tyr Thr Leu
                85                  90                  95

Phe (2) INFORMATION FOR SEQ ID NO:327:

(i) SEQUENCE CHARACTERISTICS:
       (A) LENGTH: 97 amino acids
       (B) TYPE: amino acid
       (C) STRANDEDNESS: single (D) TOPOLOGY: linear (ii) MOLECULE TYPE: peptide (xi) SEQUENCE DESCRIPTION: SEQ ID NO:327:

| Asn | Trp | Pro | Ala | Leu | Thr | Ile | Val | Val | Ile | Ile | Ile | Asn | Thr | Ile | Gly |
|---|---|---|---|---|---|---|---|---|---|---|---|---|---|---|---|
| 1 | | | | 5 | | | | | 10 | | | | | 15 | |

| Gly | Asn | Ile | Leu | Val | Ile | Met | Ala | Val | Ser | Ile | Tyr | Thr | Thr | Leu | Asp |
|---|---|---|---|---|---|---|---|---|---|---|---|---|---|---|---|
| | | | 20 | | | | | 25 | | | | | 30 | | |

| Val | Met | Leu | Cys | Thr | Ala | Thr | Ile | Leu | Asn | Leu | Leu | Ile | Thr | Leu | Phe |
|---|---|---|---|---|---|---|---|---|---|---|---|---|---|---|---|
| | | 35 | | | | | 40 | | | | | 45 | | | |

| Val | Leu | Ile | Gly | Thr | Phe | Val | Ala | Phe | Phe | Ile | Pro | Leu | Thr | Ile | Met |
|---|---|---|---|---|---|---|---|---|---|---|---|---|---|---|---|
| | 50 | | | | | 55 | | | | | 60 | | | | |

| Val | Ile | Thr | Tyr | Phe | Leu | Phe | Asn | Val | Phe | Phe | Val | Trp | Ile | Gly | Tyr |
|---|---|---|---|---|---|---|---|---|---|---|---|---|---|---|---|
| 65 | | | | | 70 | | | | | 75 | | | | | 80 |

| Val | Cys | Ser | Thr | Ser | Leu | Gly | Ile | Asn | Pro | Val | Ile | Ile | Tyr | Thr | Leu |
|---|---|---|---|---|---|---|---|---|---|---|---|---|---|---|---|
| | | | | 85 | | | | | 90 | | | | | 95 | |

Phe (2) INFORMATION FOR SEQ ID NO:328:

(i) SEQUENCE CHARACTERISTICS:
(A) LENGTH: 95 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:328:

| Asn | Trp | Pro | Ala | Leu | Thr | Ile | Val | Val | Ile | Ile | Ile | Asn | Thr | Ile | Gly |
|---|---|---|---|---|---|---|---|---|---|---|---|---|---|---|---|
| 1 | | | | 5 | | | | | 10 | | | | | 15 | |

| Gly | Asn | Ile | Leu | Val | Ile | Met | Ala | Val | Thr | Ile | Tyr | Thr | Thr | Leu | Asp |
|---|---|---|---|---|---|---|---|---|---|---|---|---|---|---|---|
| | | | 20 | | | | | 25 | | | | | 30 | | |

| Val | Met | Leu | Cys | Thr | Ala | Thr | Ile | Leu | Asn | Leu | Leu | Ile | Thr | Leu | Phe |
|---|---|---|---|---|---|---|---|---|---|---|---|---|---|---|---|
| | | 35 | | | | | 40 | | | | | 45 | | | |

| Val | Leu | Ile | Gly | Thr | Phe | Val | Ala | Phe | Phe | Ile | Pro | Leu | Thr | Ile | Met |
|---|---|---|---|---|---|---|---|---|---|---|---|---|---|---|---|
| | 50 | | | | | 55 | | | | | 60 | | | | |

| Val | Ile | Thr | Tyr | Phe | Leu | Phe | Asn | Val | Phe | Phe | Val | Trp | Ile | Gly | Tyr |
|---|---|---|---|---|---|---|---|---|---|---|---|---|---|---|---|
| 65 | | | | | 70 | | | | | 75 | | | | | 80 |

| Val | Cys | Thr | Leu | Gly | Ile | Asn | Pro | Val | Ile | Ile | Tyr | Thr | Leu | Phe |
|---|---|---|---|---|---|---|---|---|---|---|---|---|---|---|
| | | | | 85 | | | | | 90 | | | | | 95 |

(2) INFORMATION FOR SEQ ID NO:329:

(i) SEQUENCE CHARACTERISTICS:
(A) LENGTH: 97 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:329:

| Asn | Trp | Lys | Asn | Trp | Ser | Ala | Leu | Leu | Thr | Thr | Val | Val | Ile | Ile | Leu |
|---|---|---|---|---|---|---|---|---|---|---|---|---|---|---|---|
| 1 | | | | 5 | | | | | 10 | | | | | 15 | |

| Thr | Ile | Ala | Gly | Asn | Ile | Leu | Val | Ile | Met | Ala | Val | Ser | Ser | Leu | Asp |
|---|---|---|---|---|---|---|---|---|---|---|---|---|---|---|---|
| | | | 20 | | | | | 25 | | | | | 30 | | |

| Val | Met | Leu | Cys | Thr | Ala | Ser | Ile | Leu | Asn | Leu | Leu | Ile | Ser | Leu | Phe |
|---|---|---|---|---|---|---|---|---|---|---|---|---|---|---|---|
| | | 35 | | | | | 40 | | | | | 45 | | | |

| Val | Leu | Ile | Gly | Ser | Phe | Val | Ala | Phe | Phe | Ile | Pro | Leu | Thr | Ile | Met |

50                          55                              60

Val   Ile   Thr   Tyr   Phe   Leu   Phe   Asn   Val   Phe   Phe   Val   Trp   Ile   Gly   Tyr
        65                      70                      75                                  80

Val   Cys   Ser   Ser   Ser   Leu   Gly   Ile   Asn   Pro   Val   Ile   Ile   Tyr   Thr   Leu
                                85                      90                                  95

Phe ( 2 ) INFORMATION FOR SEQ ID NO:330:

( i ) SEQUENCE CHARACTERISTICS:
        ( A ) LENGTH: 98 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:330:

Ile   Thr   Ile   Thr   Val   Val   Leu   Ala   Val   Leu   Ile   Leu   Ile   Thr   Val   Ala
        1                       5                       10                                  15

Gly   Asn   Val   Val   Val   Cys   Ile   Ala   Val   Gly   Ser   Ile   Tyr   Thr   Ser   Leu
                                20                      25                                  30

Asp   Val   Met   Leu   Cys   Thr   Ala   Ser   Ile   Leu   Asn   Leu   Leu   Ile   Ser   Leu
                          35                      40                      45

Phe   Val   Leu   Ile   Gly   Ser   Phe   Val   Ala   Phe   Phe   Ile   Pro   Leu   Thr   Ile
                    50                      55                      60

Met   Val   Ile   Thr   Tyr   Phe   Leu   Phe   Asn   Val   Phe   Phe   Val   Trp   Ile   Gly
        65                      70                      75                                  80

Tyr   Val   Cys   Ser   Ser   Ser   Leu   Gly   Ile   Asn   Pro   Val   Ile   Ile   Tyr   Thr
                                85                      90                                  95

Leu   Phe ( 2 ) INFORMATION FOR SEQ ID NO:331:

( i ) SEQUENCE CHARACTERISTICS:
        ( A ) LENGTH: 93 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:331:

Thr   Leu   Thr   Leu   Val   Cys   Ile   Ala   Cys   Leu   Ser   Leu   Thr   Val   Phe   Gly
        1                       5                       10                                  15

Asn   Val   Leu   Val   Ile   Ile   Ala   Val   Phe   Ser   Leu   Asp   Val   Met   Leu   Cys
                                20                      25                                  30

Thr   Ala   Ser   Ile   Leu   Asn   Leu   Leu   Ile   Ser   Leu   Phe   Val   Leu   Ile   Gly
                    35                      40                      45

Ser   Phe   Val   Ala   Phe   Phe   Ile   Pro   Leu   Thr   Ile   Met   Val   Ile   Thr   Tyr
                    50                      55                      60

Phe   Leu   Phe   Asn   Val   Phe   Phe   Val   Trp   Ile   Gly   Tyr   Val   Cys   Ser   Ser
        65                      70                      75                                  80

Ser   Leu   Gly   Ile   Asn   Pro   Val   Ile   Ile   Tyr   Thr   Leu   Phe
                                85                      90

( 2 ) INFORMATION FOR SEQ ID NO:332:

( i ) SEQUENCE CHARACTERISTICS:
        ( A ) LENGTH: 99 amino acids
        ( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:332:

| Thr | Ala | Ala | Ile | Ala | Ala | Ala | Ile | Thr | Phe | Leu | Ile | Leu | Phe | Thr | Ile |
|---|---|---|---|---|---|---|---|---|---|---|---|---|---|---|---|
| 1 | | | | 5 | | | | | 10 | | | | | 15 | |
| Phe | Gly | Asn | Ala | Leu | Val | Ile | Ile | Ala | Val | Leu | Ser | Ile | Tyr | Thr | Ser |
| | | | 20 | | | | | 25 | | | | | 30 | | |
| Leu | Asp | Val | Met | Leu | Cys | Thr | Ala | Ser | Ile | Leu | Asn | Leu | Leu | Ile | Ser |
| | | | 35 | | | | 40 | | | | | 45 | | | |
| Leu | Phe | Val | Leu | Ile | Gly | Ser | Phe | Val | Ala | Phe | Phe | Ile | Pro | Leu | Thr |
| | | 50 | | | | 55 | | | | | 60 | | | | |
| Ile | Met | Val | Ile | Thr | Tyr | Phe | Leu | Phe | Asn | Val | Phe | Phe | Val | Trp | Ile |
| 65 | | | | | 70 | | | | | 75 | | | | | 80 |
| Gly | Tyr | Val | Cys | Ser | Ser | Ser | Leu | Gly | Ile | Asn | Pro | Val | Ile | Ile | Tyr |
| | | | | 85 | | | | | 90 | | | | | 95 | |
| Thr | Leu | Phe | | | | | | | | | | | | | |

( 2 ) INFORMATION FOR SEQ ID NO:333:

( i ) SEQUENCE CHARACTERISTICS:
( A ) LENGTH: 124 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:333:

| Ala | Ile | Ser | Val | Gly | Leu | Val | Leu | Gly | Ala | Phe | Ile | Leu | Phe | Ala | Ile |
|---|---|---|---|---|---|---|---|---|---|---|---|---|---|---|---|
| 1 | | | | 5 | | | | | 10 | | | | | 15 | |
| Val | Gly | Asn | Ile | Leu | Val | Ile | Leu | Ser | Val | Ala | Asn | Trp | Pro | Ala | Leu |
| | | | 20 | | | | | 25 | | | | | 30 | | |
| Ser | Ile | Val | Val | Ile | Ile | Ile | Asn | Thr | Ile | Gly | Gly | Asn | Ile | Leu | Val |
| | | | 35 | | | | | 40 | | | | | 45 | | |
| Ile | Met | Ala | Val | Ser | Ile | Tyr | Thr | Ser | Leu | Asp | Val | Met | Leu | Cys | Thr |
| | 50 | | | | | 55 | | | | | 60 | | | | |
| Ala | Ser | Ile | Leu | Asn | Leu | Leu | Ile | Ser | Leu | Phe | Val | Leu | Ile | Gly | Ser |
| 65 | | | | | 70 | | | | | 75 | | | | | 80 |
| Phe | Val | Ala | Phe | Phe | Ile | Pro | Leu | Thr | Ile | Met | Val | Ile | Thr | Tyr | Phe |
| | | | | 85 | | | | | 90 | | | | | 95 | |
| Leu | Phe | Asn | Val | Phe | Phe | Val | Trp | Ile | Gly | Tyr | Val | Cys | Ser | Ser | Ser |
| | | | 100 | | | | | 105 | | | | | 110 | | |
| Leu | Gly | Ile | Asn | Pro | Val | Ile | Ile | Tyr | Thr | Leu | Phe | | | | |
| | | 115 | | | | | 120 | | | | | | | | |

( 2 ) INFORMATION FOR SEQ ID NO:334:

( i ) SEQUENCE CHARACTERISTICS:
( A ) LENGTH: 95 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:334:

| Ala | Ala | Leu | Ala | Gly | Ala | Leu | Leu | Ala | Leu | Ala | Val | Leu | Ala | Thr | Val |
|---|---|---|---|---|---|---|---|---|---|---|---|---|---|---|---|
| 1 | | | | 5 | | | | | 10 | | | | | 15 | |

```
Gly  Gly  Asn  Leu  Leu  Val  Ile  Val  Ala  Ile  Ala  Ser  Leu  Asp  Val  Met
               20                      25                      30

Leu  Cys  Thr  Ala  Ser  Ile  Leu  Asn  Leu  Leu  Ile  Ser  Leu  Phe  Val  Leu
          35                      40                      45

Ile  Gly  Ser  Phe  Val  Ala  Phe  Phe  Ile  Pro  Leu  Thr  Ile  Met  Val  Ile
     50                      55                      60

Thr  Tyr  Phe  Leu  Phe  Asn  Val  Phe  Phe  Val  Trp  Ile  Gly  Tyr  Val  Cys
65                            70                      75                      80

Ser  Ser  Ser  Leu  Gly  Ile  Asn  Pro  Val  Ile  Ile  Tyr  Thr  Leu  Phe
                    85                      90                      95
```

( 2 ) INFORMATION FOR SEQ ID NO:335:

( i ) SEQUENCE CHARACTERISTICS:
        ( A ) LENGTH: 93 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:335:

```
Thr  Ala  Gly  Asp  Cys  Leu  Ile  Met  Leu  Ile  Val  Leu  Leu  Ile  Val  Ala
1                   5                      10                     15

Gly  Asn  Val  Leu  Val  Ile  Val  Ala  Ile  Ser  Leu  Asp  Val  Met  Leu  Cys
               20                      25                      30

Thr  Ala  Ser  Ile  Leu  Asn  Leu  Leu  Ile  Ser  Leu  Phe  Val  Leu  Ile  Gly
          35                      40                      45

Ser  Phe  Val  Ala  Phe  Phe  Ile  Pro  Leu  Thr  Ile  Met  Val  Ile  Thr  Tyr
     50                      55                      60

Phe  Leu  Phe  Asn  Val  Phe  Phe  Val  Trp  Ile  Gly  Tyr  Val  Cys  Ser  Ser
65                       70                      75                      80

Ser  Leu  Gly  Ile  Asn  Pro  Val  Ile  Ile  Tyr  Thr  Leu  Phe
               85                       90
```

( 2 ) INFORMATION FOR SEQ ID NO:336:

( i ) SEQUENCE CHARACTERISTICS:
        ( A ) LENGTH: 98 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:336:

```
Val  Ile  Thr  Ile  Ala  Val  Val  Thr  Ala  Val  Val  Ser  Leu  Met  Thr  Ile
1                   5                      10                     15

Val  Gly  Asn  Val  Leu  Val  Met  Ile  Ser  Phe  Ser  Ile  Tyr  Thr  Ser  Leu
               20                      25                      30

Asp  Val  Met  Leu  Cys  Thr  Ala  Ser  Ile  Leu  Asn  Leu  Leu  Ile  Ser  Leu
          35                      40                      45

Phe  Val  Leu  Ile  Gly  Ser  Phe  Val  Ala  Phe  Phe  Ile  Pro  Leu  Thr  Ile
     50                      55                      60

Met  Val  Ile  Thr  Tyr  Phe  Leu  Phe  Asn  Val  Phe  Phe  Val  Trp  Ile  Gly
65                       70                      75                      80

Tyr  Val  Cys  Ser  Ser  Ser  Leu  Gly  Ile  Asn  Pro  Val  Ile  Ile  Tyr  Thr
                    85                      90                      95

Leu  Phe
```

( 2 ) INFORMATION FOR SEQ ID NO:337:

( i ) SEQUENCE CHARACTERISTICS:
        ( A ) LENGTH: 98 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:337:

```
Met Val Phe Ile Ala Thr Val Arg Gly Ser Leu Ser Leu Val Thr Val
 1               5                  10                  15

Val Gly Asn Ile Leu Val Met Leu Ser Ile Ser Ile Tyr Thr Ser Leu
                20                  25                  30

Asp Val Met Leu Cys Thr Ala Ser Ile Leu Asn Leu Leu Ile Ser Leu
            35                  40                  45

Phe Val Leu Ile Gly Ser Phe Val Ala Phe Phe Ile Pro Leu Thr Ile
        50                  55                  60

Met Val Ile Thr Tyr Phe Leu Phe Asn Val Phe Phe Val Trp Ile Gly
65                  70                  75                  80

Tyr Val Cys Ser Ser Ser Leu Gly Ile Asn Pro Val Ile Ile Tyr Thr
                85                  90                  95

Leu Phe
```

( 2 ) INFORMATION FOR SEQ ID NO:338:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:338:

```
Trp Phe Ile Ala Phe Leu Thr Gly Ile Leu Ala Leu Val Thr Ile Ile
 1               5                  10                  15

Gly Asn Ile Leu Val Ile Val Ser Phe Ser Ile Tyr Thr Ser Leu Asp
                20                  25                  30

Val Met Leu Cys Thr Ala Ser Ile Leu Asn Leu Leu Ile Ser Leu Phe
            35                  40                  45

Val Leu Ile Gly Ser Phe Val Ala Phe Phe Ile Pro Leu Thr Ile Met
        50                  55                  60

Val Ile Thr Tyr Phe Leu Phe Asn Val Phe Phe Val Trp Ile Gly Tyr
65                  70                  75                  80

Val Cys Ser Ser Ser Leu Gly Ile Asn Pro Val Ile Ile Tyr Thr Leu
                85                  90                  95

Phe
```

( 2 ) INFORMATION FOR SEQ ID NO:339:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:339:

```
Asn Trp Pro Ala Leu Ser Ile Val Val Ile Ile Ile Asn Thr Ile Gly
 1               5                  10                  15
```

```
Gly Asn Ile Leu Val Ile Met Ala Phe Phe Ala Cys Phe Val Leu Val
            20              25              30

Leu Thr Gln Ser Ser Ile Phe Ser Leu Leu Ala Ile Ala Ile Asn Leu
        35              40              45

Leu Ile Ser Leu Phe Val Leu Ile Gly Ser Phe Val Ala Phe Phe Ile
        50              55              60

Pro Leu Thr Ile Met Val Ile Thr Tyr Phe Leu Phe Asn Val Phe Phe
65                  70              75                      80

Val Trp Ile Gly Tyr Val Cys Ser Ser Ser Leu Gly Ile Asn Pro Val
                85              90                      95

Ile Ile Tyr Thr Leu Phe
                100
```

(2) INFORMATION FOR SEQ ID NO:340:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:340:

```
Asn Trp Pro Ala Leu Ser Ile Val Val Ile Ile Ile Asn Thr Ile Gly
1               5                   10                  15

Gly Asn Ile Leu Val Ile Met Ala Phe Phe Ala Cys Phe Val Leu Val
            20              25              30

Leu Thr Gln Ser Ser Ile Phe Ser Leu Leu Ala Ile Ala Ile Phe Val
        35              40              45

Leu Ile Gly Ser Phe Val Ala Phe Phe Ile Pro Leu Thr Ile Met Val
        50              55              60

Ile Thr Tyr Phe Leu Phe Asn Val Phe Phe Val Trp Ile Gly Tyr Val
65                  70              75                      80

Cys Ser Ser Ser Leu Gly Ile Asn Pro Val Ile Ile Tyr Thr Leu Phe
                85              90              95
```

(2) INFORMATION FOR SEQ ID NO:341:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:341:

```
Asn Trp Pro Ala Leu Ser Ile Val Val Ile Ile Ile Asn Thr Ile Gly
1               5                   10                  15

Gly Asn Ile Leu Val Ile Met Ala Val Met Val Ala Cys Pro Val Leu
            20              25              30

Ile Leu Thr Gln Ser Ser Ile Ile Ala Leu Leu Ala Ile Ala Val Ser
        35              40              45

Phe Val Ala Phe Phe Ile Pro Leu Thr Ile Met Val Ile Thr Tyr Phe
    50              55              60

Leu Phe Asn Val Phe Phe Val Trp Ile Gly Tyr Val Cys Ser Ser Ser
65              70              75                      80

Leu Gly Ile Asn Pro Val Ile Ile Tyr Thr Leu Phe
                85              90
```

( 2 ) INFORMATION FOR SEQ ID NO:342:

( i ) SEQUENCE CHARACTERISTICS:
        ( A ) LENGTH: 88 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:342:

```
Asn Trp Pro Ala Leu Ser Ile Val Val Ile Ile Ile Asn Thr Ile Gly
 1               5                  10                  15
Gly Asn Ile Leu Val Ile Met Ala Val Leu Trp Leu Ala Leu Asp Tyr
            20                  25                  30
Val Ala Ser Asn Ala Ser Val Leu Asn Leu Leu Leu Ile Ser Phe Phe
            35                  40                  45
Phe Ile Pro Leu Thr Ile Met Val Ile Thr Tyr Phe Leu Phe Asn Val
    50                  55                  60
Phe Phe Val Trp Ile Gly Tyr Val Cys Ser Ser Ser Leu Gly Ile Asn
65                  70                  75                  80
Pro Val Ile Ile Tyr Thr Leu Phe
                85
```

( 2 ) INFORMATION FOR SEQ ID NO:343:

( i ) SEQUENCE CHARACTERISTICS:
        ( A ) LENGTH: 86 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:343:

```
Asn Trp Pro Ala Leu Ser Ile Val Val Ile Ile Ile Asn Thr Ile Gly
 1               5                  10                  15
Gly Asn Ile Leu Val Ile Met Ala Val Leu Tyr Val Val Ser Asn Ala
            20                  25                  30
Ser Val Met Asn Leu Leu Ile Ile Ser Ser Phe Val Ala Phe Phe Ile
            35                  40                  45
Pro Leu Thr Ile Met Val Ile Thr Tyr Phe Leu Phe Asn Val Phe Phe
    50                  55                  60
Val Trp Ile Gly Tyr Val Cys Ser Ser Ser Leu Gly Ile Asn Pro Val
65                  70                  75                  80
Ile Ile Tyr Thr Leu Phe
                85
```

( 2 ) INFORMATION FOR SEQ ID NO:344:

( i ) SEQUENCE CHARACTERISTICS:
        ( A ) LENGTH: 93 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:344:

```
Asn Trp Pro Ala Leu Ser Ile Val Val Ile Ile Ile Asn Thr Ile Gly
 1               5                  10                  15
Gly Asn Ile Leu Val Ile Met Ala Val Leu Trp Ile Ala Ile Asp Tyr
```

```
            20                          25                          30

Val  Ala  Ser  Asn  Ala  Ser  Val  Leu  Asn  Leu  Leu  Val  Ile  Ser  Phe  Gly
              35                          40                          45

Ser  Phe  Val  Ala  Phe  Phe  Ile  Pro  Leu  Thr  Ile  Met  Val  Ile  Thr  Tyr
         50                          55                          60

Phe  Leu  Phe  Asn  Val  Phe  Phe  Val  Trp  Ile  Gly  Tyr  Val  Cys  Ser  Ser
    65                          70                          75                     80

Ser  Leu  Gly  Ile  Asn  Pro  Val  Ile  Ile  Tyr  Thr  Leu  Phe
                        85                          90
```

( 2 ) INFORMATION FOR SEQ ID NO:345:

( i ) SEQUENCE CHARACTERISTICS:
        ( A ) LENGTH: 92 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:345:

```
    Asn  Trp  Pro  Ala  Leu  Ser  Ile  Val  Val  Ile  Ile  Ile  Asn  Thr  Ile  Gly
    1                    5                         10                         15

Gly  Asn  Ile  Leu  Val  Ile  Met  Ala  Val  Leu  Phe  Pro  Phe  Leu  Gln  Lys
                   20                         25                         30

Ser  Ser  Val  Gly  Ile  Thr  Val  Leu  Asn  Leu  Cys  Ala  Leu  Ser  Gly  Ser
                   35                         40                         45

Phe  Val  Ala  Phe  Phe  Ile  Pro  Leu  Thr  Ile  Met  Val  Ile  Thr  Tyr  Phe
         50                          55                         60

Leu  Phe  Asn  Val  Phe  Phe  Val  Trp  Ile  Gly  Tyr  Val  Cys  Ser  Ser  Ser
    65                          70                         75                     80

Leu  Gly  Ile  Asn  Pro  Val  Ile  Ile  Tyr  Thr  Leu  Phe
                   85                         90
```

( 2 ) INFORMATION FOR SEQ ID NO:346:

( i ) SEQUENCE CHARACTERISTICS:
        ( A ) LENGTH: 94 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:346:

```
    Asn  Trp  Pro  Ala  Leu  Ser  Ile  Val  Val  Ile  Ile  Ile  Asn  Thr  Ile  Gly
    1                    5                         10                         15

Gly  Asn  Ile  Leu  Val  Ile  Met  Ala  Val  Cys  Ile  Thr  Tyr  Leu  Gln  Tyr
                   20                         25                         30

Leu  Gly  Ile  Asn  Ala  Ser  Ser  Cys  Ser  Ile  Thr  Ala  Phe  Thr  Ile  Ile
              35                         40                         45

Gly  Ser  Phe  Val  Ala  Phe  Phe  Ile  Pro  Leu  Thr  Ile  Met  Val  Ile  Thr
         50                         55                         60

Tyr  Phe  Leu  Phe  Asn  Val  Phe  Phe  Val  Trp  Ile  Gly  Tyr  Val  Cys  Ser
    65                         70                         75                     80

Ser  Ser  Leu  Gly  Ile  Asn  Pro  Val  Ile  Ile  Tyr  Thr  Leu  Phe
                        85                         90
```

( 2 ) INFORMATION FOR SEQ ID NO:347:

( i ) SEQUENCE CHARACTERISTICS:

(A) LENGTH: 92 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:347:

| Asn | Trp | Pro | Ala | Leu | Ser | Ile | Val | Val | Ile | Ile | Ile | Asn | Thr | Ile | Gly |
|---|---|---|---|---|---|---|---|---|---|---|---|---|---|---|---|
| 1 | | | | 5 | | | | | 10 | | | | | 15 | |
| Gly | Asn | Ile | Leu | Val | Ile | Met | Ala | Val | Phe | His | Asn | Phe | Phe | Pro | Ile |
| | | | 20 | | | | | 25 | | | | | 30 | | |
| Ala | Ala | Leu | Phe | Ala | Ser | Ile | Tyr | Ser | Met | Thr | Ala | Val | Ala | Gly | Ser |
| | | 35 | | | | | 40 | | | | | 45 | | | |
| Phe | Val | Ala | Phe | Phe | Ile | Pro | Leu | Thr | Ile | Met | Val | Ile | Thr | Tyr | Phe |
| | 50 | | | | | 55 | | | | | 60 | | | | |
| Leu | Phe | Asn | Val | Phe | Phe | Val | Trp | Ile | Gly | Tyr | Val | Cys | Ser | Ser | Ser |
| 65 | | | | | 70 | | | | | 75 | | | | | 80 |
| Leu | Gly | Ile | Asn | Pro | Val | Ile | Ile | Tyr | Thr | Leu | Phe | | | | |
| | | | | 85 | | | | | 90 | | | | | | |

(2) INFORMATION FOR SEQ ID NO:348:

(i) SEQUENCE CHARACTERISTICS:
(A) LENGTH: 93 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:348:

| Asn | Trp | Pro | Ala | Leu | Ser | Ile | Val | Val | Ile | Ile | Ile | Asn | Thr | Ile | Gly |
|---|---|---|---|---|---|---|---|---|---|---|---|---|---|---|---|
| 1 | | | | 5 | | | | | 10 | | | | | 15 | |
| Gly | Asn | Ile | Leu | Val | Ile | Met | Ala | Val | Ile | Ala | Ser | Ala | Ser | Val | Ser |
| | | | 20 | | | | | 25 | | | | | 30 | | |
| Phe | Asn | Leu | Tyr | Ala | Ser | Val | Phe | Leu | Leu | Thr | Cys | Leu | Ser | Ile | Gly |
| | | 35 | | | | | 40 | | | | | 45 | | | |
| Ser | Phe | Val | Ala | Phe | Phe | Ile | Pro | Leu | Thr | Ile | Met | Val | Ile | Thr | Tyr |
| | 50 | | | | | 55 | | | | | 60 | | | | |
| Phe | Leu | Phe | Asn | Val | Phe | Phe | Val | Trp | Ile | Gly | Tyr | Val | Cys | Ser | Ser |
| 65 | | | | | 70 | | | | | 75 | | | | | 80 |
| Ser | Leu | Gly | Ile | Asn | Pro | Val | Ile | Ile | Tyr | Thr | Leu | Phe | | | |
| | | | | 85 | | | | | 90 | | | | | | |